US012624046B2

(12) United States Patent
Hirose et al.

(10) Patent No.: US 12,624,046 B2
(45) Date of Patent: May 12, 2026

(54) ORGANIC COMPOUND, LIGHT-EMITTING DEVICE, ELECTRONIC DEVICE, ELECTRONIC APPARATUS, LIGHT-EMITTING APPARATUS, AND LIGHTING APPARATUS

(71) Applicant: Semiconductor Energy Laboratory Co., Ltd., Kanagawa-ken (JP)

(72) Inventors: Tomoya Hirose, Atsugi (JP); Yasuhiro Niikura, Tokyo (JP); Hiroshi Kadoma, Sagamihara (JP); Nobuharu Ohsawa, Zama (JP); Harue Osaka, Atsugi (JP); Satoshi Seo, Sagamihara (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 941 days.

(21) Appl. No.: 17/798,499

(22) PCT Filed: Feb. 1, 2021

(86) PCT No.: PCT/IB2021/050763

§ 371 (c)(1),
(2) Date: Aug. 9, 2022

(87) PCT Pub. No.: WO2021/161127

PCT Pub. Date: Aug. 19, 2021

(65) Prior Publication Data

US 2023/0129057 A1 Apr. 27, 2023

(30) Foreign Application Priority Data

Feb. 14, 2020 (JP) ................................ 2020-023394

(51) Int. Cl.

| | |
|---|---|
| ***C07D 495/04*** | (2006.01) |
| ***C07D 491/048*** | (2006.01) |
| ***H10K 85/60*** | (2023.01) |

(52) U.S. Cl.
CPC ....... *C07D 491/048* (2013.01); *C07D 495/04* (2013.01); *H10K 85/657* (2023.02)

(58) Field of Classification Search
None
See application file for complete search history.

(56) References Cited

U.S. PATENT DOCUMENTS 9,502,656 B2 11/2016 Joseph et al.
9,553,274 B2 1/2017 Xia et al.
(Continued)

FOREIGN PATENT DOCUMENTS

CN 104292241 A 1/2015
CN 105103327 A 11/2015
(Continued)

OTHER PUBLICATIONS

International Search Report (Application No. PCT/IB2021/050763) Dated Apr. 20, 2021.

(Continued)

*Primary Examiner* — Tae H Yoon
(74) *Attorney, Agent, or Firm* — Husch Blackwell LLP

(57) ABSTRACT

An organic compound that easily exhibits thermally activated delayed fluorescence (TADF) is provided. An organic compound represented by General Formula (G1) is provided. In General Formula (G1), $R^1$ to $R^8$ are each independently any one of hydrogen, an alkyl group having 1 to 6 carbon atoms, a cycloalkyl group having 3 to 7 carbon atoms, and a substituted or unsubstituted diarylamino group; at least one of $R^1$ to $R^8$ is a substituted or unsubstituted diarylamino group; α is a substituted or unsubstituted phenylene group; n is an integer of 0 to 4; and A represents a substituted or unsubstituted benzofuropyrimidine skeleton or benzothienopyrimidine skeleton.

(Continued)

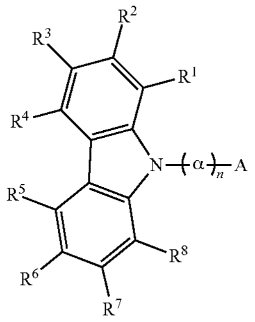

(G1)

23 Claims, 44 Drawing Sheets

(56) References Cited

U.S. PATENT DOCUMENTS

| | | | |
|---|---|---|---|
| 9,905,782 | B2 | 2/2018 | Inoue et al. |
| 10,153,437 | B2 | 12/2018 | Hirose et al. |
| 10,193,086 | B2 | 1/2019 | Inoue et al. |
| 10,230,055 | B2 | 3/2019 | Kanamoto et al. |
| 10,586,931 | B2 | 3/2020 | Kanamoto et al. |
| 10,586,932 | B2 | 3/2020 | Hosoumi et al. |
| 10,700,291 | B2 | 6/2020 | Inoue et al. |
| 10,868,258 | B2 | 12/2020 | Kurihara et al. |
| 2014/0291645 | A1 | 10/2014 | Inoue et al. |
| 2015/0021556 | A1 | 1/2015 | Xia et al. |
| 2015/0243893 | A1 | 8/2015 | Joseph et al. |
| 2018/0166641 | A1 | 6/2018 | Inoue et al. |
| 2019/0173024 | A1 | 6/2019 | Inoue et al. |
| 2020/0028091 | A1 | 1/2020 | Parham et al. |
| 2021/0013428 | A1 | 1/2021 | Inoue et al. |
| 2022/0173327 | A1 | 6/2022 | Hara et al. |

FOREIGN PATENT DOCUMENTS

| | | | | |
|---|---|---|---|---|
| CN | 109608473 | A | | 4/2019 |
| CN | 109616572 | A | | 4/2019 |
| CN | 109790173 | A | | 5/2019 |
| EP | 2 826 781 | A1 | | 1/2015 |
| EP | 2 910 555 | A1 | | 8/2015 |
| JP | 2014-209611 | A | | 11/2014 |
| JP | 2015-157808 | A | | 9/2015 |
| JP | 2016-174161 | A | | 9/2016 |
| JP | 2018-127402 | A | | 8/2018 |
| JP | 2019-069965 | A | | 5/2019 |
| JP | 2019-532952 | | | 11/2019 |
| KR | 2015-0009462 | A | | 1/2015 |
| KR | 2015-0100555 | A | | 9/2015 |
| KR | 2015-0132837 | A | | 11/2015 |
| KR | 2019-0053948 | A | | 5/2019 |
| TW | 201718614 | A | * | 6/2017 |
| WO | WO 2014/157599 | A1 | | 10/2014 |
| WO | WO 2018/060218 | A1 | | 4/2018 |

OTHER PUBLICATIONS

Written Opinion (Application No. PCT/IB2021/050763) Dated Apr. 20, 2021.

* cited by examiner

Structural Formula (100)

Structural Formula (101)

Structural Formula (102)

Structural Formula (103)

Structural Formula (104)

ORGANIC COMPOUND, LIGHT-EMITTING DEVICE, ELECTRONIC DEVICE, ELECTRONIC APPARATUS, LIGHT-EMITTING APPARATUS, AND LIGHTING APPARATUS

This application is a 371 of international application PCT/IB2021/050763 filed on Feb. 1, 2021 which is incorporated herein by reference.

TECHNICAL FIELD

One embodiment of the present invention relates to an organic compound, a light-emitting element, a light-emitting device, a display module, a lighting module, a display device, a light-emitting apparatus, an electronic apparatus, a lighting device, and an electronic device. Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting apparatus, a lighting device, a power storage device, a memory device, an imaging device, a driving method thereof, and a manufacturing method thereof.

BACKGROUND ART

Light-emitting devices (organic EL devices) including organic compounds and utilizing electroluminescence (EL) have been put into practical use. In the basic structure of such light-emitting devices, an organic compound layer containing a light-emitting material (an EL layer) is interposed between a pair of electrodes. Carriers are injected by application of voltage to the element, and recombination energy of the carriers is used, whereby light emission can be obtained from the light-emitting material.

Such light-emitting devices are of self-light-emitting type and thus have advantages over liquid crystal, such as high visibility and no need for backlight when used for pixels of a display, and are suitable as flat panel display elements. Displays including such light-emitting devices are also highly advantageous in that they can be thin and lightweight. Moreover, an extremely fast response speed is also a feature.

Since light-emitting layers of such light-emitting devices can be successively formed two-dimensionally, planar light emission can be achieved. This feature is difficult to realize with point light sources typified by incandescent lamps and LEDs or linear light sources typified by fluorescent lamps; thus, the light-emitting devices also have great potential as planar light sources, which can be applied to lighting and the like.

Displays or lighting devices using light-emitting devices can be suitably used for a variety of electronic apparatuses as described above, and research and development of light-emitting devices has progressed for more favorable characteristics (see Patent Document 1, for example).

REFERENCE

Patent Document

[Patent Document 1] Japanese Published Patent Application No. 2016-174161

SUMMARY OF THE INVENTION

Problems to be Solved by the Invention

An object of one embodiment of the present invention is to provide a novel organic compound. Alternatively, an object of one embodiment of the present invention is to provide an organic compound that easily exhibits delayed fluorescence and thermally activated delayed fluorescence (TADF). Alternatively, an object of one embodiment of the present invention is to provide an organic compound that exhibits TADF light emission. Alternatively, an object of one embodiment of the present invention is to provide an organic compound capable of providing a light-emitting element having favorable emission efficiency.

Alternatively, an object of one embodiment of the present invention is to provide a light-emitting device having favorable emission efficiency. Alternatively, an object of one embodiment of the present invention is to provide a light-emitting device that exhibits TADF light emission.

Alternatively, an object of one embodiment of the present invention is to provide a light-emitting apparatus, an electronic apparatus, a display device, and an electronic device each having low power consumption.

Note that the description of these effects does not preclude the existence of other effects. One embodiment of the present invention does not have to have all of these effects. Other effects will be apparent from the descriptions of the specification, the drawings, the claims, and the like, and other effects can be derived from the descriptions of the specification, the drawings, the claims, and the like.

It is only necessary that at least one of the above-described objects be achieved in the present invention.

Means for Solving the Problems

An embodiment of the present invention is an organic compound represented by General Formula (G1).

[Chemical Formula 2]

(G1)

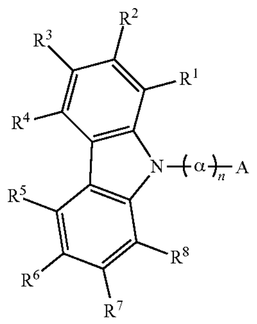

In General Formula (G1), $R^1$ to $R^8$ are each independently any one of hydrogen, an alkyl group having 1 to 6 carbon atoms, a cycloalkyl group having 3 to 7 carbon atoms, and a substituted or unsubstituted diarylamino group; at least one of $R^1$ to $R^8$ is a substituted or unsubstituted diarylamino group; α is a substituted or unsubstituted phenylene group; n is an integer of 0 to 4; and A represents a substituted or unsubstituted benzofuropyrimidine skeleton or benzothienopyrimidine skeleton.

Alternatively, an embodiment of the present invention is the organic compound in which, in the above structure, A is a group represented by General Formula (g1).

[Chemical Formula 2]

(g1)

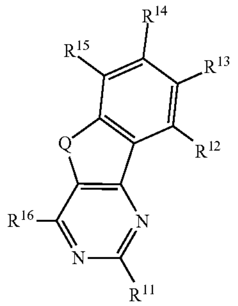

Note that in General Formula (g1), one of $R^{11}$ to $R^{16}$ is a dangling bond, and the others are each independently any of hydrogen, an alkyl group having 1 to 6 carbon atoms, a cycloalkyl group having 3 to 7 carbon atoms, and a substituted or unsubstituted aryl group having 6 to 13 carbon atoms in a ring. Furthermore, Q represents an oxygen atom or a sulfur atom.

Another embodiment of the present invention is an organic compound represented by General Formula (G2).

[Chemical Formula 3]

(G2)

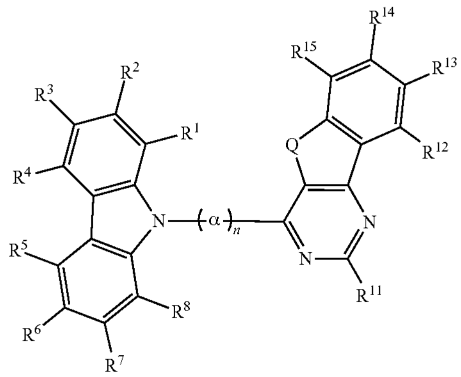

Note that in General Formula (G2), $R^1$ to $R^8$ are each independently any one of hydrogen, an alkyl group having 1 to 6 carbon atoms, a cycloalkyl group having 3 to 7 carbon atoms, and a substituted or unsubstituted diarylamino group; at least one of $R^1$ to $R^8$ is a substituted or unsubstituted diarylamino group; α is a substituted or unsubstituted phenylene group; n is an integer of 0 to 4; $R^{11}$ to $R^{15}$ are each independently any of hydrogen, an alkyl group having 1 to 6 carbon atoms, a cycloalkyl group having 3 to 7 carbon atoms, and a substituted or unsubstituted aryl group having 6 to 13 carbon atoms in a ring; and Q represents an oxygen atom or a sulfur atom.

Alternatively, another embodiment of the present invention is the organic compound in which, in the above structure, the substituted or unsubstituted diarylamino group is a group represented by General Formula (g2).

[Chemical Formula 4]

(g2)

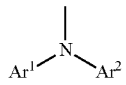

Note that in General Formula (g2), $Ar^1$ and $Ar^2$ each independently represent a substituted or unsubstituted aryl group having 6 to 13 carbon atoms in a ring.

Alternatively, another embodiment of the present invention is the organic compound in the above structure, in which one or both of $R^3$ and $R^6$ are groups represented by General Formula (g2).

Another embodiment of the present invention is an organic compound represented by a General Formula (G3).

[Chemical Formula 5]

(G3)

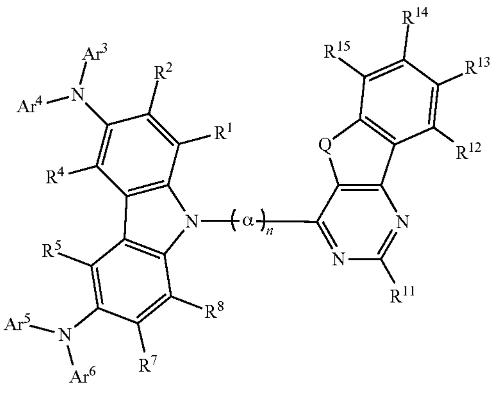

Note that in General Formula (G3), $Ar^3$ to $Ar^6$ are each independently any of a substituted or unsubstituted aryl group having 6 to 13 carbon atoms in a ring. In addition, $R^1$, $R^2$, $R^4$, $R^5$, $R^7$, and $R^8$ are each independently any one of hydrogen, an alkyl group having 1 to 6 carbon atoms, and a cycloalkyl group having 3 to 7 carbon atoms. Furthermore, a represents a substituted or unsubstituted phenylene group, and n is an integer of 0 to 4. In addition, $R^{11}$ to $R^{15}$ are each independently any of hydrogen, an alkyl group having 1 to 6 carbon atoms, a cycloalkyl group having 3 to 7 carbon atoms, and a substituted or unsubstituted aryl group having 6 to 13 carbon atoms in a ring. Furthermore, Q represents an oxygen atom or a sulfur atom.

Another embodiment of the present invention is an organic compound represented by General Formula (G4).

[Chemical Formula 6]

(G4)

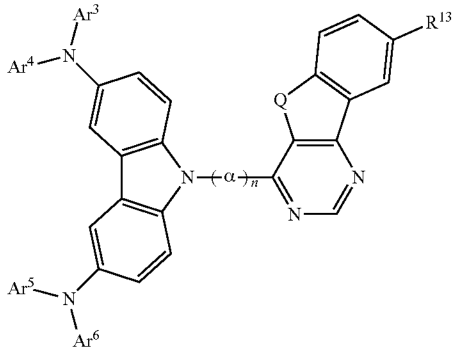

Note that in General Formula (G4), $Ar^3$ to $Ar^6$ are each independently any of a substituted or unsubstituted aryl group having 6 to 13 carbon atoms in a ring; α is a substituted or unsubstituted phenylene group; n is an integer of 0 to 4; $R^3$ is any of hydrogen, an alkyl group having 1 to 6 carbon atoms, a cycloalkyl group having 3 to 7 carbon atoms, and a substituted or unsubstituted aryl group having 6 to 13 carbon atoms in a ring; and Q represents an oxygen atom or a sulfur atom.

Alternatively, another embodiment of the present invention is an organic compound represented by a general formula (G5) below.

[Chemical Formula 7]

(G5)

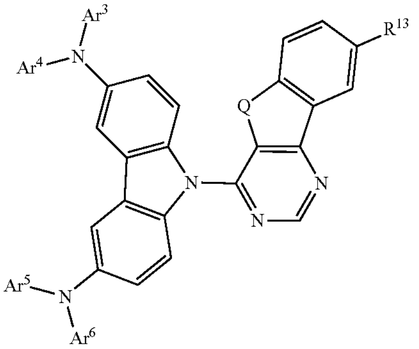

Note that in General Formula (G5), $Ar^3$ to $Ar^6$ are each independently any of a substituted or unsubstituted aryl group having 6 to 13 carbon atoms in a ring; $R^3$ is any of hydrogen, an alkyl group having 1 to 6 carbon atoms, a cycloalkyl group having 3 to 7 carbon atoms, and a substituted or unsubstituted aryl group having 6 to 13 carbon atoms in a ring; and Q represents an oxygen atom or a sulfur atom.

Alternatively, another embodiment of the present invention is an organic compound represented by Structural Formula (100).

[Chemical Formula 8]

(100)

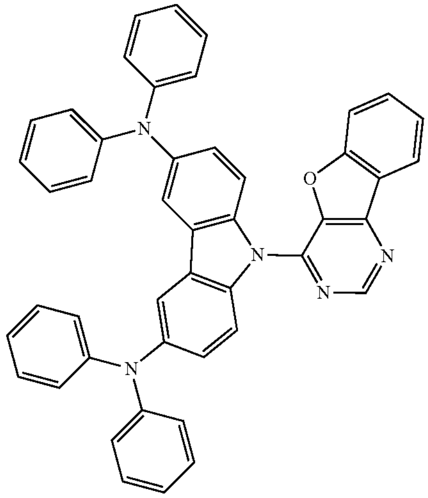

Another embodiment of the present invention is an organic compound represented by Structural Formula (101).

[Chemical Formula 9]

(101)

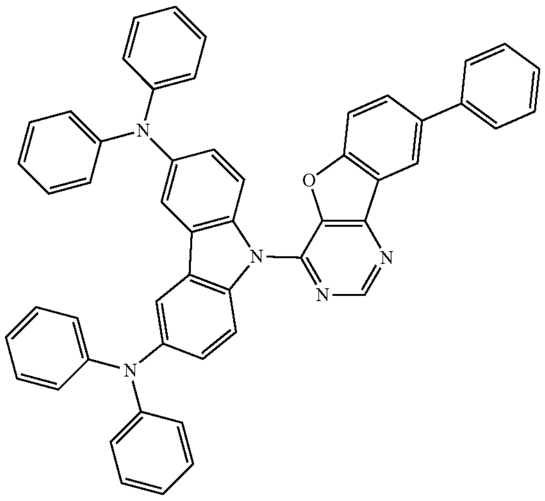

Another embodiment of the present invention is an organic compound represented by Structural Formula (102).

[Chemical Formula 10]

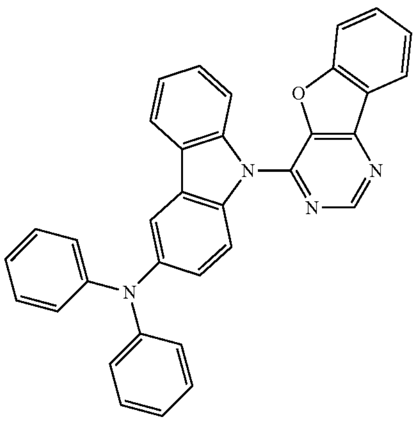

(102)

Alternatively, another embodiment of the present invention is the organic compound in the above structure, in which a difference between a lowest singlet excited level and a lowest triplet excited level is less than or equal to 0.2 eV.

Alternatively, another embodiment of the present invention is the organic compound in the above structure, in which a difference between a lowest singlet excited level and a lowest triplet excited level is less than or equal to 0.1 eV.

Alternatively, another embodiment of the present invention is the organic compound in the above structure, in which Q is an oxygen atom.

Alternatively, another embodiment of the present invention is an electronic device including a first electrode, a second electrode, and an organic layer between the first electrode and the second electrode. The organic layer includes the organic compound having the above structure.

Alternatively, another embodiment of the present invention is a light-emitting device including a first electrode, a second electrode, and an organic layer between the first electrode and the second electrode. The organic layer includes the organic compound having the above structure.

Alternatively, another embodiment of the present invention is the light-emitting device in the above structure, in which the organic layer includes a light-emitting layer and the organic compound is included in the light-emitting layer.

Alternatively, another embodiment of the present invention is the light-emitting device in the above structure, in which light emission from the organic layer is delayed fluorescence.

Alternatively, another embodiment of the present invention is the light-emitting device in the above structure, in which a transient lifetime of the delayed fluorescence is longer than or equal to 100 nanoseconds and shorter than or equal to 10 milliseconds.

Alternatively, another embodiment of the present invention is the light-emitting device in the above structure, in which the light-emitting layer further includes a fluorescent light-emitting material.

Alternatively, another embodiment of the present invention is the light-emitting device in the above structure, in which the light-emitting layer further includes a phosphorescent light-emitting material.

Another embodiment of the present invention is an electronic apparatus including the light-emitting device described in any of the above, and a sensor, an operation button, a speaker, or a microphone.

Another embodiment of the present invention is a light-emitting apparatus including the light-emitting device described in any of the above, and a transistor or a substrate.

Another embodiment of the present invention is a lighting device including the light-emitting device described in any of the above and a housing.

Note that the light-emitting apparatus in this specification includes, in its category, an image display device that uses a light-emitting device. The light-emitting apparatus may also include a module in which a light-emitting device is provided with a connector such as an anisotropic conductive film or a TCP (Tape Carrier Package), a module in which a printed wiring board is provided on the tip of a TCP, and a module in which an IC (integrated circuit) is directly mounted on a light-emitting device by a COG (Chip On Glass) method. Furthermore, in some cases, lighting equipment or the like includes the light-emitting apparatus.

Effect of the Invention

An embodiment of the present invention can provide a novel organic compound. Alternatively, an embodiment of the present invention can provide an organic compound that easily exhibits delayed fluorescence and thermally activated delayed fluorescence (TADF). Alternatively, an embodiment of the present invention can provide an organic compound that exhibits TADF light emission. Alternatively, an embodiment of the present invention can provide an organic compound capable of providing a light-emitting element having favorable emission efficiency.

Alternatively, an embodiment of the present invention can provide a light-emitting device having favorable emission efficiency. Alternatively, an embodiment of the present invention can provide a light-emitting device that exhibits TADF light emission.

Alternatively, an embodiment of the present invention can provide a light-emitting apparatus, an electronic apparatus, a display device, and an electronic device each having low power consumption.

Note that the description of these effects does not preclude the existence of other effects. One embodiment of the present invention does not have to have all of these effects. Other effects will be apparent from the descriptions of the specification, the drawings, the claims, and the like, and other effects can be derived from the descriptions of the specification, the drawings, the claims, and the like.

BRIEF DESCRIPTION OF THE DRAWINGS

FIG. 9A, FIG. 9B1, FIG. 9B2, and FIG. 9C illustrate concepts showing electronic apparatuses.

MODE FOR CARRYING OUT THE INVENTION

Figure 1A:
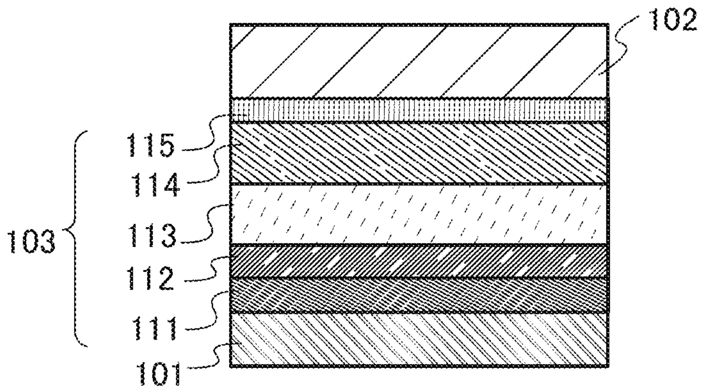
FIG. 1A, FIG. 1B, and FIG. 1C are conceptual diagrams of light-emitting devices.

Embodiments of the present invention will be described in detail below with reference to the drawings. Note that the present invention is not limited to the following description, and it will be readily appreciated by those skilled in the art that modes and details of the present invention can be modified in various ways without departing from the spirit and scope of the present invention. Thus, the present invention should not be construed as being limited to the description in the following embodiments.

Embodiment 1

For a current-excitation light-emitting device, a thermally activated delayed fluorescent (TADF) material, which can convert triplet excitation energy into light emission, has attracted attention as a highly efficient light-emitting material that replaces a phosphorescent light-emitting material. Development of a TADF material that can achieve high emission efficiency has been desired.

Unlike in an ordinary organic compound, in an organic compound that exhibits a TADF property, a difference ($\Delta E_{ST}$) between the lowest singlet excited level (S1 level) and the lowest triplet excited level (T1 level) is known to be very small. To achieve such a state, the HOMO and LUMO in a molecule need to be distributed so as to be spatially divided from each other.

An organic compound of one embodiment of the present invention has a $\Delta E_{ST}$ less than or equal to 0.2 eV, preferably less than or equal to 0.1 eV, which is very small, and is an organic compound that efficiently exhibits TADF light emission. The organic compound of one embodiment of the present invention is represented by General Formula (G1).

[Chemical Formula 11]

(G1)

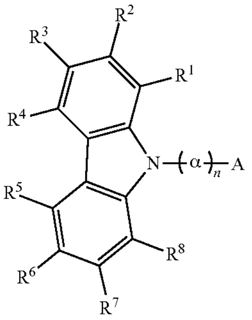

In General Formula (G1), $R^1$ to $R^8$ are each independently any one of hydrogen, an alkyl group having 1 to 6 carbon atoms, a cycloalkyl group having 3 to 7 carbon atoms, and a substituted or unsubstituted diarylamino group. Note that at least one of $R^1$ to $R^8$ is a substituted or unsubstituted diarylamino group.

In addition, a represents a substituted or unsubstituted phenylene group, and n is an integer of 0 to 4. Note that n is preferably 0 or 1, in which case the T1 level is increased. When the organic compound is used as an energy donor for a green-light-emitting material in a phosphorescent light-emitting device or an exciton capture type fluorescent element, the T1 level is required to be further higher; from this point of view, n is preferably 0. Alternatively, n is preferably 1 from the viewpoint of more reducing the energy of $\Delta E_{ST}$.

Note that A represents a substituted or unsubstituted benzofuropyrimidine skeleton or a substituted or unsubstituted benzothienopyrimidine skeleton. The benzofuropyrimidine skeleton can also be represented as Formula (g1). In General Formula (g1), Q represents an oxygen atom or a sulfur atom.

[Chemical Forrmula 12]

(g1)

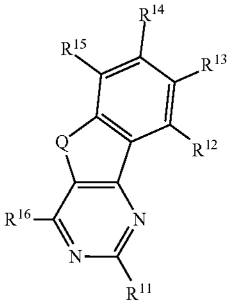

In General Formula (g1), one of $R^{11}$ to $R^{16}$ is a dangling bond, and bonded to a or a nitrogen atom of a carbazolyl group in General Formula (G1). The others are each independently any of hydrogen, an alkyl group having 1 to 6 carbon atoms, a cycloalkyl group having 3 to 7 carbon atoms, and a substituted or unsubstituted aryl group having 6 to 13 carbon atoms in a ring.

In General Formula (g1), the dangling bond is preferably $R^6$, in which case synthesis is facilitated and stability is improved. That is, the organic compound of one embodiment of the present invention is preferably an organic compound represented by General Formula (G2).

[Chemical Formula 13]

(G2)

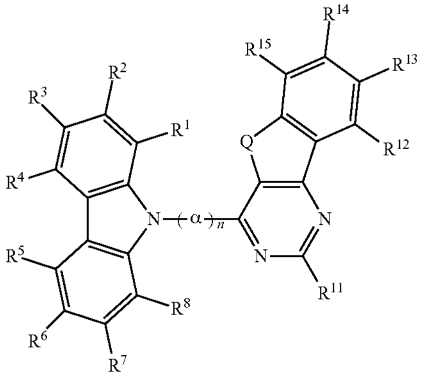

In General Formula (G2), $R^1$ to $R^8$ are each independently any one of hydrogen, an alkyl group having 1 to 6 carbon atoms, a cycloalkyl group having 3 to 7 carbon atoms, and a substituted or unsubstituted diarylamino group. Note that at least one of $R^1$ to $R^8$ is a substituted or unsubstituted diarylamino group.

In addition, α represents a substituted or unsubstituted phenylene group, and n is an integer of 0 to 4.

In addition, $R^{11}$ to $R^{15}$ are each independently any of hydrogen, an alkyl group having 1 to 6 carbon atoms, a cycloalkyl group having 3 to 7 carbon atoms, and a substituted or unsubstituted aryl group having 6 to 13 carbon atoms in a ring. Furthermore, Q represents an oxygen atom or a sulfur atom.

In General Formulae (G1) and (G2), the substituted or unsubstituted diarylamino group that is at least one of $R^1$ to $R^8$ is preferably a group represented by General Formula (g2).

[Chemical Formula 14]

(g2)

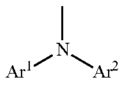

In this specification, $Ar^1$ and $Ar^2$ each independently represent a substituted or unsubstituted aryl group having 6 to 13 carbon atoms in a ring.

In General Formulae (G1) and (G2), one or two of $R^1$ to $R^8$ are preferably groups represented by General Formula (g2) and one or both of $R^3$ and $R^6$ are preferably groups represented by General Formula (g2). In General Formulae (G1) and (G2), two of $R^1$ to $R^8$ are preferably groups represented by General Formula (g2). Specifically, the organic compound of one embodiment of the present invention is preferably an organic compound represented by General Formula (G3).

[Chemical Formula 15]

(G3)

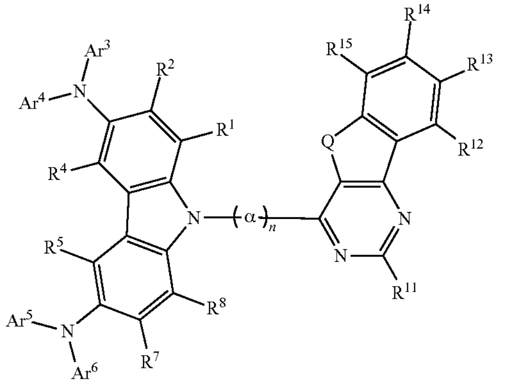

Note that in General Formula (G3), $Ar^3$ to $Ar^6$ are each independently any of a substituted or unsubstituted aryl group having 6 to 13 carbon atoms in a ring.

In addition, $R^1$, $R^2$, $R^4$, $R^5$, $R^7$, and $R^8$ are each independently any one of hydrogen, an alkyl group having 1 to 6 carbon atoms, and a cycloalkyl group having 3 to 7 carbon atoms.

Furthermore, α is a substituted or unsubstituted phenylene group, and n is an integer of 0 to 4.

In addition, $R^{11}$ to $R^{15}$ are each independently any of hydrogen, an alkyl group having 1 to 6 carbon atoms, a cycloalkyl group having 3 to 7 carbon atoms, and a substituted or unsubstituted aryl group having 6 to 13 carbon atoms in a ring. Furthermore, Q represents an oxygen atom or a sulfur atom.

In General Formula (G3), $R^1$, $R^2$, $R^4$, $R^5$, $R^7$, $R^8$, $R^{11}$, $R^{12}$, $R^{14}$ and $R^{15}$ are each preferably hydrogen, in which case the T1 level is increased and stability is improved. That is, the organic compound of one embodiment of the present invention is preferably an organic compound represented by General Formula (G4).

[Chemical Formula 16]

(G4)

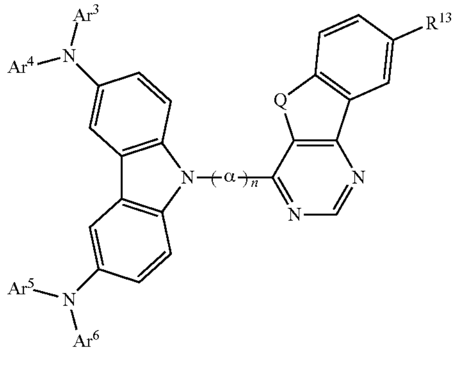

Note that in General Formula (G4), $Ar^3$ to $Ar^6$ are each independently any of a substituted or unsubstituted aryl group having 6 to 13 carbon atoms in a ring.

Furthermore, α is a substituted or unsubstituted phenylene group, and n is an integer of 0 to 4.

In addition, $R^{13}$ is any of hydrogen, an alkyl group having 1 to 6 carbon atoms, a cycloalkyl group having 3 to 7 carbon atoms, and a substituted or unsubstituted aryl group having 6 to 13 carbon atoms in a ring. In addition, Q represents an oxygen atom or a sulfur atom.

In the organic compounds represented by General Formulae (G1) to (G4), α is preferably an unsubstituted phenylene group.

In the organic compounds represented by General Formulae (G1) to (G4), n is preferably 1 or 0, in which case the T1 level is increased, and n is further preferably 0. That is, the organic compound of one embodiment of the present invention is preferably an organic compound represented by General Formula (G5).

[Chemical Formula 17]

(G5)

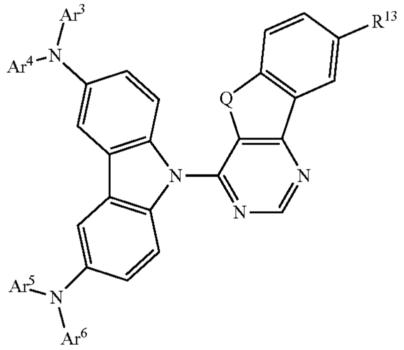

Note that in General Formula (G5), $Ar^3$ to $Ar^6$ are each independently any of a substituted or unsubstituted aryl group having 6 to 13 carbon atoms in a ring.

In addition, $R^{13}$ is any of hydrogen, an alkyl group having 1 to 6 carbon atoms, a cycloalkyl group having 3 to 7 carbon atoms, and a substituted or unsubstituted aryl group having 6 to 13 carbon atoms in a ring. Furthermore, Q represents an oxygen atom or a sulfur atom.

In this specification, specific examples of the alkyl group having 1 to 6 carbon atoms include a methyl group, an ethyl group, a propyl group, an isopropyl group, a butyl group, a tert-butyl group, a pentyl group, and a hexyl group. Specific examples of the cycloalkyl group having 3 to 7 carbon atoms include a cyclopropyl group, and a cyclohexyl group. Specific examples of the aryl group having 6 to 13 carbon atoms in a ring include a phenyl group, a biphenyl group, a naphthyl group, and a fluorenyl group.

In this specification, when the expression "substituted or unsubstituted" is used and a substituent is included, the substituent refers to an alkyl group having 1 to 6 carbon atoms or a cycloalkyl group having 3 to 7 carbon atoms.

The organic compound of one embodiment of the present invention with the above structure is an organic compound where the $\Delta E_{ST}$ is small and reverse intersystem crossing easily occurs, whereby TADF light emission can be easily obtained and light is emitted with favorable efficiency. A light-emitting device using the organic compound can be a light-emitting device which emits light with extremely favorable efficiency. Note that in a light-emitting device using the organic compound of one embodiment of the present invention, a delayed fluorescence component is observed in measurement of transient EL and the transient lifetime is longer than or equal to 100 nanoseconds and shorter than or equal to 10 milliseconds, preferably longer than or equal to 1 microsecond and shorter than or equal to 10 microseconds.

Specific examples of the organic compound with the above structure are shown.
[Chemical Formula 18]
(100)
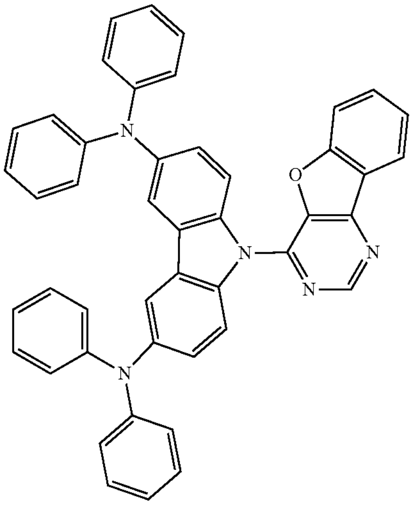
(101)
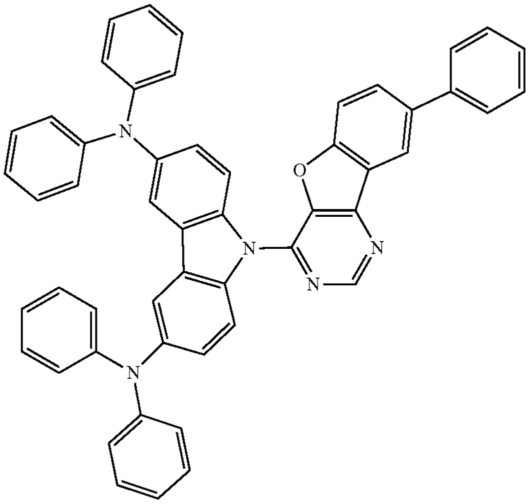
(102)
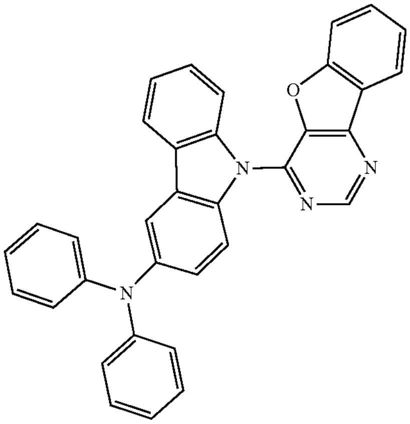
(103)
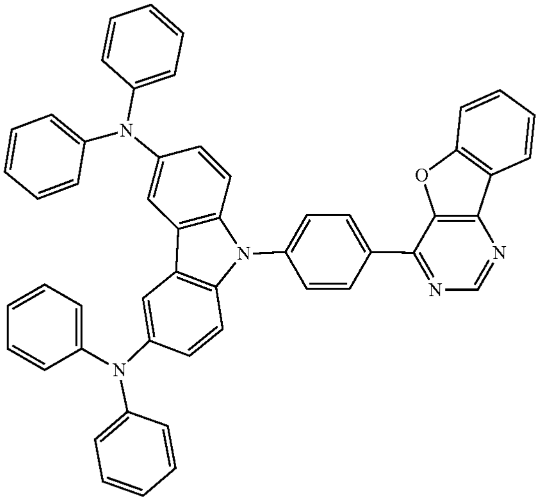
(104)
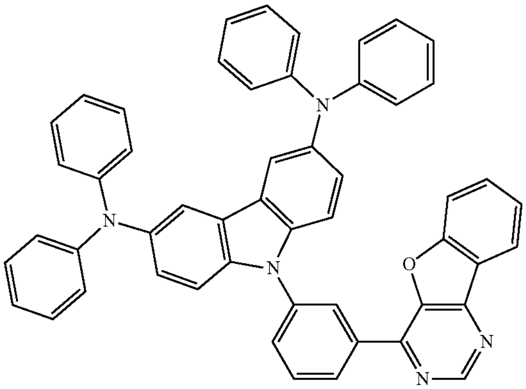
(105)
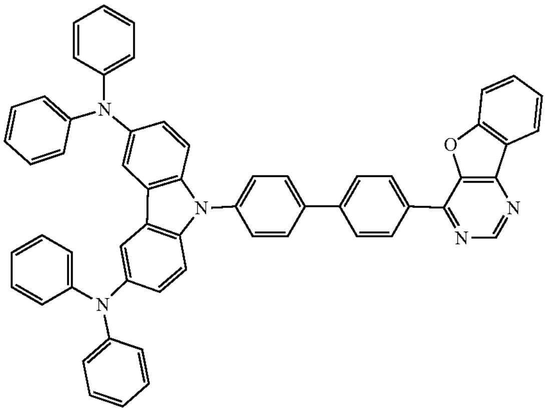

-continued
(106)
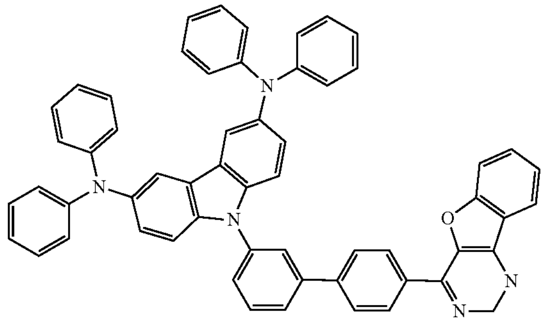
(107)
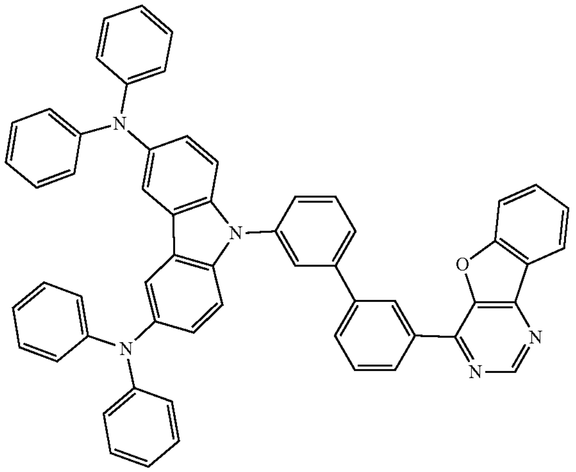
(108)
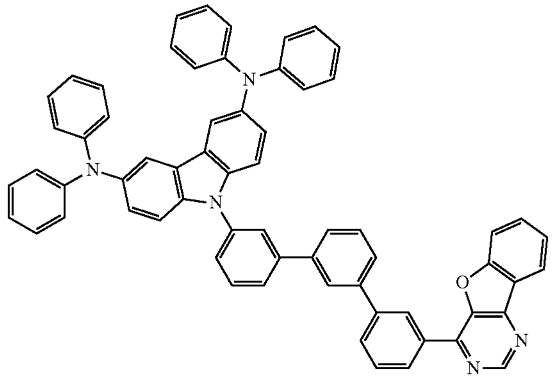
[Chemical Formula 19]
(109)
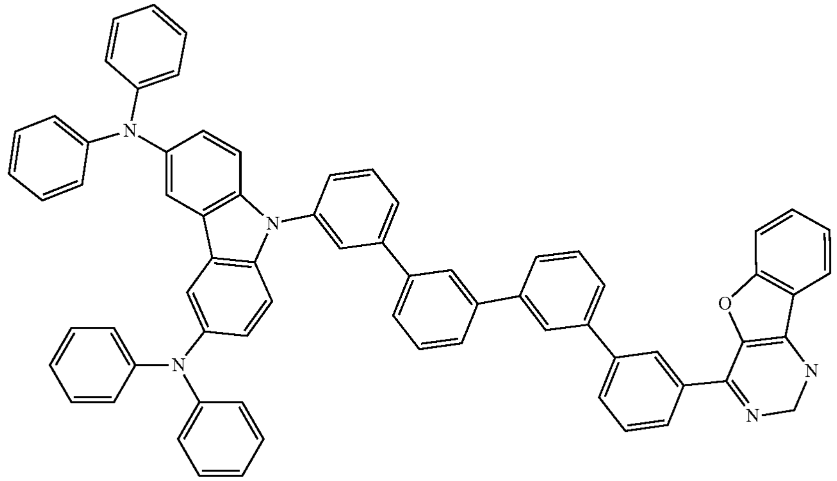

-continued
(110)
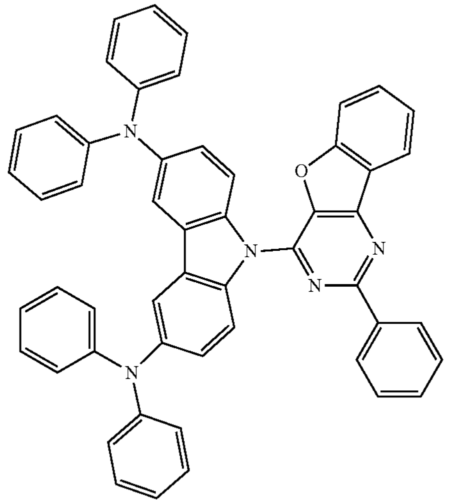
(111)
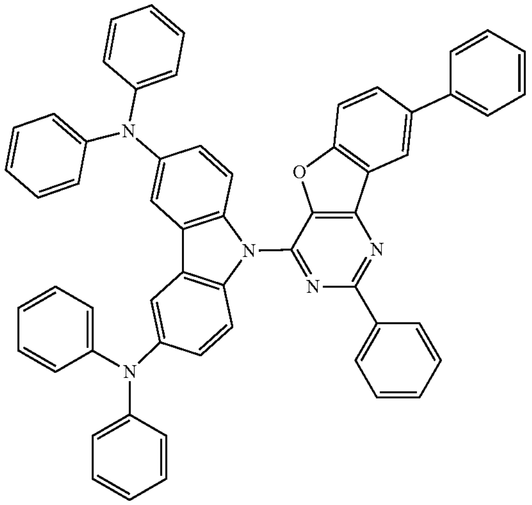
(112)
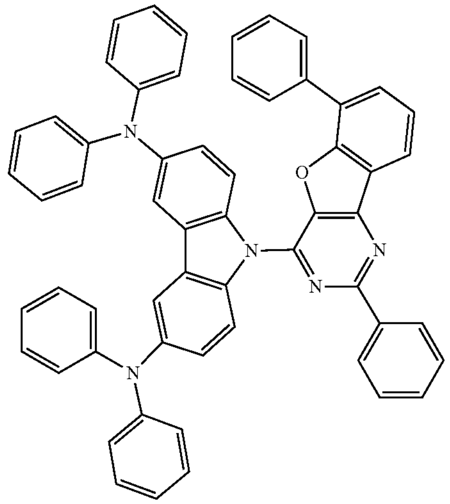
(113)
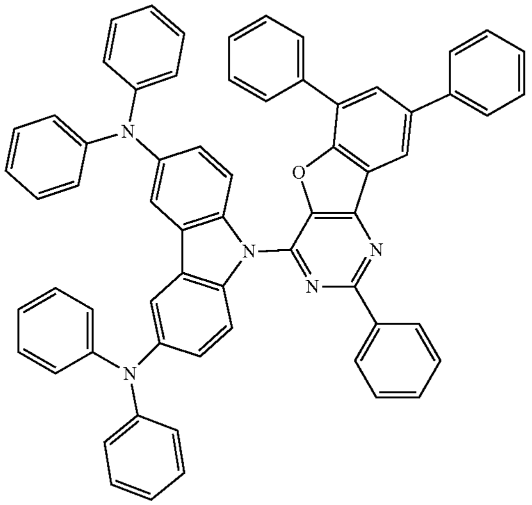
(114)
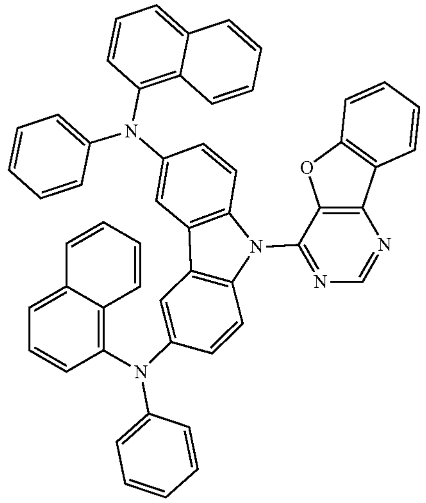
(115)
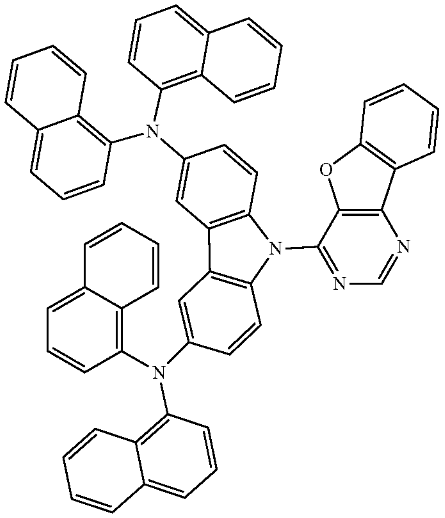

-continued
(116)
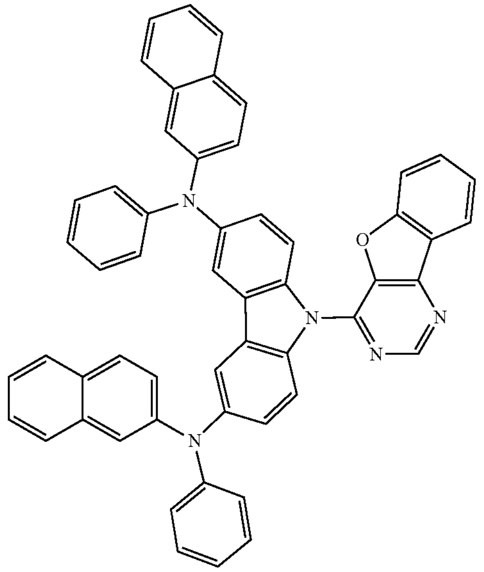
[Chemical Formula 20]
(117)
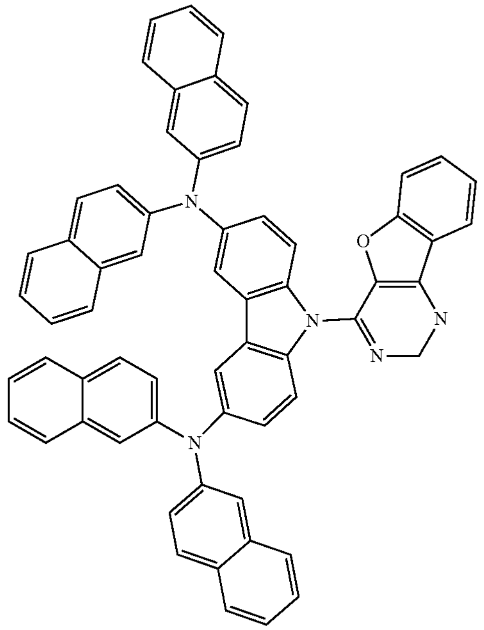

-continued
(118)
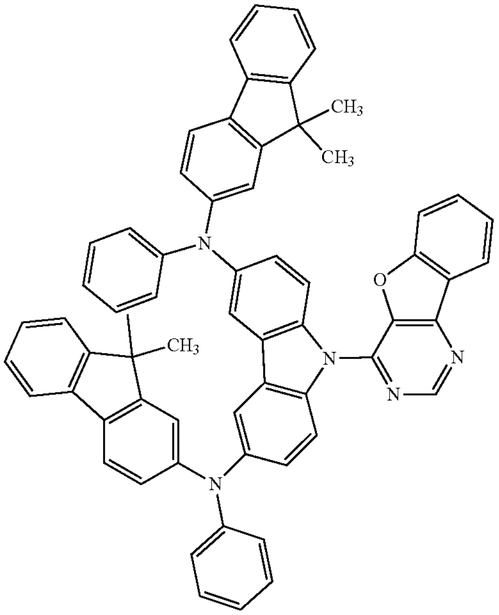
(119)
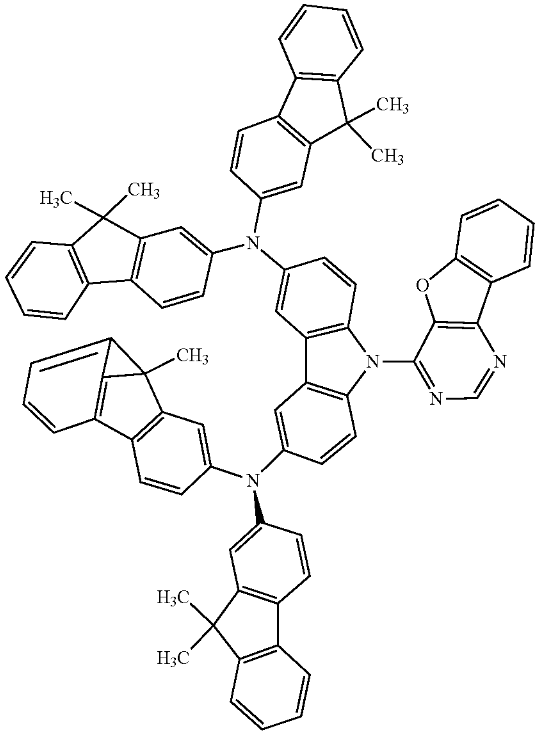
(120)
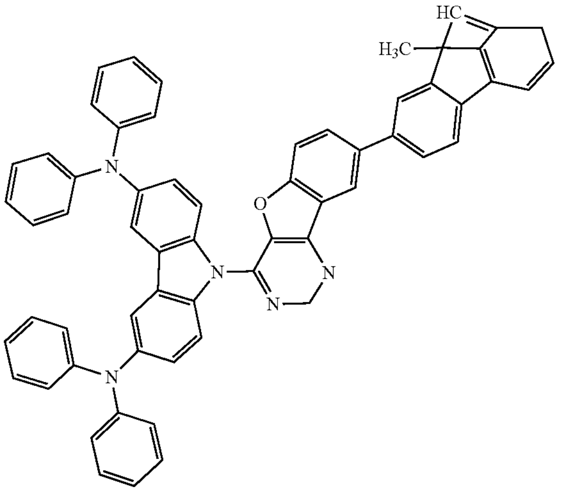
(121)
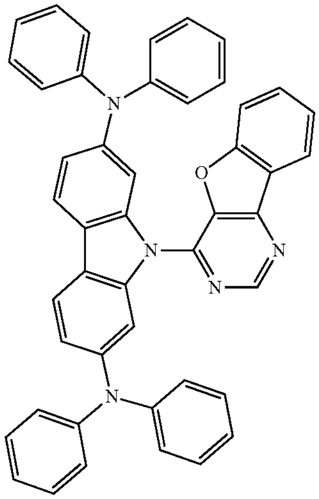

-continued
(122)
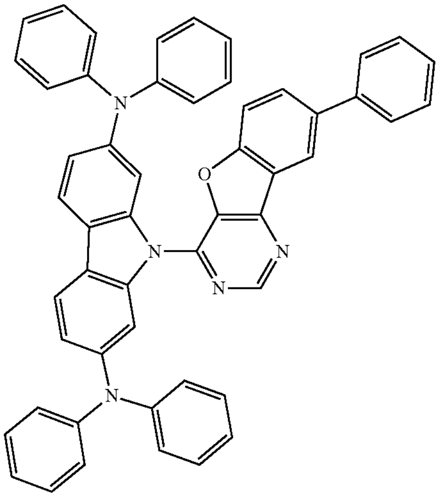
(123)
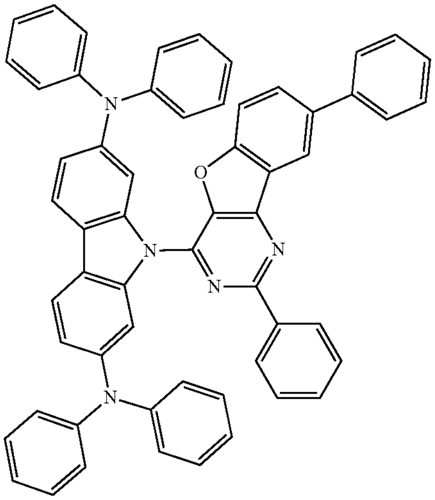
(124)
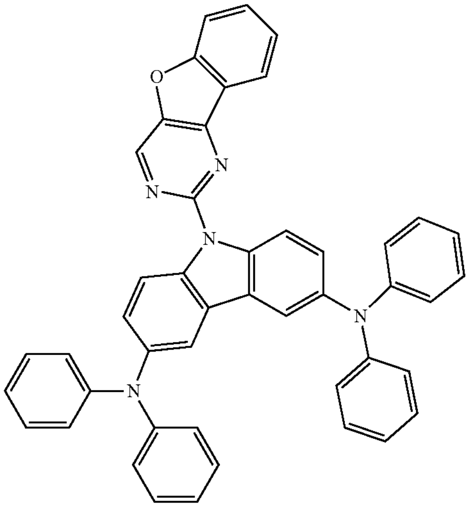
(125)
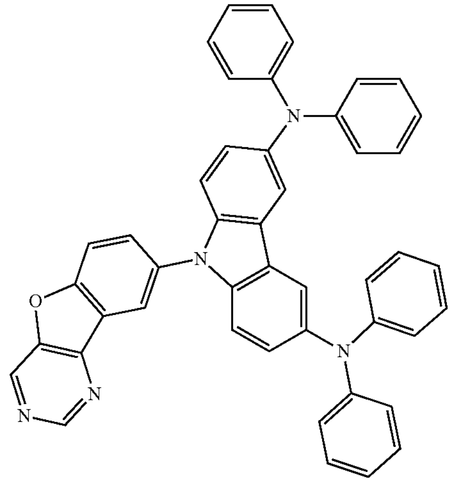
[Chemical Formula 21]
(126)
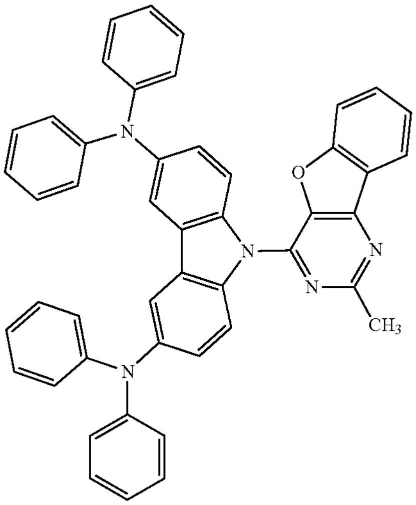
(127)
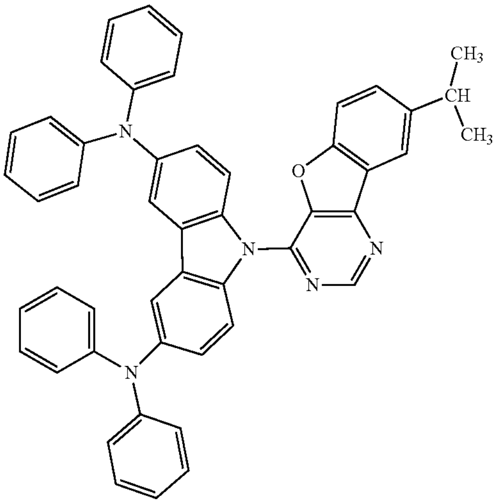

-continued
(128)
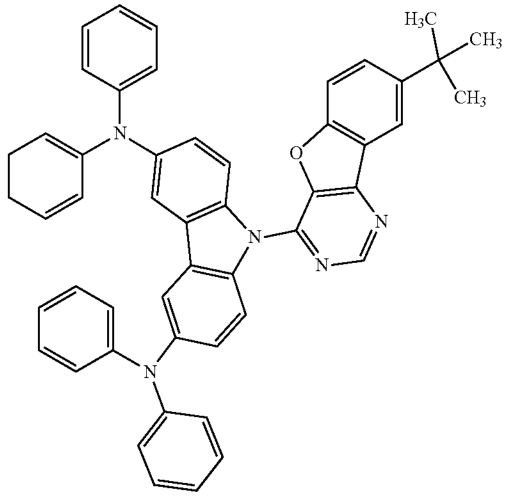
(129)
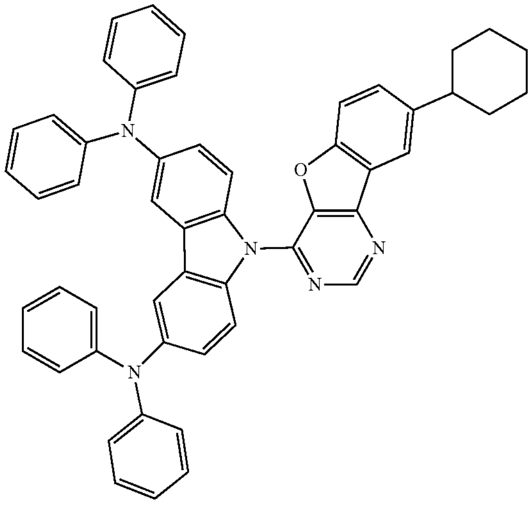
(130)
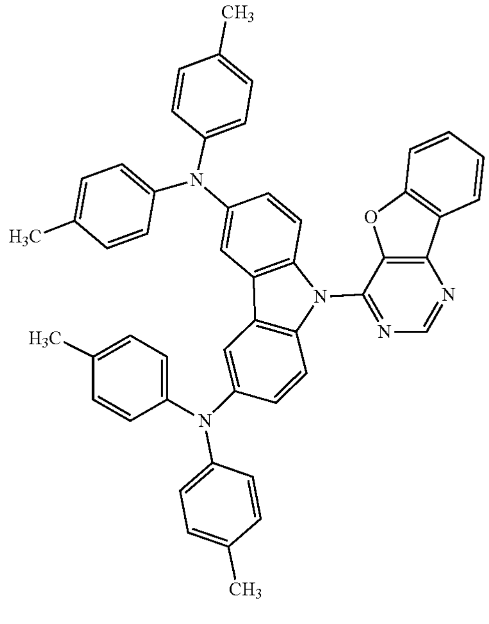
(131)
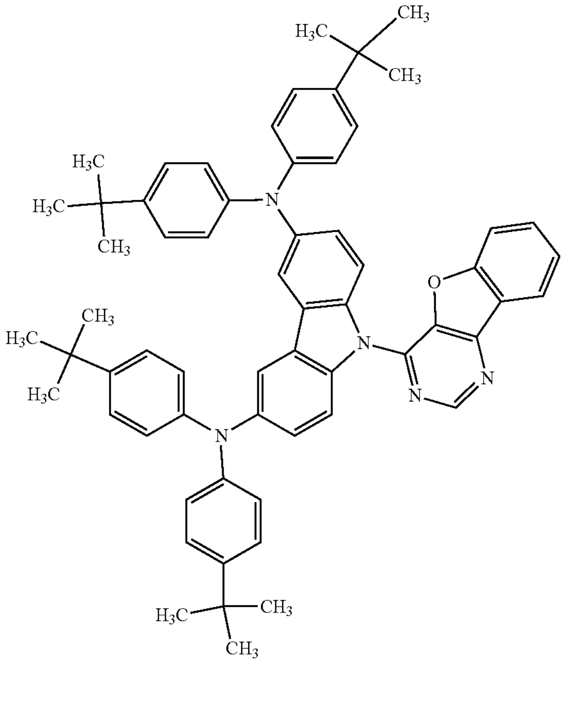

-continued
(132)
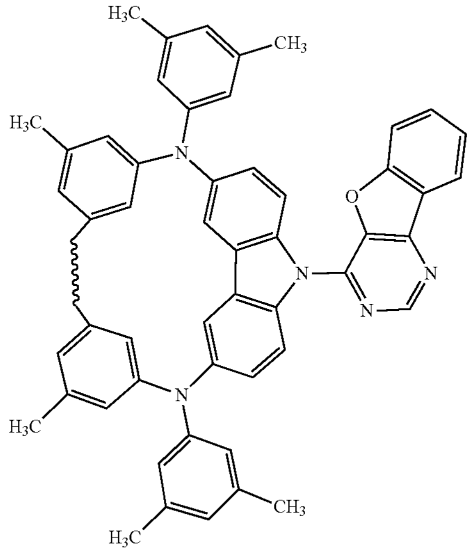
[Chemical Formula 22]
(133)
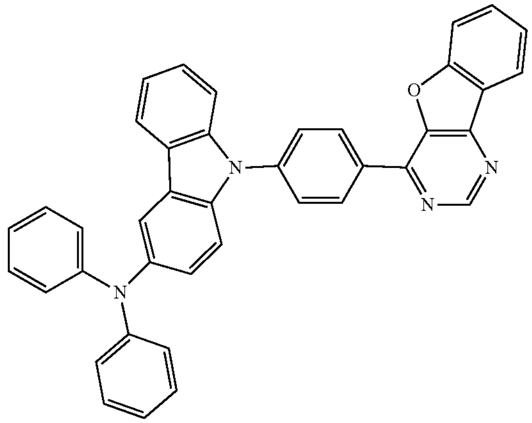
(134)
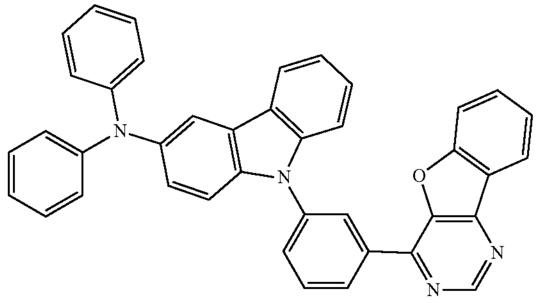
(135)
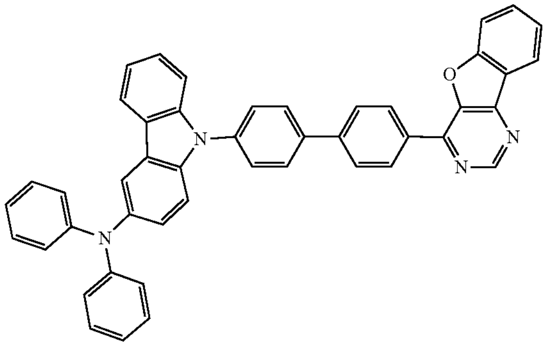

-continued
(136)
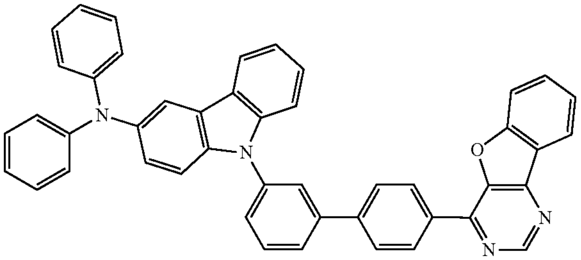
(137)
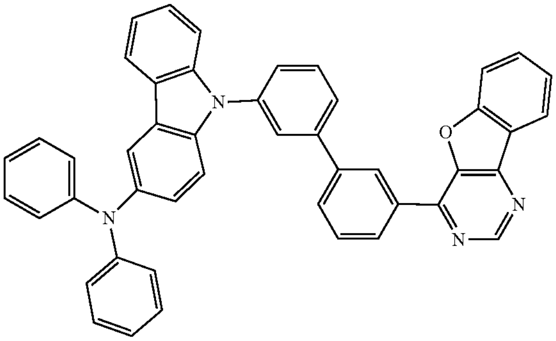
(138)
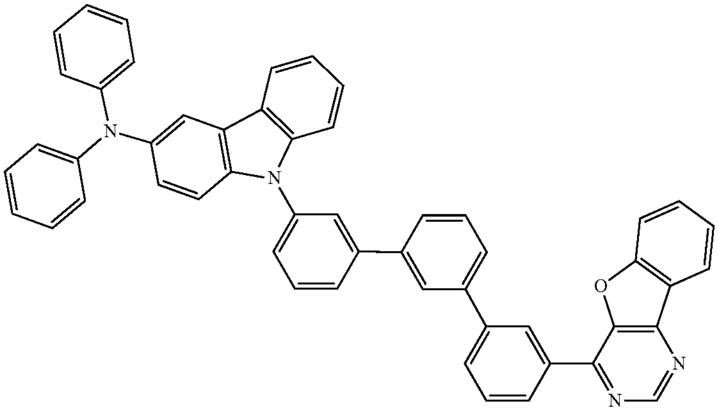
(139)
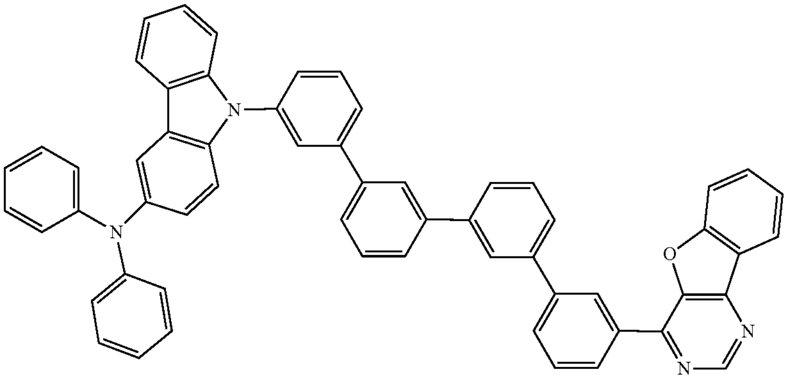
(140)
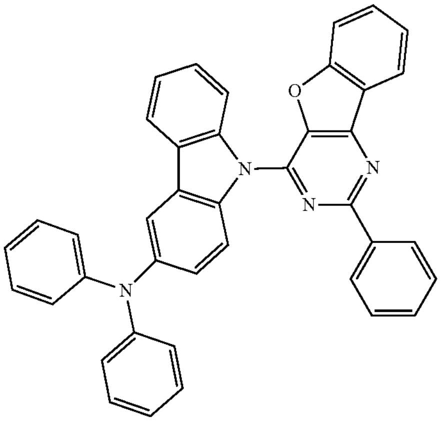

-continued
[Chemical Formula 23]
(141)
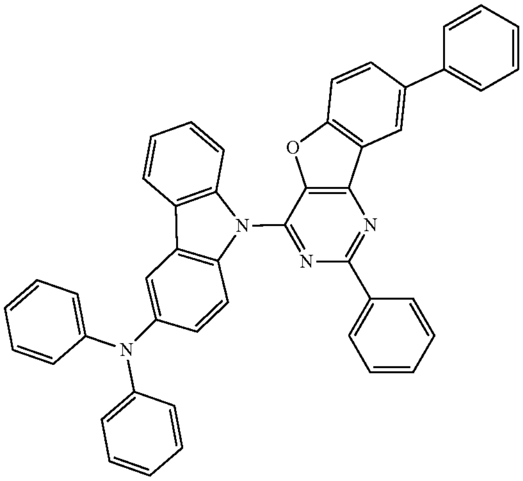
(142)
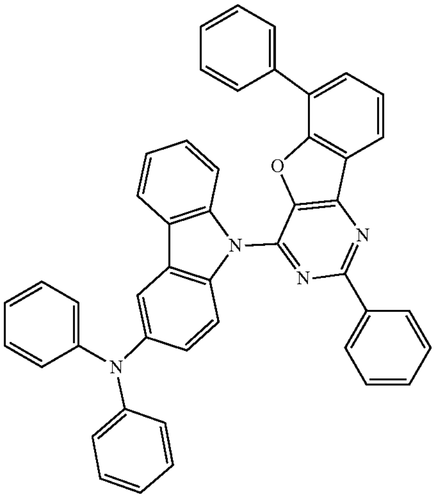
(143)
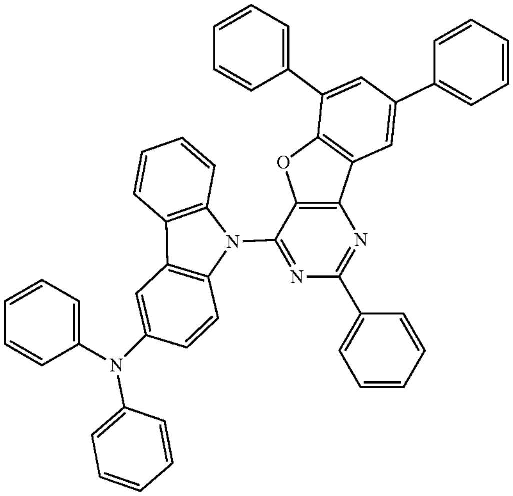
(144)
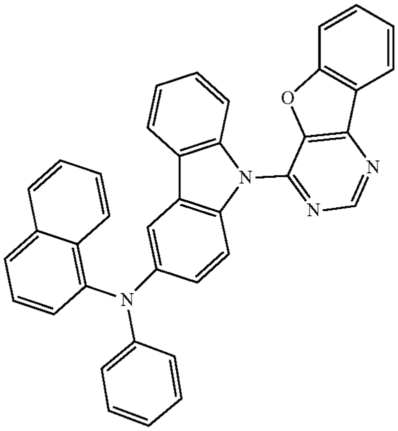
(145)
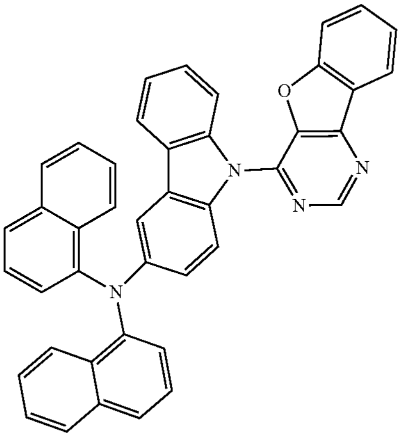

-continued
(146)
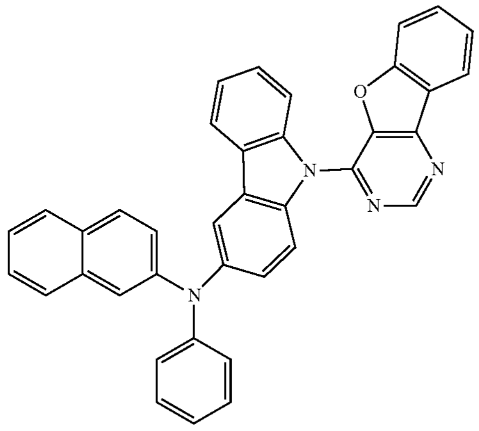
(147)
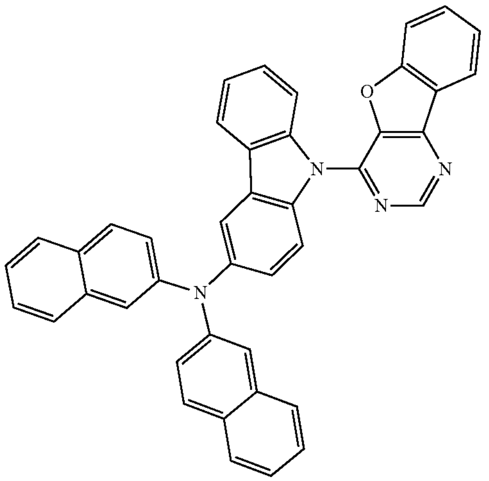
(148)
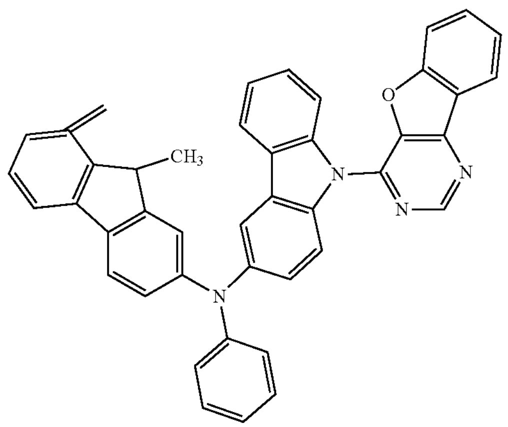
(149)
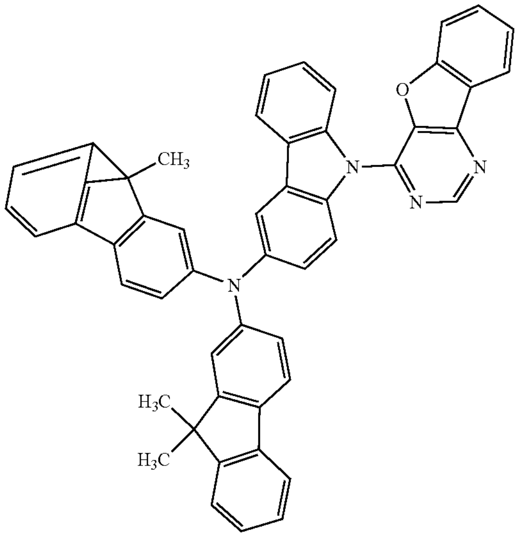
(150)
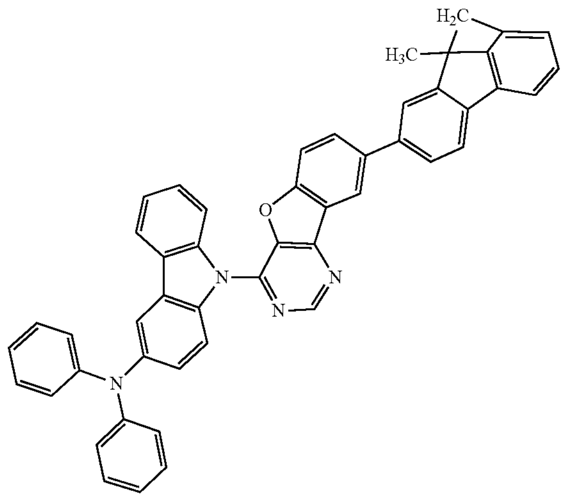
(151)
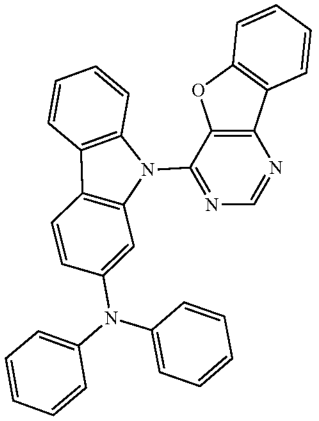

-continued
(152)
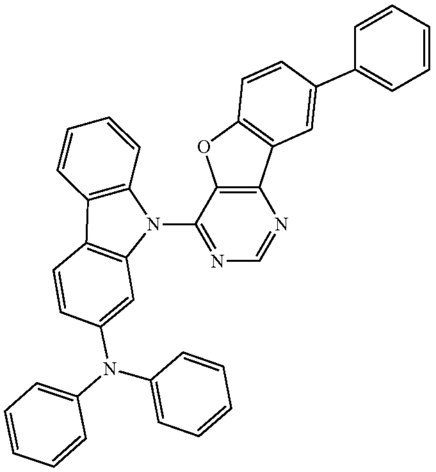
[Chemical Formula 24]
(153)
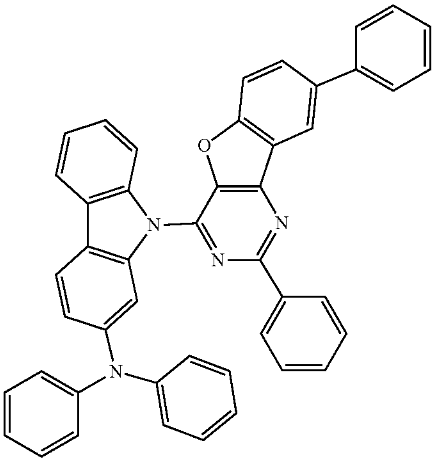
(154)
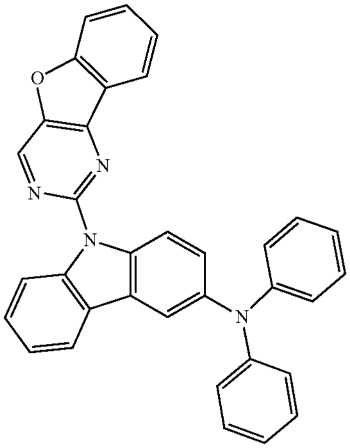
(155)
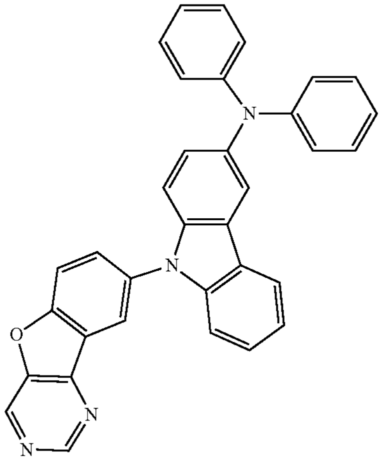

-continued
(156)
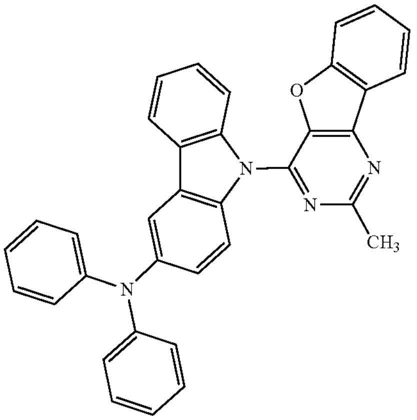
(157)
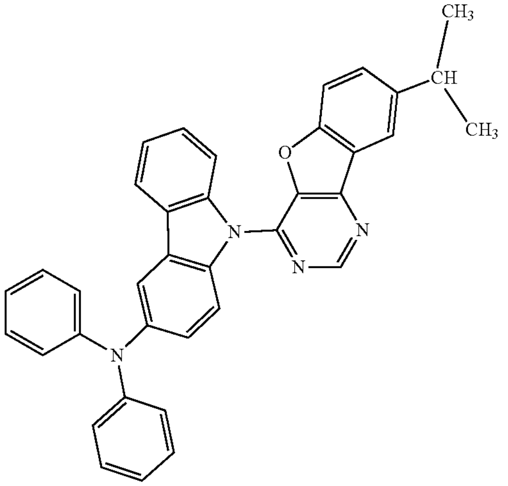
(158)
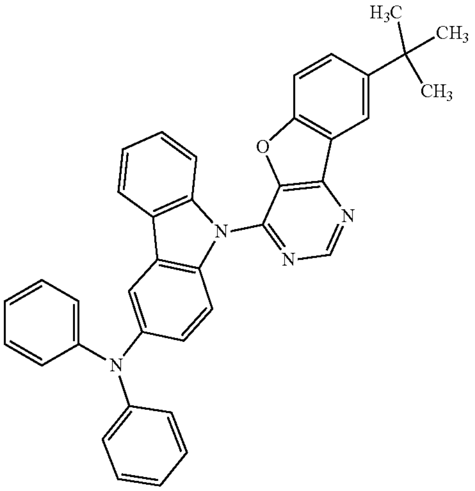
(159)
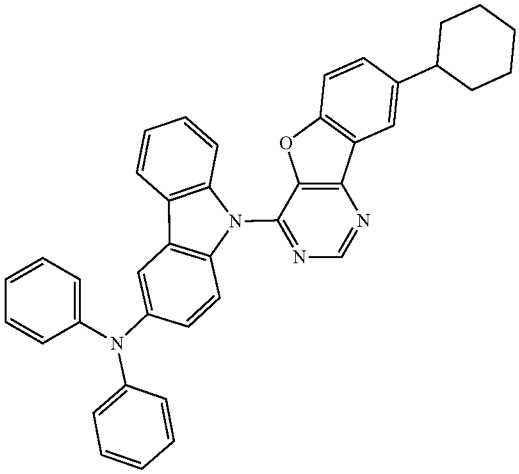
(160)
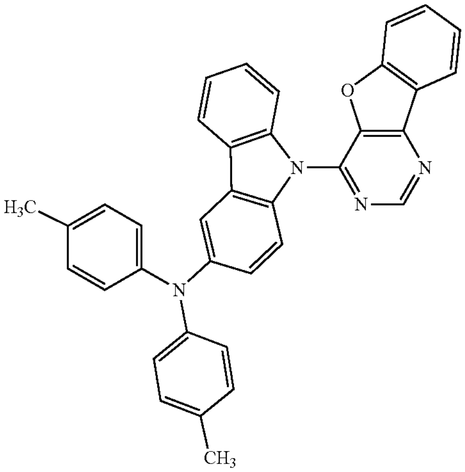
(161)
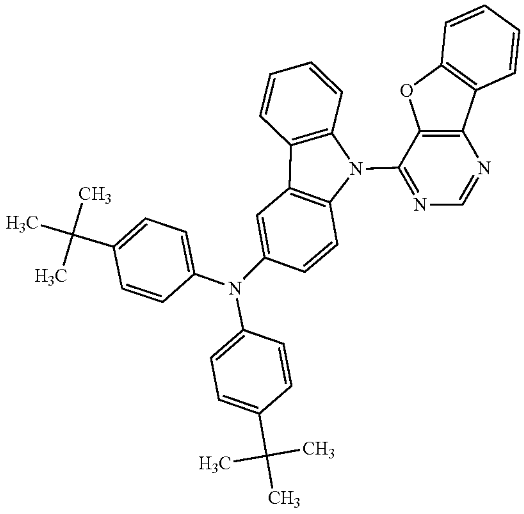

-continued (162)

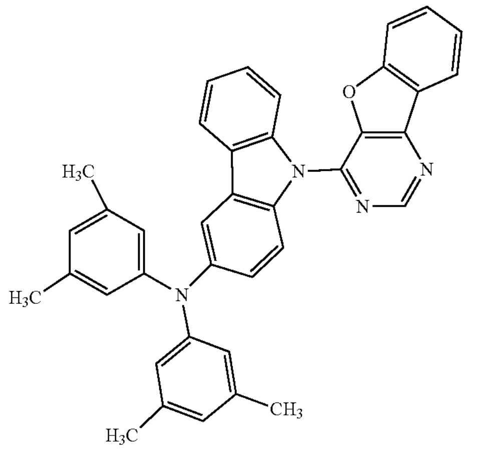

[Chemical Formula 25]

(200)

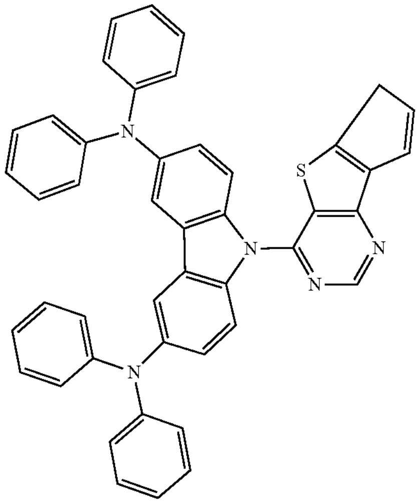

(201)

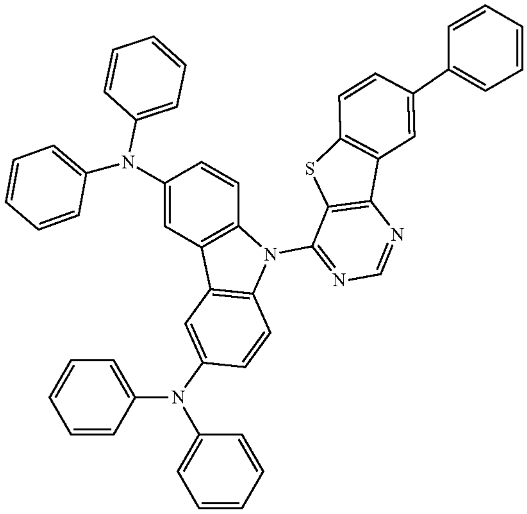

(202)

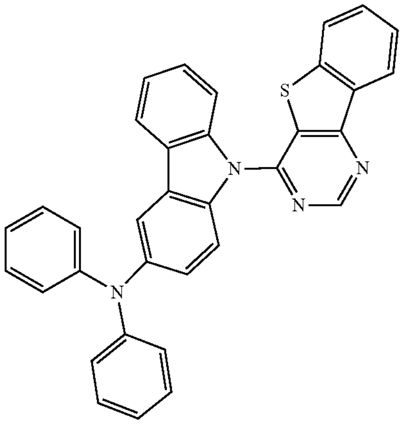

Next, an example of a method for synthesizing the organic compound represented by General Formula (G1) is described. As shown in the synthesis scheme below, an organoboron compound or a boronic acid of a carbazole derivative (Compound 1) is coupled with a halide of a benzothienopyrimidine derivative or a benzothienopyrimidine derivative or with a benzofuropyrimidine derivative or a benzofuropyrimidine derivative having triflate as a substituent (Compound 2) by a Suzuki-Miyaura reaction, whereby the compound represented by General Formula (G1) can be obtained. Note that in the synthesis scheme shown below, $R^1$ to $R^8$ are each independently any one of hydrogen, an alkyl group having 1 to 6 carbon atoms, a cycloalkyl group having 3 to 7 carbon atoms, and a substituted or unsubstituted diarylamino group. Note that at least one of $R^1$ to $R^8$ is a substituted or unsubstituted diarylamino group. In addition, α represents a substituted or unsubstituted phenylene group, and n is an integer of 0 to 4. Note that A represents a substituted or unsubstituted benzofuropyrimidine skeleton or a substituted or unsubstituted benzothienopyrimidine skeleton.

[Chemical Formula 26]

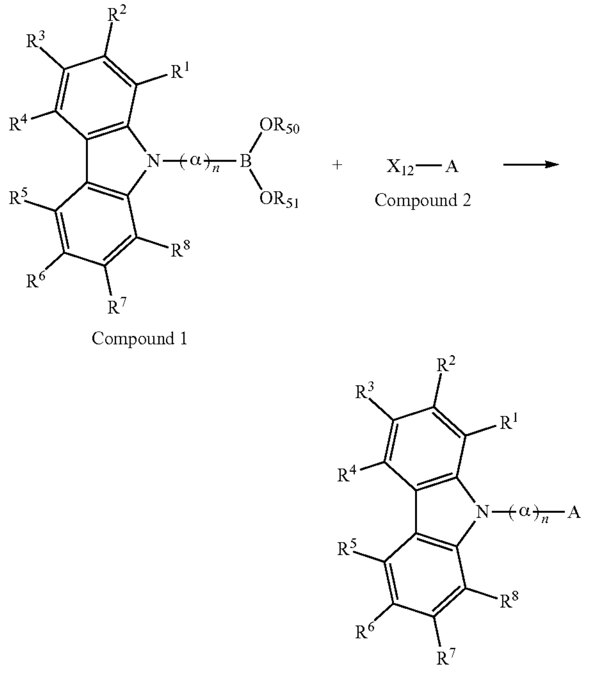

Compound 1

Compound 2

(G1)

In the above synthesis scheme, $X^{12}$ represents a halogen such as chlorine, bromine, or iodine or a triflate group. When $X^{12}$ represents a halogen, chlorine, bromine, or iodine is particularly preferable.

In addition, $R^{50}$ and $R^{51}$ each independently represent any of hydrogen and an alkyl group having 1 to 6 carbon atoms, and $R^{50}$ and $R^{51}$ may be bonded with each other to form a ring.

Examples of a palladium catalyst that can be used in the reaction represented by the above synthesis scheme include palladium (II) acetate, tetrakis (triphenylphosphine) palladium (0), and bis (triphenylphosphine) palladium (II) dichloride.

Examples of a ligand in the above palladium catalyst include di(1-adamantyl)-n-butylphosphine, tri(ortho-tolyl) phosphine, triphenylphosphine, and tricyclohexylphosphine.

Examples of the base that can be used in the reaction represented by the above synthesis scheme include an organic base such as sodium tert-butoxide and an inorganic base such as potassium carbonate or sodium carbonate.

Examples of a solvent that can be used in the reaction represented by the above synthesis scheme include a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; a mixed solvent of water and an ether such as ethylene glycol dimethyl ether; and a mixed solvent of an ether such as ethylene glycol dimethyl ether and alcohol such as ethanol. Note that the solvent that can be used is not limited to these. It is more preferable to use a mixed solvent of toluene and water or toluene, ethanol, and water; a mixed solvent of water and an ether such as ethylene glycol dimethyl ether; or a mixed solvent of an ether such as ethylene glycol dimethyl ether and alcohol such as ethanol.

As a coupling reaction that can be used in the above synthesis scheme, the Suzuki-Miyaura coupling reaction using the organoboron compound or boronic acid represented by Compound 1 may be replaced with a cross coupling reaction using an organoaluminum compound, an organozirconium compound, an organozinc compound, an organotin compound, or the like. In the reaction shown in the above synthesis scheme, an organoboron compound or a boronic compound of a benzofuropyrimidine derivative or a benzothienopyrimidine derivative may be coupled with a halide of a carbazole derivative or with a carbazole derivative having triflate as a substituent by a Suzuki-Miyaura reaction.

The compound represented by General Formula (G1) can also be synthesized by a synthesis method described in an example.

Embodiment 2

In this embodiment, a light-emitting device of one embodiment of the present invention is described.

FIG. 1A is a diagram illustrating a light-emitting device of one embodiment of the present invention. The light-emitting device of one embodiment of the present invention includes a first electrode 101, a second electrode 102, and an EL layer 103. The EL layer 103 includes the organic compound described in Embodiment 1.

The EL layer 103 includes a light-emitting layer 113, and the light-emitting layer 113 contains a light-emitting material. A hole-injection layer 111 and a hole-transport layer 112 are provided between the light-emitting layer 113 and the first electrode 101. The organic compound described in Embodiment 1 efficiently emits light by TADF, and thus is preferably used as the light-emitting material.

The light-emitting layer 113 may include a host material in addition to the light-emitting material. The host material is an organic compound having a carrier-transport property. The host material is not limited to one kind of material, and a plurality of kinds of materials may be included. In such a structure, the plurality of kinds of organic compounds are preferably an organic compound having an electron-transport property and an organic compound having a hole-transport property, in which case the carrier balance in the light-emitting layer 113 can be adjusted. The plurality of organic compounds may be organic compounds each having an electron-transport property (or a hole-transport property), and when the carrier-transport properties thereof are different from each other, the carrier-transport property of the light-emitting layer 113 can also be adjusted. Proper adjustment of the carrier balance can provide a long-life light-emitting device and a light-emitting device having favorable emission efficiency. The plurality of organic compounds that are host materials may form an exciplex, or the host material and the light-emitting material may form an exciplex. Formation of the exciplex having an appropriate emission wavelength allows efficient energy transfer to the light-emitting material, achieving a light-emitting device with favorable efficiency and a long lifetime.

In the case where the host material and the light-emitting material form an exciplex and light is emitted, an element having efficiency higher (e.g., external quantum efficiency higher by 7% or more) than that of an ordinary fluorescent element is sometimes obtained. Also in this case, delayed fluorescence is observed from the light-emitting element.

The organic compound of one embodiment of the present invention has a bipolar property and can also be suitably used as the host material in the light-emitting layer. The organic compound of one embodiment of the present invention can convert triplet excitation energy into singlet excitation energy because of its TADF property. The converted singlet excitation energy is transferred to a fluorescent light-emitting material to cause light emission, which means that triplet excitation energy can be converted into light emission. This achieves a fluorescent light-emitting device with very favorable emission efficiency (a so-called exciton capture type fluorescent element). Furthermore, since the light-emitting device is provided by a stable fluorescent light-emitting material, the light-emitting device can easily have a long lifetime.

Note that although FIG. 1A illustrates an electron-transport layer 114 and an electron-injection layer 115 in the EL layer 103 in addition to the light-emitting layer 113, the hole-injection layer 111, and the hole-transport layer 112, the structure of the light-emitting device is not limited thereto. Any of these layers may be omitted or a layer having another function may be included.

Next, examples of specific structures and materials of the aforementioned light-emitting device will be described. As described above, the light-emitting device of one embodiment of the present invention includes, between the pair of electrodes of the first electrode 101 and the second electrode 102, the EL layer 103 including a plurality of layers; the EL layer 103 includes the organic compound disclosed in Embodiment 1 in any of the layers.

The first electrode 101 is preferably formed using a metal, an alloy, or a conductive compound having a high work function (specifically, 4.0 eV or more), a mixture thereof, or the like. Specifically, for example, indium oxide-tin oxide (ITO: Indium Tin Oxide), indium oxide-tin oxide containing silicon or silicon oxide, indium oxide-zinc oxide, indium oxide containing tungsten oxide and zinc oxide (IWZO), and the like can be given. These conductive metal oxide films are usually formed by a sputtering method but may also be formed by application of a sol-gel method or the like. An example of the formation method is a method in which indium oxide-zinc oxide is formed by a sputtering method using a target in which 1 to 20 wt % zinc oxide is added to indium oxide. Indium oxide containing tungsten oxide and zinc oxide (IWZO) can also be formed by a sputtering method using a target containing 0.5 to 5 wt % tungsten oxide and 0.1 to 1 wt % zinc oxide with respect to indium oxide. Alternatively, gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride), and the like can be given. Graphene can also be used. Note that when a composite material described later is used for a layer that is in contact with the first electrode 101 in the EL layer 103, an electrode material can be selected regardless of its work function.

Figure 1B:
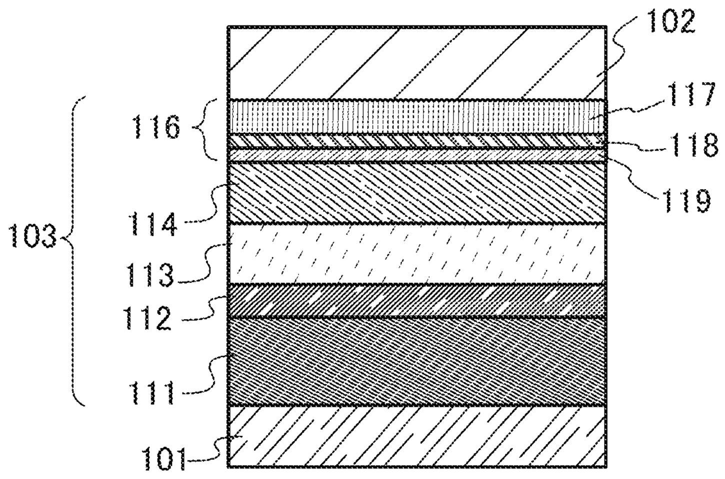

Although the EL layer 103 preferably has a stacked-layer structure, there is no particular limitation on the stacked-layer structure, and various layer structures such as a hole-injection layer, a hole-transport layer, a light-emitting layer, an electron-transport layer, an electron-injection layer, a carrier-blocking layer, an exciton-blocking layer, and a charge-generation layer can be employed. In this embodiment, two kinds of structures are described as examples: the structure including the electron-transport layer 114 and the electron-injection layer 115 in addition to the hole-injection layer 111, the hole-transport layer 112, and the light-emitting layer 113 as illustrated in FIG. 1A; and the structure including the electron-transport layer 114 and a charge-generation layer 116 in addition to the hole-injection layer 111, the hole-transport layer 112, and the light-emitting layer 113 as illustrated in FIG. 1B. Materials forming the layers are specifically described below.

The hole-injection layer 111 contains a substance having an acceptor property. Either an organic compound or an inorganic compound can be used as the substance having an acceptor property.

As the substance having an acceptor property, a compound having an electron-withdrawing group (a halogen group or a cyano group) can be used; 7,7,8,8-tetracyano-2,3,5,6-tetrafluoroquinodimethane (abbreviation: $F_4$-TCNQ), chloranil, 2,3,6,7,10,11-hexacyano-1,4,5,8,9,12-hexaazatriphenylene (abbreviation: HAT-CN), 1,3,4,5,7,8-hexafluorotetracyano-naphthoquinodimethane (abbreviation: F6-TCNNQ), 2-(7-dicyanomethylene-1,3,4,5,6,8,9,10-octafluoro-7H-pyren-2-ylidene)malononitrile, and the like can be given. A compound in which electron-withdrawing groups are bonded to a condensed aromatic ring having a plurality of heteroatoms, such as HAT-CN, is particularly preferable because it is thermally stable. A [3]radialene derivative having an electron-withdrawing group (in particular, a halogen group such as a fluoro group, or a cyano group) has a very high electron-accepting property and thus is preferable. Specific examples include α,α,α"-1,2,3-cyclopropanetriylidenetris[4-cyano-2,3,5,6-tetrafluorobenzeneacetonitrile], α,α,α"-1,2,3-cyclopropanetriylidenetris[2,6-dichloro-3,5-difluoro-4-(trifluoromethyl)benzeneacetonitrile], and α,α,α"-1,2,3-cyclopropanetriylidenetris[2,3,4,5,6-pentafluorobenzeneacetonitrile]. The organic compound having an acceptor property is an easy-to-use material because evaporation is easy and its film can be easily formed.

As the substance having an acceptor property, molybdenum oxide, vanadium oxide, ruthenium oxide, tungsten oxide, manganese oxide, or the like can be used, other than the above-described organic compounds.

Alternatively, the hole-injection layer 111 can be formed using a phthalocyanine-based complex compound such as phthalocyanine (abbreviation: $H_2$Pc) or copper phthalocyanine (CuPc), an aromatic amine compound such as 4,4'-bis[N-(4-diphenylaminophenyl)-N-phenylamino]biphenyl (abbreviation: DPAB) or N,N'-bis{4-[bis(3-methylphenyl)amino]phenyl}-N,N'-diphenyl-(1,1'-biphenyl)-4,4'-diamine (abbreviation: DNTPD), or a high molecule such as poly(3,4-ethylenedioxythiophene)/poly(styrenesulfonic acid) (PEDOT/PSS). The sub stance having an acceptor property can extract electrons from an adjacent hole-transport layer (or hole-transport material) by the application of an electric field.

Alternatively, a composite material in which a material having a hole-transport property contains the above-described substance having an acceptor property can be used for the hole-injection layer 111. By using a composite material in which a material having a hole-transport property contains a substance having an acceptor property, a material used to form an electrode can be selected regardless of its work function. In other words, besides a material having a high work function, a material having a low work function can also be used for the first electrode 101.

As the material having a hole-transport property used for the composite material, any of a variety of organic compounds such as aromatic amine compounds, carbazole derivatives, aromatic hydrocarbons, and high molecular compounds (e.g., oligomers, dendrimers, or polymers) can be used. Note that the material having a hole-transport property used for the composite material preferably has a hole mobility of $1\times10^{-6}$ $cm^2/Vs$ or higher. Organic compounds which can be used as the material having a hole-transport property in the composite material are specifically given below.

Examples of the aromatic amine compounds that can be used for the composite material include N,N'-di(p-tolyl)-N, N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis {4-[bis(3-methylphenyl)amino]phenyl}-N,N'-diphenyl-(1,1'-biphenyl)-4, 4'-diamine (abbreviation: DNTPD), and 1,3,5-tris[N-(4-diphenylaminophenyl)-N-phenylamino]benzene (abbreviation: DPA3B). Specific examples of the carbazole derivative include 3-[N-(9-phenylcarbazol-3-yl)-N-phenylamino]-9-phenylcarbazole (abbreviation: PCzPCA1), 3,6-bis[N-(9-phenylcarbazol yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)]phenyl-10-phenylanthracene (abbreviation: CzPA), and 1,4-bis[4-(N-carbazolyl)phenyl]-2,3,5,6-tetraphenylbenzene. Examples of the aromatic hydrocarbon include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis (4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9, 10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra (tert-butyl)perylene. Other examples include pentacene and coronene. The aromatic hydrocarbon may have a vinyl skeleton. Examples of the aromatic hydrocarbon having a vinyl group include 4,4'-bis(2,2-diphenylvinyl)biphenyl (abbreviation: DPVBi) and 9,10-bis[4-(2,2-diphenylvinyl)phenyl]anthracene (abbreviation: DPVPA).

Other examples include high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis (phenyl)benzidine] (abbreviation: Poly-TPD).

The material having a hole-transport property used for the composite material further preferably has any of a carbazole skeleton, a dibenzofuran skeleton, a dibenzothiophene skeleton, and an anthracene skeleton. In particular, an aromatic amine having a substituent that includes a dibenzofuran ring or a dibenzothiophene ring, an aromatic monoamine that has a naphthalene ring, or an aromatic monoamine in which a 9-fluorenyl group is bonded to nitrogen of the amine through an arylene group may be used. Note that these second organic compounds are preferably substances having an N,N-bis(4-biphenyl)amino group because a light-emitting device with a long lifetime can be manufactured. Specific examples of the above second organic compound include N-(4-biphenyl)-6,N-diphenylbenzo[b]naphtho[1,2-d]furan-8-amine (abbreviation: BnfABP), N,N-bis(4-biphenyl)-6-phenylbenzo[b]naphtho[1,2-d]furan-8-amine (abbreviation: BBABnf), 4,4'-bis(6-phenylbenzo[b]naphtho[1,2-d]furan-8-yl)-4"-phenyltriphenylamine (abbreviation: BnfBB1BP), N,N-bis(4-biphenyl)benzo[b]naphtho[1,2-d]furan-6-amine (abbreviation: BBABnf(6)), N,N-bis(4-biphenyl)benzo[b] naphtho[1,2-d]furan-8-amine (abbreviation: BBABnf(8)), N,N-bis(4-biphenyl)benzo[b]naphtho[2,3-d]furan-4-amine (abbreviation: BBABnf(II)(4)), N,N-bis[4-(dibenzofuran-4-yl)phenyl]-4-amino-p-terphenyl (abbreviation: DBfBB1TP), N-[4-(dibenzothiophen-4-yl)phenyl]-N-phenyl-4-biphenylamine (abbreviation: ThBA1BP), 4-(2-naphthyl)-4',4"-diphenyltriphenylamine (abbreviation: BBAβNB), 4-[4-(2-naphthyl)phenyl]-4',4"-diphenyltriphenylamine (abbreviation: BBAβNBi), 4,4'-diphenyl-4"-(6;1'-binaphthyl-2-yl)triphenylamine (abbreviation: BBAαNβNB), 4,4'-diphenyl-4"-(7;1'-binaphthyl-2-yl)triphenylamine (abbreviation: BBAαNβNB-03), 4,4'-diphenyl-4"-(7-phenyl)naphthyl-2-yl)triphenylamine (abbreviation: BBAPβNB-03), 4,4'-diphenyl-4"-(6;2'-binaphthyl-2-yl)triphenylamine (abbreviation: BBA(βN2)B), 4,4'-diphenyl-4"-(7;2'-binaphthyl-2-yl)triphenylamine (abbreviation: BBA (βN2)B-03), 4,4'-diphenyl-4"-(4;2'-binaphthyl-1-yl) triphenylamine (abbreviation: BBAβNαNB), 4,4'-diphenyl-4"-(5;2'-binaphthyl-1-yl)triphenylamine (abbreviation: BBAβNαNB-02), 4-(4-biphenylyl)-4'-(2-naphthyl)-4"-phenyltriphenylamine (abbreviation: TPBiAβNB), 4-(3-biphenylyl)-4'-[4-(2-naphthyl)phenyl]-4"-phenyltriphenylamine (abbreviation: mTPBiAβNBi), 4-(4-biphenylyl)-4'-[4-(2-naphthyl)phenyl]-4"-phenyltriphenylamine (abbreviation: TPBiAβNBi), 4-phenyl-4'-(1-naphthyl)triphenylamine (abbreviation: αNBA1BP), 4,4'-bis(1-naphthyl)triphenylamine (abbreviation: αNBB1BP), 4,4'-diphenyl-4"-[4'-(carbazol-9-yl)biphenyl-4-yl]triphenylamine (abbreviation: YGTBi1BP), 4'-[4-(3-phenyl-9H-carbazol-9-yl)phenyl]tris (1,1'-biphenyl-4-yl)amine (abbreviation: YGTBi1BP-02), 4-diphenyl-4'-(2-naphthyl)-4"-{9-(4-biphenylyl) carbazole)}triphenylamine (abbreviation: YGTBiβNB), N-[4-(9-phenyl-9H-carbazol-3-yl)phenyl]-N-[4-(1-naphthyl)phenyl]-9,9'-spirobi[9H-fluoren]-2-amine (abbreviation: PCBNBSF), N,N-bis(4-biphenylyl)-9,9'-spirobi[9H-fluoren]-2-amine (abbreviation: BBASF), N,N-bis(1,1'-biphenyl-4-yl)-9,9'-spirobi[9H-fluoren]-4-amine (abbreviation: BBASF(4)), N-(1,1'-biphenyl-2-yl)-N-(9,9-dimethyl-9H-fluoren-2-yl)-9,9'-spiro-bi[9H-fluoren]-4-amine (abbreviation: oFBiSF), N-(4-biphenyl)-N-(dibenzofuran-4-yl)-9,9-dimethyl-9H-fluoren-2-amine (abbreviation: FrBiF), N-[4-(1-naphthyl)phenyl]-N-[3-(6-phenyldibenzofuran-4-yl)phenyl]-1-naphthylamine (abbreviation: mPDBfBNBN), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-[4-(9-phenylfluoren-9-yl)phenyl]triphenylamine (abbreviation: BPAFLBi), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), N-phenyl-N-[4-(9-phenyl-9H-carbazol-3-yl)phenyl]spiro-9,9'-bifluoren-2-amine (abbreviation: PCBASF), N-(1,1'-biphenyl-4-yl)-9,9-dimethyl-N-[4-(9-phenyl-9H-carbazol-3-yl)phenyl]-9H-fluoren-2-amine (abbreviation: PCBBiF), N,N-bis(9,9-dimethyl-9H-fluoren-2-yl)-9,9'-spirobi[9H-fluoren]-4-amine, N,N-bis(9,9-dimethyl-9H-fluoren-2-yl)-9,9'-spirobi[9H-fluoren]-3-amine, N,N-bis(9,9-dimethyl-9H-fluoren-2-yl)-9,9'-spirobi[9H-fluoren]-2-amine, and N,N-bis(9,9-dimethyl-9H-fluoren-2-yl)-9,9'-spirobi[9H-fluoren]-1-amine.

Note that it is further preferable that the material having a hole-transport property used for the composite material have a relatively deep HOMO level greater than or equal to −5.7 eV and less than or equal to −5.4 eV. The relatively deep HOMO level of the material having a hole-transport property used for the composite material makes it easy to inject holes into the hole-transport layer 112 and to obtain a light-emitting device with a long lifetime.

Note that mixing the above composite material with a fluoride of an alkali metal or an alkaline earth metal (the proportion of fluorine atoms in the layer is preferably greater than or equal to 20%) can lower the refractive index of the layer. This also enables a layer with a low refractive index to be formed in the EL layer 103, leading to higher external quantum efficiency of the light-emitting device.

The formation of the hole-injection layer 111 can improve the hole-injection property, whereby a light-emitting device having a low driving voltage can be obtained.

The hole-transport layer 112 contains a material having a hole-transport property. The material having a hole-transport property preferably has a hole mobility of $1\times10^{-6}$ $cm^2/Vs$ or more. As the material having a hole-transport property, a compound having an aromatic amine skeleton, such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)-triphenylamine (abbreviation: PCBANB), 4,4'-di(1-naphthyl)-4"-(9-phenyl-9H-carbazol yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), or N-phenyl-N-[4-(9-phenyl-9H-carbazol-3-yl)phenyl]spiro-9,9'-bifluoren-2-amine (abbreviation: PCBASF), a compound having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP), a compound having a thiophene skeleton, such as 4,4',4"-(benzene-1,3,5-triyl)tri(dibenzothiophene) (abbreviation: DB T3P-II), 2,8-diphenyl-4-[4-(9-phenyl-9H-fluoren-9-yl)phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV), and a compound having a furan skeleton, such as 4,4',4"-(benzene-1,3,5-triyl)tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II) can be given. Among the above, the compound having an aromatic amine skeleton and the compound having a carbazole skeleton are preferable because these have favorable reliability, have high hole-transport properties, and contribute to a reduction in driving voltage. Note that any of the substances given as examples of the material having a hole-transport property that is used for the composite material for the hole-injection layer 111 can also be suitably used as the material included in the hole-transport layer 112. The organic compound described in Embodiment 1 can be highly suitably used as the material included in the hole-transport layer 112 because of its high hole-transport property. Furthermore, since the organic compound described in Embodiment 1 has a high hole-transport property, even when the hole-transport layer 112 is formed to have a large thickness of 100 nm or more, a light-emitting device with a small increase in driving voltage and favorable element characteristics can be provided. The large thickness of the hole-transport layer 112 facilitates appropriate formation of a microcavity structure because it allows the optical length between electrodes to be adjusted easily.

The light-emitting layer 113 contains a light-emitting substance and a host material. The light-emitting layer 113 may additionally contain other materials. Furthermore, the light-emitting layer 113 may be a stack of two layers with different compositions.

The light-emitting substance may be fluorescent substances, phosphorescent substances, substances exhibiting thermally activated delayed fluorescence (TADF), or other light-emitting substances. The organic compound of one embodiment of the present invention is a substance that efficiently exhibits TADF.

Examples of a material that can be used as a fluorescent substance in the light-emitting layer 113 include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-(tert-butyl)perylene (abbreviation: TBP), 4-(10-phenyl-9-anthryl)-4'-(9-phenyl-9H-carbazol-3-yl)triphenylamine (abbreviation: PCBAPA), N,N"-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N",N",N"',N"'-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-c]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), N,N'-(pyrene-1,6-diyl)bis[(6,N-diphenylbenzo[b]naphtho[1,2-d]furan)-8-amine] (abbreviation: 1,6BnfAPrn-03), 3,10-bis[N-(9-phenyl-9H-carbazol-2-yl)-N-phenylamino]naphtho[2,3-b; 6,7-b']bisbenzofuran (abbreviation: 3,10PCA2Nbf(IV)-02), and 3,10-bis[N-(dibenzofuran-3-yl)-N-phenylamino]naphtho[2,3-b; 6,7-b']bisbenzofuran (abbreviation: 3,10FrA2Nbf(IV)-02). In particular, a condensed aromatic diamine compound typified by a pyrenediamine compound such as 1,6FLPAPrn, 1,6mMemFLPAPrn, and 1,6BnfAPrn-03 is preferable because of its high hole-trapping property, high emission efficiency, and high reliability. Fluorescent substances other than those can also be used.

In the case where a phosphorescent substance is used as a light-emitting substance in the light-emitting layer 113, examples of a material that can be used include an organometallic iridium complex having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: $[Ir(mpptz-dmp)_3]$), tris(5-methyl-3,4-diphenyl-4H-1,2,4-triazolato)iridium(III) (abbreviation: $[Ir(Mptz)_3]$), and tris[4-(3-biphenyl)-5-isopropyl-3-phenyl-4H-1,2,4-triazolato]iridium(III) (abbreviation: $[Ir(iPrptz-3b)_3]$); an organometallic iridium complex having a 1H-triazole skeleton, such as tris[3-methyl-1-(2-methylphenyl)-5-phenyl-1H-1,2,4-triazolato]iridium(III) (abbreviation: $[Ir(Mptz1-mp)_3]$) and tris(1-methyl-5-phenyl-3-propyl-1H-1,2,4-triazolato)iridium(III) (abbreviation: $[Ir(Prptz1-Me)_3]$); an organometallic iridium complex having an imidazole skeleton, such as fac-tris[1-(2,6-diisopropylphenyl)-2-phenyl-1H-imidazole]iridium(III) (abbreviation: $[Ir(iPrpmi)_3]$) and tris[3-(2,6-dimethylphenyl)-7-methylimidazo[1,2-f]phenanthridinato]iridium(III) (abbreviation: $[Ir(dmpimpt-Me)_3]$); and an organometallic iridium complex in which a phenylpyridine derivative having an electron-withdrawing group is a ligand, such as bis[2-(4',6'-difluorophenyl)pyridinato-N,$C^2$]iridium(III) tetrakis(1-pyrazolyl)borate (abbreviation: FIr6), bis[2-(4',6'-difluorophenyl)pyridinato-N,$C^2$]iridium(III) picolinate (abbreviation: Flrpic), bis{2-[3',5'-bis(trifluoromethyl)phenyl]pyridinato-N,$C^2$}iridium(III) picolinate (abbreviation: $[Ir(CF_3ppy)_2(pic)]$), and bis[2-(4',6'-difluorophenyl)pyridinato-N,$C^2$]iridium(III) acetylacetonate (abbreviation: FIracac). These are compounds exhibiting blue phosphorescent light, and are compounds having an emission wavelength peak at 440 nm to 520 nm.

Examples also include an organometallic iridium complex having a pyrimidine skeleton, such as tris(4-methyl-6-phenylpyrimidinato)iridium(III) (abbreviation: $[Ir(mppm)_3]$), tris(4-t-butyl-6-phenylpyrimidinato)iridium(III) (abbreviation: $[Ir(tBuppm)_3]$), (acetylacetonato)bis(6-methyl-4-phenylpyrimidinato)iridium(III) (abbreviation: $[Ir(mppm)_2(acac)]$), (acetylacetonato)bis(6-tert-butyl-4-phenylpyrimidinato)iridium(III) (abbreviation: $[Ir(tBuppm)_2(acac)]$), (acetylacetonato)bis[6-(2-norbornyl)-4-phenylpyrimidinato]iridium(III) (abbreviation: $[Ir(nbppm)_2(acac)]$), (acetylacetonato)bis[5-methyl-6-(2-methylphenyl)-4-phenylpyrimidinato]iridium(III) (abbreviation: $[Ir(mpmppm)_2(acac)]$), or (acetylacetonato)bis(4,6-diphenylpyrimidinato)iridium(III) (abbreviation: $[Ir(dppm)_2(acac)]$), an organometallic iridium complex having a pyrazine skeleton, such as (acetylacetonato)bis(3,5-dimethyl-2-phenylpyrazinato)iridium(III) (abbreviation: $[Ir(mppr-Me)_2(acac)]$) or (acetylacetonato)bis(5-isopropyl-3-methyl-2-phenylpyrazinato)iridium(III) (abbreviation: $[Ir(mppr-iPr)_2(acac)]$), an organometallic iridium complex having a pyridine skeleton, such as tris(2-phenylpyridinato-N,$C^{2'}$)iridium(III) (abbreviation: $[Ir(ppy)_3]$), bis(2-phenylpyridinato-N,$C^{2'}$)iridium(III) acetylacetonate (abbreviation: $[Ir(ppy)_2(acac)]$), bis(benzo[h]quinolinato)iridium(III) acetylacetonate (abbreviation: $[Ir(bzq)_2(acac)]$), tris(benzo[h]quinolinato)iridium(III) (abbreviation: $[Ir(bzq)_3]$), tris(2-phenylquinolinato-N,$C^{2'}$)iridium(III) (abbreviation: $[Ir(pq)_3]$), bis(2-phenylquinolinato-N,$C^{2'}$)iridium(III) acetylacetonate (abbreviation: $[Ir(pq)_2(acac)]$), [2-d3-methyl-(2-pyridinyl-κN)benzofuro[2,3-b]pyridine-κC]bis[2-(5-d3-methyl-2-pyridyl-κN2)phenyl-κ]iridium(III) (abbreviation: [Ir(5mppy-d3)2(mbfpypy-d3)]), or [2-d3-methyl-(2-pyridinyl-κN)benzofuro[2,3-b]pyridine-κC]bis[2-(2-pyridinyl-κN)phenyl-κC]iridium(III) (abbreviation: [Ir(ppy)2(mbfpypy-d3)]), and a rare earth metal complex such as tris(acetylacetonato)(monophenanthroline)terbium(III) (abbreviation: $[Tb(acac)_3(Phen)]$). These are compounds that mainly exhibit green phosphorescent light, and have an emission wavelength peak at 500 nm to 600 nm. Note that an organometallic iridium complex having a pyrimidine skeleton is particularly preferable because of its distinctively high reliability and emission efficiency.

Examples also include an organometallic iridium complex having a pyrimidine skeleton, such as (diisobutyrylmethanato)bis[4,6-bis(3-methylphenyl)pyrimidinato]iridium(III) (abbreviation: $[Ir(5mdppm)_2(dibm)]$), bis[4,6-bis(3-methylphenyl)pyrimidinato] (dipivaloylmethanato)iridium(III) (abbreviation: $[Ir(5mdppm)_2(dpm)]$), or bis[4,6-di(naphthalen-1-yl)pyrimidinato](dipivaloylmethanato)iridium(III) (abbreviation: $[Ir(d1npm)_2(dpm)]$), an organometallic iridium complex having a pyrazine skeleton, such as (acetylacetonato)bis(2,3,5-triphenylpyrazinato)iridium(III) (abbreviation: $[Ir(tppr)_2(acac)]$), bis(2,3,5-triphenylpyrazinato)(dipivaloylmethanato)iridium(III) (abbreviation: $[Ir(tppr)_2(dpm)]$), or (acetylacetonato)bis[2,3-bis(4-fluorophenyl)quinoxalinato]iridium(III) (abbreviation: $[Ir(Fdpq)_2(acac)]$), an organometallic iridium complex having a pyridine skeleton, such as tris(1-phenylisoquinolinato-N,$C^{2'}$)iridium(III) (abbreviation: $[Ir(piq)_3]$) or bis(1-phenylisoquinolinato-N,$C^{2'}$)iridium(III) acetylacetonate (abbreviation: $[Ir(piq)_2(acac)]$), a platinum complex such as 2,3,7,8,12,13,17,18-octaethyl-21H,23H-porphyrin platinum(II) (abbreviation: PtOEP), and a rare earth metal complex such as tris(1,3-diphenyl-1,3-propanedionato)(monophenanthroline)europium(III) (abbreviation: [Eu(DBM)$_3$(Phen)]) or tris[1-(2-thenoyl)-3,3,3-trifluoroacetonato](monophenanthroline)europium(III) (abbreviation: [Eu(TTA)$_3$(Phen)]). These are compounds exhibiting red phosphorescent light, and have an emission peak at 600 nm to 700 nm. Furthermore, from the organometallic iridium complex having a pyrazine skeleton, red light emission with favorable chromaticity can be obtained.

Besides the above-described phosphorescent light-emitting substances, other known phosphorescent substances may be selected and used.

As the substance that exhibits TADF (TADF material), a fullerene, a derivative thereof, an acridine, a derivative thereof, an eosin derivative, or the like can be used. Other examples include a metal-containing porphyrin containing magnesium (Mg), zinc (Zn), cadmium (Cd), tin (Sn), platinum (Pt), indium (In), palladium (Pd), or the like. Examples of the metal-containing porphyrin include a protoporphyrin-tin fluoride complex ($SnF_2$(Proto IX)), a mesoporphyrin-tin fluoride complex ($SnF_2$(Meso IX)), a hematoporphyrin-tin fluoride complex ($SnF_2$(Hemato IX)), a coproporphyrin tetramethyl ester-tin fluoride complex ($SnF_2$(Copro III-4Me)), an octaethylporphyrin-tin fluoride complex ($SnF_2$(OEP)), an etioporphyrin-tin fluoride complex ($SnF_2$(Etio I)), and an octaethylporphyrin-platinum chloride complex ($PtCl_2$(OEP)), which are represented by the following structural formulae. Note that the organic compound of one embodiment of the present invention is also a TADF material.

[Chemical Formula 27]

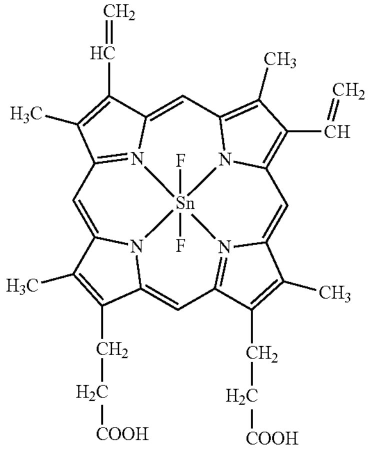

$SnF_2$(Proto IX)

-continued

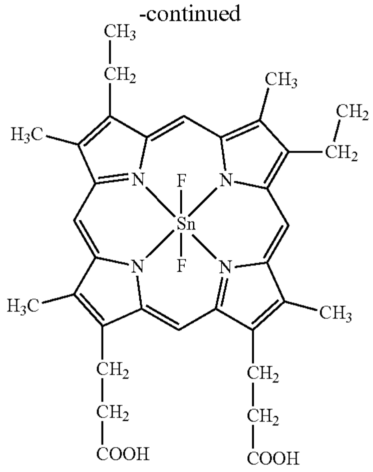

$SnF_2$(Meso IX)

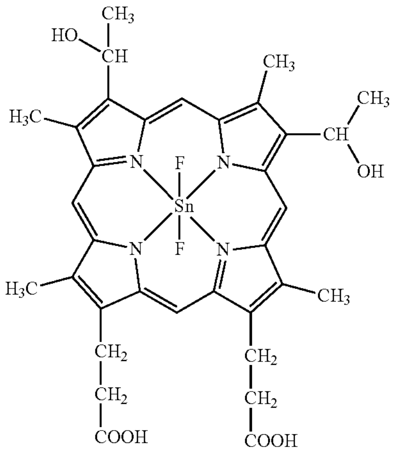

$SnF_2$(Hemato IX)

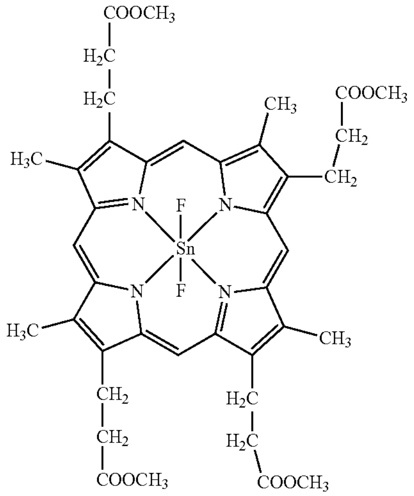

$SnF_2$(Copro III-4Me)

-continued

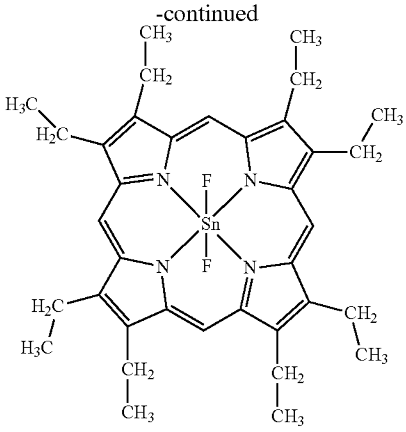

$SnF_2(OEP)$

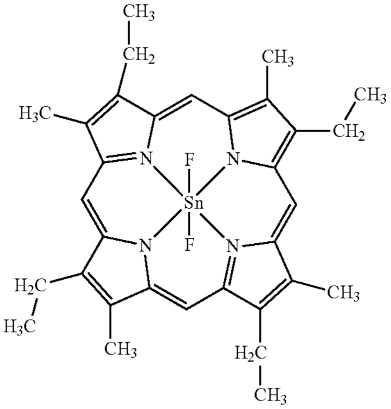

$SnF_2$(Etio I)

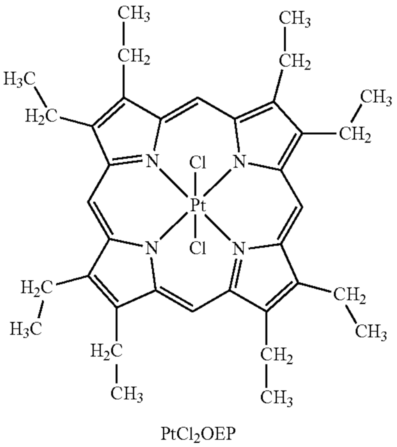

$PtCl_2OEP$

Alternatively, a heterocyclic compound having one or both of a π-electron rich heteroaromatic ring and a π-electron deficient heteroaromatic ring that is represented by the following structural formulae, such as 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazine-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA) can be used. These heterocyclic compounds are preferable because of having both a high electron-transport property and a high hole-transport property owing to the π-electron rich heteroaromatic ring and the π-electron deficient heteroaromatic ring. Among skeletons having a π-electron deficient heteroaromatic ring, a pyridine skeleton, a diazine skeleton (a pyrimidine skeleton, a pyrazine skeleton, and a pyridazine skeleton), and a triazine skeleton are particularly preferable because of their stability and favorable reliability. In particular, a benzofuropyrimidine skeleton, a benzothienopyrimidine skeleton, a benzofuropyrazine skeleton, and a benzothienopyrazine skeleton are preferable because of their high acceptor property and favorable reliability. Among skeletons having a π-electron rich heteroaromatic ring, an acridine skeleton, a phenoxazine skeleton, a phenothiazine skeleton, a furan skeleton, a thiophene skeleton, and a pyrrole skeleton have stability and favorable reliability; therefore, at least one of these skeletons is preferably included. Note that a dibenzofuran skeleton and a dibenzothiophene skeleton are preferable as the furan skeleton and the thiophene skeleton, respectively. As the pyrrole skeleton, an indole skeleton, a carbazole skeleton, an indolocarbazole skeleton, a bicarbazole skeleton, and a 3-(9-phenyl-9H-carbazol-3-yl)-9H-carbazole skeleton are particularly preferable. Note that a substance in which a π-electron rich heteroaromatic ring and a π-electron deficient heteroaromatic ring are directly bonded to each other is particularly preferable because the electron-donating property of the π-electron rich heteroaromatic ring and the electron-accepting property of the π-electron deficient heteroaromatic ring are both increased and the energy difference between the S1 level and the T1 level becomes small, and thus TADF can be obtained efficiently. Note that an aromatic ring to which an electron-withdrawing group such as a cyano group is bonded may be used instead of the π-electron deficient heteroaromatic ring. As a π-electron rich skeleton, an aromatic amine skeleton, a phenazine skeleton, or the like can be used. As a π-electron deficient skeleton, a xanthene skeleton, a thioxanthene dioxide skeleton, an oxadiazole skeleton, a triazole skeleton, an imidazole skeleton, an anthraquinone skeleton, a boron-containing skeleton such as phenylborane or boranthrene, an aromatic ring or a heteroaromatic ring having a nitrile group or a cyano group, such as benzonitrile or cyanobenzene, a carbonyl skeleton such as benzophenone, a phosphine oxide skeleton, a sulfone skeleton, or the like can be used. As described above, a π-electron deficient skeleton and a π-electron rich skeleton can be used instead of at least one of the π-electron deficient heteroaromatic ring and the π-electron rich heteroaromatic ring.

[Chemical Formula 28]
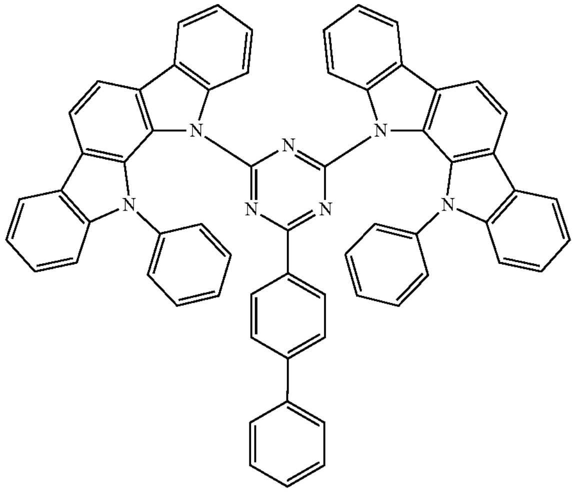
PIC-TRZ
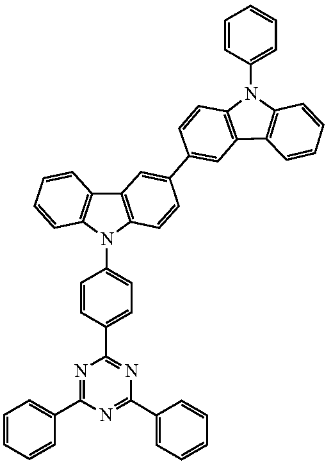
PCCzPTzn
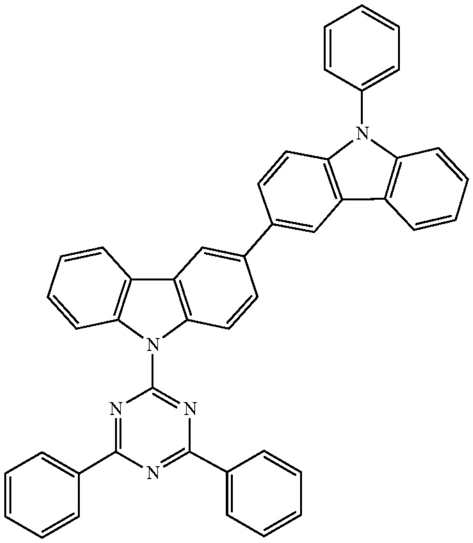
PCCzTzn
-continued
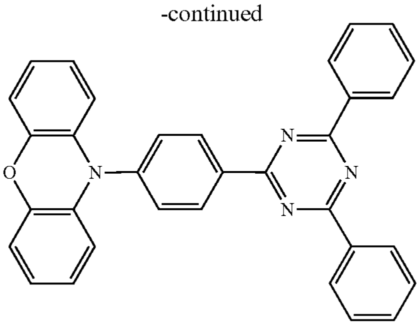
PXZ-TRZ
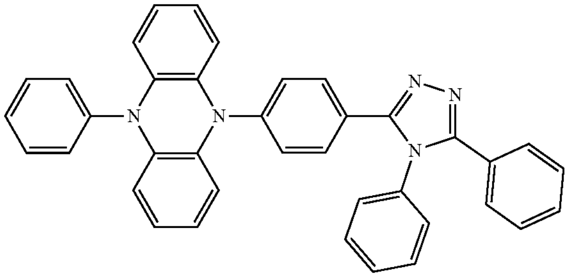
PPZ-3TPT
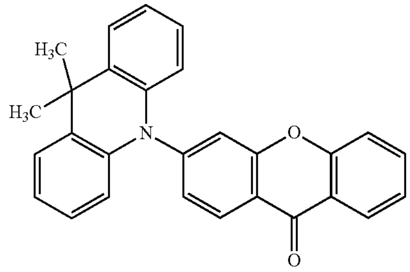
ACRXTN
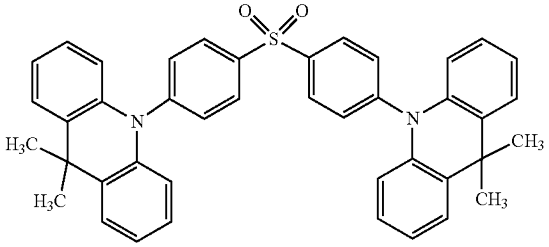
DMAC-DPS
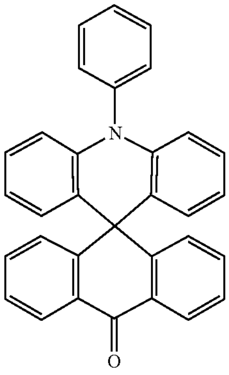
ACRSA
Note that the TADF material is a material that has a small difference ($\Delta E_{ST}$) between the S1 level and the T1 level and has a function of converting triplet excitation energy into singlet excitation energy by reverse intersystem crossing. Thus, it is possible to upconvert triplet excitation energy into singlet excitation energy (reverse intersystem crossing) using a little thermal energy and to efficiently generate a singlet excited state. In addition, the triplet excitation energy can be converted into light emission.

An exciplex whose excited state is formed by two kinds of substances has an extremely $\Delta E_{ST}$ and has a function of a TADF material that can convert triplet excitation energy into singlet excitation energy.

Note that a phosphorescent spectrum observed at low temperatures (e.g., 77 K to 10 K) is used for an index of the T1 level. When the level of energy with a wavelength of the line obtained by extrapolating a tangent to the fluorescent spectrum at a tail on the short wavelength side is the S1 level and the level of energy with a wavelength of the line obtained by extrapolating a tangent to the phosphorescent spectrum at a tail on the short wavelength side is the T1 level, the difference between the S1 level and the T1 level of the TADF material is preferably less than or equal to 0.3 eV, further preferably less than or equal to 0.2 eV, still further preferably less than or equal to 0.01 eV.

When the TADF material is used as a light-emitting substance, the S1 level of the host material is preferably higher than the S1 level of the TADF material. In addition, the T1 level of the host material is preferably higher than the T1 level of the TADF material.

As the host material in the light-emitting layer, various carrier-transport materials such as a material having an electron-transport property, a material having a hole-transport property, and the TADF material can be used. Note that the organic compound of one embodiment of the present invention has a bipolar property and can also be suitably used as the host material.

The material having a hole-transport property is preferably an organic compound having an amine skeleton or a π-electron rich heteroaromatic ring skeleton. Examples include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)-triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol yl)phenyl]fluoren-2-amine (abbreviation: PCBAF), or N-phenyl-N-[4-(9-phenyl-9H-carbazol yl)phenyl]spiro-9,9'-bifluoren-2-amine (abbreviation: PCBASF), a compound having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP), a compound having a thiophene skeleton, such as 4,4',4"-(benzene-1,3,5-triyl)tri(dibenzothiophene) (abbreviation: DB T3P-II), 2,8-diphenyl-4-[4-(9-phenyl-9H-fluoren-9-yl)phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV), and a compound having a furan skeleton, such as 4,4',4"-(benzene-1,3,5-triyl)tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II).

Among the above, the compound having an aromatic amine skeleton and the compound having a carbazole skeleton are preferable because these have favorable reliability, have high hole-transport properties, and contribute to a reduction in driving voltage.

As the material having an electron-transport property, for example, a metal complex such as bis(10-hydroxybenzo[h]quinolinato)beryllium(II) (abbreviation: $BeBq_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ); or an organic compound having a π-electron deficient heteroaromatic ring skeleton is preferable. Examples of the organic compound having a π-electron deficient heteroaromatic ring skeleton include a heterocyclic compound having a polyazole skeleton, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-1H-benzimidazole) (abbreviation: TPBI), or 2-[3-(dib enzothiophen-4-yl)phenyl]-1-phenyl-1H-benzimidazole (abbreviation: mDBT-BIm-II), a heterocyclic compound having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f, h]quinoxaline (abbreviation: 2mCzBPDBq), 4,6-bis[3-(phenanthren-9-yl)phenyl]pyrimidine (abbreviation: 4,6mPnP2Pm), 4,6-bis[3-(4-dibenzothienyl)phenyl]pyrimidine (abbreviation: 4,6mDBTP2Pm-II), or 4,8-bis[3-(dibenzothiophen-4-yl)phenyl]benzo[h]quinazoline (abbreviation: 4,8mDBtP2Bqn), and a heterocyclic compound having a pyridine skeleton, such as 3,5-bis[3-(9H-carbazol yl)phenyl]pyridine (abbreviation: 35DCzPPy) or 1,3,5-tri[3-(3-pyridyl)phenyl]benzene (abbreviation: TmPyPB). Among the above, the heterocyclic compound having a diazine skeleton and the heterocyclic compound having a pyridine skeleton have favorable reliability and thus are preferable. In particular, the heterocyclic compound having a diazine (pyrimidine or pyrazine) skeleton has a high electron-transport property and contributes to a reduction in driving voltage.

As the TADF material that can be used as the host material, the above-mentioned materials given as TADF materials can also be used. When the TADF material is used as the host material, triplet excitation energy generated in the TADF material is converted into singlet excitation energy by reverse intersystem crossing and transferred to the light-emitting substance, whereby the emission efficiency of the light-emitting device can be increased. At this time, the TADF material functions as an energy donor, and the light-emitting substance functions as an energy acceptor.

This is very effective in the case where the light-emitting substance is a fluorescent substance. In that case, the S1 level of the TADF material is preferably higher than the S1 level of the fluorescent substance in order to achieve high emission efficiency. Furthermore, the T1 level of the TADF material is preferably higher than the S1 level of the fluorescent substance. Therefore, the T1 level of the TADF material is preferably higher than the T1 level of the fluorescent substance.

It is also preferable to use a TADF material that exhibits light emission overlapping with the wavelength of a lowest-energy-side absorption band of the fluorescent substance. This enables smooth transfer of excitation energy from the TADF material to the fluorescent substance and accordingly enables efficient light emission, which is preferable.

In order that singlet excitation energy is efficiently generated from the triplet excitation energy by reverse intersystem crossing, carrier recombination preferably occurs in the TADF material. It is also preferable that the triplet excitation energy generated in the TADF material not be transferred to the triplet excitation energy of the fluorescent substance. For that reason, the fluorescent substance preferably has a protective group around a luminophore (a skeleton that causes light emission) of the fluorescent substance. As the protective group, a substituent having no π bond and saturated hydrocarbon are preferably used. Specific examples include an alkyl group having 3 to 10 carbon atoms, a substituted or unsubstituted cycloalkyl group having 3 to 10 carbon atoms, and a trialkylsilyl group having 3 to 10 carbon atoms. It is further preferable that the fluorescent substance have a plurality of protective groups. The substituent having no 7C bond has a poor carrier-transport property; thus, the TADF material and the luminophore of the fluorescent substance can be made away from each other with little influence on carrier transportation or carrier recombination. Here, the luminophore refers to an atomic group (skeleton) that causes light emission in a fluorescent substance. The luminophore is preferably a skeleton having a π bond, further preferably includes an aromatic ring, and still further preferably includes a condensed aromatic ring or a condensed heteroaromatic ring. Examples of the condensed aromatic ring or the condensed heteroaromatic ring include a phenanthrene skeleton, a stilbene skeleton, an acridone skeleton, a phenoxazine skeleton, and a phenothiazine skeleton. Specifically, a fluorescent substance having any of a naphthalene skeleton, an anthracene skeleton, a fluorene skeleton, a chrysene skeleton, a triphenylene skeleton, a tetracene skeleton, a pyrene skeleton, a perylene skeleton, a coumarin skeleton, a quinacridone skeleton, and a naphthobisbenzofuran skeleton is preferable because of its high fluorescence quantum yield.

In the case where a fluorescent substance is used as the light-emitting substance, a material having an anthracene skeleton is suitable for the host material. The use of a substance having an anthracene skeleton as a host material for a fluorescent substance makes it possible to achieve a light-emitting layer with favorable emission efficiency and durability. As the substance having an anthracene skeleton that is used as the host material, a substance having a diphenylanthracene skeleton, in particular, a substance having a 9,10-diphenylanthracene skeleton, is preferable because of its chemical stability. The host material preferably has a carbazole skeleton because the hole-injection and hole-transport properties are improved; further preferably, the host material has a benzocarbazole skeleton in which a benzene ring is further condensed to carbazole because the HOMO level thereof is shallower than that of carbazole by approximately 0.1 eV and thus holes enter the host material easily. In particular, the host material having a dibenzocarbazole skeleton is preferable because its HOMO level is shallower than that of carbazole by approximately 0.1 eV so that holes enter the host material easily, the hole-transport property is improved, and the heat resistance is increased. Accordingly, a substance that has both a 9,10-diphenylanthracene skeleton and a carbazole skeleton (or a benzocarbazole skeleton or a dibenzocarbazole skeleton) is further preferable as the host material. Note that in terms of the hole-injection and hole-transport properties described above, instead of a carbazole skeleton, a benzofluorene skeleton or a dibenzofluorene skeleton may be used. Examples of such a substance include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl anthryl)phenyl]-7H-dibenzo[c,g]carbazole (abbreviation: cgDBCzPA), 6-[3-(9,10-diphenyl anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), and 9-(1-naphthyl)-10-[4-(2-naphthyl)phenyl]anthracene (abbreviation: αN-βNPAnth). In particular, CzPA, cgDBCzPA, 2mBnfPPA, and PCzPA are preferably selected because they exhibit favorable characteristics.

Note that a host material may be a material of a mixture of a plurality of kinds of substances; in the case of using a mixed host material, it is preferable to mix a material having an electron-transport property with a material having a hole-transport property. When the material having an electron-transport property is mixed with the material having a hole-transport property, the transport property of the light-emitting layer 113 can be easily adjusted and a recombination region can be easily controlled. The weight ratio of the content of the material having a hole-transport property to the content of the material having an electron-transport property may be 1:19 to 19:1. Note that the organic compounds described in Embodiment 1 can be suitably used as the material having an electron-transport property in the mixed host material.

Note that a phosphorescent substance can be used as part of the mixed material. When a fluorescent substance is used as the light-emitting substance, a phosphorescent substance can be used as an energy donor for supplying excitation energy to the fluorescent substance.

An exciplex may be formed by these mixed materials. A combination is preferably selected so as to form an exciplex that exhibits light emission overlapping with the wavelength of a lowest-energy-side absorption band of a light-emitting substance, because energy can be transferred smoothly and light emission can be efficiently obtained. The use of the structure is preferable because the driving voltage is also be reduced.

Note that at least one of the materials forming an exciplex may be a phosphorescent substance. In this case, triplet excitation energy can be efficiently converted into singlet excitation energy by reverse intersystem crossing.

A combination of a material having an electron-transport property and a material having a hole-transport property whose HOMO level is higher than or equal to the HOMO level of the material having an electron-transport property is preferable for forming an exciplex efficiently. In addition, the LUMO level of the material having a hole-transport property is preferably higher than or equal to the LUMO level of the material having an electron-transport property. Note that the LUMO levels and the HOMO levels of the materials can be derived from the electrochemical characteristics (the reduction potentials and the oxidation potentials) of the materials that are measured by cyclic voltammetry (CV).

Note that the formation of an exciplex can be confirmed by a phenomenon in which the emission spectrum of the mixed film in which the material having a hole-transport property and the material having an electron-transport property are mixed is shifted to the longer wavelength side than the emission spectrum of each of the materials (or has another peak on the longer wavelength side), observed by comparison of the emission spectrum of the material having a hole-transport property, the emission spectrum of the material having an electron-transport property, and the emission spectrum of the mixed film of these materials, for example. Alternatively, the formation of an exciplex can be confirmed by a difference in transient response, such as a phenomenon in which the transient photoluminescence (PL) lifetime of the mixed film has longer lifetime components or has a larger proportion of delayed components than that of each of the materials, observed by comparison of the transient PL of the material having a hole-transport property, the transient PL of the material having an electron-transport property, and the transient PL of the mixed film of these materials. The transient PL can be rephrased as transient electroluminescence (EL). That is, the formation of an exciplex can also be confirmed by a difference in transient response observed by comparison of the transient EL of the material having a hole-transport property, the transient EL of the material having an electron-transport property, and the transient EL of the mixed film of these materials.

The electron-transport layer 114 is a layer containing a substance having an electron-transport property. As the substance having an electron-transport property, it is possible to use any of the above-listed substances having electron-transport properties that can be used as the host material.

The electron mobility of the electron-transport layer 114 in the case where the square root of the electric field strength [V/cm] is 600 is preferably higher than or equal to $1\times10^{-7}$ $cm^2/Vs$ and lower than or equal to $5\times10^{-5}$ $cm^2/Vs$. Lowering the electron-transport property of the electron-transport layer 114 enables control of the amount of electrons injected into the light-emitting layer and can prevent the light-emitting layer from having excess electrons. The electron-transport layer preferably includes a material having an electron-transport property and an alkali metal, an alkaline earth metal, a compound thereof, or a complex thereof. It is particularly preferable that this structure be employed when the hole-injection layer is formed using a composite material that includes a material having a hole-transport property with a relatively deep HOMO level of −5.7 eV or higher and −5.4 eV or lower, in which case a long lifetime can be achieved. Here, the material having an electron-transport property preferably has a HOMO level of higher than or equal to −6.0 eV. The material having an electron-transport property is preferably an organic compound having an anthracene skeleton and is further preferably an organic compound having both an anthracene skeleton and a heterocyclic skeleton. The heterocyclic skeleton is preferably a nitrogen-containing five-membered ring skeleton or a nitrogen-containing six-membered ring skeleton, and particularly preferably a nitrogen-containing five-membered ring skeleton or a nitrogen-containing six-membered ring skeleton including two heteroatoms in the ring, such as a pyrazole ring, an imidazole ring, an oxazole ring, a thiazole ring, a pyrazine ring, a pyrimidine ring, or a pyridazine ring. In addition, it is preferable that the alkali metal itself, the alkaline earth metal itself, the compound thereof, and the complex thereof have an 8-hydroxyquinolinato structure. Specific examples include 8-hydroxyquinolinato-lithium (abbreviation: Liq) and 8-hydroxyquinolinato-sodium (abbreviation: Naq). In particular, a complex of a monovalent metal ion, especially a complex of lithium is preferable, and Liq is further preferable. Note that in the case where the 8-hydroxyquinolinato structure is included, a methyl-substituted product (e.g., a 2-methyl-substituted product or a 5-methyl-substituted product) thereof or the like can also be used. There is preferably a difference in the concentration (including 0) of the alkali metal itself, the alkaline earth metal itself, the compound thereof, or the complex thereof in the electron-transport layer in the thickness direction.

As the electron-injection layer 115, a layer containing an alkali metal, an alkaline earth metal, or a compound thereof, such as lithium fluoride (LiF), cesium fluoride (CsF), calcium fluoride ($CaF_2$), or 8-hydroxyquinolinato-lithium (abbreviation: Liq), may be provided between the electron-transport layer 114 and the second electrode 102. An electride or a layer that is formed using a substance having an electron-transport property and that includes an alkali metal, an alkaline earth metal, or a compound thereof can be used as the electron-injection layer 115. Examples of the electride include a substance in which electrons are added at high concentration to a mixed oxide of calcium and aluminum.

Note that as the electron-injection layer 115, it is possible to use a layer that contains a substance having an electron-transport property (preferably an organic compound having a bipyridine skeleton) and contains a fluoride of the alkali metal or the alkaline earth metal at a concentration higher than or equal to that at which the electron-injection layer 115 becomes in a microcrystalline state (50 wt % or higher). Since the layer has a low refractive index, a light-emitting device having more favorable external quantum efficiency can be provided.

Instead of the electron-injection layer 115, the charge-generation layer 116 may be provided (FIG. 1B). The charge-generation layer 116 refers to a layer capable of injecting holes into a layer in contact therewith on the cathode side and injecting electrons into a layer in contact therewith on the anode side when supplied with a potential. The charge-generation layer 116 includes at least a P-type layer 117. The P-type layer 117 is preferably formed using the composite materials given above as the material that can form the hole-injection layer 111. The P-type layer 117 may be formed by stacking a film containing the above acceptor material as a material included in the composite material and a film containing the above hole-transport material. When a potential is applied to the P-type layer 117, electrons are injected into the electron-transport layer 114 and holes are injected into the second electrode 102 that is a cathode; thus, the light-emitting device operates.

Note that one or both of an electron-relay layer 118 and an electron-injection buffer layer 119 are preferably provided in the charge-generation layer 116 in addition to the P-type layer 117.

The electron-relay layer 118 contains at least a substance having an electron-transport property and has a function of preventing an interaction between the electron-injection buffer layer 119 and the P-type layer 117 to transfer electrons smoothly. The LUMO level of the substance having an electron-transport property contained in the electron-relay layer 118 is preferably between the LUMO level of an acceptor substance in the P-type layer 117 and the LUMO level of a substance contained in a layer of the electron-transport layer 114 in contact with the charge-generation layer 116. A specific energy level of the LUMO level of the substance having an electron-transport property used for the electron-relay layer 118 may be higher than or equal to −5.0 eV, preferably higher than or equal to −5.0 eV and lower than or equal to −3.0 eV. Note that as the substance having an electron-transport property used for the electron-relay layer 118, a phthalocyanine-based material or a metal complex having a metal-oxygen bond and an aromatic ligand is preferably used.

For the electron-injection buffer layer 119, a substance having a high electron-injection property, such as an alkali metal, an alkaline earth metal, a rare earth metal, or a compound thereof (an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)), can be used.

In the case where the electron-injection buffer layer 119 is formed so as to contain the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound thereof (an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)). Note that as the substance having an electron-transport property, a material similar to the above-described material forming the electron-transport layer 114 can be used for the formation.

As a substance forming the second electrode 102, a metal, an alloy, an electrically conductive compound, or a mixture thereof having a low work function (specifically, 3.8 eV or less) or the like can be used. As specific examples of such a cathode material, elements belonging to Group 1 or Group 2 of the periodic table, such as alkali metals, e.g., lithium (Li) and cesium (Cs)), magnesium (Mg), calcium (Ca), and strontium (Sr), alloys containing these (MgAg and AlLi), rare earth metals such as europium (Eu) and ytterbium (Yb), alloys containing these rare earth metals, and the like can be given. However, when the electron-injection layer is provided between the second electrode 102 and the electron-transport layer, as the second electrode 102, a variety of conductive materials such as Al, Ag, ITO, or indium oxide-tin oxide containing silicon or silicon oxide can be used regardless of their work functions. Films of these conductive materials can be formed by a dry process such as a vacuum evaporation method or a sputtering method, an inkjet method, a spin coating method, or the like. Alternatively, the films may be formed by a wet process using a sol-gel method or a wet process using a paste of a metal material.

Various methods can be used as a method for forming the EL layer 103 regardless of whether it is a dry process or a wet process. For example, a vacuum evaporation method, a gravure printing method, an offset printing method, a screen printing method, an ink-jet method (a droplet discharge method), a spin coating method, or the like may be used.

Different deposition methods may be used to form the electrodes or the layers described above.

The structure of the layers provided between the first electrode 101 and the second electrode 102 is not limited to the above structure. However, a structure is preferable in which a light-emitting region where holes and electrons recombine is provided at a position away from the first electrode 101 and the second electrode 102 so as to prevent quenching caused by the proximity of the light-emitting region and a metal used for electrodes and carrier-injection layers.

Furthermore, in order to inhibit energy transfer from an exciton generated in the light-emitting layer, it is preferable to form the hole-transport layer and the electron-transport layer that are in contact with the light-emitting layer 113, particularly a carrier-transport layer closer to the recombination region in the light-emitting layer 113, using the light-emitting material of the light-emitting layer or a substance having a wider band gap than the light-emitting material included in the light-emitting layer.

Here, a method of forming an EL layer 786 by a droplet discharge method is described with reference to FIG. 2. FIG. 2A to FIG. 2D are cross-sectional views illustrating the method for forming an EL layer 786.

Figure 2A:
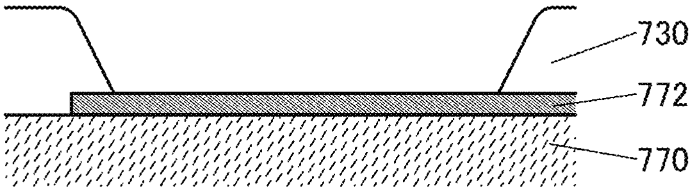
FIG. 2A, FIG. 2B, FIG. 2C, and FIG. 2D illustrate an example of a method for manufacturing a light-emitting device.
Figure 2B:
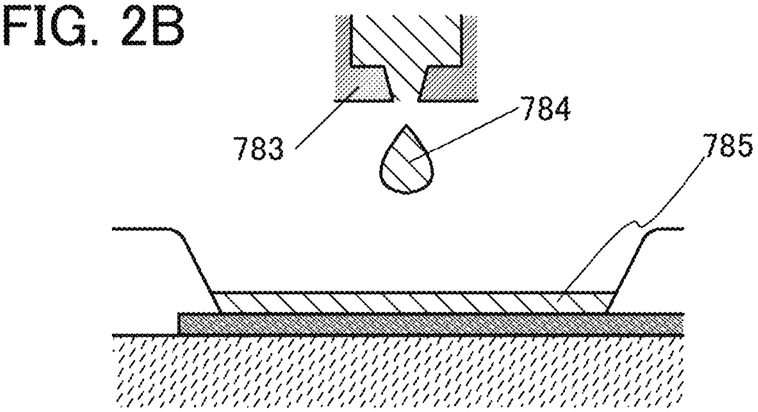

First, a conductive film 772 is formed over a planarization insulating film 770, and an insulating film 730 is formed to cover part of the conductive film 772 (see FIG. 2A).

Then, a droplet 784 is discharged from a droplet discharge apparatus 783 to the conductive film 772 exposed in an opening of the insulating film 730, so that a layer 785 containing a composition is formed. The droplet 784 is a composition containing a solvent and is attached onto the conductive film 772 (see FIG. 2B).

Note that the step of discharging the droplet 784 may be performed under reduced pressure.

Figure 2C:
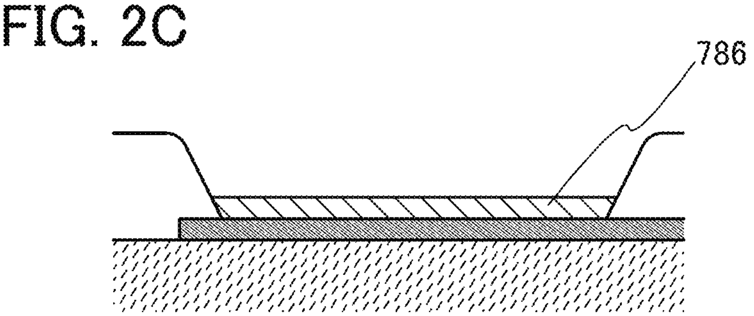

Then, the solvent is removed from the layer 785 containing the composition, and the layer is solidified to form the EL layer 786 (see FIG. 2C).

As the solvent removing method, a drying process or a heating process may be performed.

Figure 2D:
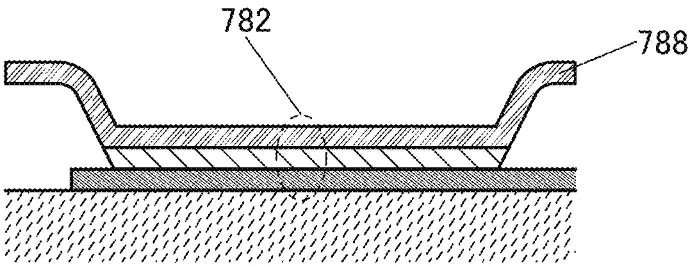

Next, a conductive film 788 is formed over the EL layer 786; thus, a light-emitting device 782 is formed (see FIG. 2D).

When the EL layer 786 including a light-emitting substance is formed by a droplet discharge method in this manner, the composition can be selectively discharged; accordingly, waste of the material can be reduced. Furthermore, a lithography process or the like for shaping is not needed, and thus, the process can be simplified and cost reduction can be achieved.

The droplet discharge method mentioned above is a general term for a method with a droplet discharge means such as a nozzle having a composition discharge outlet or a head having one or a plurality of nozzles.

Figure 3:
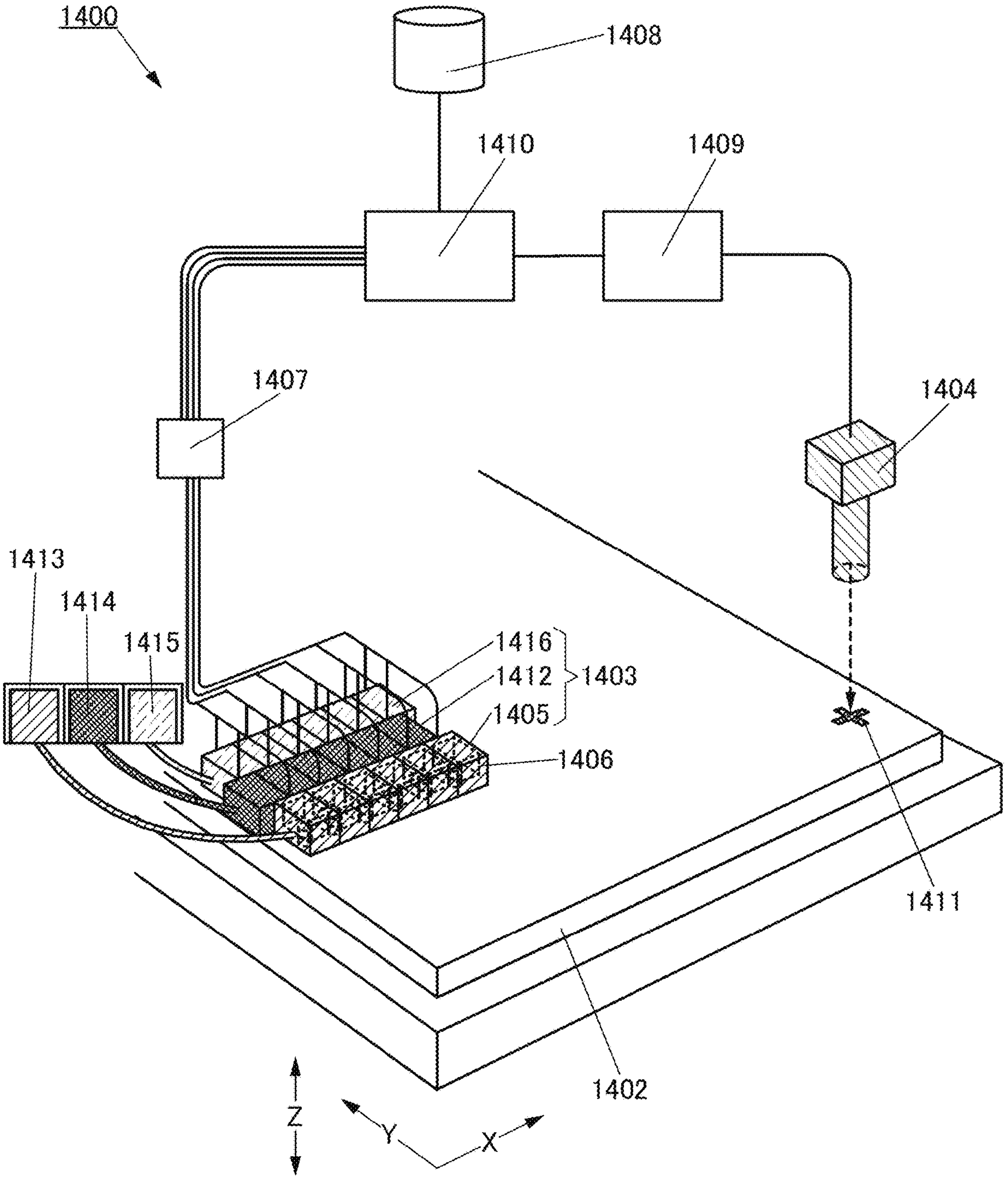
FIG. 3 illustrates an example of a method for manufacturing a light-emitting device.

Next, a droplet discharge apparatus used for the droplet discharge method will be described with reference to FIG. 3. FIG. 3 is a conceptual diagram illustrating a droplet discharge apparatus 1400.

The droplet discharge apparatus 1400 includes a droplet discharge means 1403. In addition, the droplet discharge means 1403 includes a head 1405, a head 1412, and a head 1416.

The head 1405, the head 1412, and the head 1416 are connected to a control means 1407 that is controlled by a computer 1410; thus, a preprogrammed pattern can be drawn.

The drawing may be conducted at a timing, for example, based on a marker 1411 formed over a substrate 1402. Alternatively, the reference point may be determined on the basis of an outer edge of the substrate 1402. Here, the marker 1411 is detected by an imaging means 1404 and converted into a digital signal by an image processing means 1409. The computer 1410 recognizes the digital signal, generates a control signal, and transmits the control signal to the control means 1407.

An image sensor or the like utilizing a charge coupled device (CCD) or a complementary metal-oxide-semiconductor (CMOS) can be used as the imaging means 1404. Note that information about a pattern to be formed over the substrate 1402 is stored in a storage medium 1408, and on the basis of the information, a control signal is transmitted to the control means 1407, and each of the head 1405, the head 1412, and the head 1416 of the droplet discharge means 1403 can be individually controlled. The head 1405, the head 1412, and the head 1416 are supplied with a material to be discharged from a material supply source 1413, a material supply source 1414, and a material supply source 1415 through pipes, respectively.

Inside the head 1405, the head 1412, and the head 1416, a structure including a space to be filled with a liquid material, as indicated by a dotted line 1406, and a nozzle serving as a discharge outlet is employed. Although not illustrated, the inside structures of the head 1412 and the head 1416 are similar to that of the head 1405. When the nozzle sizes of the head 1405, the head 1412, and the head 1416 are different from each other, different materials with different widths can be discharged simultaneously. Each head can discharge a plurality of light-emitting materials or the like to draw a pattern. In the case of drawing over a large area, the same material can be simultaneously discharged to be drawn from a plurality of nozzles in order to improve throughput. When a large substrate is used, the head 1405, the head 1412, and the head 1416 can freely scan the substrate in the directions of arrows X, Y, and Z in FIG. 3, a region in which a pattern is drawn can be freely set, and the same patterns can be drawn on one substrate.

Furthermore, the step of discharging the composition may be performed under reduced pressure. The substrate may be heated at the time of discharging. The discharge of the composition is followed by one or both steps of drying and baking. Both the drying and baking steps are heat treatments but different in purpose, temperature, and time. The drying step and the baking step are performed under normal pressure or reduced pressure by laser irradiation, rapid thermal annealing, heating in a heating furnace, or the like. Note that there is no particular limitation on the timing of the heat treatment and the number of times of the heat treatment. The temperature for adequately performing the drying and baking steps depends on the material of the substrate and the properties of the composition.

In the above-described manner, the EL layer 786 can be formed with the droplet discharge apparatus.

In the case where the EL layer 786 is fabricated with the droplet discharge apparatus, when the EL layer 786 is formed by a wet method using a composition in which any of a variety of organic materials and organic-inorganic halide perovskite materials are dissolved or dispersed in a solvent, various organic solvents can be used to serve as a composition for application. As the organic solvents that can be used for the composition, a variety of organic solvents such as benzene, toluene, xylene, mesitylene, tetrahydrofuran, dioxane, ethanol, methanol, n-propanol, isopropanol, n-butanol, t-butanol, acetonitrile, dimethylsulfoxide, dimethylformamide, chloroform, methylene chloride, carbon tetrachloride, ethyl acetate, hexane, and cyclohexane can be used. In particular, a less polar benzene derivative such as benzene, toluene, xylene, or mesitylene is preferably used because a solution with a suitable concentration can be obtained and a material contained in ink can be prevented from deteriorating due to oxidation or the like. Furthermore, in light of the uniformity of a formed film and the uniformity of film thickness, the boiling point is preferably 100° C. or higher, and toluene, xylene, or mesitylene is further preferable.

Note that the above-described structure can be combined with another embodiment or another structure in this embodiment as appropriate. Although the method of forming the EL layer 786 as a single layer is illustrated in FIG. 2 and FIG. 3, the EL layer 786 may be formed as stacked layers. In this case, to form the stacked layers, a wet method such as a droplet discharge method may be performed more than once or may be combined with an evaporation method. It is preferable that the layers including the hole-injection (-transport) layer to the light-emitting layer be formed by a wet method such as a droplet discharge method and the layers including the electron-transport layer to the cathode be formed by a dry method such as an evaporation method or a sputtering method.

Next, an embodiment of a light-emitting device with a structure where a plurality of light-emitting units are stacked (also referred to as a stacked-type element or a tandem element) will be described with reference to FIG. 1C. This light-emitting device is a light-emitting device including a plurality of light-emitting units between an anode and a cathode. One light-emitting unit has substantially the same structure as that of the EL layer 103, which is illustrated in FIG. 1A. In other words, the light-emitting device illustrated in FIG. 1C can be called a light-emitting device including a plurality of light-emitting units, and the light-emitting device illustrated in FIG. 1A or FIG. 1B can be called a light-emitting device including one light-emitting unit.

Figure 1C:
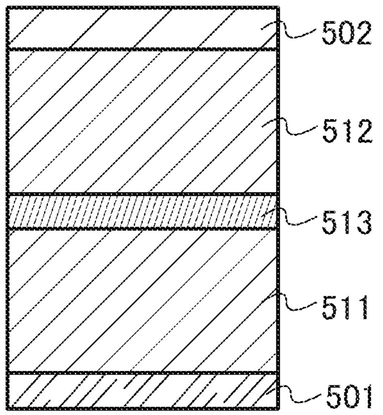

In FIG. 1C, a first light-emitting unit 511 and a second light-emitting unit 512 are stacked between an anode 501 and a cathode 502, and a charge-generation layer 513 is provided between the first light-emitting unit 511 and the second light-emitting unit 512. The anode 501 and the cathode 502 correspond, respectively, to the first electrode 101 and the second electrode 102 in FIG. 1A, and the same substance as what is given in the description for FIG. 1A can be used. Furthermore, the first light-emitting unit 511 and the second light-emitting unit 512 may have the same structure or different structures.

The charge-generation layer 513 has a function of injecting electrons into one of the light-emitting units and injecting holes into the other of the light-emitting units when a voltage is applied to the anode 501 and the cathode 502. That is, in FIG. 1C, any layer can be used as the charge-generation layer 513 as long as the layer injects electrons into the first light-emitting unit 511 and injects holes into the second light-emitting unit 512 in the case where a voltage is applied such that the potential of the anode is higher than the potential of the cathode.

The charge-generation layer 513 is preferably formed with a structure similar to that of the charge-generation layer 116 described with reference to FIG. 1B. A composite material of an organic compound and a metal oxide has an excellent carrier-injection property and an excellent carrier-transport property; thus, low-voltage driving and low-current driving can be achieved. Note that in the case where the anode-side surface of a light-emitting unit is in contact with the charge-generation layer 513, the charge-generation layer 513 can also serve as a hole-injection layer of the light-emitting unit; therefore, a hole-injection layer is not necessarily provided in the light-emitting unit.

In the case where the electron-injection buffer layer 119 is provided in the charge-generation layer 513, the electron-injection buffer layer 119 serves as an electron-injection layer in the light-emitting unit on the anode side; therefore, an electron-injection layer is not necessarily formed in the light-emitting unit on the anode side.

The light-emitting device having two light-emitting units is described with reference to FIG. 1C; however, the same can also be applied to a light-emitting device in which three or more light-emitting units are stacked. With a plurality of light-emitting units partitioned by the charge-generation layer 513 between a pair of electrodes as in the light-emitting device according to this embodiment, it is possible to provide a long-life element that can emit light with high luminance at a low current density. Moreover, a light-emitting apparatus that can be driven at a low voltage and has low power consumption can be achieved.

Furthermore, when emission colors of the light-emitting units are different, light emission of a desired color can be obtained from the light-emitting device as a whole. For example, in a light-emitting device having two light-emitting units, emission colors of red and green are obtained in the first light-emitting unit and an emission color of blue is obtained in the second light-emitting unit, whereby a light-emitting device that emits white light as the whole light-emitting device can be obtained.

The above-described layers and electrodes such as the EL layer 103, the first light-emitting unit 511, the second light-emitting unit 512, and the charge-generation layer can be formed by a method such as an evaporation method (including a vacuum evaporation method), a droplet discharge method (also referred to as an ink-jet method), a coating method, or a gravure printing method. Those may include a low molecular material, a middle molecular material (including an oligomer and a dendrimer), or a high molecular material.

Embodiment 3

In this embodiment, a light-emitting apparatus using the light-emitting device described in Embodiment 2 will be described.

Figure 4A:
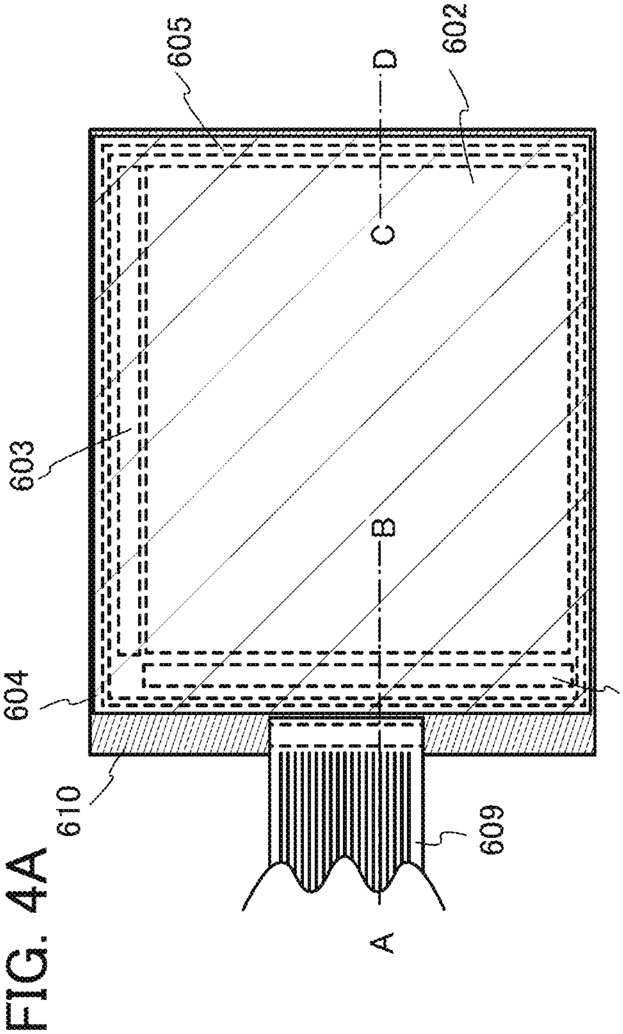
FIG. 4A and FIG. 4B are conceptual diagrams of an active matrix light-emitting apparatus.
Figure 4B:
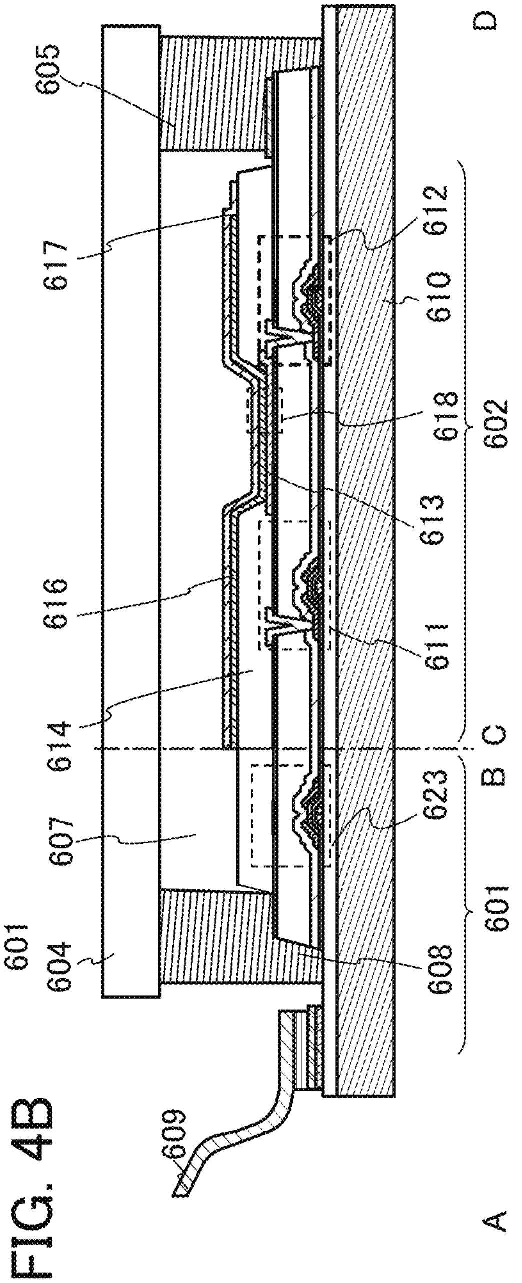

In this embodiment, a light-emitting apparatus fabricated using the light-emitting device described in Embodiment 2 will be described with reference to FIG. 4. Note that FIG. 4A is a top view illustrating the light-emitting apparatus, and FIG. 4B is a cross-sectional view taken along A-B and C-D in FIG. 4A. This light-emitting apparatus includes a driver circuit portion (source line driver circuit) 601, a pixel portion 602, and a driver circuit portion (gate line driver circuit) 603, which are to control light emission of a light-emitting device and are illustrated with dotted lines. Furthermore, 604 denotes a sealing substrate, 605 denotes a sealant, and the inside surrounded by the sealant 605 is a space 607.

Note that a lead wiring 608 is a wiring for transmitting signals to be input to the source line driver circuit 601 and the gate line driver circuit 603 and receiving a video signal, a clock signal, a start signal, a reset signal, and the like from an FPC (flexible printed circuit) 609 serving as an external input terminal. Although only the FPC is illustrated here, a printed wiring board (PWB) may be attached to this FPC. The light-emitting apparatus in this specification includes not only the light-emitting apparatus itself but also the apparatus provided with the FPC or the PWB.

Next, a cross-sectional structure will be described with reference to FIG. 4B. The driver circuit portion and the pixel portion are formed over an element substrate 610. Here, the source line driver circuit 601, which is the driver circuit portion, and one pixel of the pixel portion 602 are illustrated.

The element substrate 610 may be fabricated using a substrate containing glass, quartz, an organic resin, a metal, an alloy, a semiconductor, or the like, or a plastic substrate formed of FRP (Fiber Reinforced Plastic), PVF (polyvinyl fluoride), polyester, an acrylic resin, or the like.

There is no particular limitation on the structure of transistors used in pixels and driver circuits. For example, an inverted staggered transistor or a staggered transistor may be used. Furthermore, top-gate transistors or bottom-gate transistors may be used. There is no particular limitation on a semiconductor material used for the transistors, and for example, silicon, germanium, silicon carbide, gallium nitride, or the like can be used. Alternatively, an oxide semiconductor containing at least one of indium, gallium, and zinc, such as In—Ga—Zn-based metal oxide, may be used.

There is no particular limitation on the crystallinity of a semiconductor material used for the transistors, and any of an amorphous semiconductor or a semiconductor having crystallinity (a microcrystalline semiconductor, a polycrystalline semiconductor, a single-crystal semiconductor, and a semiconductor partly including crystal regions) may be used. A semiconductor having crystallinity is preferably used, in which case deterioration of the transistor characteristics can be suppressed.

Here, an oxide semiconductor is preferably used for semiconductor devices such as the transistors provided in the pixels and driver circuits and transistors used for touch sensors described later, and the like. In particular, an oxide semiconductor having a wider band gap than silicon is preferably used. The use of an oxide semiconductor having a wider band gap than silicon can reduce the off-state current of the transistors.

The oxide semiconductor preferably contains at least indium (In) or zinc (Zn). Further preferably, the oxide semiconductor contains an oxide represented by an In-M-Zn-based oxide (M represents a metal such as Al, Ti, Ga, Ge, Y, Zr, Sn, La, Ce, or Hf).

As a semiconductor layer, it is particularly preferable to use an oxide semiconductor film including a plurality of crystal parts whose c-axes are aligned perpendicular to a surface on which the semiconductor layer is formed or the top surface of the semiconductor layer and in which the adjacent crystal parts have no grain boundary.

The use of such a material for the semiconductor layer makes it possible to achieve a highly reliable transistor in which a change in the electrical characteristics is reduced.

Charge accumulated in a capacitor through a transistor including the above-described semiconductor layer can be retained for a long time because of the low off-state current of the transistor. The use of such a transistor in pixels allows a driver circuit to stop while the gray level of an image displayed on each display region is maintained. As a result, an electronic apparatus with significantly reduced power consumption can be achieved.

For stable characteristics of the transistor or the like, a base film is preferably provided. The base film can be formed to be a single-layer or a stacked-layer using an inorganic insulating film such as a silicon oxide film, a silicon nitride film, a silicon oxynitride film, or a silicon nitride oxide film. The base film can be formed by a sputtering method, a CVD (Chemical Vapor Deposition) method (e.g., a plasma CVD method, a thermal CVD method, or an MOCVD (Metal Organic CVD) method), an ALD (Atomic Layer Deposition) method, a coating method, a printing method, or the like. Note that the base film is not necessarily provided when not needed.

Note that an FET 623 is illustrated as a transistor formed in the driver circuit portion 601. The driver circuit can be formed using various circuits such as a CMOS circuit, a PMOS circuit, and an NMOS circuit. Although a driver-integrated type in which the driver circuit is formed over the substrate is described in this embodiment, the driver circuit is not necessarily formed over the substrate and can be formed outside.

The pixel portion 602 is formed with a plurality of pixels including a switching FET 611, a current control FET 612, and a first electrode 613 electrically connected to a drain of the current control FET 612; however, without being limited thereto, a pixel portion in which three or more FETs and a capacitor are combined may be employed.

Note that an insulator 614 is formed to cover an end portion of the first electrode 613. The insulator 614 can be formed using a positive photosensitive acrylic resin film here.

In order to improve the coverage with an EL layer or the like to be formed later, the insulator 614 is formed so as to have a curved surface with curvature at its upper end portion or lower end portion. For example, in the case where a positive photosensitive acrylic resin is used as a material for the insulator 614, only the upper end portion of the insulator 614 preferably has a curved surface with a curvature radius (0.2 μm to 3 μm). As the insulator 614, either a negative photosensitive resin or a positive photosensitive resin can be used.

An EL layer 616 and a second electrode 617 are formed over the first electrode 613. Here, as a material used for the first electrode 613 functioning as an anode, a material with a high work function is desirably used. For example, a single-layer film of an ITO film, an indium tin oxide film containing silicon, an indium oxide film containing zinc oxide at 2 to 20 wt %, a titanium nitride film, a chromium film, a tungsten film, a Zn film, a Pt film, or the like, a stacked layer of titanium nitride film and a film containing aluminum as its main component, a three-layer structure of a titanium nitride film, a film containing aluminum as its main component, and a titanium nitride film, or the like can be used. Note that the stacked-layer structure achieves low wiring resistance, a favorable ohmic contact, and a function as an anode.

The EL layer 616 is formed by any of a variety of methods such as an evaporation method using an evaporation mask, an inkjet method, and a spin coating method. Alternatively, a material included in the EL layer 616 may be a low molecular compound or a high molecular compound (including an oligomer or a dendrimer).

As a material used for the second electrode 617, which is formed over the EL layer 616 and functions as a cathode, a material with a low work function (e.g., Al, Mg, Li, Ca, or an alloy or a compound thereof (e.g., MgAg, MgIn, or AlLi)) is preferably used. Note that in the case where light generated in the EL layer 616 passes through the second electrode 617, it is preferable to use, for the second electrode 617, a stacked layer of a thin metal film and a transparent conductive film (e.g., ITO, indium oxide containing zinc oxide at 2 to 20 wt %, indium tin oxide containing silicon, or zinc oxide (ZnO)).

Note that a light-emitting device 618 is formed with the first electrode 613, the EL layer 616, and the second electrode 617. The light-emitting device is the light-emitting device described in Embodiment 2. A plurality of light-emitting devices are formed in the pixel portion, and the light-emitting apparatus of this embodiment may include both the light-emitting device described in Embodiment 2 and a light-emitting device having a different structure.

The sealing substrate 604 and the element substrate 610 are attached to each other using the sealant 605, so that a structure is employed in which a light-emitting device 618 is provided in the space 607 surrounded by the element substrate 610, the sealing substrate 604, and the sealant 605. The space 607 is filled with a filler; it is filled with an inert gas (e.g., nitrogen or argon) in some cases, and filled with the sealant in some cases. The structure of the sealing substrate in which a recessed portion is formed and a desiccant is provided is preferable because deterioration due to the influence of moisture can be inhibited.

Note that an epoxy-based resin or glass frit is preferably used for the sealant 605. Furthermore, these materials are preferably materials that transmit moisture or oxygen as little as possible. As the material used for the sealing substrate 604, in addition to a glass substrate and a quartz substrate, a plastic substrate formed of FRP (Fiber Reinforced Plastics), PVF (polyvinyl fluoride), polyester, an acrylic resin, or the like can be used.

Although not illustrated in FIG. 4, a protective film may be provided over the second electrode. The protective film may be formed using an organic resin film or an inorganic insulating film. The protective film may be formed so as to cover an exposed portion of the sealant 605. The protective film may be provided so as to cover surfaces and side surfaces of the pair of substrates and exposed side surfaces of a sealing layer, an insulating layer, and the like.

For the protective film, a material that is less likely to transmit an impurity such as water can be used. Thus, diffusion of an impurity such as water from the outside into the inside can be effectively inhibited.

As a material included in the protective film, an oxide, a nitride, a fluoride, a sulfide, a ternary compound, a metal, a polymer, or the like can be used; for example, it is possible to use a material containing aluminum oxide, hafnium oxide, hafnium silicate, lanthanum oxide, silicon oxide, strontium titanate, tantalum oxide, titanium oxide, zinc oxide, niobium oxide, zirconium oxide, tin oxide, yttrium oxide, cerium oxide, scandium oxide, erbium oxide, vanadium oxide, indium oxide, or the like; a material containing aluminum nitride, hafnium nitride, silicon nitride, tantalum nitride, titanium nitride, niobium nitride, molybdenum nitride, zirconium nitride, gallium nitride, or the like; or a material containing a nitride containing titanium and aluminum, an oxide containing titanium and aluminum, an oxide containing aluminum and zinc, a sulfide containing manganese and zinc, a sulfide containing cerium and strontium, an oxide containing erbium and aluminum, an oxide containing yttrium and zirconium, or the like.

The protective film is preferably formed using a deposition method that enables favorable step coverage. One such method is an atomic layer deposition (ALD) method. A material that can be formed by an ALD method is preferably used for the protective film. With the use of an ALD method, a dense protective film with reduced defects such as cracks and pinholes or with a uniform thickness can be formed. Furthermore, damage caused to a process member in forming the protective film can be reduced.

By an ALD method, a uniform protective film with few defects can be formed even on a surface with a complex uneven shape or upper, side, and lower surfaces of a touch panel.

As described above, the light-emitting apparatus fabricated using the light-emitting device described in Embodiment 2 can be obtained.

For the light-emitting apparatus in this embodiment, the light-emitting device described in Embodiment 2 is used and thus a light-emitting apparatus having favorable characteristics can be obtained. Specifically, since the light-emitting device described in Embodiment 2 has favorable emission efficiency, the light-emitting apparatus with low power consumption can be obtained.

Figure 5A:
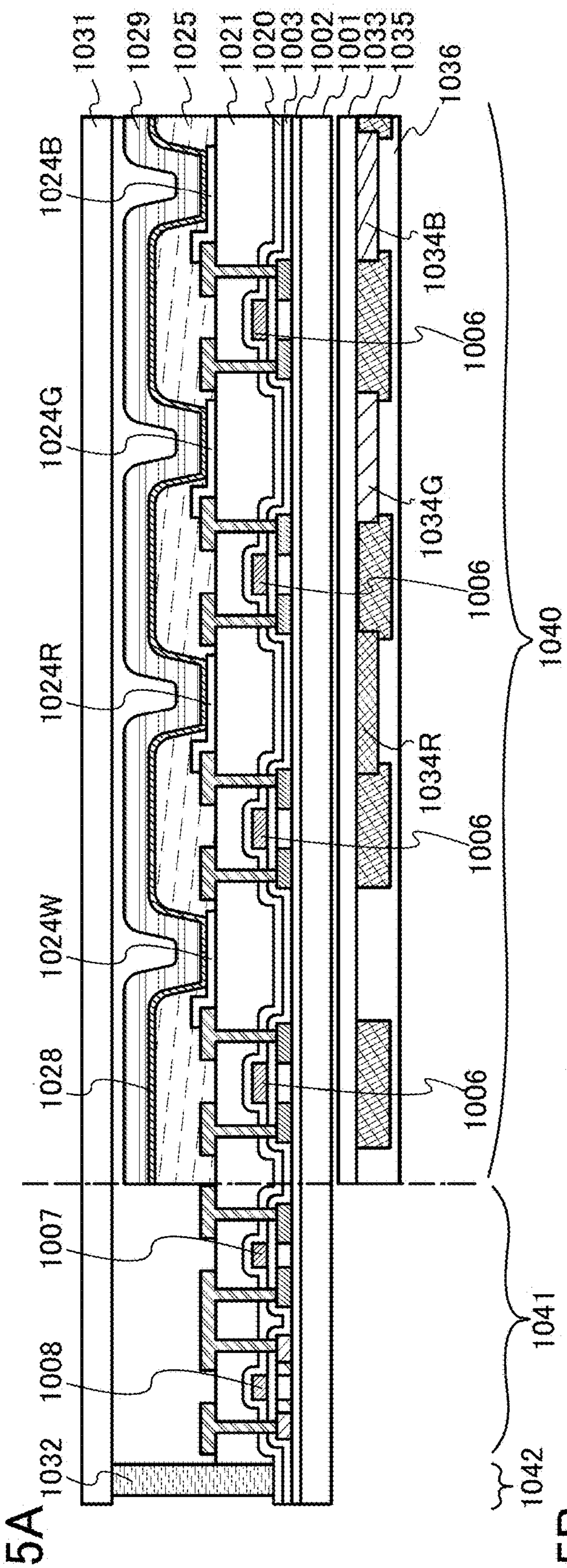
FIG. 5A and FIG. 5B are conceptual diagrams of active matrix light-emitting apparatuses.

FIG. 5 illustrates examples of a light-emitting apparatus in which full color display is achieved by formation of a light-emitting device exhibiting white light emission and provision of coloring layers (color filters) and the like. FIG. 5A illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of the light-emitting devices, a partition 1025, an EL layer 1028, a second electrode 1029 of the light-emitting devices, a sealing substrate 1031, a sealant 1032, and the like.

In FIG. 5A, coloring layers (a red coloring layer 1034R, a green coloring layer 1034G, and a blue coloring layer 1034B) are provided on a transparent base material 1033. A black matrix 1035 may be additionally provided. The transparent base material 1033 provided with the coloring layers and the black matrix is positioned and fixed to the substrate 1001. Note that the coloring layers and the black matrix 1035 are covered with an overcoat layer 1036. In FIG. 5A, a light-emitting layer from which light is emitted to the outside without passing through the coloring layer and light-emitting layers from which light is emitted to the outside, passing through the coloring layers of the respective colors are shown. Since light that does not pass through the coloring layer is white and light that passes through the coloring layer is red, green, or blue, an image can be expressed by pixels of the four colors.

Figure 5B:
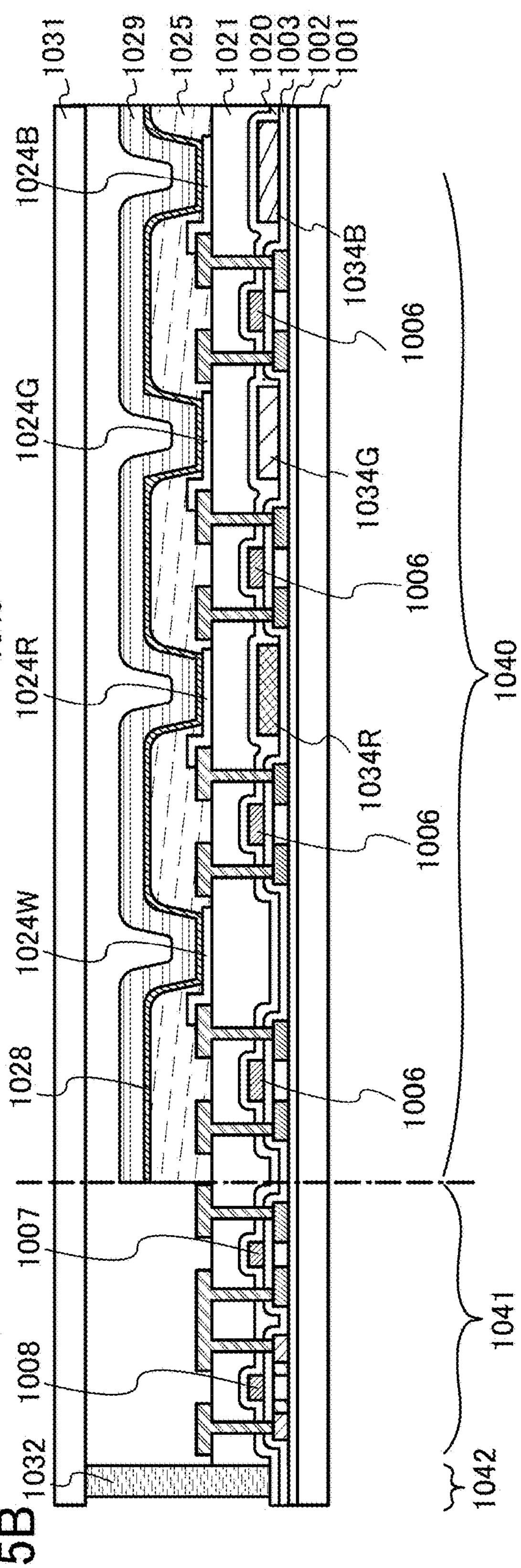

FIG. 5B shows an example in which the coloring layers (the red coloring layer 1034R, the green coloring layer 1034G, and the blue coloring layer 1034B) are formed between the gate insulating film 1003 and the first interlayer insulating film 1020. The coloring layers may be provided between the substrate 1001 and the sealing substrate 1031 in this manner.

Figure 6:
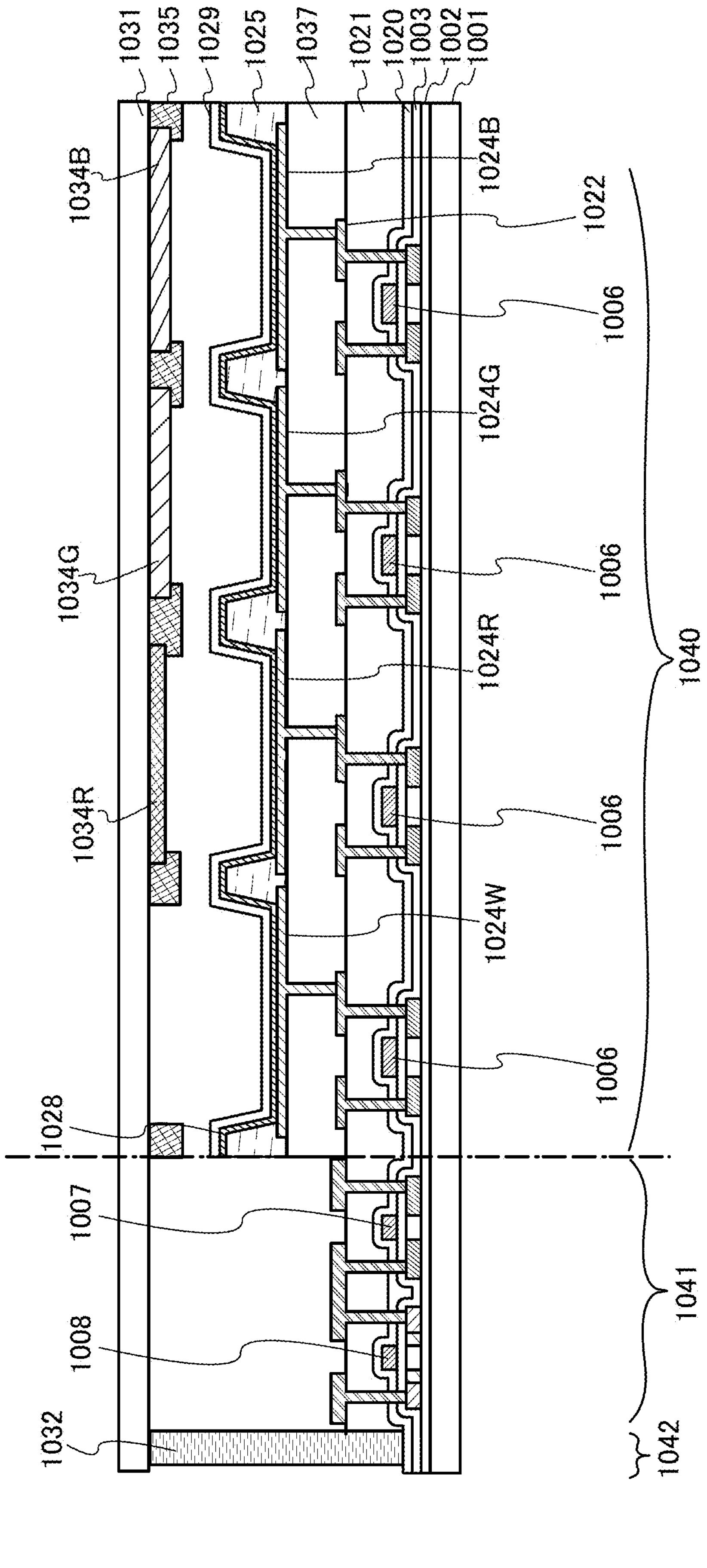
FIG. 6 is a conceptual diagram of an active matrix light-emitting apparatus.

The above-described light-emitting apparatus is a light-emitting apparatus having a structure in which light is extracted to the substrate 1001 side where the FETs are formed (a bottom-emission type), but may be a light-emitting apparatus having a structure in which light emission is extracted to the sealing substrate 1031 side (a top-emission type). FIG. 6 shows a cross-sectional view of a top-emission light-emitting apparatus. In this case, a substrate that does not transmit light can be used as the substrate 1001. The top-emission light-emitting apparatus is formed in a manner similar to that of the bottom-emission light-emitting apparatus until a connection electrode which connects the FET and the anode of the light-emitting device is formed. Then, a third interlayer insulating film 1037 is formed to cover an electrode 1022. This insulating film may have a planarization function. The third interlayer insulating film 1037 can be formed using a material similar to that for the second interlayer insulating film or using any other known materials.

The first electrodes 1024W, 1024R, 1024G, and 1024B of the light-emitting devices are each an anode here, but may each be a cathode. Furthermore, in the case of the top-emission light-emitting apparatus illustrated in FIG. 6, the first electrodes are preferably reflective electrodes. The structure of the EL layer 1028 is such a structure as that of the EL layer 103 described in Embodiment 2, and an element structure with which white light emission can be obtained.

In the case of such a top-emission structure as in FIG. 6, sealing can be performed with the sealing substrate 1031 on which the coloring layers (the red coloring layer 1034R, the green coloring layer 1034G, and the blue coloring layer 1034B) are provided. The sealing substrate 1031 may be provided with the black matrix 1035 which is positioned between pixels. The coloring layers (the red coloring layer 1034R, the green coloring layer 1034G, and the blue coloring layer 1034B) and the black matrix may be covered with the overcoat layer 1036. Note that a light-transmitting substrate is used as the sealing substrate 1031. Although an example in which full color display is performed using four colors of red, green, blue, and white is shown here, there is no particular limitation and full color display may be performed using four colors of red, yellow, green, and blue or three colors of red, green, and blue.

In the top-emission-type light-emitting apparatus, a microcavity structure can be favorably employed. A light-emitting device with a microcavity structure can be obtained with the use of a reflective electrode as the first electrode and a semi-transmissive and semi-reflective electrode as the second electrode. The light-emitting device with a microcavity structure includes at least an EL layer between the reflective electrode and the semi-transmissive and semi-reflective electrode, which includes at least a light-emitting layer serving as a light-emitting region.

Note that the reflective electrode is a film having a visible light reflectivity of 40% to 100%, preferably 70% to 100%, and a resistivity of $1\times10^{-2}$ Ω/cm or lower. In addition, the semi-transmissive and semi-reflective electrode is a film having a visible light reflectivity of 20% to 80%, preferably 40% to 70%, and a resistivity of $1\times10^{-2}$ Ωcm or lower.

Light emitted from the light-emitting layer included in the EL layer is reflected and resonated by the reflective electrode and the semi-transmissive and semi-reflective electrode.

In the light-emitting device, by changing thicknesses of the transparent conductive film, the above-described composite material, the carrier-transport material, and the like, the optical path length between the reflective electrode and the semi-transmissive and semi-reflective electrode can be changed. Thus, light with a wavelength that is resonated between the reflective electrode and the semi-transmissive and semi-reflective electrode can be intensified while light with a wavelength that is not resonated therebetween can be attenuated.

Note that light that is reflected back by the reflective electrode (first reflected light) considerably interferes with light that directly enters the semi-transmissive and semi-reflective electrode from the light-emitting layer (first incident light); therefore, the optical path length between the reflective electrode and the light-emitting layer is preferably adjusted to $(2n-1)\lambda/4$ (n is a natural number of 1 or larger and λ is a wavelength of light emission to be amplified). By adjusting the optical path length, the phases of the first reflected light and the first incident light can be aligned with each other and the light emitted from the light-emitting layer can be further amplified.

Note that in the above structure, the EL layer may include a plurality of light-emitting layers or may include a single light-emitting layer; for example, in combination with the structure of the above-described tandem light-emitting device, a plurality of EL layers each including a single or a plurality of light-emitting layer(s) may be provided in one light-emitting device with a charge-generation layer interposed between the EL layers.

With the microcavity structure, emission intensity with a specific wavelength in the front direction can be increased, whereby power consumption can be reduced. Note that in the case of a light-emitting apparatus which displays images with subpixels of four colors, red, yellow, green, and blue, the light-emitting apparatus can have favorable characteristics because a microcavity structure suitable for wavelengths of the corresponding color is employed in each subpixel, in addition to the effect of an improvement in luminance owing to yellow light emission.

For the light-emitting apparatus in this embodiment, the light-emitting device described in Embodiment 2 is used and thus a light-emitting apparatus having favorable characteristics can be obtained. Specifically, since the light-emitting device described in Embodiment 2 has favorable emission efficiency, the light-emitting apparatus with low power consumption can be obtained.

Figure 7A:
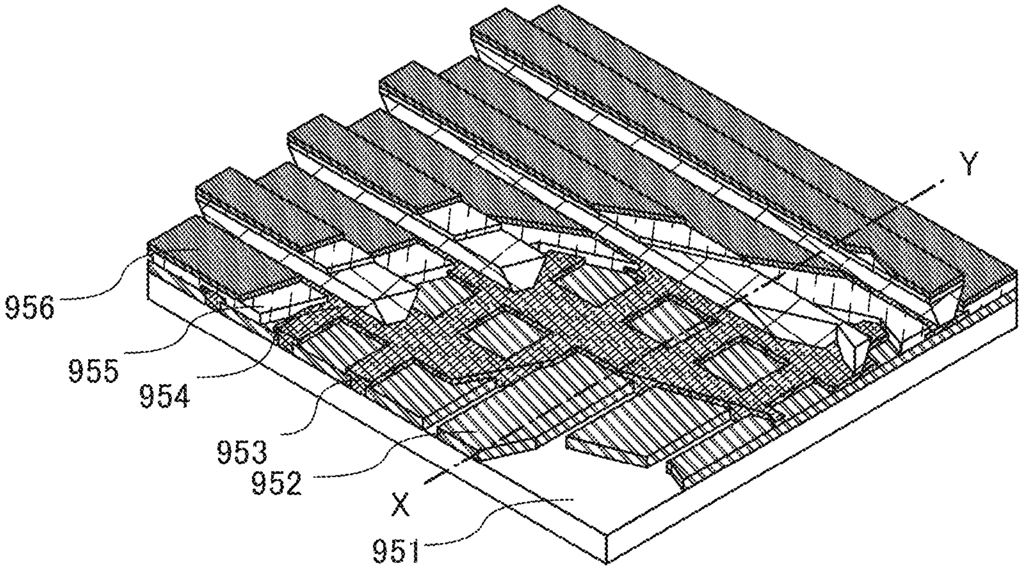
FIG. 7A and FIG. 7B are conceptual diagrams of a passive matrix light-emitting apparatus.
Figure 7B:
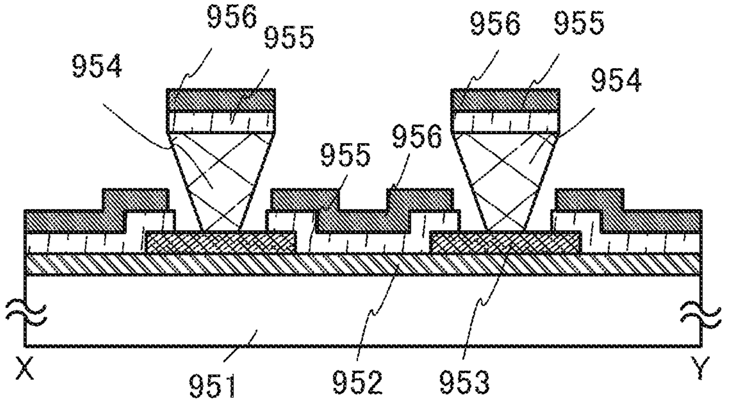

The active matrix light-emitting apparatus is described above, whereas a passive matrix light-emitting apparatus is described below. FIG. 7 illustrates a passive matrix light-emitting apparatus fabricated using the present invention. Note that FIG. 7A is a perspective view illustrating the light-emitting apparatus, and FIG. 7B is a cross-sectional view taken along X-Y in FIG. 7A. In FIG. 7, over a substrate 951, an EL layer 955 is provided between an electrode 952 and an electrode 956. An end portion of the electrode 952 is covered with an insulating layer 953. A partition layer 954 is provided over the insulating layer 953. Sidewalls of the partition layer 954 are aslope such that the distance between one sidewall and the other sidewall is gradually narrowed toward the surface of the substrate. That is, a cross section in the short side direction of the partition layer 954 is a trapezoidal shape, and the lower side (the side facing the same direction as the plane direction of the insulating layer 953 and touching the insulating layer 953) is shorter than the upper side (the side facing the same direction as the plane direction of the insulating layer 953, and not touching the insulating layer 953). By providing the partition layer 954 in this manner, defects of the light-emitting device due to static charge or the like can be prevented. The passive-matrix light-emitting apparatus also uses the light-emitting device described in Embodiment 2; thus, the light-emitting apparatus can have favorable reliability or low power consumption.

Since many minute light-emitting devices arranged in a matrix can each be controlled in the light-emitting apparatus described above, the light-emitting apparatus can be suitably used as a display device for displaying images.

This embodiment can be freely combined with any of the other embodiments.

Embodiment 4

Figure 8A:
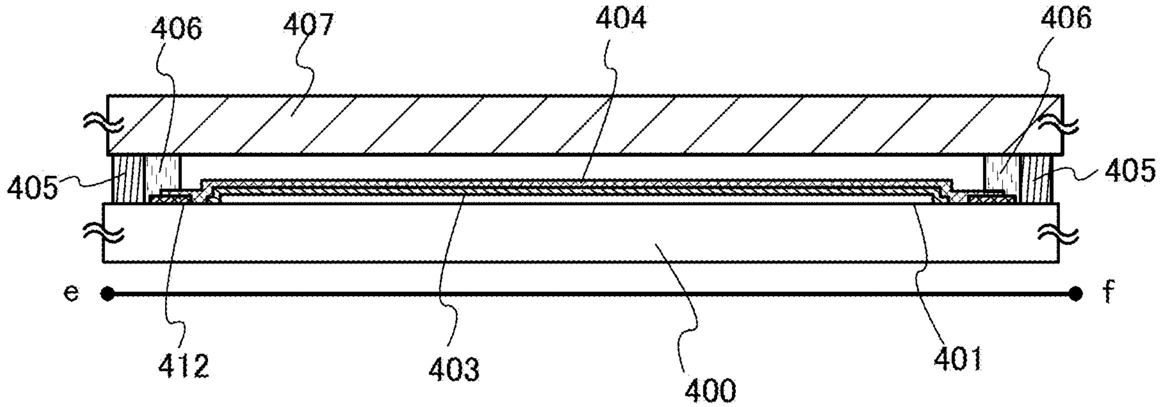
FIG. 8A and FIG. 8B are diagrams showing a lighting device.
Figure 8B:
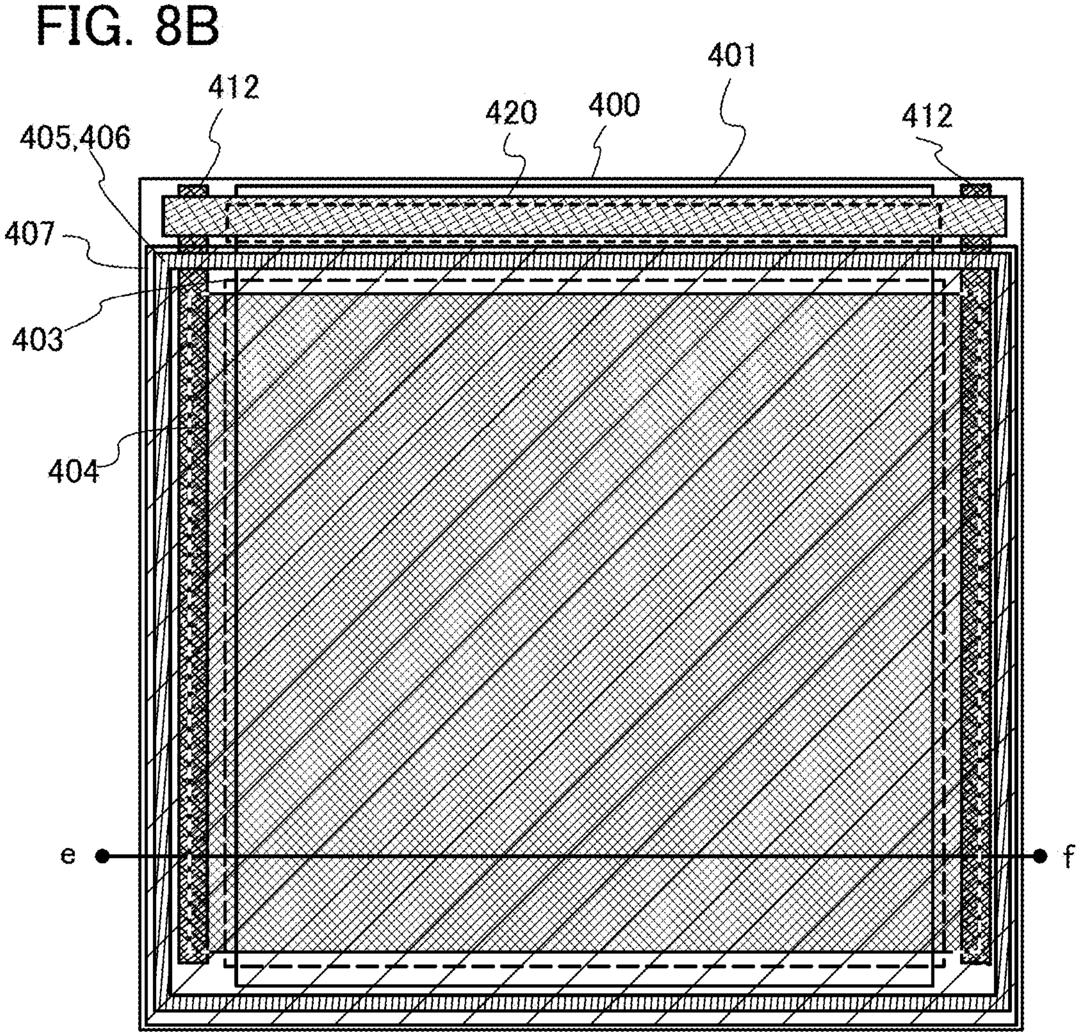

In this embodiment, an example in which the light-emitting device described in Embodiment 2 is used for a lighting device will be described with reference to FIG. 8. FIG. 8B is a top view of the lighting device, and FIG. 8A is a cross-sectional view taken along e-f in FIG. 8B.

In the lighting device in this embodiment, a first electrode 401 is formed over a substrate 400 which is a support and has a light-transmitting property. The first electrode 401 corresponds to the first electrode 101 in Embodiment 2. In the case where light emission is extracted from the first electrode 401 side, the first electrode 401 is formed with a material having a light-transmitting property.

A pad 412 for supplying a voltage to a second electrode 404 is formed over the substrate 400.

An EL layer 403 is formed over the first electrode 401. The EL layer 403 has a structure corresponding to the structure of the EL layer 103 in Embodiment 2, or the structure in which the first light-emitting unit 511 and the second light-emitting unit 512 are combined with the charge-generation layer 513. Note that for these structures, the corresponding description can be referred to.

The second electrode 404 is formed to cover the EL layer 403. The second electrode 404 corresponds to the second electrode 102 in Embodiment 2. In the case where light-emission is extracted from the first electrode 401 side, the second electrode 404 is formed with a material having high reflectivity. The second electrode 404 is supplied with a voltage when connected to the pad 412.

As described above, the lighting device described in this embodiment includes a light-emitting device including the first electrode 401, the EL layer 403, and the second electrode 404. Since the light-emitting device is a light-emitting device with high emission efficiency, the lighting device in this embodiment can be a lighting device with low power consumption.

The substrate 400 over which the light-emitting device having the above structure is formed is fixed to a sealing substrate 407 with sealants 405 and 406 and sealing is performed, whereby the lighting device is completed. It is possible to use only either the sealant 405 or 406. In addition, the inner sealant 406 (not shown in FIG. 8B) can be mixed with a desiccant, which enables moisture to be adsorbed, resulting in improved reliability.

When parts of the pad 412 and the first electrode 401 are provided to extend to the outside of the sealants 405 and 406, those can serve as external input terminals. An IC chip 420 mounted with a converter or the like may be provided over the external input terminals.

The lighting device described in this embodiment uses the light-emitting device described in Embodiment 2 as an EL device; thus, the light-emitting apparatus can have low power consumption.

Embodiment 5

In this embodiment, examples of electronic apparatuses each partly including the light-emitting device described in Embodiment 2 are described. The light-emitting device described in Embodiment 2 is a light-emitting device with favorable emission efficiency and low power consumption. As a result, the electronic apparatuses described in this embodiment can be electronic apparatuses each including a light-emitting portion with low power consumption.

Examples of electronic apparatuses to which the light-emitting device is applied include a television devices (also referred to as TV or television receivers), monitors for computers and the like, cameras such as digital cameras and digital video cameras, digital photo frames, mobile phones (also referred to as portable telephones or portable telephone devices), portable game machines, portable information terminals, audio playback devices, and large game machines such as pin-ball machines. Specific examples of these electronic apparatuses are shown below.

Figure 9A:
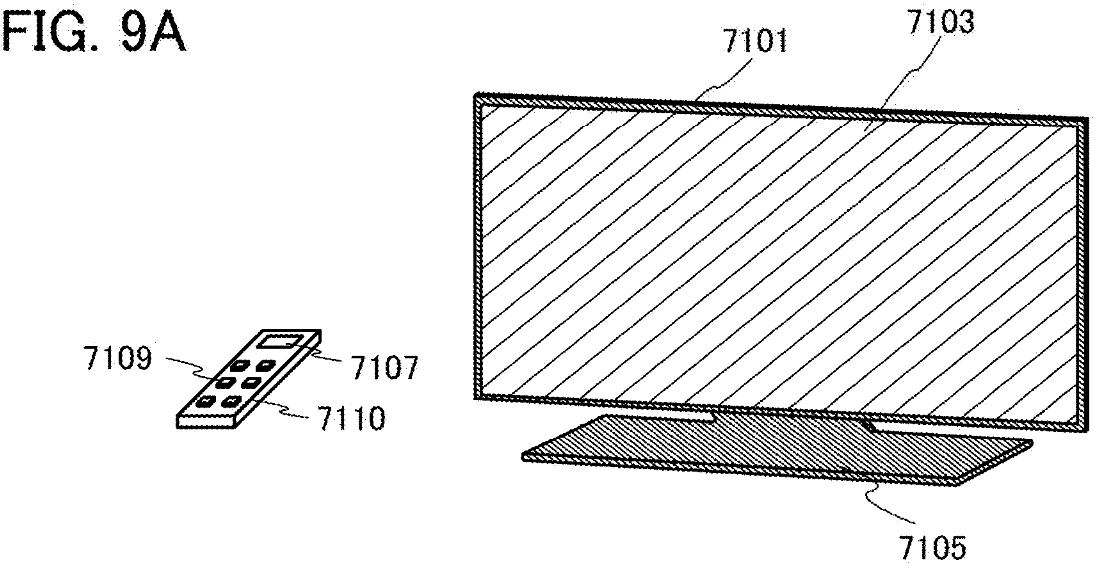
Figure 9A:
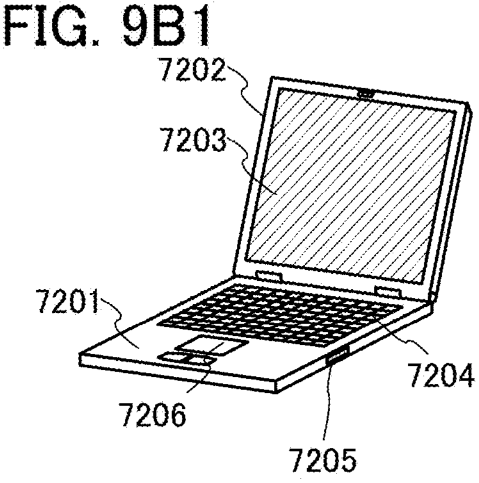
Figure 9A:
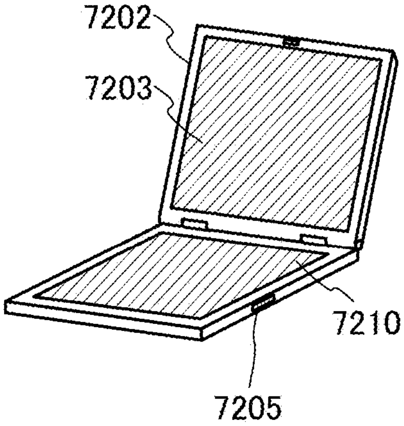

FIG. 9A shows an example of a television device. In the television device, a display portion 7103 is incorporated in a housing 7101. Here, a structure in which the housing 7101 is supported by a stand 7105 is shown. Images can be displayed on the display portion 7103, and the light-emitting devices described in Embodiment 2 are arranged in a matrix in the display portion 7103.

The television device can be operated with an operation switch of the housing 7101 or a separate remote controller 7110. With operation keys 7109 of the remote controller 7110, channels and volume can be operated and images displayed on the display portion 7103 can be operated. Furthermore, a structure may be employed in which the remote controller 7110 is provided with a display portion 7107 for displaying data output from the remote controller 7110.

Note that the television device has a structure of including a receiver, a modem, and the like. With the use of the receiver, a general television broadcast can be received, and moreover, when the television device is connected to a communication network with or without a wire via the modem, one-way (from a sender to a receiver) or two-way (between a sender and a receiver or between receivers) data communication can be performed.

FIG. 9B1 is a computer which includes a main body 7201, a housing 7202, a display portion 7203, a keyboard 7204, an external connection port 7205, a pointing device 7206, and the like. Note that this computer is fabricated using the light-emitting devices described in Embodiment 2 arranged in a matrix in the display portion 7203. The computer in FIG. 9B1 may be such a mode as illustrated in FIG. 9B2. The computer in FIG. 9B2 is provided with a second display portion 7210 instead of the keyboard 7204 and the pointing device 7206. The second display portion 7210 is of a touch-panel type, and input can be performed by operating display for input displayed on the second display portion 7210 with a finger or a dedicated pen. The second display portion 7210 can also display images other than the display for input. The display portion 7203 may also be a touch panel. Connecting the two screens with a hinge can prevent troubles such as a crack in or damage to the screens caused when the computer is stored or carried.

Figure 9C:
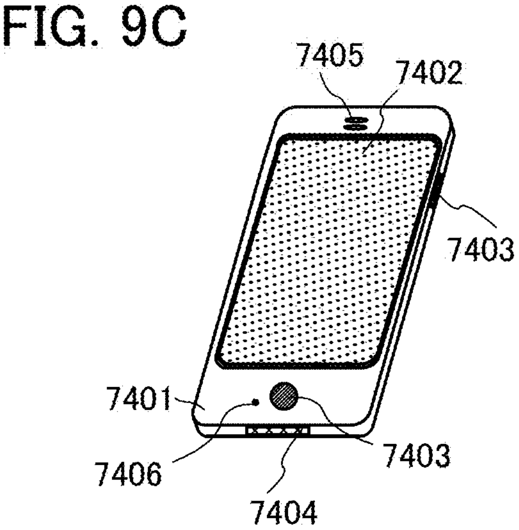

FIG. 9C shows an example of a portable terminal. A mobile phone includes operation buttons 7403, an external connection port 7404, a speaker 7405, a microphone 7406, and the like in addition to a display portion 7402 incorporated in a housing 7401. Note that a mobile phone includes the display portion 7402 which is fabricated by arranging the light-emitting devices described in Embodiment 2 in a matrix.

The portable terminal illustrated in FIG. 9C may have a structure in which information can be input by touching the display portion 7402 with a finger or the like. In this case, operations such as making a call and creating an e-mail can be performed by touching the display portion 7402 with a finger or the like.

The display portion 7402 has mainly three screen modes. The first one is a display mode mainly for displaying images, and the second one is an input mode mainly for inputting data such as text. The third one is a display+input mode in which two modes of the display mode and the input mode are combined.

For example, in the case of making a call or creating an e-mail, a text input mode mainly for inputting text is selected for the display portion 7402 so that an operation of inputting text displayed on the screen may be performed. In this case, it is preferable to display a keyboard or number buttons on the entire screen of the display portion 7402.

When a sensing device including a sensor for sensing inclination, such as a gyroscope sensor or an acceleration sensor, is provided inside the portable terminal, screen display of the display portion 7402 can be automatically changed by determining the orientation of the portable terminal (vertically or horizontally).

The screen modes are changed by touching the display portion 7402 or operating the operation buttons 7403 of the housing 7401. Alternatively, the screen modes can be changed depending on the kind of image displayed on the display portion 7402. For example, when a signal of an image displayed on the display portion is moving image data, the screen mode is changed to the display mode, and when the signal is text data, the screen mode is changed to the input mode.

Moreover, in the input mode, when input by the touch operation of the display portion 7402 is not performed for a certain period while a signal sensed by an optical sensor in the display portion 7402 is sensed, the screen mode may be controlled so as to be changed from the input mode to the display mode.

The display portion 7402 can also function as an image sensor. For example, an image of a palm print, a fingerprint, or the like is taken when the display portion 7402 is touched with the palm or the finger, whereby personal authentication can be performed. Furthermore, by using a backlight which emits near-infrared light or a sensing light source which emits near-infrared light in the display portion, an image of a finger vein, a palm vein, or the like can be taken.

Figure 10A:
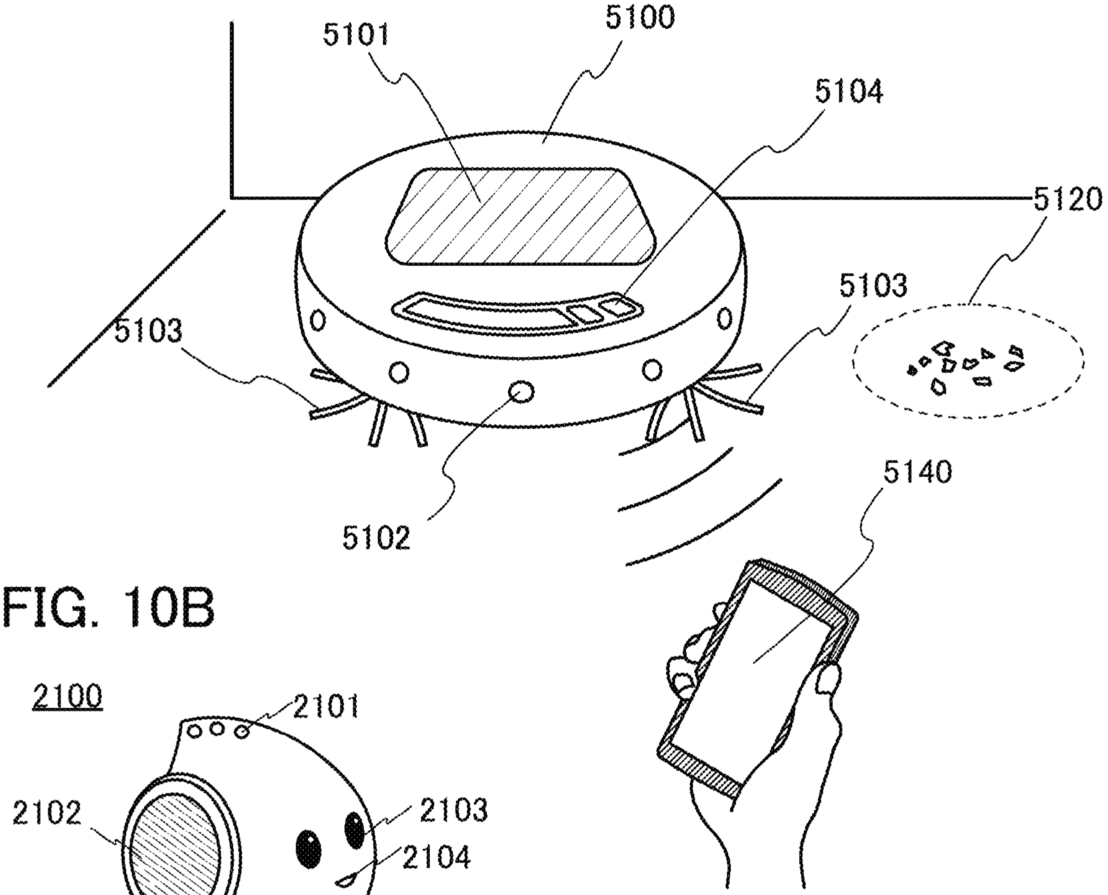
FIG. 10A, FIG. 10B, and FIG. 10C illustrate concepts showing electronic apparatuses.

FIG. 10A is a schematic view showing an example of a cleaning robot.

A cleaning robot 5100 includes a display 5101 placed on its top surface, a plurality of cameras 5102 placed on its side surface, a brush 5103, and operation buttons 5104. Although not illustrated, the bottom surface of the cleaning robot 5100 is provided with a tire, an inlet, and the like. Furthermore, the cleaning robot 5100 includes various sensors such as an infrared sensor, an ultrasonic sensor, an acceleration sensor, a piezoelectric sensor, an optical sensor, and a gyroscope sensor. In addition, the cleaning robot 5100 has a wireless communication means.

The cleaning robot 5100 is self-propelled, detects dust 5120, and sucks up the dust through the inlet provided on the bottom surface.

The cleaning robot 5100 can judge whether there is an obstacle such as a wall, furniture, or a step by analyzing images taken by the cameras 5102. When an object that is likely to be caught in the brush 5103, such as a wire, is detected by image analysis, the rotation of the brush 5103 can be stopped.

The display 5101 can display the remaining capacity of a battery, the amount of vacuumed dust, and the like. The display 5101 may display a path on which the cleaning robot 5100 has run. The display 5101 may be a touch panel, and the operation buttons 5104 may be provided on the display 5101.

The cleaning robot 5100 can communicate with a portable electronic apparatus 5140 such as a smartphone. The portable electronic apparatus 5140 can display images taken by the cameras 5102. Accordingly, an owner of the cleaning robot 5100 can monitor the room even from the outside. The display on the display 5101 can be checked by the portable electronic apparatus such as a smartphone.

The light-emitting apparatus of one embodiment of the present invention can be used for the display 5101.

Figure 10B:
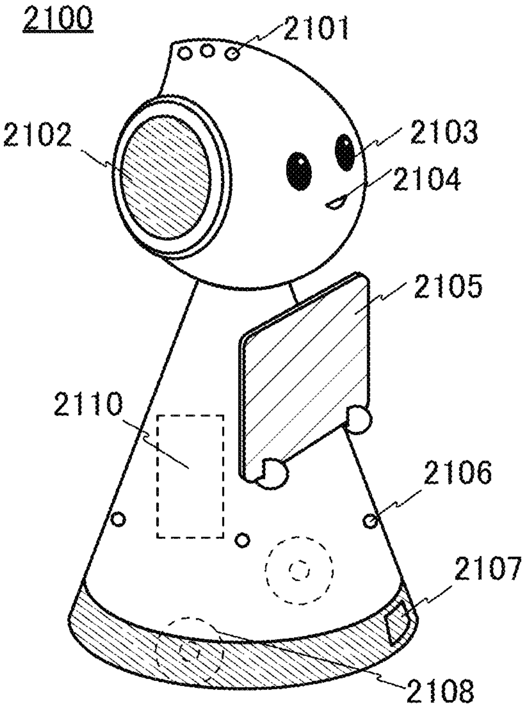

A robot 2100 illustrated in FIG. 10B includes an arithmetic device 2110, an illuminance sensor 2101, a microphone 2102, an upper camera 2103, a speaker 2104, a display 2105, a lower camera 2106, an obstacle sensor 2107, and a moving mechanism 2108.

The microphone 2102 has a function of detecting a speaking voice of a user, an environmental sound, and the like. The speaker 2104 also has a function of outputting sound. The robot 2100 can communicate with a user using the microphone 2102 and the speaker 2104.

The display 2105 has a function of displaying various kinds of information. The robot 2100 can display information desired by a user on the display 2105. The display 2105 may be provided with a touch panel. Moreover, the display 2105 may be a detachable information terminal, in which case charging and data communication can be performed when the display 2105 is set at the home position of the robot 2100.

The upper camera 2103 and the lower camera 2106 each have a function of taking an image of the surroundings of the robot 2100. The obstacle sensor 2107 can detect the presence of an obstacle in the direction where the robot 2100 advances with the moving mechanism 2108. The robot 2100 can move safely by recognizing the surroundings with the upper camera 2103, the lower camera 2106, and the obstacle sensor 2107. The light-emitting apparatus of one embodiment of the present invention can be used for the display 2105.

Figure 10C:
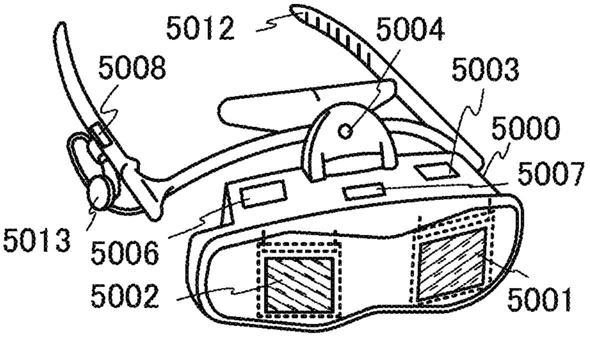

FIG. 10C shows an example of a goggle-type display. The goggle-type display includes, for example, a housing 5000, a display portion 5001, a speaker 5003, an LED lamp 5004, a connection terminal 5006, a sensor 5007 (a sensor having a function of measuring force, displacement, position, speed, acceleration, angular velocity, rotational frequency, distance, light, liquid, magnetism, temperature, a chemical substance, sound, time, hardness, an electric field, current, voltage, power, radiation, flow rate, humidity, gradient, oscillation, odor, or infrared ray), a microphone 5008, a display portion 5002, a support 5012, and an earphone 5013.

The light-emitting apparatus of one embodiment of the present invention can be used for the display portion 5001 and the display portion 5002.

Figure 11:
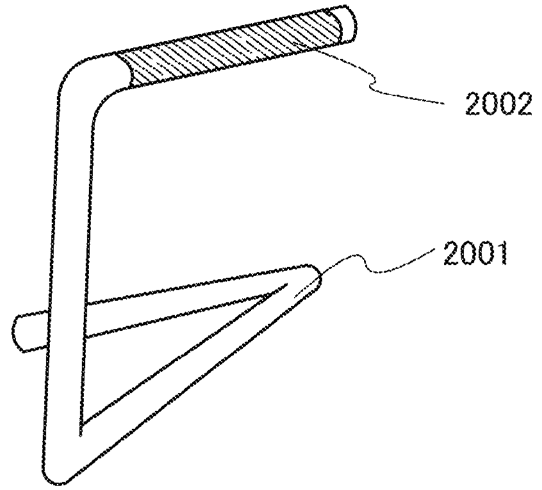
FIG. 11 illustrates a concept showing a lighting device.

FIG. 11 shows an example in which the light-emitting device described in Embodiment 2 is used for a table lamp which is a lighting device. The table lamp illustrated in FIG. 11 includes a housing 2001 and a light source 2002, and the lighting device described in Embodiment 3 may be used for the light source 2002.

Figure 12:
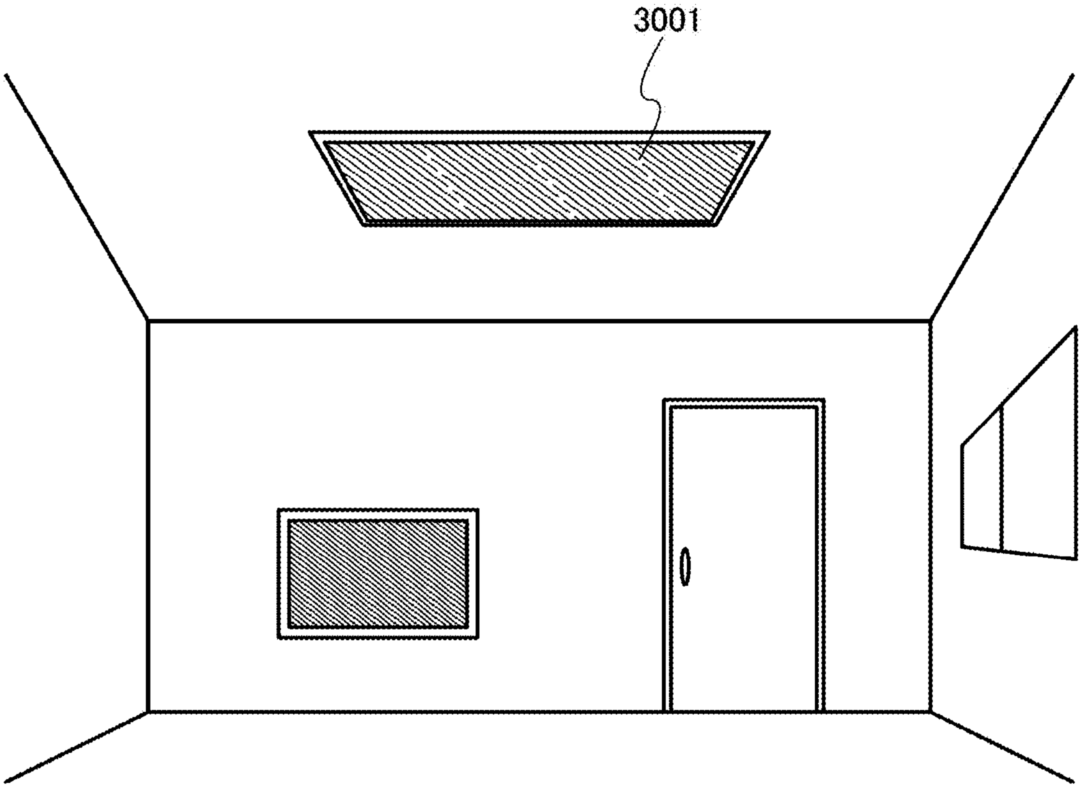
FIG. 12 illustrates a concept showing a lighting device.

FIG. 12 shows an example in which the light-emitting device described in Embodiment 2 is used for an indoor lighting device 3001. Since the light-emitting device described in Embodiment 2 is a light-emitting device with high emission efficiency, the lighting device can have low power consumption. Furthermore, the light-emitting device described in Embodiment 2 can have a larger area, and thus can be used for a large-area lighting device. Furthermore, the light-emitting device described in Embodiment 2 is thin, and thus can be used for a lighting device having a reduced thickness.

Figure 13:
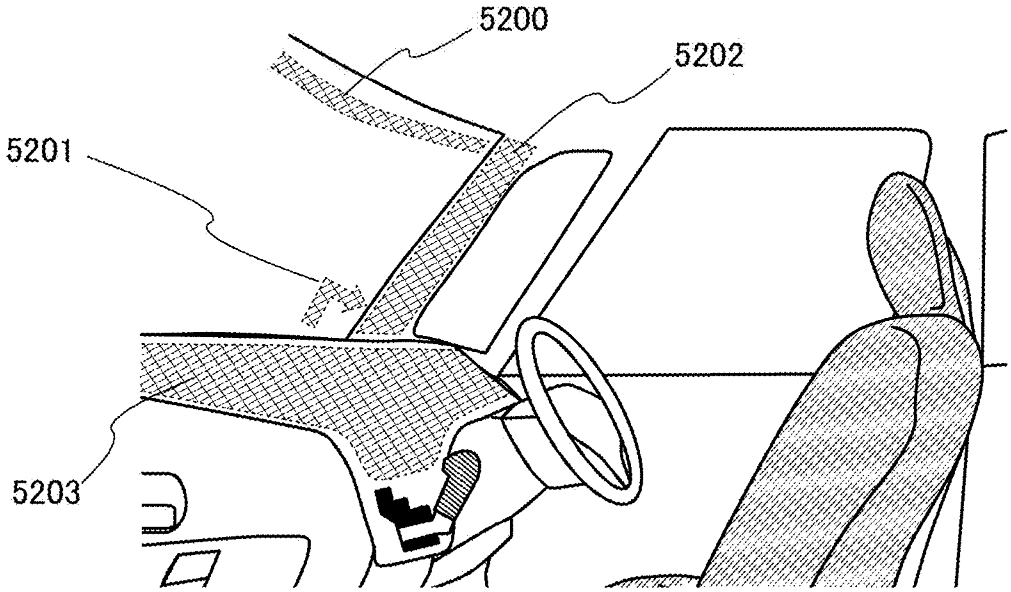
FIG. 13 illustrates a concept showing in-vehicle display apparatuses and lighting devices.

The light-emitting device described in Embodiment 2 can also be incorporated in an automobile windshield or an automobile dashboard. FIG. 13 illustrates one mode in which the light-emitting device described in Embodiment 2 is used for a windshield and a dashboard of an automobile. A display region 5200 to a display region 5203 are each display provided using the light-emitting device described in Embodiment 2.

The display region 5200 and the display region 5201 are display devices provided in the automobile windshield, in which the light-emitting devices described in Embodiment 2 are incorporated. When the light-emitting devices described in Embodiment 2 are fabricated using electrodes having light-transmitting properties as a first electrode and a second electrode, what is called see-through display devices, through which the opposite side can be seen, can be obtained. See-through display can be provided without hindering the vision even when being provided in the automobile windshield. Note that in the case where a driving transistor or the like is provided, a transistor having a light-transmitting property, such as an organic transistor using an organic semiconductor material or a transistor using an oxide semiconductor, is preferably used.

The display region 5202 is a display device provided in a pillar portion, in which the light-emitting devices described in Embodiment 2 are incorporated. The display region 5202 can compensate for the view hindered by the pillar by displaying an image taken by an imaging means provided on the car body. Similarly, the display region 5203 provided in the dashboard portion can compensate for the view hindered by the car body by displaying an image taken by an imaging means provided on the outside of the automobile. Thus, blind areas can be compensated for and the safety can be enhanced. Showing an image so as to compensate for the area that cannot be seen makes it possible to confirm safety more naturally and comfortably.

The display region 5203 can provide a variety of kinds of information such as navigation data, a speedometer, a tachometer, and the like. The content or layout of the display can be changed freely in accordance with the preference of a user. Note that such information can also be provided on the display region 5200 to the display region 5202. The display region 5200 to the display region 5203 can also be used as lighting devices.

Figure 14A:
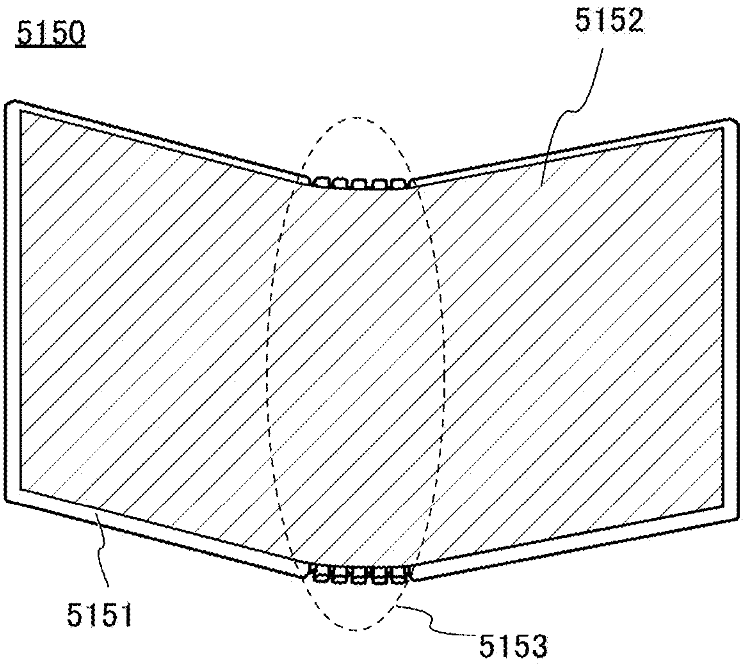
FIG. 14A and FIG. 14B illustrate a concept showing an electronic apparatus.
Figure 14B:
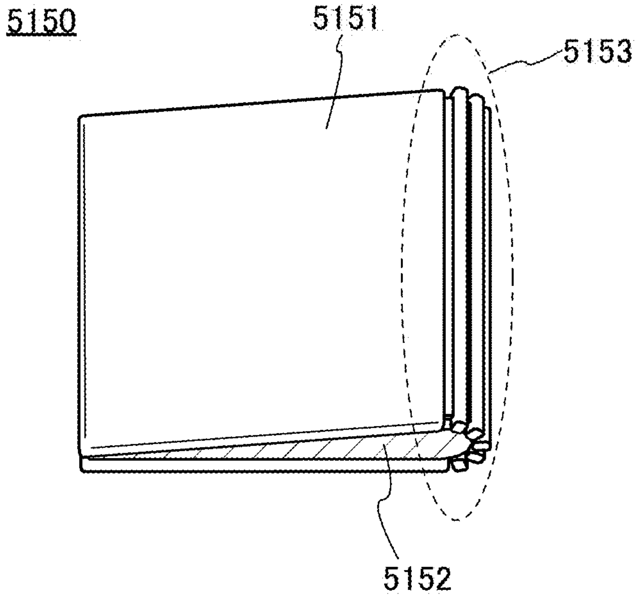

FIG. 14A and FIG. 14B illustrate a foldable portable information terminal 5150. The foldable portable information terminal 5150 includes a housing 5151, a display region 5152, and a bend portion 5153. FIG. 14A illustrates the portable information terminal 5150 that is opened. FIG. 14B illustrates the portable information terminal that is folded. The portable information terminal 5150 is compact in size and has excellent portability when folded, despite its large display region 5152.

The display region 5152 can be folded in half with the bend portion 5153. The bend portion 5153 includes a flexible member and a plurality of supporting members, and when the display region is folded, the flexible member expands and the bend portion 5153 has a radius of curvature of 2 mm or more, preferably 3 mm or more.

Note that the display region 5152 may be a touch panel (an input/output device) including a touch sensor (an input device). The light-emitting apparatus of one embodiment of the present invention can be used for the display region 5152.

Figure 15A:
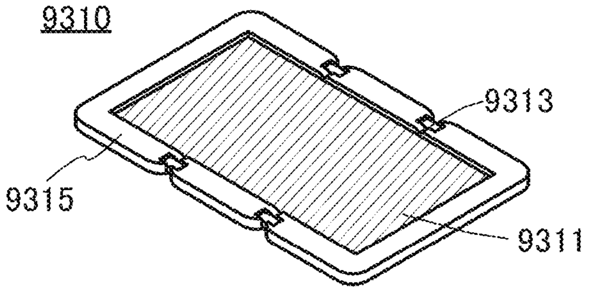
FIG. 15A, FIG. 15B, and FIG. 15C illustrates a concept showing an electronic apparatus.
Figure 15B:
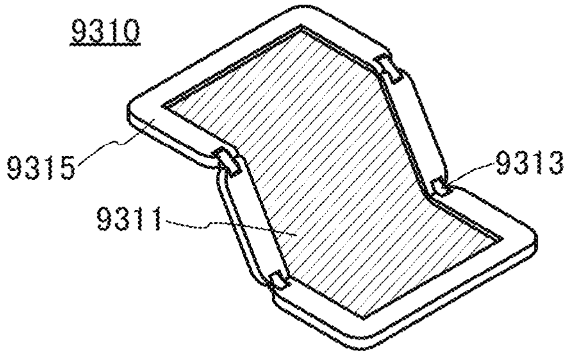
Figure 15C:
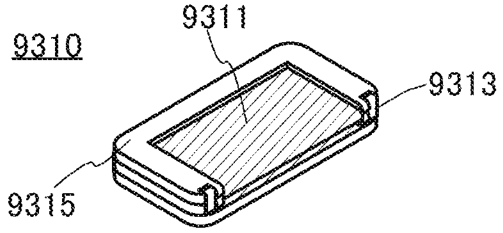

FIG. 15A to FIG. 15C illustrate a foldable portable information terminal 9310. FIG. 15A illustrates the portable information terminal 9310 that is opened. FIG. 15B illustrates the portable information terminal 9310 that is in the state of being changed from one of an opened state and a folded state to the other. FIG. 15C illustrates the portable information terminal 9310 that is folded. The portable information terminal 9310 is excellent in portability when folded, and is excellent in display browsability when opened because of a seamless large display region.

A display panel 9311 is supported by three housings 9315 joined together by hinges 9313. Note that the display panel 9311 may be a touch panel (an input/output device) including a touch sensor (an input device). By folding the display panel 9311 at the hinges 9313 between two housings 9315, the portable information terminal 9310 can be reversibly changed in shape from the opened state to the folded state. A light-emitting apparatus of one embodiment of the present invention can be used for the display panel 9311.

The organic compound of one embodiment of the present invention can be used for an electronic element such as an organic thin film solar cell (OPV) or an organic photo diode (OPD). Specifically, the organic compound can be used in a carrier-transport layer or a carrier-injection layer because the organic compound has a carrier-transport property. In addition, a mixed film of the organic compound and an acceptor substance can be used as a charge-generation layer. The organic compound is photoexcited and thus can be used as a power generation layer or an active layer.

Note that the structures described in this embodiment can be combined with the structures described in any of Embodiment 1 to Embodiment 4 as appropriate.

As described above, the application range of the light-emitting apparatus including the light-emitting device described in Embodiment 2 is wide so that this light-emitting apparatus can be applied to electronic apparatuses in a variety of fields. With the use of the light-emitting device described in Embodiment 2, an electronic apparatus with low power consumption can be obtained.

Example 1

Synthesis Example 1

In this example, a method for synthesizing 4-[3,6-bis(N,N-diphenylamino)carbazol-9-yl]benzofuro[3,2-d]pyrimidine (abbreviation: 4DPhA2CzBfpm), which is represented by Structural Formula (100) in Embodiment 1, is described in detail. The structural formula of 4DPhA2CzBfpm is shown below.

[Chemical Formula 29]

(100)

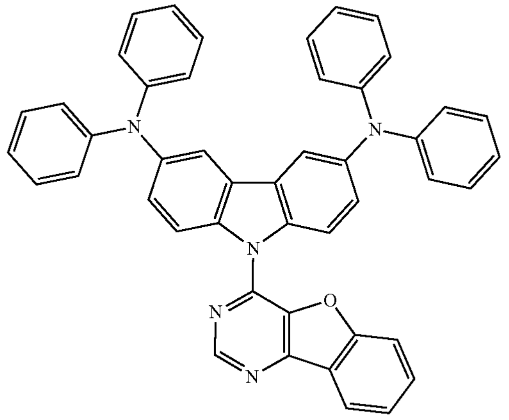

4DPhA2CzBfpm

Synthesis of 4-[3,6-bis(N,N-diphenylamino)carbazol-9-yl]benzofuro[3,2-d]pyrimidine (Abbreviation: 4DPhA2CzBfpm)

After the air in a 50 mL three-neck flask was replaced with nitrogen, 79 mg (2.0 mmol) of sodium hydride (NaH) and 15 mL of dehydrated N,N-dimethylformamide (abbreviation: DMF) were added, and the mixture was stirred at 0° C. To this, 0.72 g (1.4 mmol) of 3,6-bis(N,N-diphenylamino)carbazole was added and the mixture was stirred at 0° C. for 30 minutes. After that, 0.27 g (1.3 mmol) of 4-chlorobenzofuro[3,2-d]pyrimidine was added, and the mixture was stirred at room temperature for 18 hours. After a predetermined time elapsed, water was added to this mixture, and a precipitated solid was collected by suction filtration. The obtained solid was purified by silica gel column chromatography (toluene:ethyl acetate=4:1 as a developing solvent) and further recrystallized with a mixed solvent of ethyl acetate and methanol to give 0.62 g (0.93 mmol) of a target yellow solid in a yield of 71%. The synthesis scheme of this synthesis example is shown below.

[Chemical Formula 30]

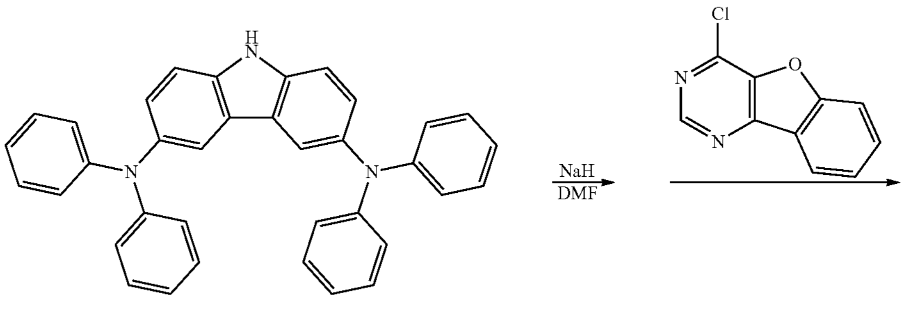

-continued

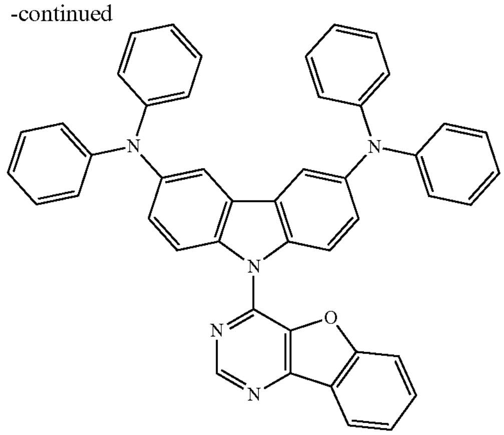

By a train sublimation method, 0.61 g of the obtained yellow solid was purified by sublimation. The sublimation purification was performed under the conditions where the pressure was 3.4 Pa and the argon flow rate was 5 mL/min at 290° C. After the sublimation purification, 0.55 g of a yellow powder of 4DPhA2CzBfpm was obtained at a collection rate of 84%.

Figure 16A:
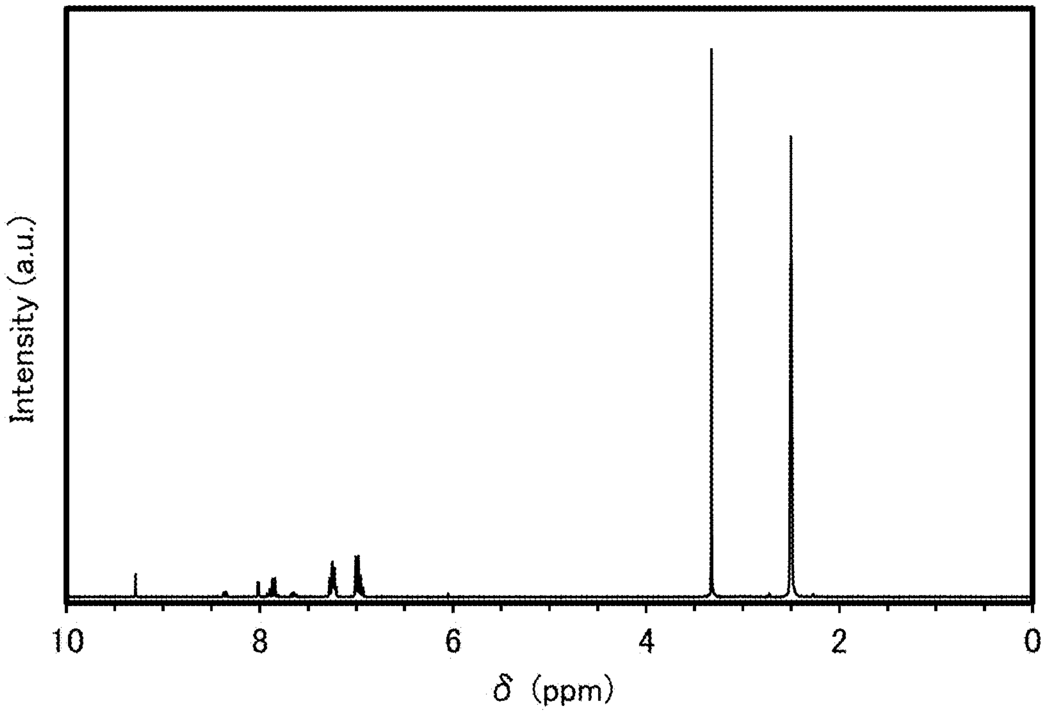
FIG. 16A and FIG. 16B are $^1$H NMR charts of 4DPhA2CzBfpm.
Figure 16B:
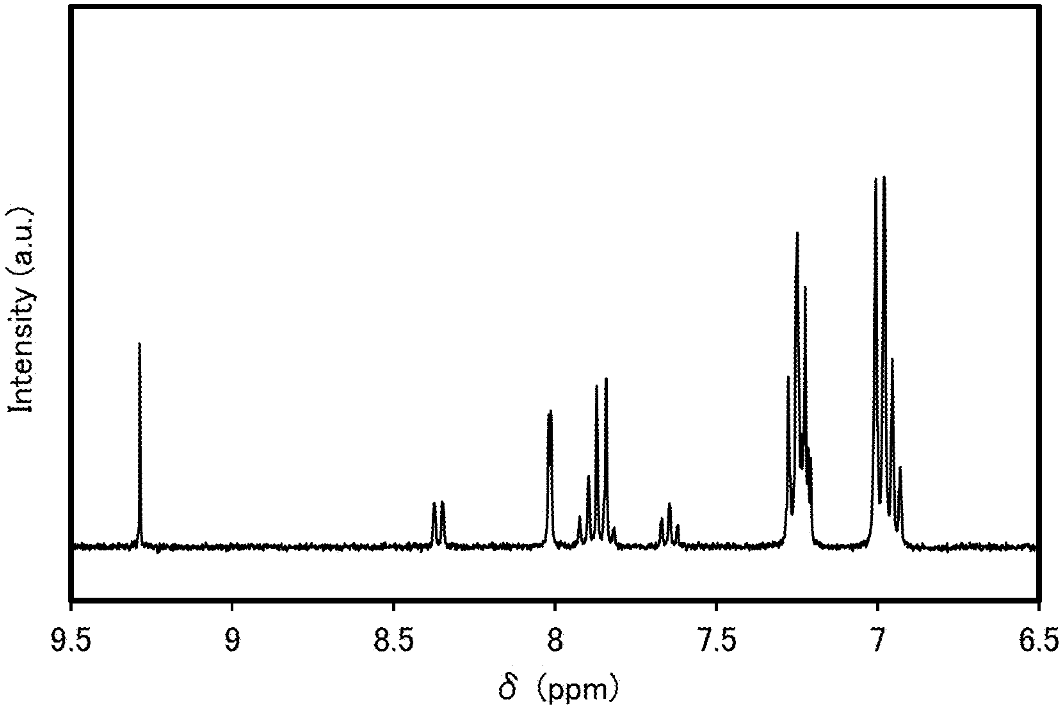

FIG. 16A and FIG. 16B show measurement results by nuclear magnetic resonance spectroscopy ($^1$H NMR) of the obtained compound. Note that FIG. 16B is a graph where the range from 6.5 ppm to 9.5 ppm in FIG. 16A is enlarged. In addition, numerical data is shown below. $^1$H NMR (DMSO-d6, 300 MHz): δ=6.92-7.03 (m, 12H), 7.20-7.29 (m, 10H), 7.61-7.68 (m, 1H), 7.81-7.93 (m, 4H), 8.02 (d, J=2.2 Hz, 2H), 8.36 (d, J=7.3 Hz, 1H), 9.29 (s, 1H).

Figure 17:
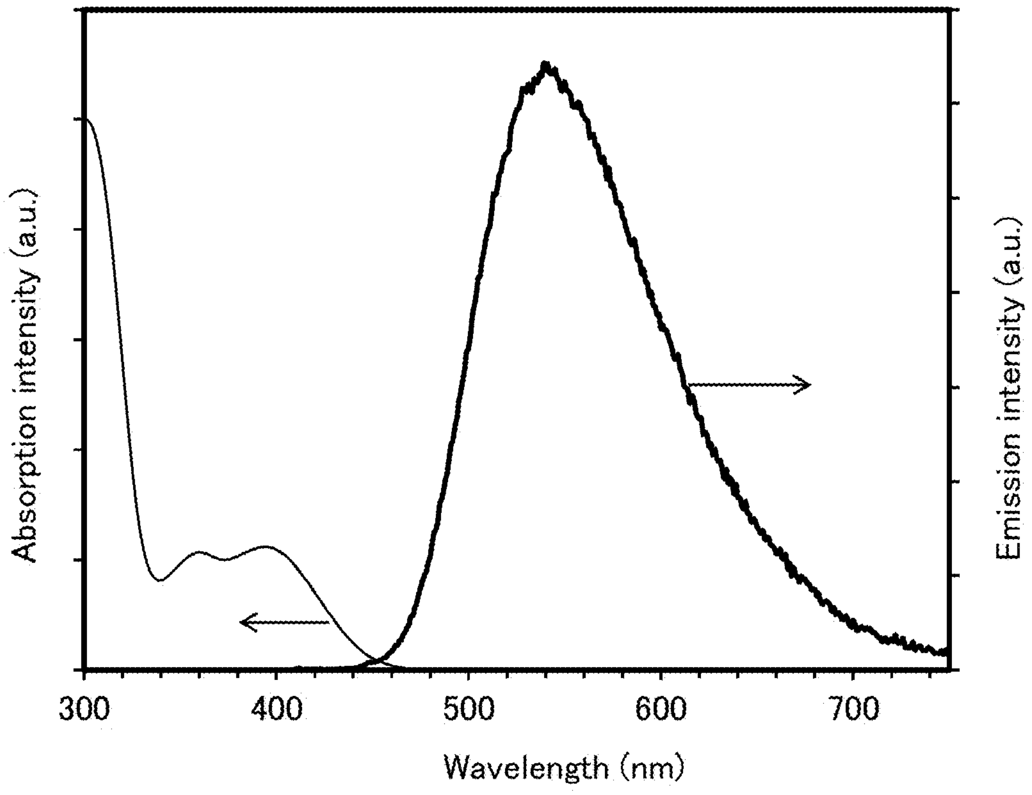
FIG. 17 shows an absorption spectrum and an emission spectrum of 4DPhA2CzBfpm in a solution state.

Next, FIG. 17 shows the measurement results of an absorption spectrum and an emission spectrum of 4DPhA2CzBfpm in a toluene solution. The absorption spectrum of the toluene solution was measured with an ultraviolet-visible light spectrophotometer (V550, manufactured by JASCO Corporation), and the spectrum from which the measured spectrum of toluene alone put in a quartz cell was subtracted was shown. The emission spectrum was measured with a fluorescence spectrophotometer (FP-920, manufactured by JASCO Corporation).

Figure 18:
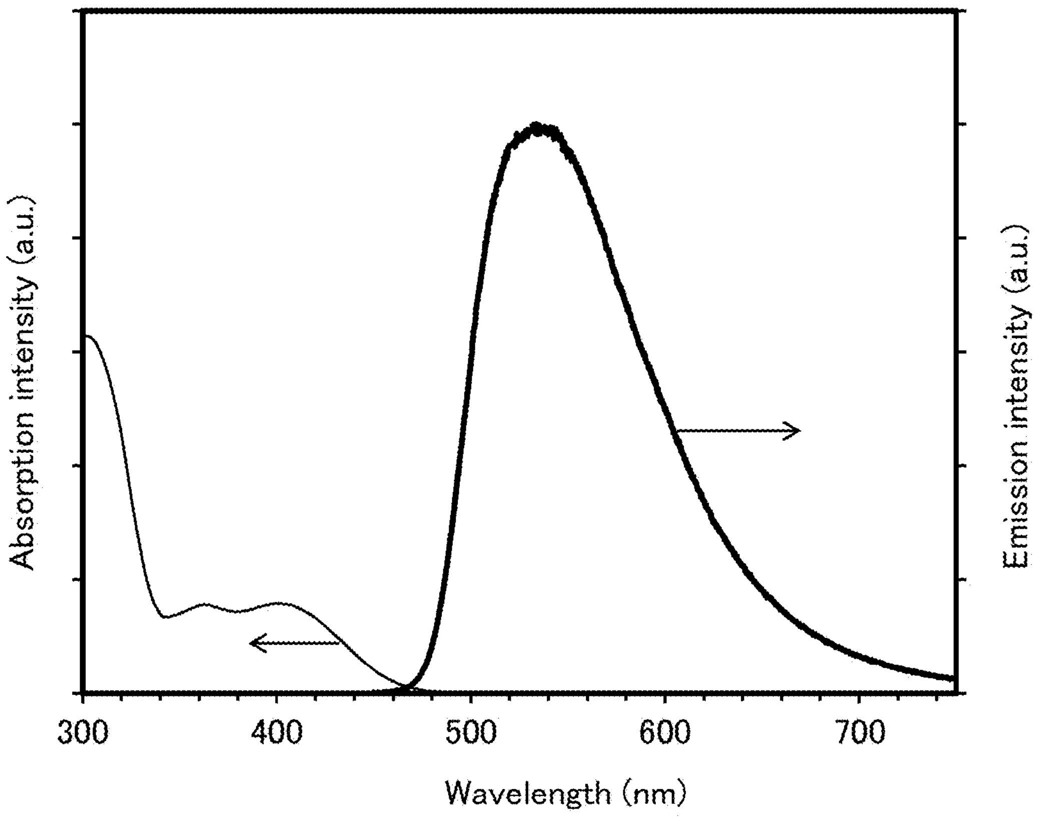
FIG. 18 shows an absorption spectrum and an emission spectrum of 4DPhA2CzBfpm in a thin film state.
Figure 19:
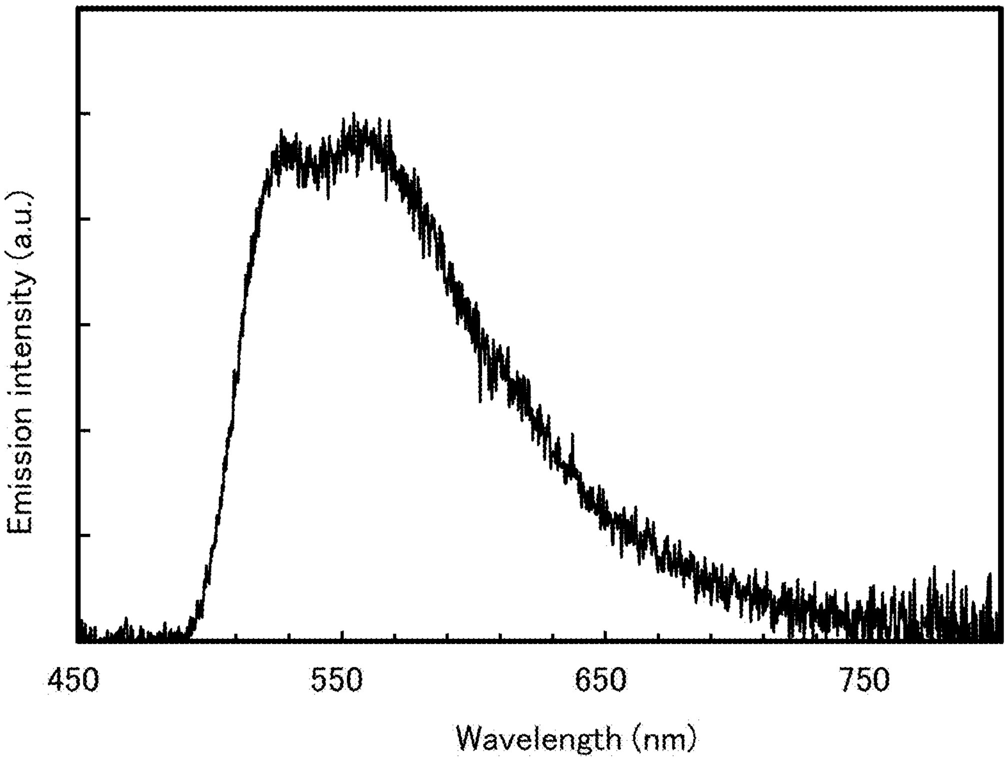
FIG. 19 shows a phosphorescence spectrum of 4DPhA2CzBfpm.

FIG. 18 shows an absorption spectrum and a fluorescence spectrum of 4DPhA2CzBfpm in a thin film state, and FIG. 19 shows a phosphorescence spectrum thereof. The absorption spectrum was measured with a spectrophotometer (U4100 Spectrophotometer, manufactured by Hitachi High-Technologies Corporation). The solid thin film for measurement of the absorption spectrum was formed over a quartz substrate by a vacuum evaporation method. Measurements of the fluorescence spectrum and the phosphorescence spectrum were performed with a PL microscope LabRAM HR-PL (produced by HORIBA, Ltd.). The measurement temperature was 10 K, a He—Cd laser (325 nm) was used as excitation light, and a CCD detector was used as a detector. A thin film as a sample was used for the measurements after the thin film was formed over a quartz substrate to a thickness of approximately 50 nm and another quartz substrate was attached to the quartz substrate from the evaporation surface in a nitrogen atmosphere. Since this measurement of the emission spectra was performed at a low temperature (10 K), phosphorescence was partly observed in the normal measurement of emission spectrum, in addition to fluorescence, which is the main emission component. In the measurement of the time-resolved emission spectra (20 ms to 120 ms integration after illumination of the excited light) in which light emission with a long lifetime is focused on, the obtained spectra were mainly regarded as phosphorescence.

FIG. 17 shows that the toluene solution of 4DPhA2CzBfpm has an absorption peak at 394 nm and an emission wavelength peak at 539 nm (excitation wavelength: 394 nm). As shown in FIG. 18, the thin film of 4DPhA2CzBfpm exhibits absorption peaks at 401 nm, 363 nm, and 301 nm and a fluorescence spectrum peaks at around 530 nm (excitation wavelength: 325 nm). As shown in FIG. 19, the peak on the shortest wavelength side of the phosphorescence spectrum of 4DPhA2CzBfpm is present at 527 nm, which indicates that it is a substance with a high T1 level. Note that although the wavelength of the read peak value of phosphorescence is shorter than the wavelength of the read peak value of fluorescence, the phosphorescence spectrum has a shape more slightly shifted to the longer wavelength as a whole than the fluorescence spectrum. These results show that 4DPhA2CzBfpm emits green light and can be used as a light-emitting material or a host material for a fluorescent light-emitting material or a phosphorescent light-emitting material.

An index of the T1 level can be calculated using a phosphorescence spectrum. The level of energy with a wavelength of the line obtained by extrapolating a tangent to the phosphorescence spectrum at a tail on the short wavelength side can be regarded as the T1 level. An index of the S1 level can be calculated using a fluorescence spectrum. The level of energy with a wavelength of the line obtained by extrapolating a tangent to the fluorescence spectrum at a tail on the short wavelength side can be regarded as the S1 level.

The T1 level of 4DPhA2CzBfpm is calculated to be 2.49 eV as in FIG. 19, and the S1 level is calculated to be 2.58 eV as in FIG. 18. The results show that $\Delta E_{ST}$, which is the difference between the S1 level and T1 level of 4DPhA2CzBfpm, is 0.08 eV. In general, the $\Delta E_{ST}$ of a material having a TADF property is preferably 0.2 eV or less, and thus the $\Delta E_{ST}$ of 4DPhA2CzBfpm is found to be a value small enough to have a TADF property.

Example 2

Synthesis Example 2

In this synthesis example, a method for synthesizing 8-phenyl-4-[3,6-bis(N,N-diphenylamino)carbazol-9-yl]benzofuro[3,2-d]pyrimidine (abbreviation: 8Ph-4DPhA2CzBfpm), which is represented by Structural Formula (101) in Embodiment 1, is described in detail. The structural formula of 8Ph-4DPhA2CzBfpm is shown below.

[Chemical Formula 31]

(101)

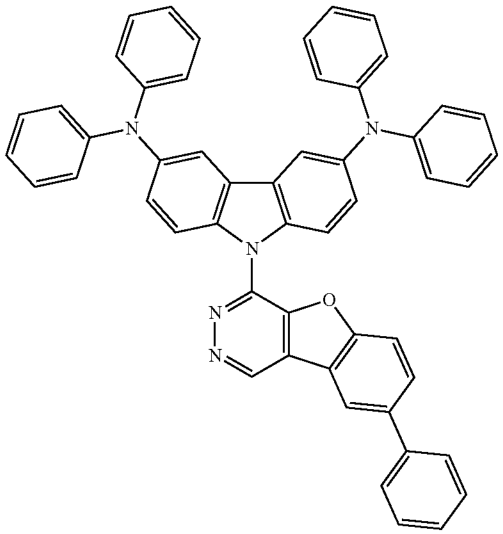

8Ph-4DPhA2CzBfpm

[Chemical Formula 32]

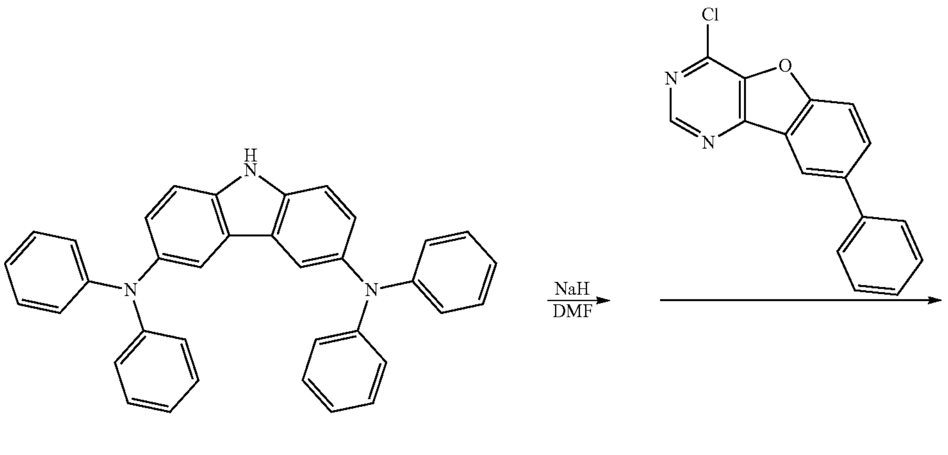

Synthesis of 8-phenyl-4-[3,6-bis(N,N-diphenylamino)carbazol-9-yl]benzofuro[3,2-d]pyrimidine (Abbreviation: 8Ph-4DPhA2CzBfpm)

After the air in a 100 mL three-neck flask was replaced with nitrogen, 130 mg (3.4 mmol) of sodium hydride (NaH) and 30 mL of dehydrated N,N-dimethylformamide (abbreviation: DMF) were added, and the mixture was stirred at 0° C. To this, 1.2 g (2.5 mmol) of 3,6-bis(N,N-diphenylamino) carbazole was added and the mixture was stirred at 0° C. for 30 minutes. After that, 0.63 g (2.2 mmol) of 4-chloro-8-phenylbenzofuro[3,2-d]pyrimidine was added, and the mixture was stirred at room temperature for 110 hours. After a predetermined time elapsed, water was added to this reaction mixture, and a precipitated solid was collected by suction filtration. The obtained solid was purified by silica gel column chromatography (toluene:ethyl acetate=4:1 as a developing solvent) and further recrystallized with a mixed solvent of toluene and methanol to give 1.5 g of a target yellow solid in a yield of 91%. The synthesis scheme of this synthesis example is shown below.

-continued

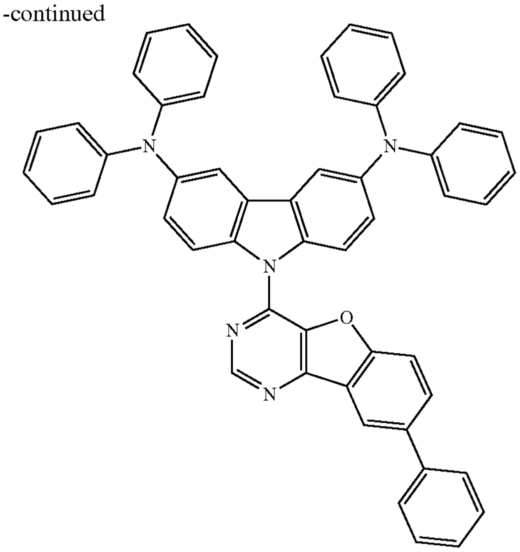

By a train sublimation method, 1.5 g of the obtained yellow solid was purified by sublimation. The sublimation purification was performed under the conditions where the pressure was 3.1 Pa and the argon flow rate was 5 mL/min at 335° C. After the sublimation purification, 1.4 g of a yellow powder of 8Ph-4DPhA2CzBfpm was obtained at a collection rate of 93%.

Figure 20A:
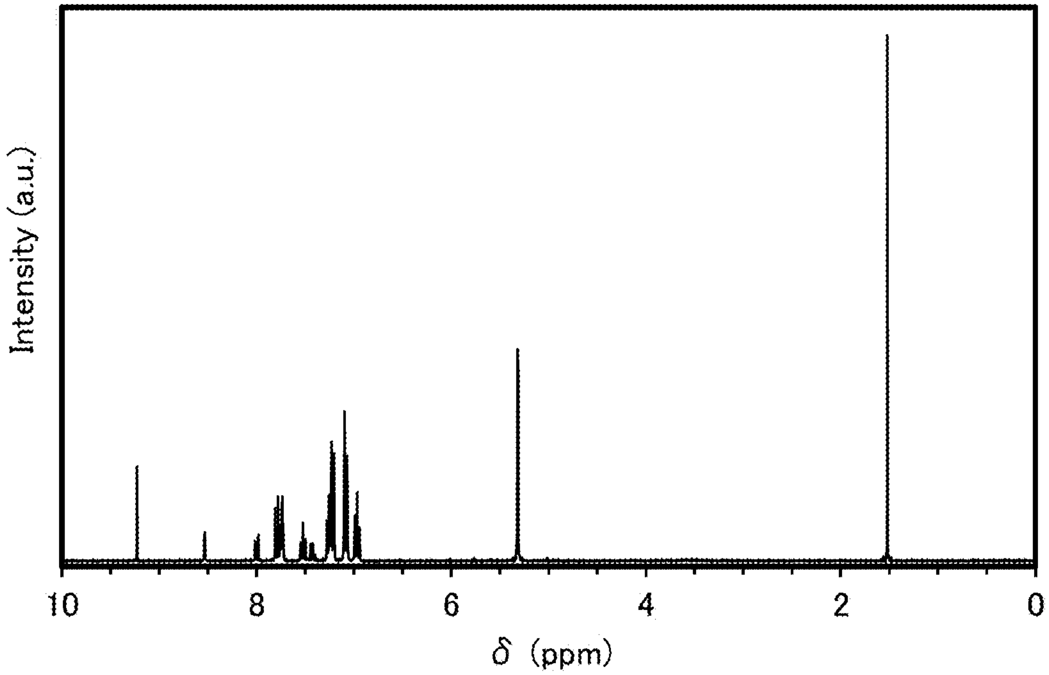
FIG. 20A and FIG. 20B are $^1$H NMR charts of 8Ph-4DPhA2CzBfpm.
Figure 20B:
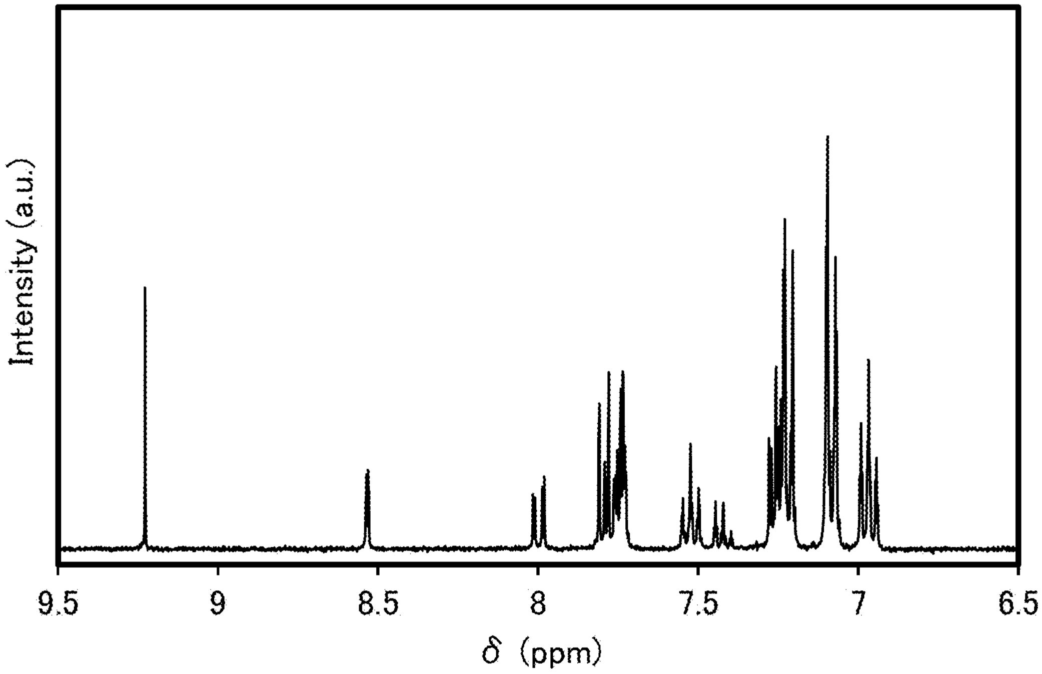

FIG. 20A and FIG. 20B show measurement results by nuclear magnetic resonance spectroscopy ($^1$H NMR) of the obtained compound. Note that FIG. 20B is a graph where the range from 6.5 ppm to 9.5 ppm in FIG. 20A is enlarged. In addition, numerical data is shown below. $^1$H NMR ($CD_2Cl_2$, 300 MHz): δ=6.93-7.01 (m, 4H), 7.05-7.12 (m, 8H), 7.19-7.29 (m, 10H), 7.39-7.46 (m, 1H), 7.49-7.56 (m, 2H), 7.72-7.82 (m, 7H), 8.00 (dd, J=1.8 Hz, 8.8 Hz, 1H), 8.53 (d, J=2.2 Hz, 1H), 9.23 (s, 1H).

Figure 21:
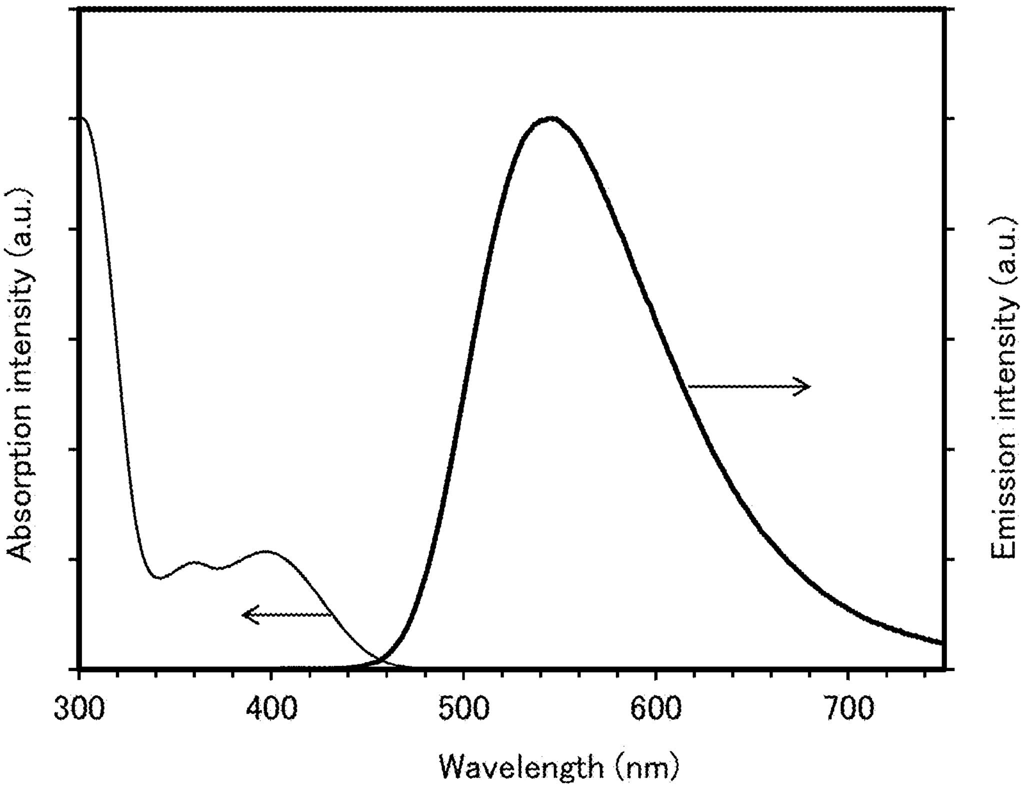
FIG. 21 shows an absorption spectrum and an emission spectrum of 8Ph-4DPhA2CzBfpm in a solution state.

Next, FIG. 21 shows the measurement results of an absorption spectrum and an emission spectrum of 8Ph-4DPhA2CzBfpm in a toluene solution. The absorption spectrum of the toluene solution was measured with an ultraviolet-visible light spectrophotometer (V550, manufactured by JASCO Corporation), and the spectrum from which the measured spectrum of toluene alone put in a quartz cell was subtracted was shown. The emission spectrum was measured with a fluorescence spectrophotometer (FP-8600, manufactured by JASCO Corporation).

Figure 22:
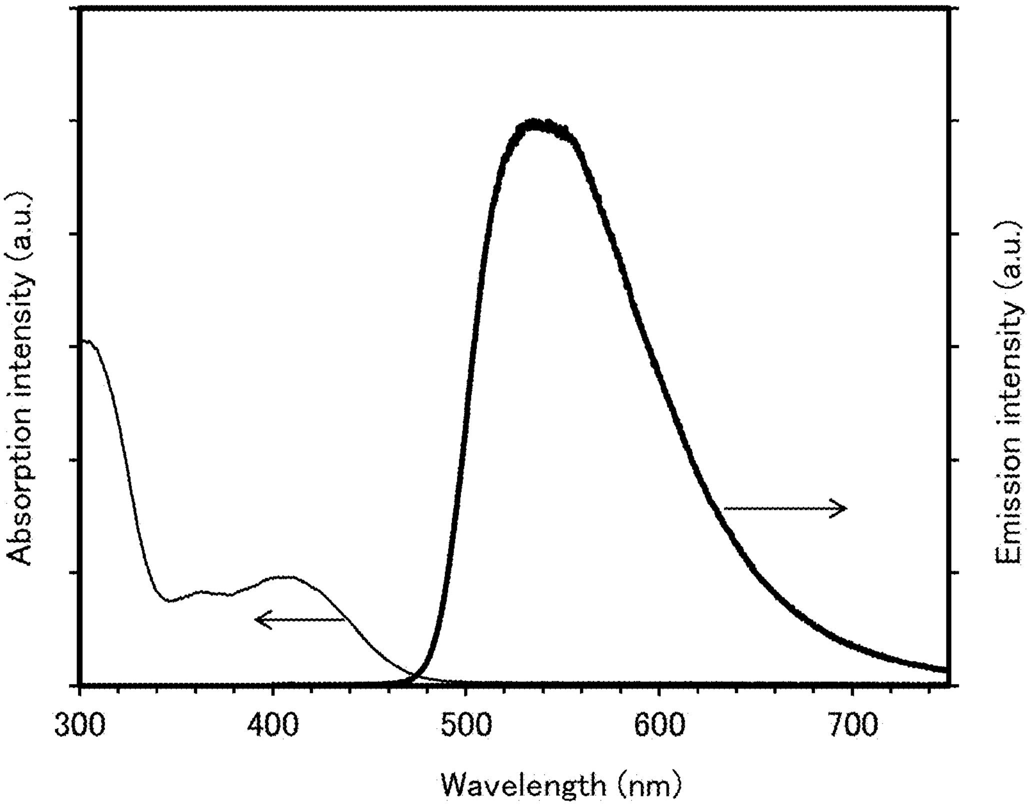
FIG. 22 shows an absorption spectrum and an emission spectrum of 8Ph-4DPhA2CzBfpm in a thin film state.
Figure 23:
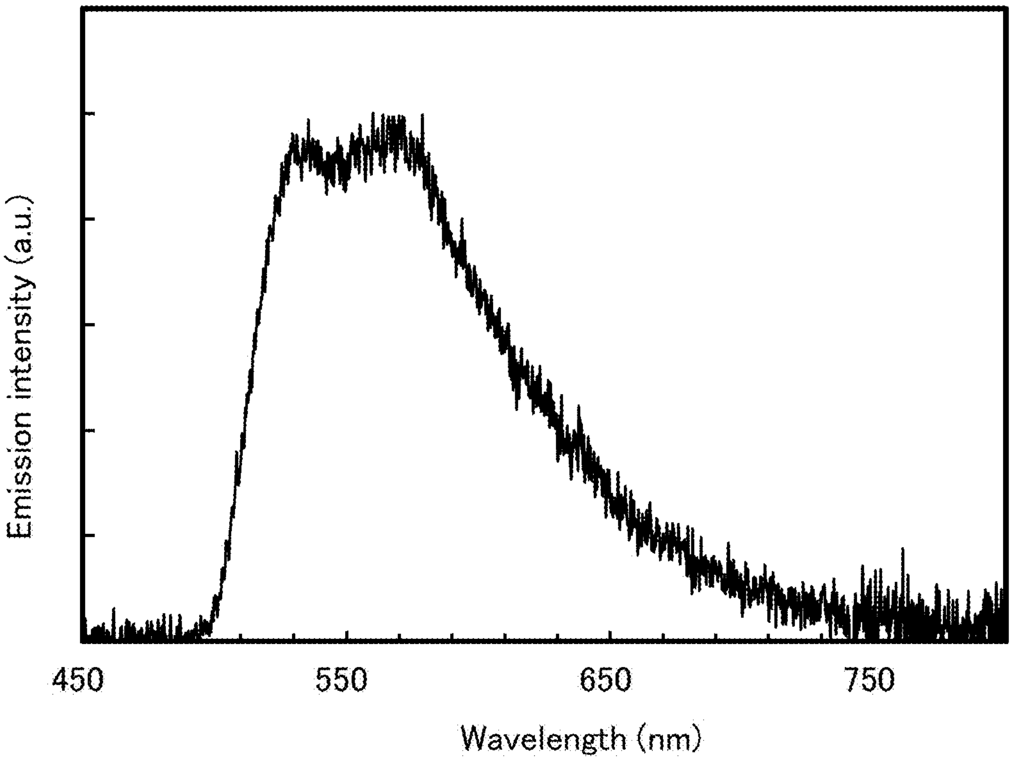
FIG. 23 shows a phosphorescence spectrum of 8Ph-4DPhA2CzBfpm.

FIG. 22 shows an absorption spectrum and a fluorescence spectrum of 8Ph-4DPhA2CzBfpm in a thin film state, and FIG. 23 shows a phosphorescence spectrum thereof. The absorption spectrum was measured with a spectrophotometer (U4100 Spectrophotometer, manufactured by Hitachi High-Technologies Corporation). The solid thin film for measurement of the absorption spectrum was formed over a quartz substrate by a vacuum evaporation method. Measurements of the fluorescence spectrum and phosphorescence spectrum of the thin film were performed with a PL microscope LabRAM HR-PL (produced by HORIBA, Ltd.). The measurement temperature was 10 K, a He—Cd laser (325 nm) was used as excitation light, and a CCD detector was used as a detector. A thin film as a sample was used for the measurements after the thin film was formed over a quartz substrate to a thickness of approximately 50 nm and another quartz substrate was attached to the quartz substrate from the evaporation surface in a nitrogen atmosphere. Since this measurement of the emission spectra was performed at a low temperature (10 K), phosphorescence was partly observed in the normal measurement of emission spectrum, in addition to fluorescence, which is the main emission component. In the measurement of the time-resolved emission spectra (20 ms to 120 ms integration after illumination of the excited light) in which light emission with a long lifetime is focused on, the obtained spectra were mainly regarded as phosphorescence.

FIG. 21 shows that the toluene solution of 8Ph-4DPhA2CzBfpm has absorption peaks at 397 nm and 360 nm and an emission wavelength peak at 545 nm (excitation wavelength: 397 nm). As shown in FIG. 22, the thin film of 8Ph-4DPhA2CzBfpm exhibits absorption peaks at 410 nm, 363 nm, and 301 nm and a fluorescence spectrum peaks at around 530 nm (excitation wavelength: around 325 nm). As shown in FIG. 23, the peak on the shortest wavelength side of the phosphorescence spectrum of 8Ph-4DPhA2CzBfpm is present at 531 nm, which indicates that it is a substance with a high T1 level. Note that although the read peak value of phosphorescence is more at the shorter wavelength side than that of fluorescence, the phosphorescence spectrum has a shape more slightly shifted to the longer wavelength as a whole than the fluorescence spectrum. These results show that 8Ph-4DPhA2CzBfpm emits green light and can be used as a light-emitting material or a host material for a fluorescent light-emitting material or a phosphorescent light-emitting material.

An index of the T1 level can be calculated using a phosphorescence spectrum. The level of energy with a wavelength of the line obtained by extrapolating a tangent to the phosphorescence spectrum at a tail on the short wavelength side can be regarded as the T1 level. An index of the S1 level can be calculated using a fluorescence spectrum. The level of energy with a wavelength of the line obtained by extrapolating a tangent to the fluorescence spectrum at a tail on the short wavelength side can be regarded as the S1 level.

The T1 level of 8Ph-4DPhA2CzBfpm is calculated to be 2.48 eV as in FIG. 23, and the S1 level is calculated to be 2.56 eV as in FIG. 22. The results show that $\Delta E_{ST}$, which is the difference between the T1 level and S1 level of 8Ph- 4DPhA2CzBfpm, is 0.08 eV. In general, the $\Delta E_{ST}$ of a material having a TADF property is preferably 0.2 eV or less, and thus the $\Delta E_{ST}$ of 8Ph-4DPhA2CzBfpm is found to be a value small enough to have a TADF property.

Example 3

Synthesis Example 3

In this synthesis example, a method for synthesizing 4-[3-(N,Ndiphenylamino)carbazol-9-yl]benzofuro[3,2-di]pyrimidine (abbreviation: 4DPhACzBfpm), which is represented by Structural Formula (102) in Embodiment 1, is described in detail. The structural formula of 4DPhACzBfpm is shown below.

[Chemical Formula 33]

(102)

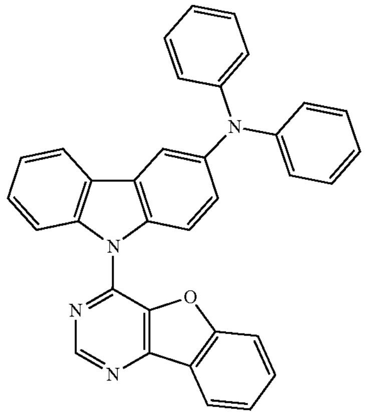

4DPhACzBfpm

Synthesis of 4-[3-(N,Ndiphenylamino)carbazol-9-yl]benzofuro[3,2-di]pyrimidine (Abbreviation: 4DPhACzBfpm)

After the air in a 50 mL three-neck flask was replaced with nitrogen, 82 mg (2.0 mmol) of sodium hydride (NaH) and 15 mL of dehydrated N,N-dimethylformamide (abbreviation: DMF) were added, and the mixture was stirred at 0° C. To this, 0.50 g (1.5 mmol) of 3-(N,N-diphenylamino)carbazole was added and the mixture was stirred at 0° C. for 30 minutes. After that, 0.28 g (1.4 mmol) of 4-chlorobenzofuro[3,2-d]pyrimidine was added, and the mixture was stirred at room temperature for 18 hours. After a predetermined time elapsed, water was added to this mixture, and a precipitated solid was collected by suction filtration. The obtained solid was purified by silica gel column chromatography (toluene: ethyl acetate=4:1 as a developing solvent) to give 0.76 g of a target yellow solid. A methanol suspension of the obtained solid was irradiated with ultrasonic waves, and a solid was collected by suction filtration, whereby 0.50 g (0.99 mmol) of a target yellow solid was obtained in a yield of 73%. The synthesis scheme of this synthesis example is shown below.

[Chemical Formula 34]

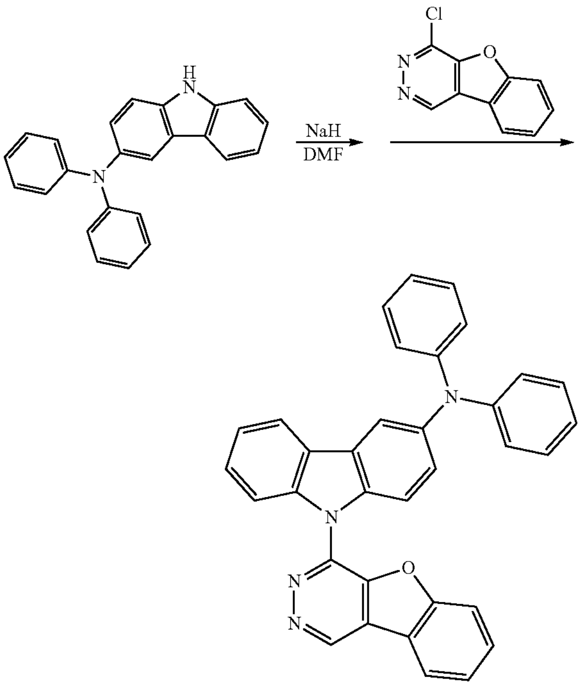

By a train sublimation method, 0.49 g of the obtained yellow solid was purified by sublimation. The sublimation purification was performed under the conditions where the pressure was 3.4 Pa and the argon flow rate was 5 mL/min at 235° C. After the sublimation purification, 0.36 g of a yellow powder of 4DPhACzBfpm was obtained at a collection rate of 74%.

Figure 24A:
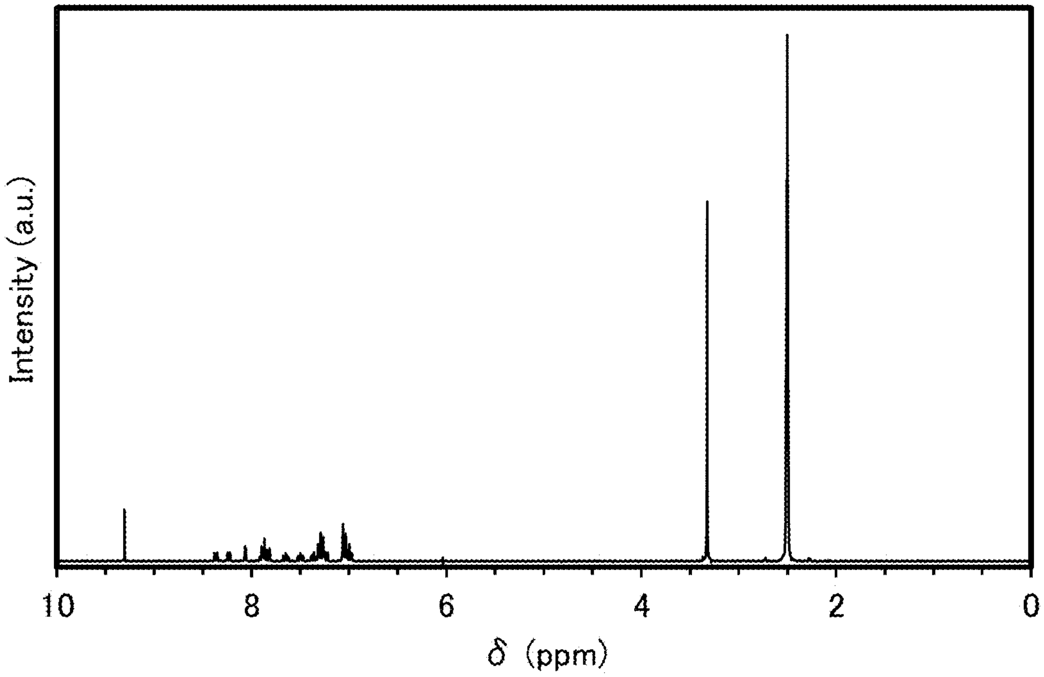
FIG. 24A and FIG. 24B are $^1$H NMR charts of 4DPhACzBfpm.
Figure 24B:
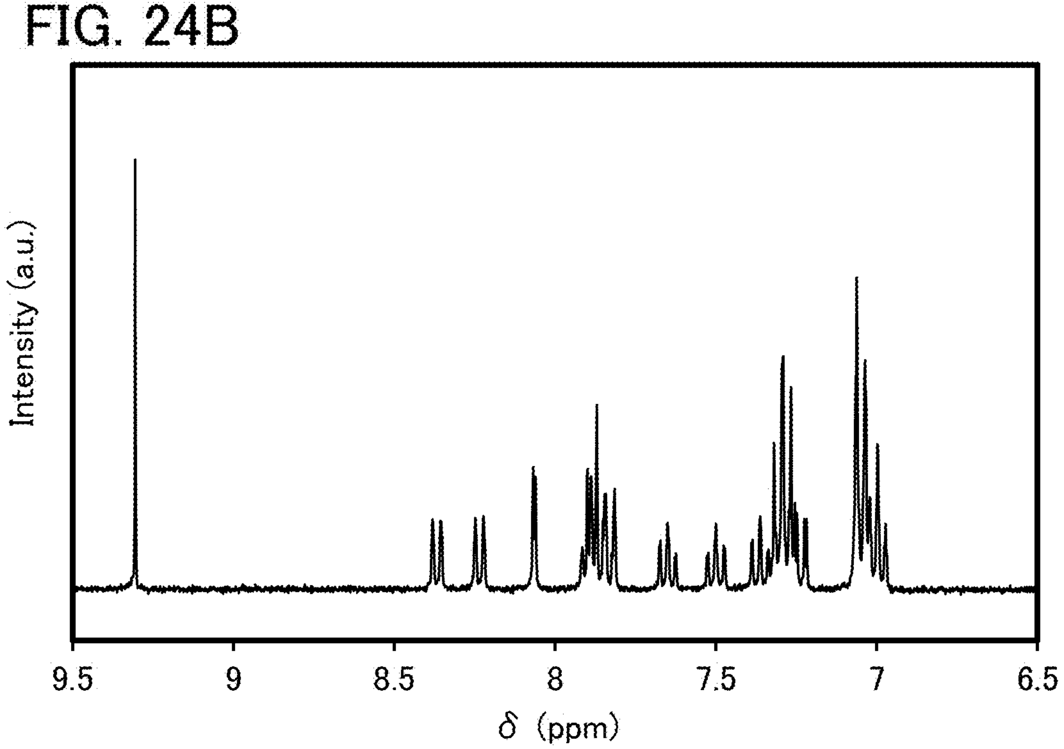

FIG. 24A and FIG. 24B show measurement results by nuclear magnetic resonance spectroscopy ($^1$H-NMR) of the obtained compound. Note that FIG. 24B is a graph where the range from 6.5 ppm to 9.5 ppm in FIG. 24A is enlarged. In addition, numerical data is shown below. $^1$H NMR (DMSO-d6, 300 MHz): δ=6.97-7.08 (m, 6H), 7.21-7.40 (m, 6H), 7.46-7.54 (m, 1H), 7.61-7.68 (m, 1H), 7.80-7.93 (m, 4H), 8.07 (d, J=1.8 Hz, 1H), 8.24 (d, J=7.3 Hz, 1H), 8.37 (d, J=7.3 Hz, 1H), 9.31 (s, 1H).

Figure 25:
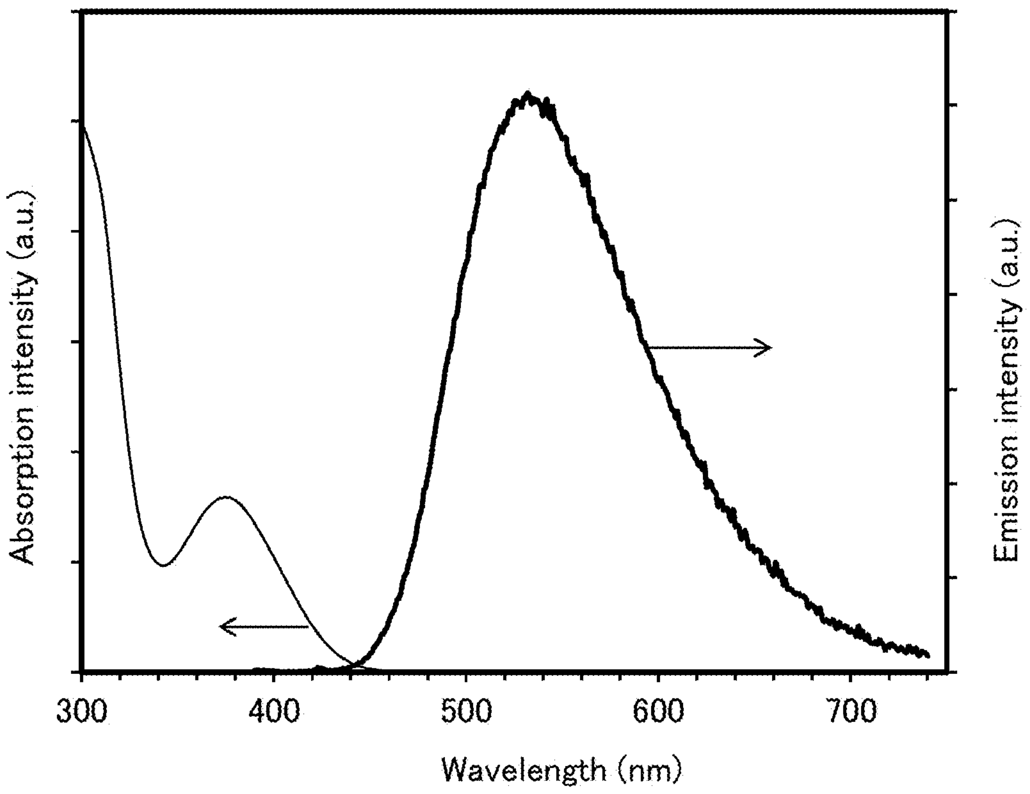
FIG. 25 shows an absorption spectrum and an emission spectrum of 4DPhACzBfpm in a solution state.

Next, FIG. 25 shows the measurement results of an absorption spectrum and an emission spectrum of 4DPhACzBfpm in a toluene solution. The absorption spectrum of the toluene solution was measured with an ultra-violet-visible light spectrophotometer (V550, manufactured by JASCO Corporation), and the spectrum from which the measured spectrum of toluene alone put in a quartz cell was subtracted was shown. The emission spectrum was measured with a fluorescence spectrophotometer (FP-920, manufactured by JASCO Corporation).

Figure 26:
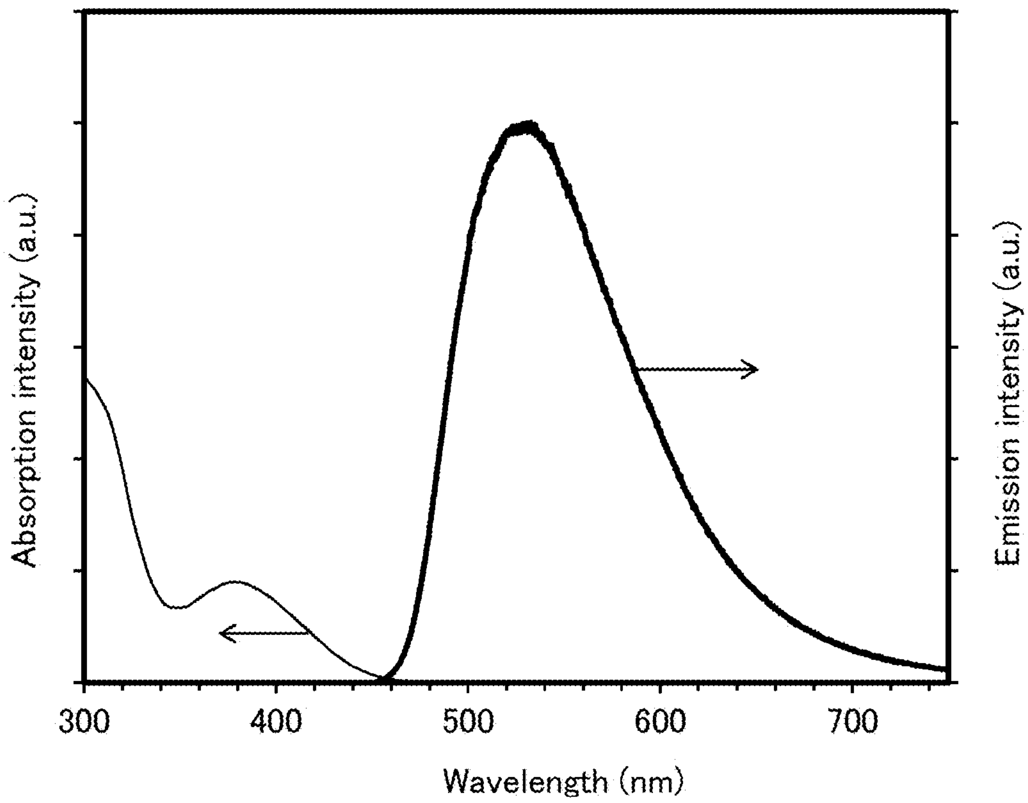
FIG. 26 shows an absorption spectrum and an emission spectrum of 4DPhACzBfpm in a thin film state.
Figure 27:
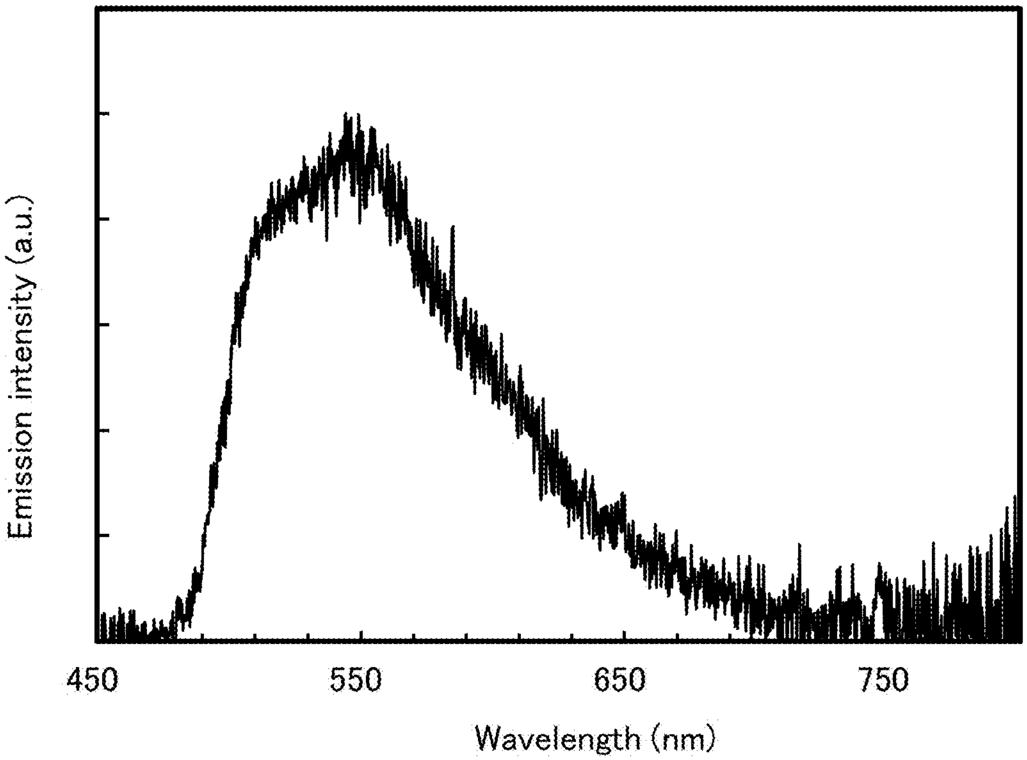
FIG. 27 shows a phosphorescence spectrum of 4DPhACzBfpm.

FIG. 26 shows an absorption spectrum and a fluorescence spectrum of 4DPhACzBfpm in a thin film state, and FIG. 27 shows a phosphorescence spectrum thereof. The absorption spectrum was measured with a spectrophotometer (U4100 Spectrophotometer, manufactured by Hitachi High-Technologies Corporation). The solid thin film for measurement of the absorption spectrum was formed over a quartz substrate by a vacuum evaporation method. Measurements of the fluorescence spectrum and the phosphorescence spectrum were performed with a PL microscope LabRAM HR-PL (produced by HORIBA, Ltd.). The measurement temperature was 10 K, a He—Cd laser (325 nm) was used as excitation light, and a CCD detector was used as a detector. A thin film as a sample was used for the measurements after the thin film was formed over a quartz substrate to a thickness of approximately 50 nm and another quartz substrate was attached to the quartz substrate from the evaporation surface in a nitrogen atmosphere. Since this measurement of the emission spectra was performed at a low temperature (10 K), phosphorescence was partly observed in the normal measurement of emission spectrum, in addition to fluorescence, which is the main emission component. In the measurement of the time-resolved emission spectra (20 ms to 120 ms integration after illumination of the excited light) in which light emission with a long lifetime is focused on, the obtained spectra were mainly regarded as phosphorescence.

FIG. 25 shows that the toluene solution of 4DPhACzBfpm has an absorption peak at 375 nm and an emission wavelength peak at 532 nm (excitation wavelength: 375 nm). As shown in FIG. 26, the thin film of 4DPhACzBfpm exhibits absorption peaks at 379 nm and 293 nm and a fluorescence spectrum peaks at around 525 nm (excitation wavelength: 325 nm). As shown in FIG. 27, the peak on the shortest wavelength side of the phosphorescence spectrum of 4DPhACzBfpm is present at 521 nm, which indicates that it is a substance with a high T1 level. Note that although the read peak value of phosphorescence is more at the shorter wavelength side than that of fluorescence, the phosphorescence spectrum has a shape more slightly shifted to the longer wavelength as a whole than the fluorescence spectrum. These results show that 4DPhACzBfpm emits green light and can be used as a light-emitting material or a host material for a fluorescent light-emitting material or a phosphorescent light-emitting substance.

An index of the T1 level can be calculated using a phosphorescence spectrum. The level of energy with a wavelength of the line obtained by extrapolating a tangent to the phosphorescence spectrum at a tail on the short wavelength side can be regarded as the T1 level. An index of the S1 level can be calculated using a fluorescence spectrum. The level of energy with a wavelength of the line obtained by extrapolating a tangent to the fluorescence spectrum at a tail on the short wavelength side can be regarded as the S1 level.

The T1 level of 4DPhACzBfpm is calculated to be 2.56 eV as in FIG. 27, and the S1 level is calculated to be 2.64 eV as in FIG. 26. The results show that $\Delta E_{ST}$, which is the difference between the T1 level and S1 level of 4DPhACzBfpm, is 0.08 eV. In general, the $\Delta E_{ST}$ of a material having a TADF property is preferably 0.2 eV or less, and thus the $\Delta E_{ST}$ of 4DPhACzBfpm is found to be a value small enough to have a TADF property.

Example 4

In this example, distribution of the lowest unoccupied molecular orbital (LUMO) level and distribution of the highest occupied molecular orbital (HOMO) level in organic compounds represented by Structural Formulae (100) to (104), which are organic compounds of one embodiment of the present invention, were examined by molecular orbital calculation.

[Chemical Formula 35]

(100)

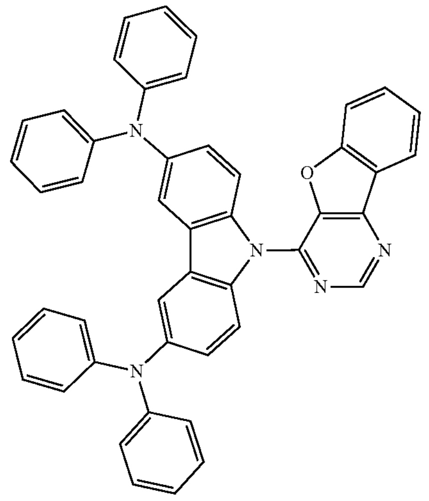

(101)

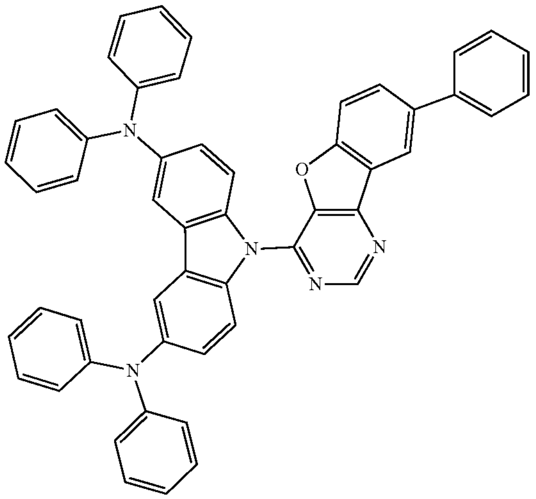

(102)

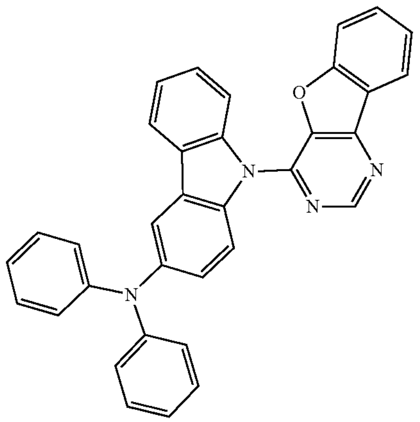

-continued (103)

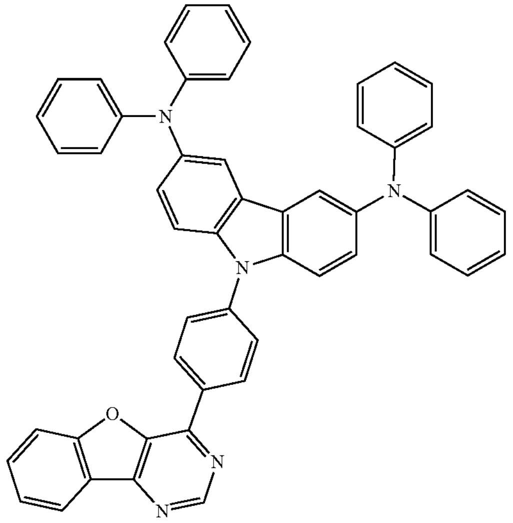

(104)

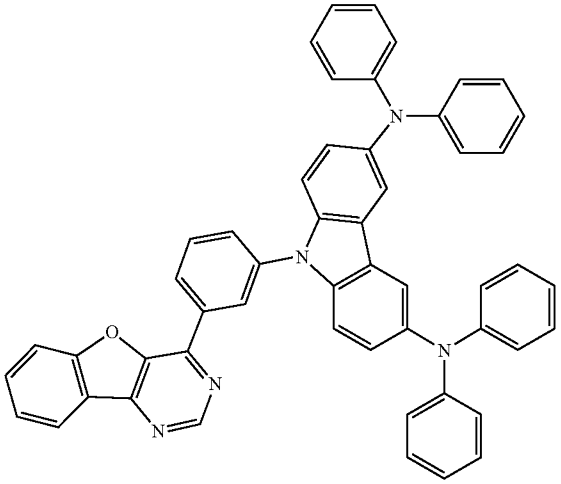

First, the most stable structure in the singlet ground state was calculated using the density functional theory (DFT). At this time, vibration analysis was conducted on each of the most stable structures. As a basis function, 6-311G was applied to all the atoms. Furthermore, to improve calculation accuracy, the p function and the d function as polarization basis sets were added to hydrogen atoms and atoms other than hydrogen atoms, respectively. As a functional, B3LYP is used. Each of the HOMO level and the LUMO level of the most stable singlet structure calculated was calculated. In the DFT, the total energy of the molecules is represented as the sum of potential energy, electrostatic energy between electrons, electronic kinetic energy, and exchange-correlation energy including all the complicated interactions between electrons. Also in the DFT, exchange-correlation interaction is approximated by a functional (meaning a function of another function) of one electron potential represented in terms of electron density; thus, electron states can be obtained with higher accuracy.

Note that Gaussian 09 was used as a quantum chemistry computational program. A high performance computer (Altix 4700, manufactured by SGI Japan, Ltd.) was used for the calculations.

Figure 28:
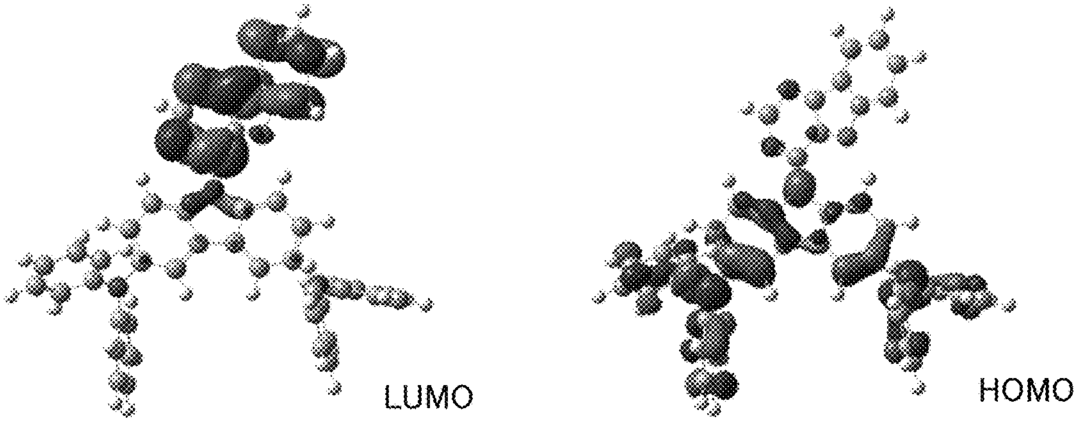
FIG. 28 shows HOMO and LUMO distributions of organic compounds represented by Structural Formulae (100) to (102).
Figure 28:
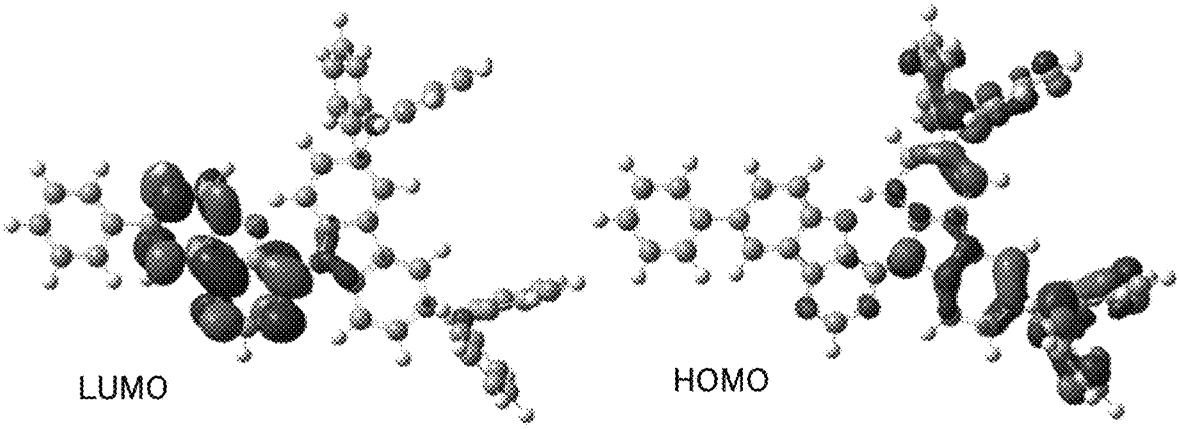
Figure 28:
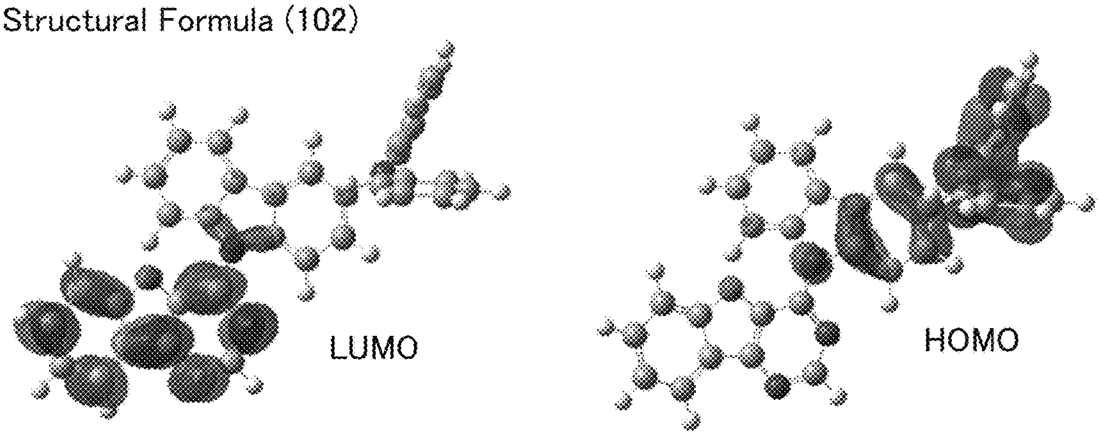
Figure 29:
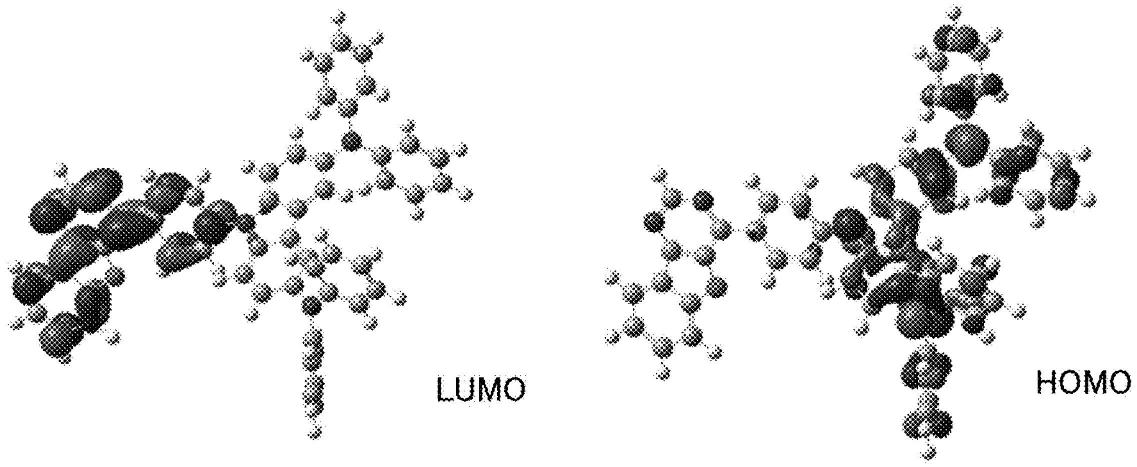
FIG. 29 shows HOMO and LUMO distributions of organic compounds represented by Structural Formulae (103) and (104).
Figure 29:
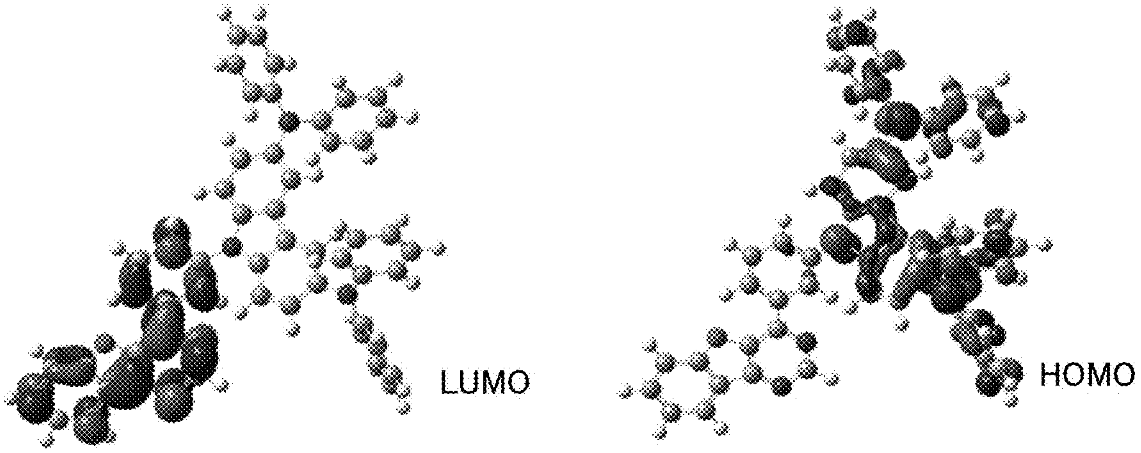

FIG. 28 and FIG. 29 show the results. As shown in FIG. 28 and FIG. 29, in the above-described five substances which are organic compounds of one embodiment of the present invention, the LUMO level mainly in the benzofuropyrimidine skeleton and the HOMO level mainly in the carbazole skeleton and the diphenylamine skeleton are spatially divided from each other.

The organic compounds represented by Structural Formula (103) and Structural Formula (104) in which the carbazole skeleton is bonded to the benzofuropyrimidine skeleton through a phenylene group exhibit smaller $\Delta E_{ST}$ than the organic compound represented by Structural Formula (100) in which bonding is formed without a phenylene group (their respective calculated values: 0.09 eV, 0.02 eV, and 0.18 eV). Furthermore, Structural Formula (104) in which the phenylene group is substituted at the meta-position exhibits smaller $\Delta E_{ST}$ than Structural Formula (103) in which the phenylene group is substituted at the para-position. Note that such $\Delta E_{ST}$ was obtained by calculation of a difference between the lowest singlet excitation energy (S1) and the lowest triplet excitation energy (T1) using the most stable structure of the singlet ground state by time-dependent density functional theory (TD-DFT). As a basis function, 6-311G (d,p) was used, and as a functional, B3LYP was used.

In order that TADF occur, reverse intersystem crossing from T1 to S1 needs to be preferentially caused at a rate higher than the rate of non-radiative deactivation from T1 to S0. This can be effectively done by reducing the energy difference $\Delta E_{ST}$ between the S1 and T1 states. To reduce $\Delta E_{ST}$, the density of overlap between the HOMO and the LUMO is reduced, and a molecular design where the HOMO and the LUMO are spatially divided is said to be effective.

The five substances, which are organic compounds of one embodiment of the present invention, can be said to be exactly the organic compounds that have the above-mentioned molecular structure. In particular, the organic compounds represented by Structural Formulae (100) to (102) synthesized in Example 1 to Example 3, in each of which $\Delta E_{ST}$ actually measured was as small as 0.08 eV, were found to be organic compounds with a high TADF property.

Example 5

In this example, Light-emitting device 1 using the organic compound of one embodiment of the present invention will be described. Structural formulae of organic compounds used in Light-emitting device 1 are shown below.

[Chemical Formula 36]

(i)

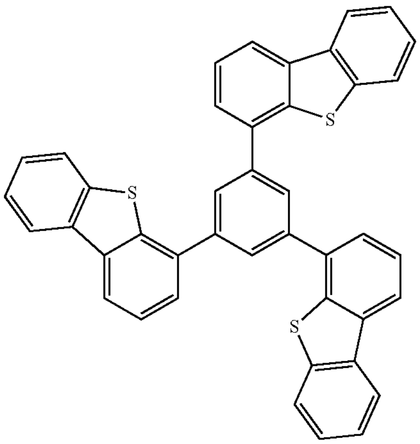

DBT3P-II (ii)

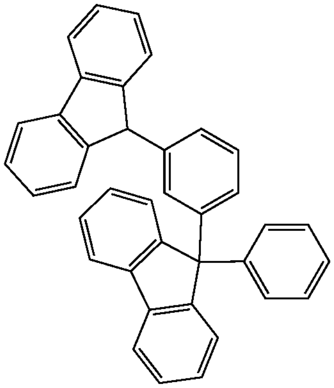

mCzFLP (iii)

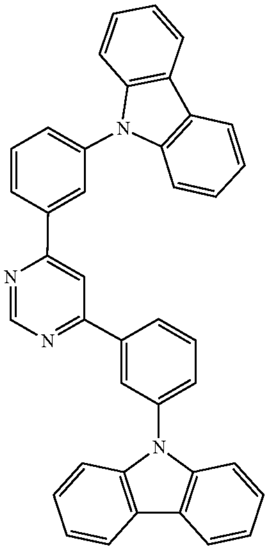

4,6mCzP2Pm

-continued (100)

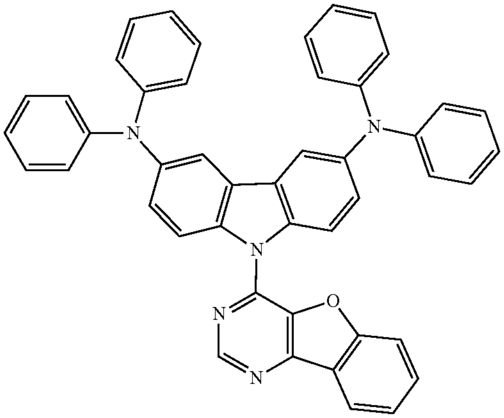

4DPhA2CzBfpm (iv)

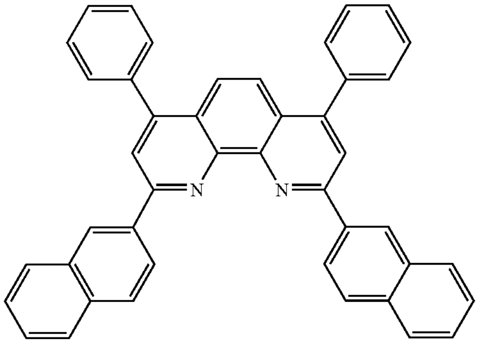

NBPhen (Method for Fabricating Light-Emitting Device 1)

First, indium tin oxide containing silicon oxide (ITSO) was deposited over a glass substrate by a sputtering method, so that the first electrode 101 was formed. Note that the film thickness was 70 nm and the area of the electrode was 2 mm×2 mm.

Next, in pretreatment for forming the light-emitting device over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to approximately $10^{-4}$ Pa, vacuum baking at 170° C. for 30 minutes was performed in a heating chamber in the vacuum evaporation apparatus, and then the substrate was cooled down for approximately 30 minutes.

Next, the substrate over which the first electrode 101 was formed was fixed to a substrate holder provided in the vacuum evaporation apparatus so that the surface over which the first electrode 101 was formed faced downward, and 4,4',4"-(benzene-1,3,5-triyl)tri(dibenzothiophene) (abbreviation: DBT3P-II) represented by Structural Formula (i) and molybdenum(VI) oxide were co-evaporated over the first electrode 101 to have a weight ratio of 1:0.5 (=DBT3P-II: molybdenum oxide) to a thickness of 40 nm by an evaporation method using resistance heating, whereby the hole-injection layer 111 was formed.

Next, as the hole-transport layer 112, 9-[3-(9-phenyl-9H-fluoren-9-yl)phenyl]9H-carbazole (abbreviation: mCzFLP) represented by Structural Formula (ii) was deposited over the hole-injection layer 111 by evaporation to a thickness of 20 nm.

Then, 9,9'-(pyrimidine-4,6-diyldi-3,1-phenyl ene)bis(9H-carbazole) (abbreviation: 4,6mCzP2Pm) represented by Structural Formula (iii) and 4-[3,6-bis(N,N-diphenylamino) carbazol-9-yl]benzofuro[3,2-d]pyrimidine (abbreviation: 4DPhA2CzBfpm) represented by Structural Formula (100) were deposited by co-evaporation to a thickness of 30 nm at a weight ratio of 1:0.1 (=4,6mCzP2Pm:4DPhA2CzBfpm), so that the light-emitting layer 113 was formed.

After that, over the light-emitting layer 113, 4,6mCzP2Pm was formed to a thickness of 20 nm, and then, 2,9-di(2-naphthyl)-4,7-diphenyl-1,10-phenanthroline (abbreviation: NBPhen) represented by Structural Formula (iv) was deposited by evaporation to a thickness of 15 nm, whereby the electron-transport layer 114 was formed.

After the formation of the electron-transport layer 114, lithium fluoride (LiF) was deposited by evaporation to a thickness of 1 nm to form the electron-injection layer 115, and then aluminum was deposited by evaporation to a thickness of 200 nm to form the second electrode 102, whereby a light-emitting device 1 of this example was fabricated.

The element structure of the light-emitting device is listed in the following table.

TABLE 1

| | Hole-injection layer 40 nm | Hole-transport layer 20 nm | Light-emitting layer 30 nm | Electron-transport layer 1 20 nm | Electron-transport layer 2 15 nm |
|---|---|---|---|---|---|
| Light-emitting device 1 | DBT3P-II:molybdenum oxide (1:0.5) | mCzFLP | 4,6mCzP2Pm:4DPhA2CzBfpm (1:0.1) | 4,6mCzP2Pm | NBPhen |

The light-emitting device was subjected to sealing with a glass substrate (a sealant was applied to surround the element, and at the time of sealing, UV treatment was performed first and heat treatment was performed at 80° C. for one hour) in a glove box containing a nitrogen atmosphere so that the light-emitting device was not exposed to the air. Then, the initial characteristics were measured.

Figure 30:
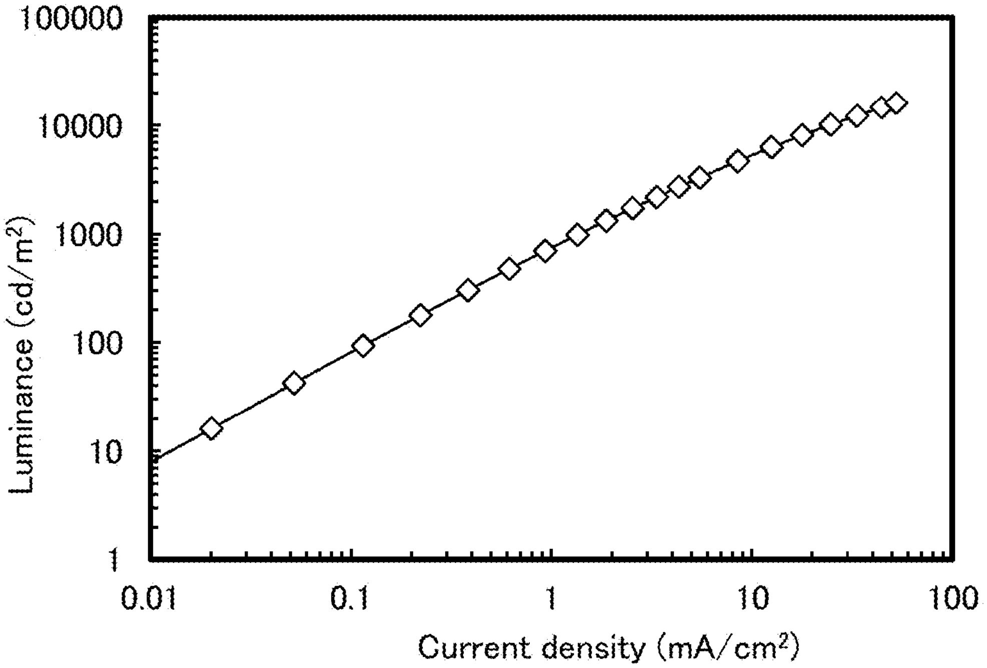
FIG. 30 is a graph showing luminance-current density characteristics of Light-emitting device 1.
Figure 31:
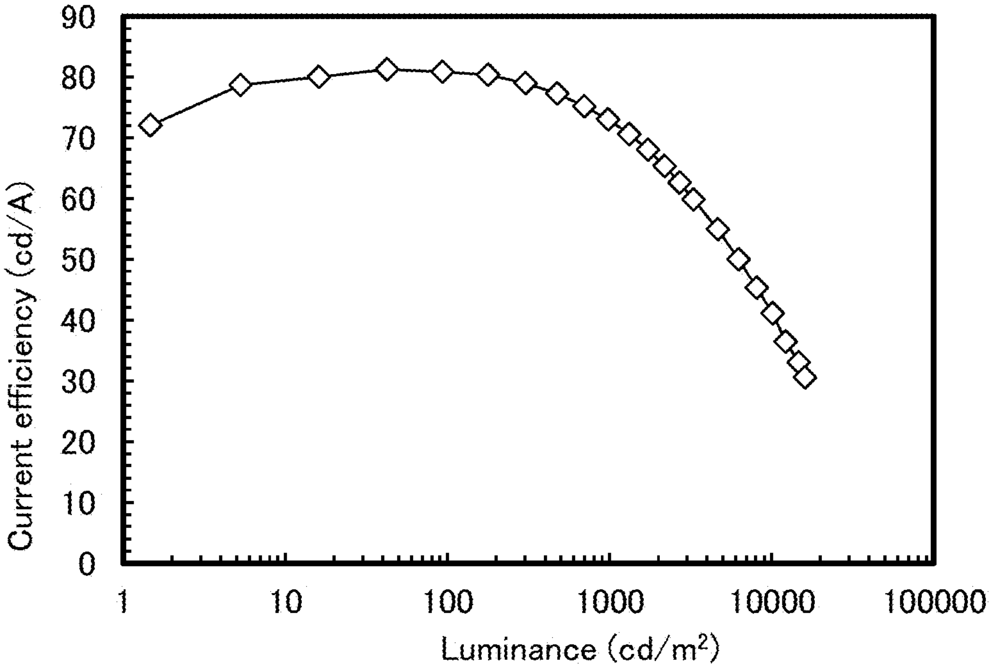
FIG. 31 is a graph showing current efficiency-luminance characteristics of Light-emitting device 1.
Figure 32:
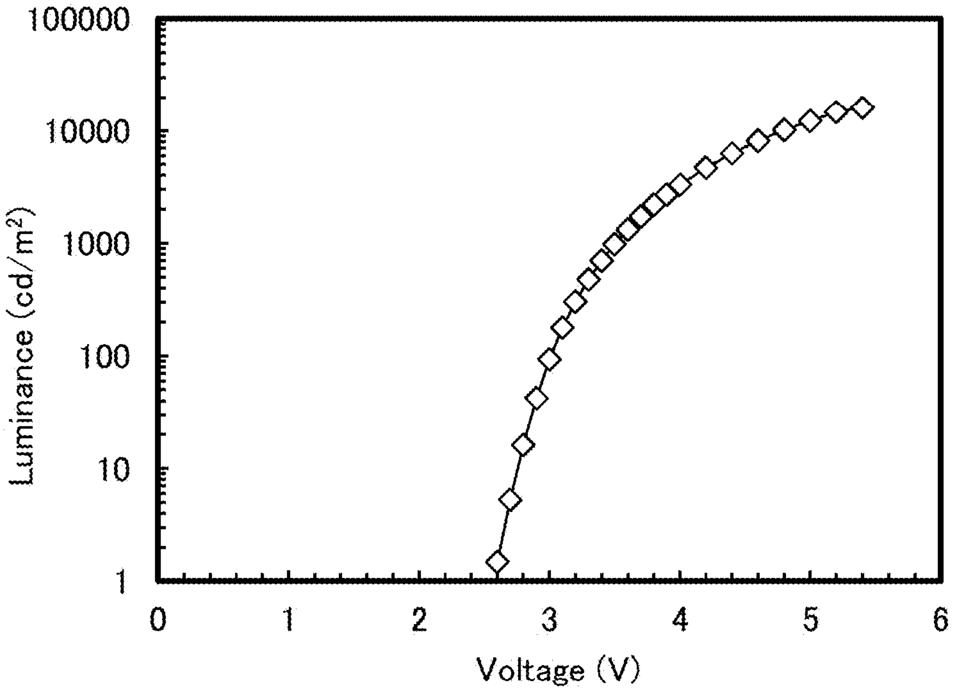
FIG. 32 is a graph showing luminance-voltage characteristics of Light-emitting device 1.
Figure 33:
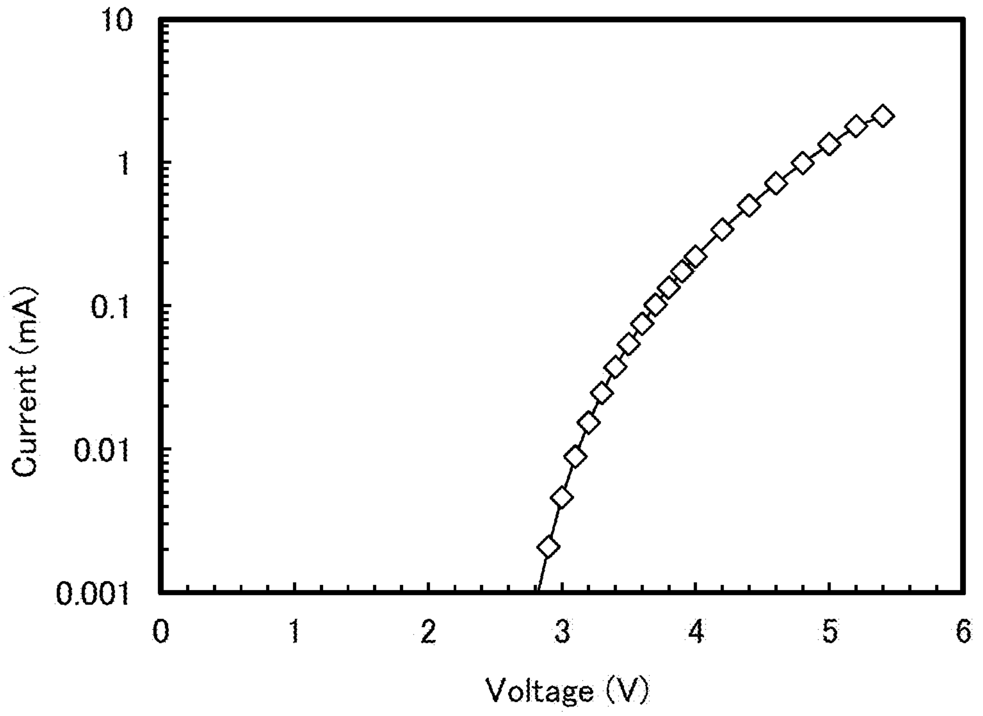
FIG. 33 is a graph showing current-voltage characteristics of Light-emitting device 1.
Figure 34:
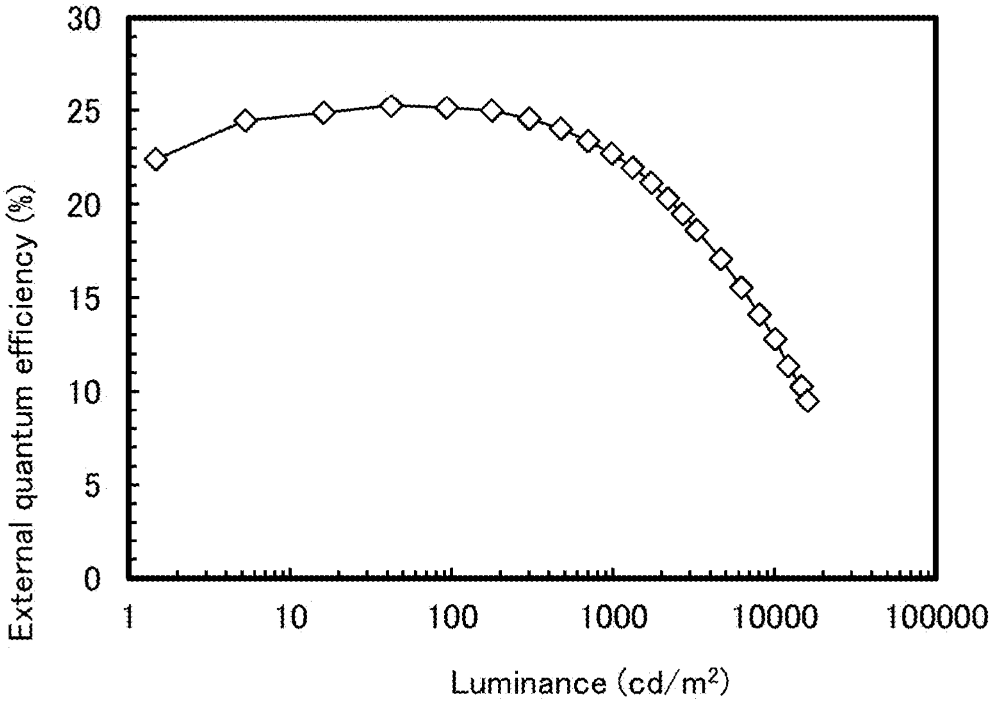
FIG. 34 is a graph showing external quantum efficiency-luminance characteristics of Light-emitting device 1.
Figure 35:
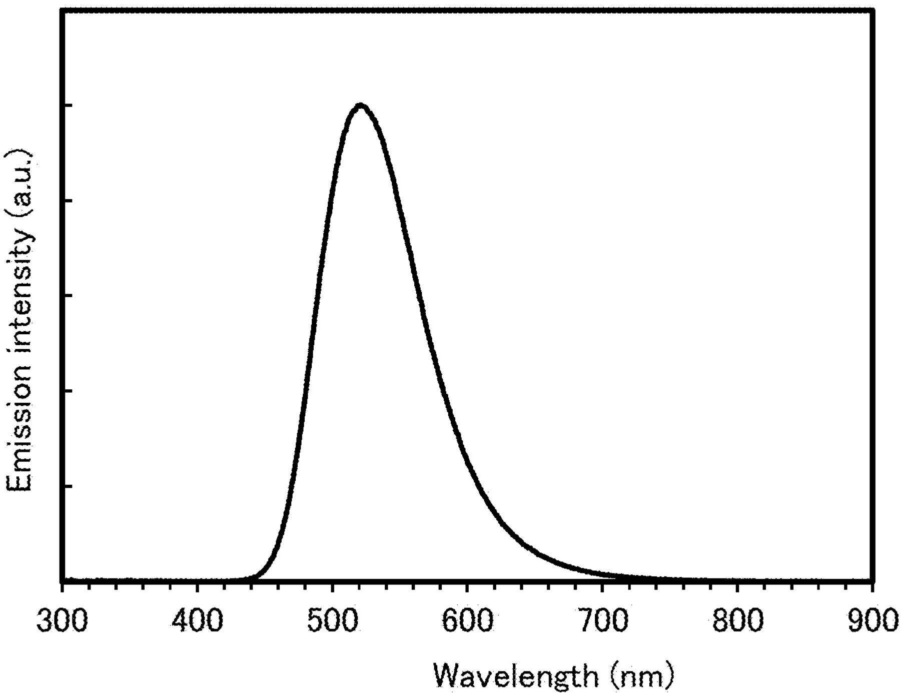
FIG. 35 is a graph showing an emission spectrum of Light-emitting device 1.

FIG. 30 shows the luminance-current density characteristics of Light-emitting device 1; FIG. 31, the current efficiency-luminance characteristics; FIG. 32, the luminance-voltage characteristics; FIG. 33, the current-voltage characteristics; FIG. 34, the external quantum efficiency-luminance characteristics; and FIG. 35, the emission spectrum. Main characteristics of Light-emitting device 1 at approximately 1000 cd/$m^2$ are listed below.

TABLE 2

| | Voltage (V) | Current (mA) | Current density (mA/$cm^2$) | Chromaticity x | Chromaticity y | Current efficiency (cd/A) | External efficiency (%) |
|---|---|---|---|---|---|---|---|
| Light-emitting device 1 | 3.5 | 0.05 | 1.3 | 0.28 | 0.59 | 73.0 | 22.7 |

It is found from FIG. 30 to FIG. 34 that Light-emitting device 1 of one embodiment of the present invention is a light-emitting element having favorable characteristics with very high efficiency such as high external quantum efficiency of a maximum of 25% or higher. This is a value significantly exceeding the theoretical limit of fluorescent light emission in current excitation and indicates that energy from triplet excitons contributes to light emission.

Light-emitting device 1, in which the HOMO and LUMO of 4DPhA2CzBfpm used as the light-emitting material are present in the spatially divided state in a molecule as described in Example 4, is an organic compound with small $\Delta E_{ST}$ as in the measurement in Example 1. This indicates that 4DPhA2CzBfpm is a substance that easily exhibits TADF.

Figure 36A:
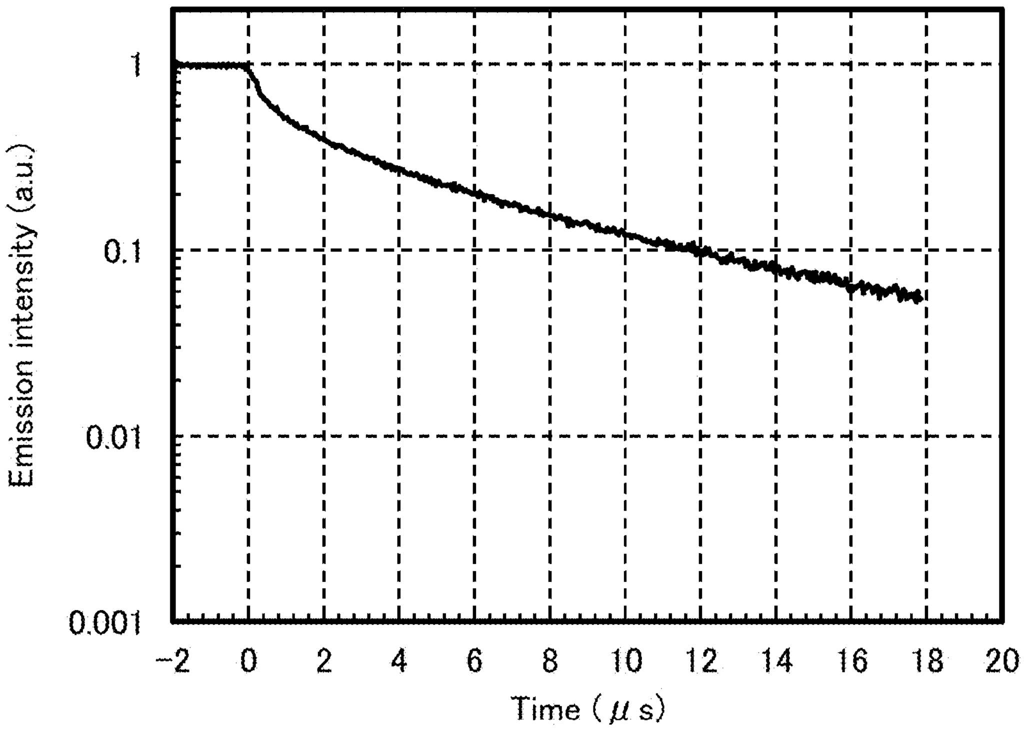
FIG. 36A and FIG. 36B are graphs showing transient EL characteristics of Light-emitting device 1.
Figure 36B:
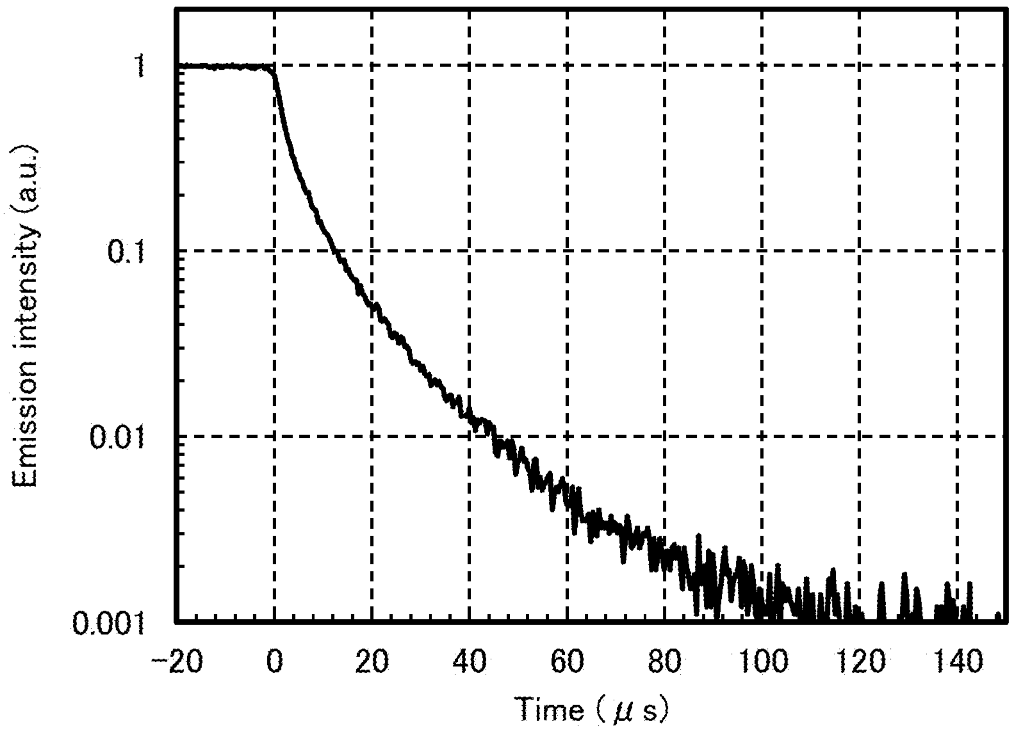

FIG. 36A and FIG. 36B show the measurement results of the transient EL characteristics of Light-emitting device 1. A picosecond fluorescence lifetime measurement system (manufactured by Hamamatsu Photonics K.K.) was used for the measurements. In the measurement, a square wave pulse voltage was applied to the light-emitting device, and time-resolved measurement of light emission, which was attenuated from the falling of the voltage, was performed with a streak camera. The measurement was conducted at room temperature (25° C.).

In FIG. 36A and FIG. 36B, the vertical axis represents the emission intensity normalized to that in a state where carriers were steadily injected (when the pulse voltage is ON). The horizontal axis represents time elapsed after the falling of the pulse voltage. Note that FIG. 36A and FIG. 36B differ in measurement time range.

From the transient EL characteristics shown in FIG. 36A and FIG. 36B, at least an emission component that attenuates promptly with a fluorescence lifetime (transient lifetime) of approximately 0.4 μs and an emission component that attenuates late with a fluorescence lifetime of approximately 9 μs were observed from Light-emitting device 1. Of these, the emission component with a fluorescence lifetime of 9 μs is delayed fluorescence based on reverse intersystem crossing, and Light-emitting device 1 is found to exhibit TADF. This indicates that using 4DPhA2CzBfpm as a light-emitting material causes TADF and allows triplet excitons to contribute to light emission, and accordingly Light-emitting device 1 can emit light with extremely favorable emission efficiency.

Example 6

In this example, Light-emitting device 2 using the organic compound of one embodiment of the present invention will be described. Structural formulae of organic compounds used in Light-emitting device 2 are shown below.

[Chemical Formula 37]

(i)

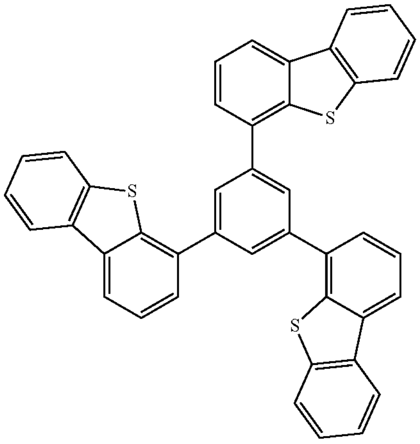

DBT3P-II (ii)

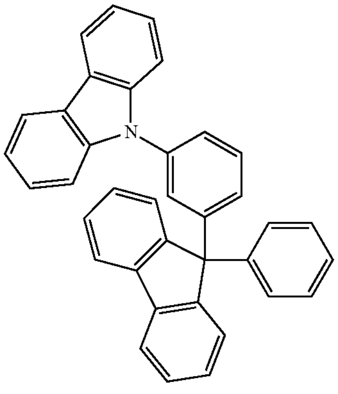

mCzFLP

-continued (v)

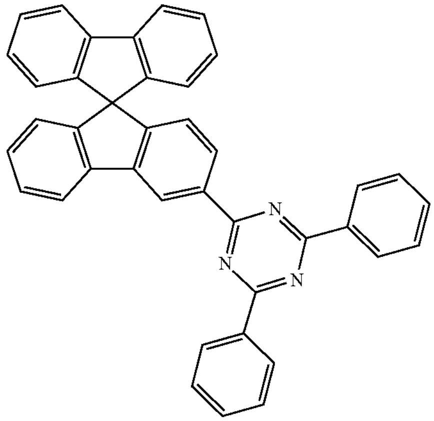

SF3-TZN (iii)

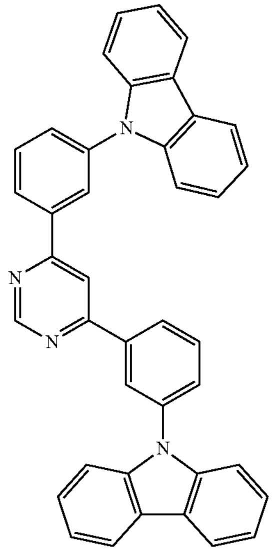

4,6mCzP2Pm (101)

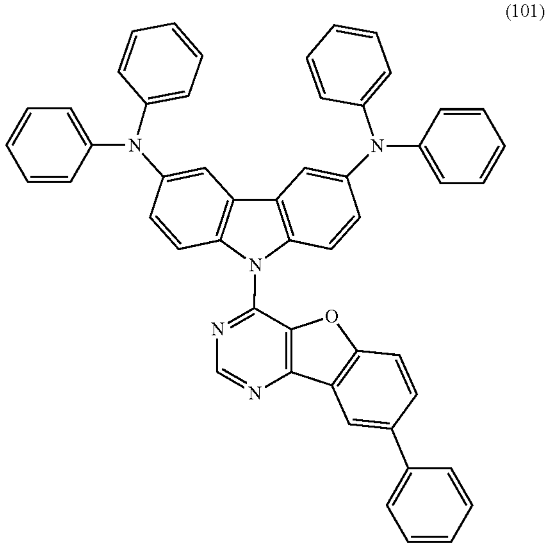

8Ph-4DPhA2CzBfpm

-continued (iv)

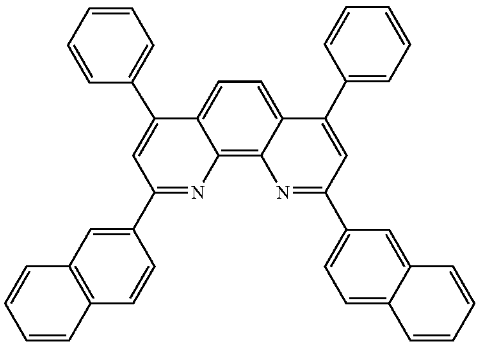

NBPhen (Method for Fabricating Light-Emitting Device 2)

First, indium tin oxide containing silicon oxide (ITSO) was deposited over a glass substrate by a sputtering method, so that the first electrode 101 was formed. Note that the film thickness was 70 nm and the area of the electrode was 2 mm×2 mm.

Next, in pretreatment for forming the light-emitting device over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to approximately $10^{-4}$ Pa, vacuum baking at 170° C. for 30 minutes was performed in a heating chamber in the vacuum evaporation apparatus, and then the substrate was cooled down for approximately 30 minutes.

Next, the substrate over which the first electrode 101 was formed was fixed to a substrate holder provided in the vacuum evaporation apparatus so that the surface over which the first electrode 101 was formed faced downward, and 4,4',4"-(benzene-1,3,5-triyl)tri(dibenzothiophene) (abbreviation: DBT3P-II) represented by Structural Formula (i) and molybdenum(VI) oxide were co-evaporated over the first electrode 101 to have a weight ratio of 1:0.5 (=DBT3P-II: molybdenum oxide) to a thickness of 40 nm by an evaporation method using resistance heating, whereby the hole-injection layer 111 was formed.

Next, as the hole-transport layer 112, 9-[3-(9-phenyl-9H-fluoren-9-yl)phenyl]9H-carbazole (abbreviation: mCzFLP) represented by Structural Formula (ii) was deposited over the hole-injection layer 111 by evaporation to a thickness of 20 nm.

Then, 2-(9,9'-spirobi[fluoren]-3-yl)-4,6-diphenyl-1,3,5-triazine (abbreviation: SF3-TZN) represented by Structural Formula (v) and 8-phenyl-4-[3,6-bis(N,N-diphenylamino) carbazol-9-yl]benzofuro[3,2-d]pyrimidine (abbreviation: 8Ph-4DPhA2CzBfpm) represented by Structural Formula (101) were deposited by co-evaporation to a thickness of 30 nm at a weight ratio of 1:0.1 (=SF3-TZN:8Ph-4DPhA2CzBfpm), so that the light-emitting layer 113 was formed.

After that, over the light-emitting layer 113, 4,6-bis[3-(9H-carbazol-9-yl)phenyl]pyrimidine (abbreviation: 4,6mCzP2Pm) represented by Structural Formula (iii) was formed to a thickness of 20 nm, and then, 2,9-di(2-naphthyl)-4,7-diphenyl-1,10-phenanthroline (abbreviation: NBPhen) represented by Structural Formula (iv) was deposited by evaporation to a thickness of 15 nm, whereby the electron-transport layer 114 was formed.

After the formation of the electron-transport layer 114, lithium fluoride (LiF) was deposited by evaporation to a thickness of 1 nm to form the electron-injection layer 115, and then aluminum was deposited by evaporation to a thickness of 200 nm to form the second electrode 102, whereby a light-emitting device 2 of this example was fabricated.

The element structure of the light-emitting device is listed in the following table.

TABLE 3

| | | | | Electron-transport layer | |
|---|---|---|---|---|---|
| | Hole-injection layer | Hole-transport layer | Light-emitting layer | 1 | 2 |
| | 40 nm | 20 nm | 30 nm | 20 nm | 15 nm |
| Light-emitting device 2 | DBT3P-II:molybdenum oxide (1:0.5) | mCzFLP | SF3-Tzn:8Ph-4DPhA2CzBfpm (1:0.1) | 4,6mCzP2Pm | NBPhen |

The light-emitting device was subjected to sealing with a glass substrate (a sealant was applied to surround the element, and at the time of sealing, UV treatment was performed first and heat treatment was performed at 80° C. for one hour) in a glove box containing a nitrogen atmosphere so that the light-emitting device was not exposed to the air. Then, the initial characteristics were measured.

Figure 37:
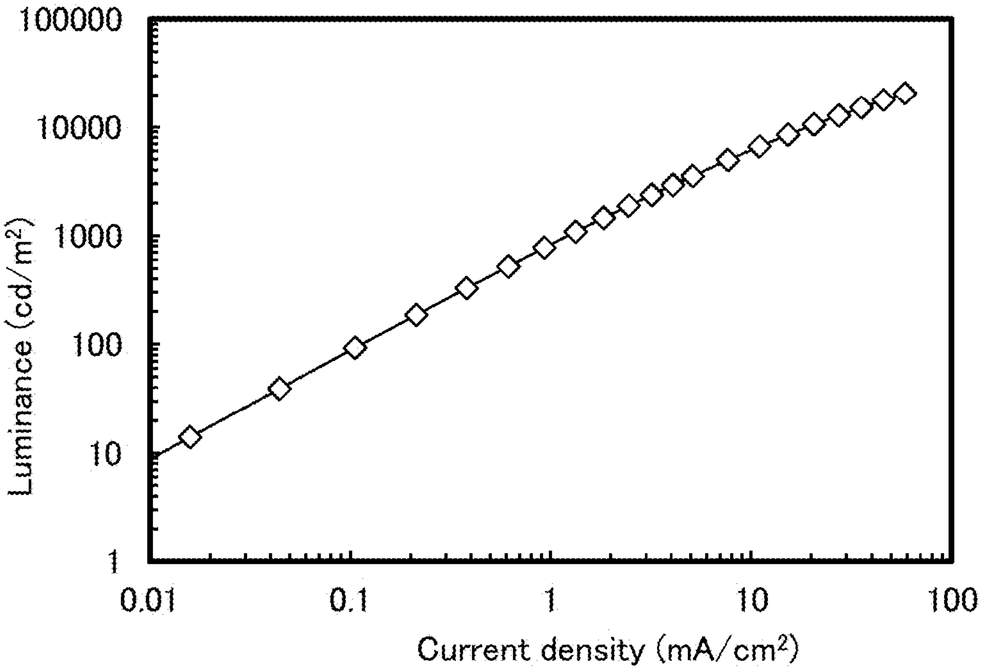
FIG. 37 is a graph showing luminance-current density characteristics of Light-emitting device 2.
Figure 38:
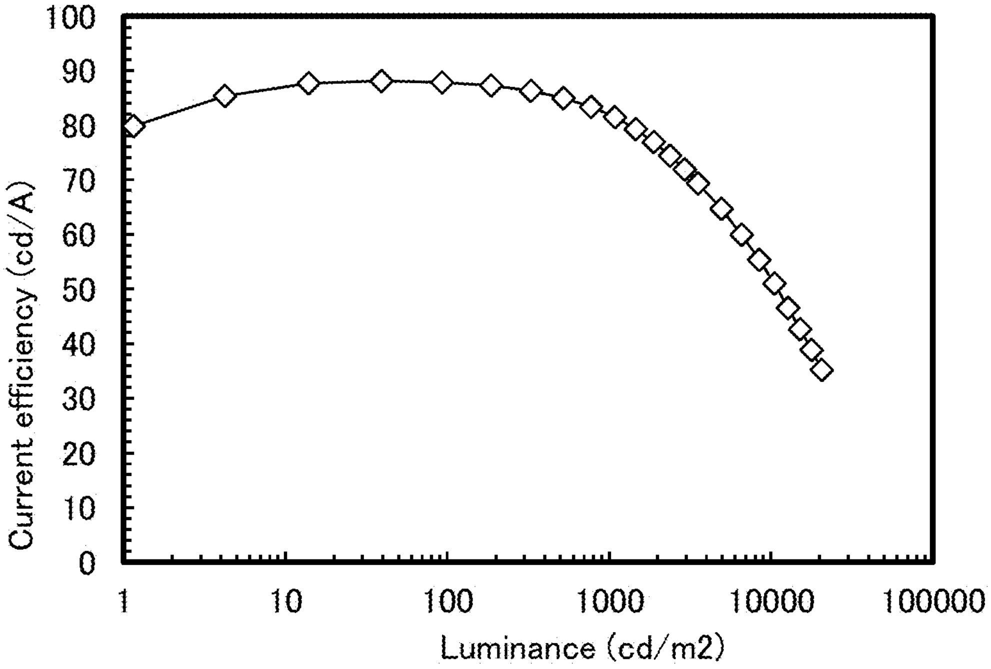
FIG. 38 is a graph showing current efficiency-luminance characteristics of Light-emitting device 2.
Figure 39:
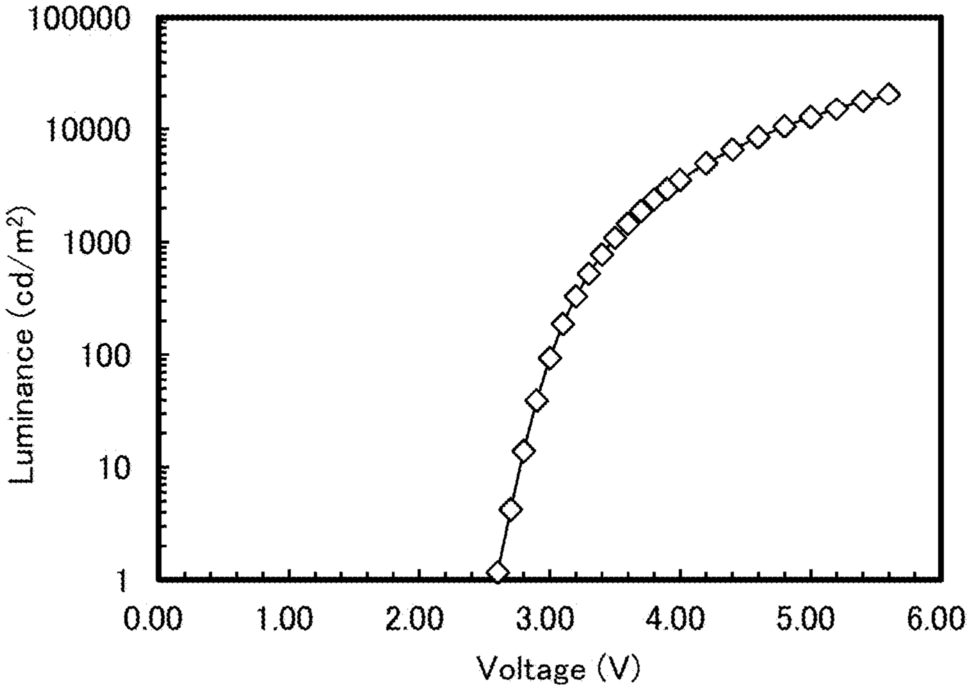
FIG. 39 is a graph showing luminance-voltage characteristics of Light-emitting device 2.
Figure 40:
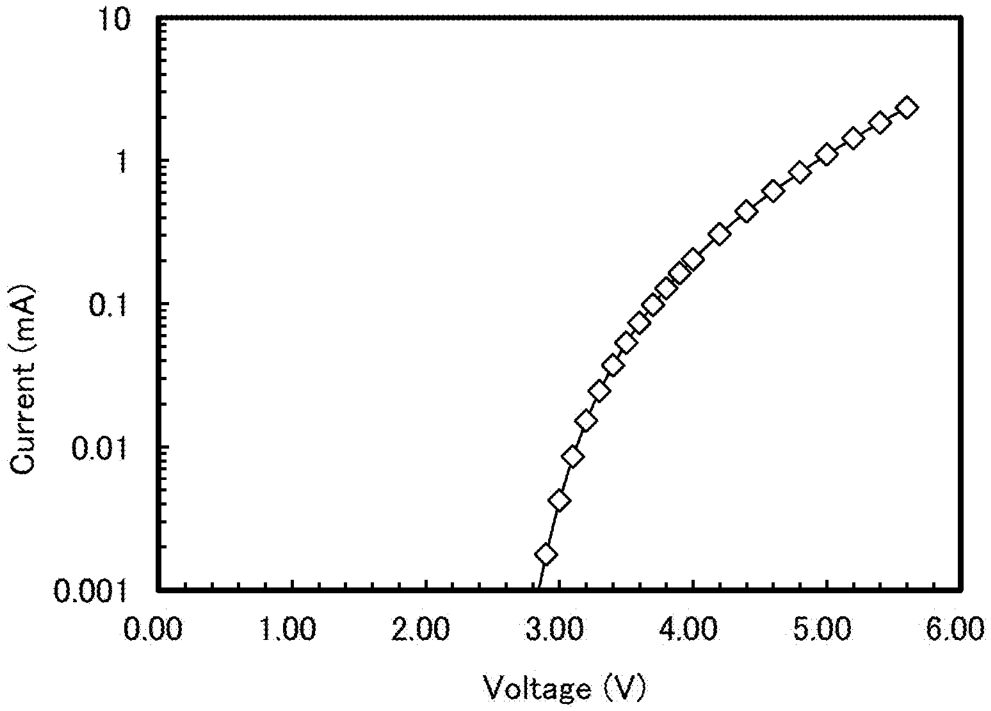
FIG. 40 is a graph showing current-voltage characteristics of Light-emitting device 2.
Figure 41:
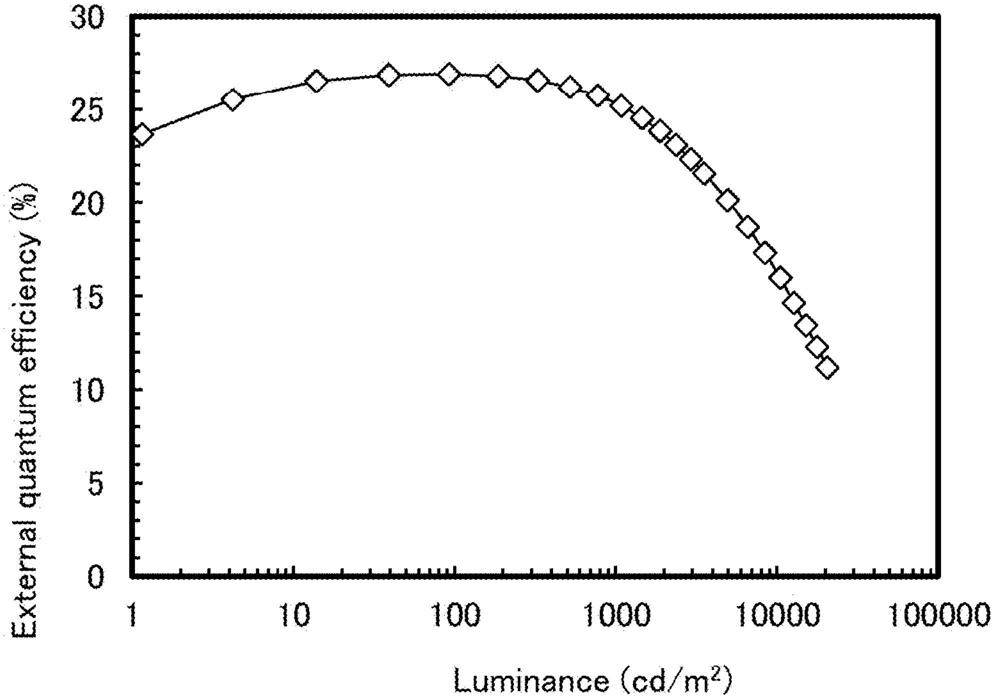
FIG. 41 is a graph showing external quantum efficiency-luminance characteristics of Light-emitting device 2.
Figure 42:
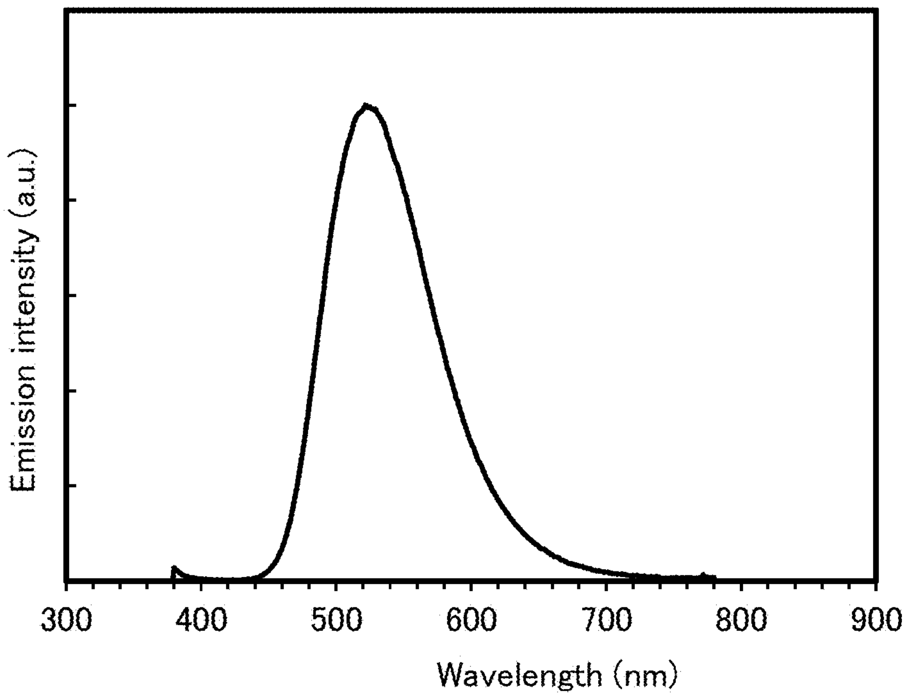
FIG. 42 is a graph showing an emission spectrum of Light-emitting device 2.

FIG. 37 shows the luminance-current density characteristics of Light-emitting device 2; FIG. 38, the current efficiency-luminance characteristics; FIG. 39, the luminance-voltage characteristics; FIG. 40, the current-voltage characteristics; FIG. 41, the external quantum efficiency-luminance characteristics; and FIG. 42, the emission spectrum. Main characteristics of Light-emitting device 2 at approximately 1000 cd/$m^2$ are listed below.

TABLE 4

| | Voltage (V) | Current (mA) | Current density (mA/$cm^2$) | Chromaticity x | Chromaticity y | Current efficiency (cd/A) | External efficiency (%) |
|---|---|---|---|---|---|---|---|
| Light-emitting device 2 | 3.5 | 0.05 | 1.3 | 0.30 | 0.57 | 81.5 | 25.2 |

It is found from FIG. 37 to FIG. 41 that Light-emitting device 2 of one embodiment of the present invention is a light-emitting element having favorable characteristics with very high efficiency such as high external quantum efficiency of a maximum of 25% or higher. This is a value significantly exceeding the theoretical limit of fluorescent light emission in current excitation and indicates that energy from triplet excitons contributes to light emission.

Light-emitting device 2, in which the HOMO and the LUMO of 8Ph-4DPhA2CzBfpm used as the light-emitting material are present in the spatially divided state in a molecule as described in Example 4, is an organic compound where $\Delta E_{ST}$ is small as in the measurement in Example 2 and reverse intersystem crossing easily occurs. Hence, it can be considered that 8Ph-4DPhA2CzBfpm is a substance that easily exhibits TADF, using 8Ph-4DPhA2CzBfpm as a light-emitting material causes TADF and allows triplet excitons to contribute to light emission, and accordingly Light-emitting device 2 can emit light with extremely favorable emission efficiency.

Example 7

In this example, Light-emitting device 3 using the organic compound of one embodiment of the present invention will be described. Structural formulae of organic compounds used in Light-emitting device 3 are shown below.

[Chemical Formula 38]

(i)

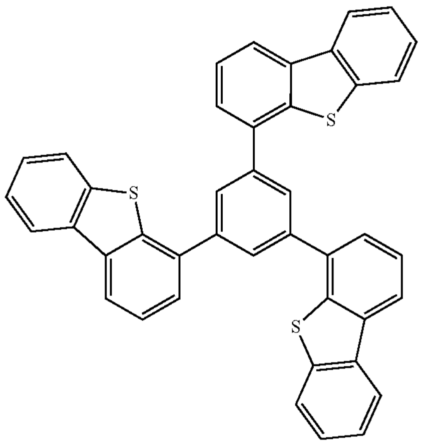

DBT3P-II (ii)

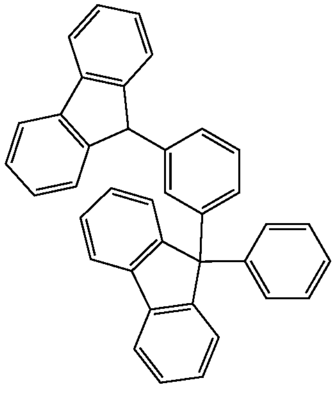

mCzFLP

-continued (iii)

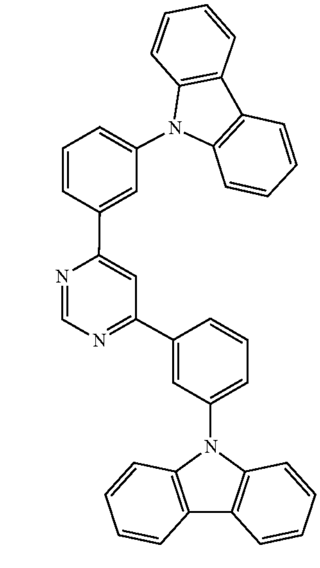

4,6mCzP2Pm (102)

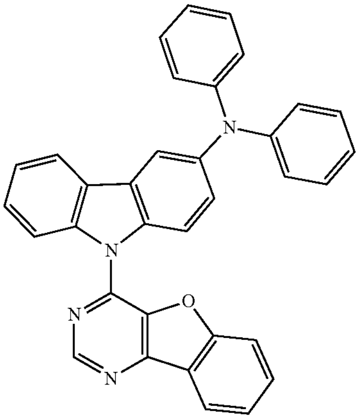

4DPhACzBfpm

-continued (iv)

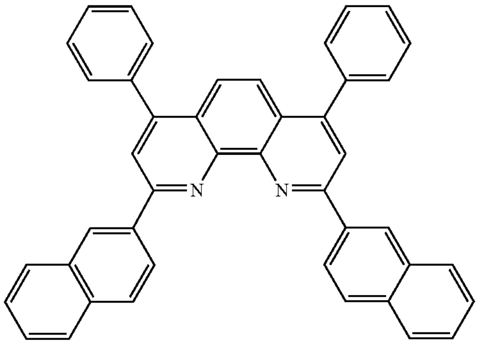

NBPhen

First, indium tin oxide containing silicon oxide (ITSO) was deposited over a glass substrate by a sputtering method, so that the first electrode 101 was formed. Note that the film thickness was 70 nm and the area of the electrode was 2 mm×2 mm.

Next, in pretreatment for forming the light-emitting device over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to approximately $10^{-4}$ Pa, vacuum baking at 170° C. for 30 minutes was performed in a heating chamber in the vacuum evaporation apparatus, and then the substrate was cooled down for approximately 30 minutes.

Next, the substrate over which the first electrode 101 was formed was fixed to a substrate holder provided in the vacuum evaporation apparatus so that the surface over which the first electrode 101 was formed faced downward, and 4,4',4"-(benzene-1,3,5-triyl)tri(dibenzothiophene) (abbreviation: DBT3P-II) represented by Structural Formula (i) and molybdenum(VI) oxide were co-evaporated over the first electrode 101 to have a weight ratio of 1:0.5 (=DBT3P-II: molybdenum oxide) to a thickness of 40 nm by an evaporation method using resistance heating, whereby the hole-injection layer 111 was formed.

Next, as the hole-transport layer 112, 9-[3-(9-phenyl-9H-fluoren-9-yl)phenyl]9H-carbazole (abbreviation: mCzFLP) represented by Structural Formula (ii) was deposited over the hole-injection layer 111 by evaporation to a thickness of 20 nm.

Then, 4,6-bis[3-(9H-carbazol-9-yl)phenyl]pyrimidine (abbreviation: 4,6mCzP2Pm) represented by Structural Formula (iii) and 4-[3-(N,Ndiphenylamino)carbazol-9-yl]benzofuro[3,2-d]pyrimidine (abbreviation: 4DPhACzBfpm) represented by Structural Formula (102) were deposited by co-evaporation to a thickness of 30 nm at a weight ratio of 1:0.1 (=4,6mCzP2Pm:4DPhACzBfpm), so that the light-emitting layer 113 was formed.

After that, over the light-emitting layer 113, 4,6mCzP2Pm was formed to a thickness of 20 nm, and then, 2,9-di(2-naphthyl)-4,7-diphenyl-1,10-phenanthroline (abbreviation: NBPhen) represented by Structural Formula (iv) was deposited by evaporation to a thickness of 15 nm, whereby the electron-transport layer 114 was formed.

After the formation of the electron-transport layer 114, lithium fluoride (LiF) was deposited by evaporation to a thickness of 1 nm to form the electron-injection layer 115, and then aluminum was deposited by evaporation to a thickness of 200 nm to form the second electrode 102, whereby a light-emitting device 3 of this example was fabricated.

The element structure of the light-emitting device is listed in the following table.

TABLE 5

| | Hole-injection layer 40 nm | Hole-transport layer 20 nm | Light-emitting layer 30 nm | Electron-transport layer 1 20 nm | Electron-transport layer 2 15 nm |
|---|---|---|---|---|---|
| Light-emitting device 3 | DBT3P-II:molybdenum oxide (1:0.5) | mCzFLP | 4,6mCzP2Pm:4DPhACzBfpm (1:0.1) | 4,6mCzP2Pm | NBPhen |

The light-emitting device was subjected to sealing with a glass substrate (a sealant was applied to surround the element, and at the time of sealing, UV treatment was performed first and heat treatment was performed at 80° C. for one hour) in a glove box containing a nitrogen atmosphere so that the light-emitting device was not exposed to the air. Then, the initial characteristics were measured.

Figure 43:
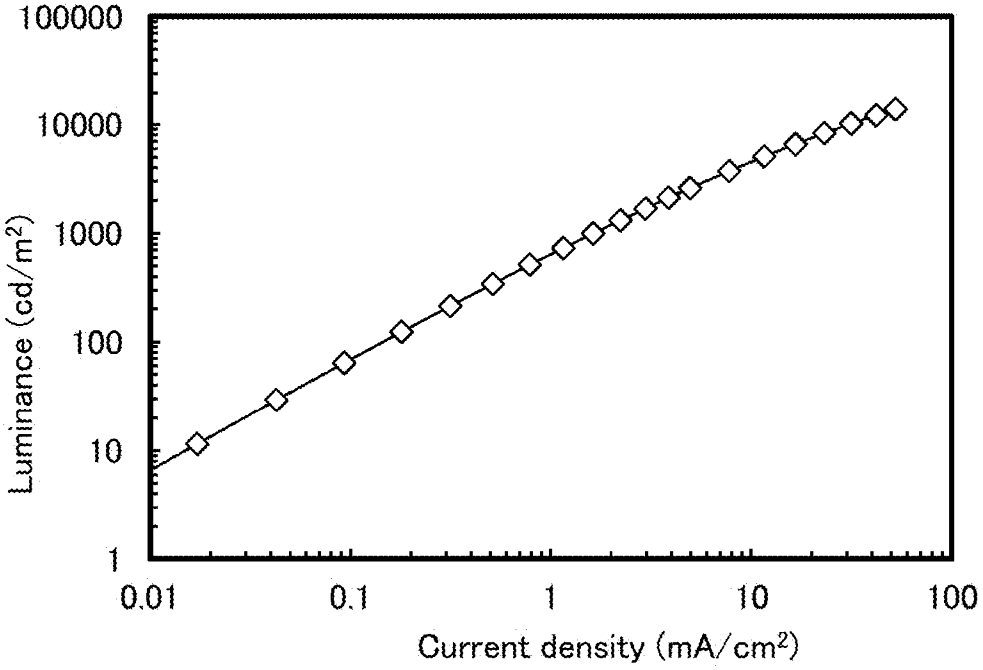
FIG. 43 is a graph showing luminance-current density characteristics of Light-emitting device 3.
Figure 44:
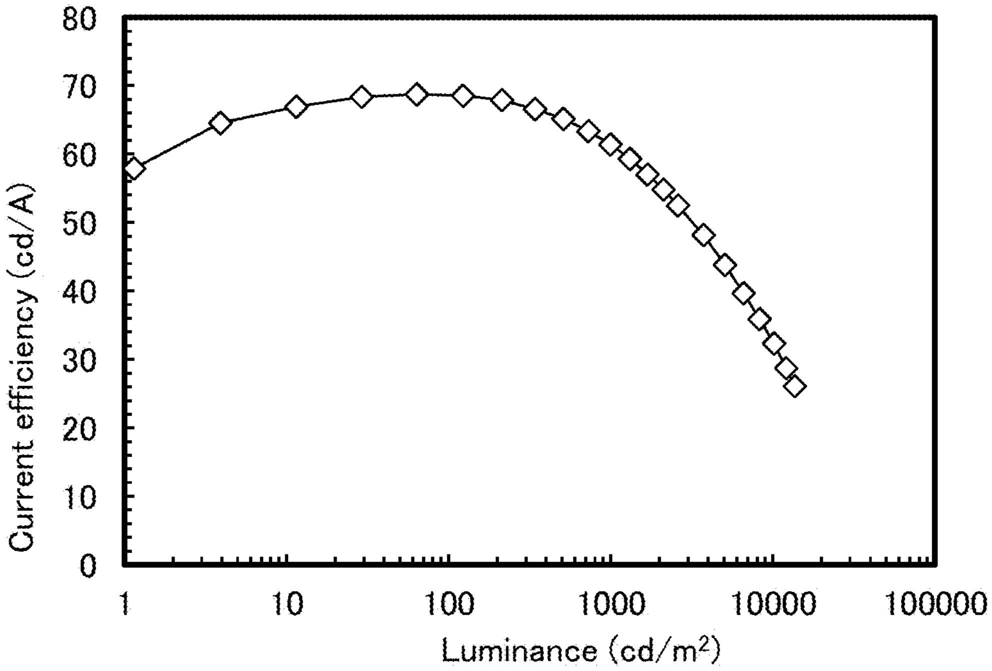
FIG. 44 is a graph showing current efficiency-luminance characteristics of Light-emitting device 3.
Figure 45:
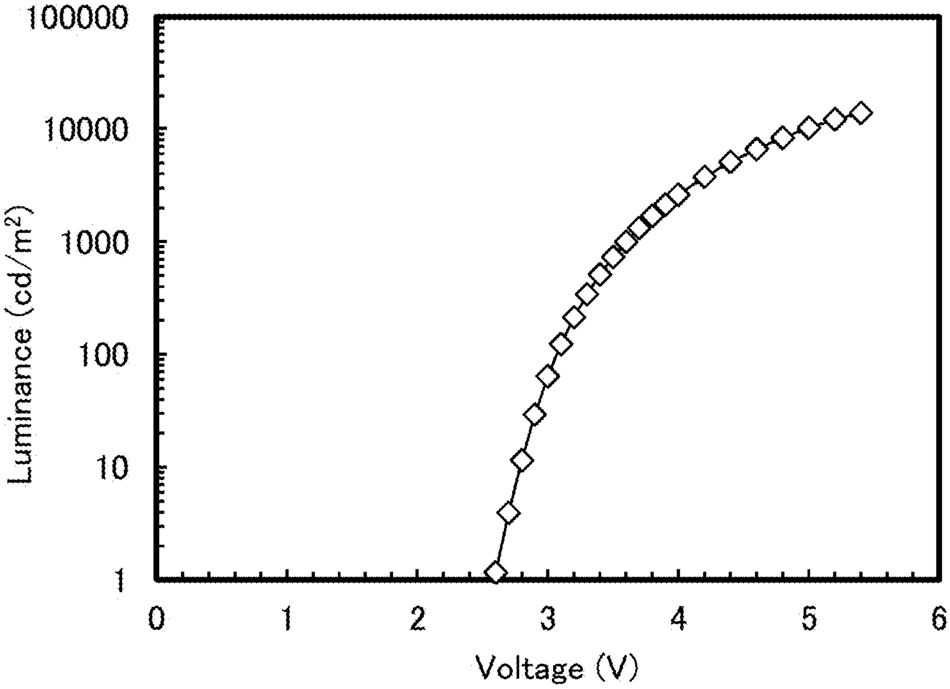
FIG. 45 is a graph showing luminance-voltage characteristics of Light-emitting device 3.
Figure 46:
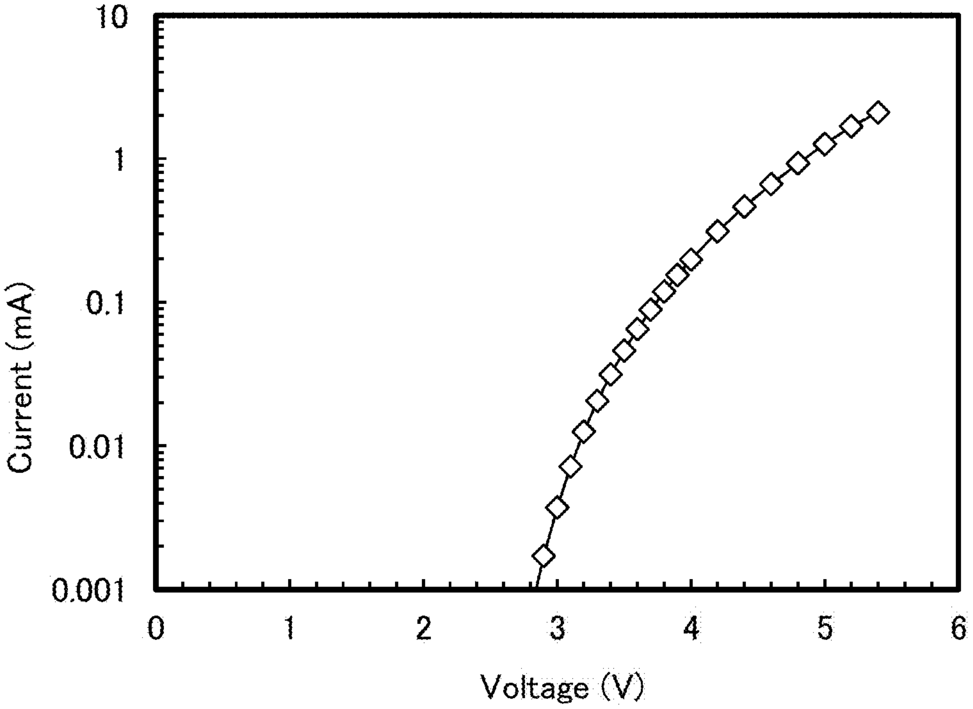
FIG. 46 is a graph showing current-voltage characteristics of Light-emitting device 3.
Figure 47:
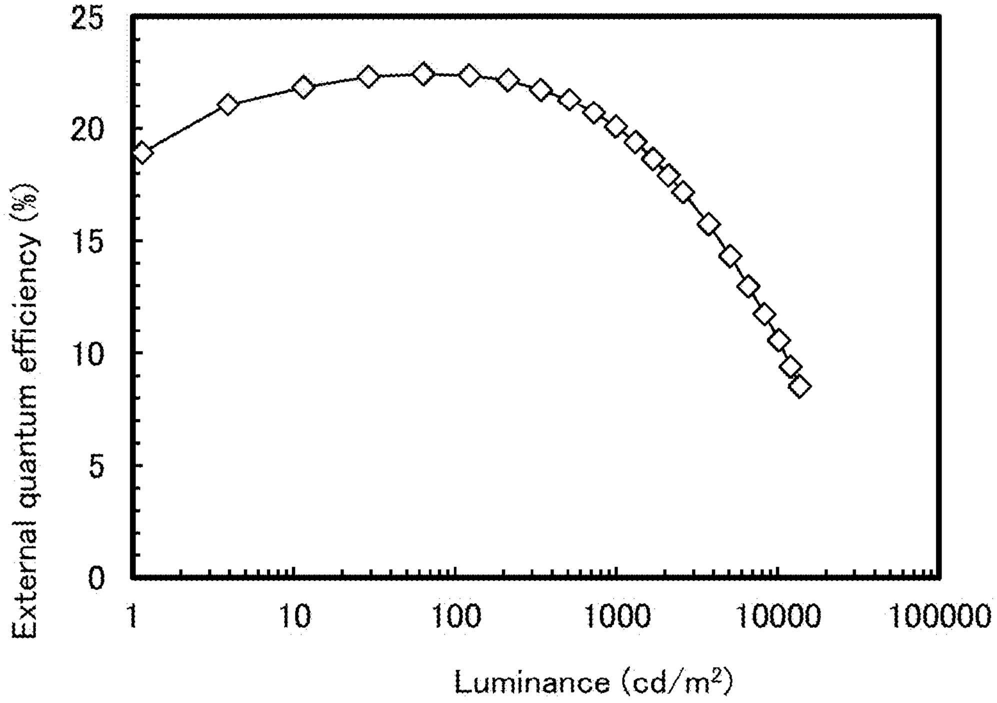
FIG. 47 is a graph showing external quantum efficiency-luminance characteristics of Light-emitting device 3.
Figure 48:
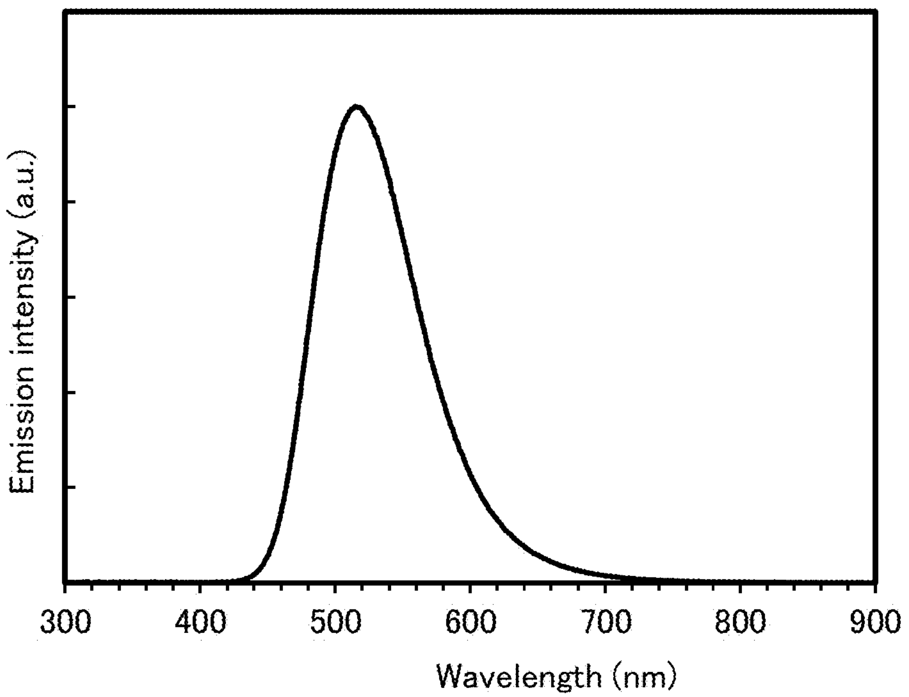
FIG. 48 is a graph showing an emission spectrum of Light-emitting device 3.

FIG. 43 shows the luminance-current density characteristics of Light-emitting device 3; FIG. 44, the current efficiency-luminance characteristics; FIG. 45, the luminance-voltage characteristics; FIG. 46, the current-voltage characteristics; FIG. 47, the external quantum efficiency-luminance characteristics; and FIG. 48, the emission spectrum. Main characteristics of Light-emitting device 3 at approximately 1000 cd/$m^2$ are listed below.

TABLE 6

| | Voltage (V) | Current (mA) | Current density (mA/$cm^2$) | Chromaticity x | Chromaticity y | Current efficiency (cd/A) | External efficiency (%) |
|---|---|---|---|---|---|---|---|
| Light-emitting device 3 | 3.6 | 0.06 | 1.6 | 0.27 | 0.56 | 61.4 | 20.1 |

It is found from FIG. 43 to FIG. 47 that Light-emitting device 3 of one embodiment of the present invention is a light-emitting element having favorable characteristics with very high efficiency such as high external quantum efficiency of a maximum of 20% or higher. This is a value significantly exceeding the theoretical limit of fluorescent light emission in current excitation and indicates that energy from triplet excitons contributes to light emission.

Light-emitting device 3, in which the HOMO and LUMO of 4DPhACzBfpm used as the light-emitting material are present in the spatially divided state in a molecule as described in Example 4, is an organic compound with small $\Delta E_{ST}$ as in the measurement in Example 3. This indicates that 4DPhACzBfpm is a substance that easily exhibits TADF.

Figure 49A:
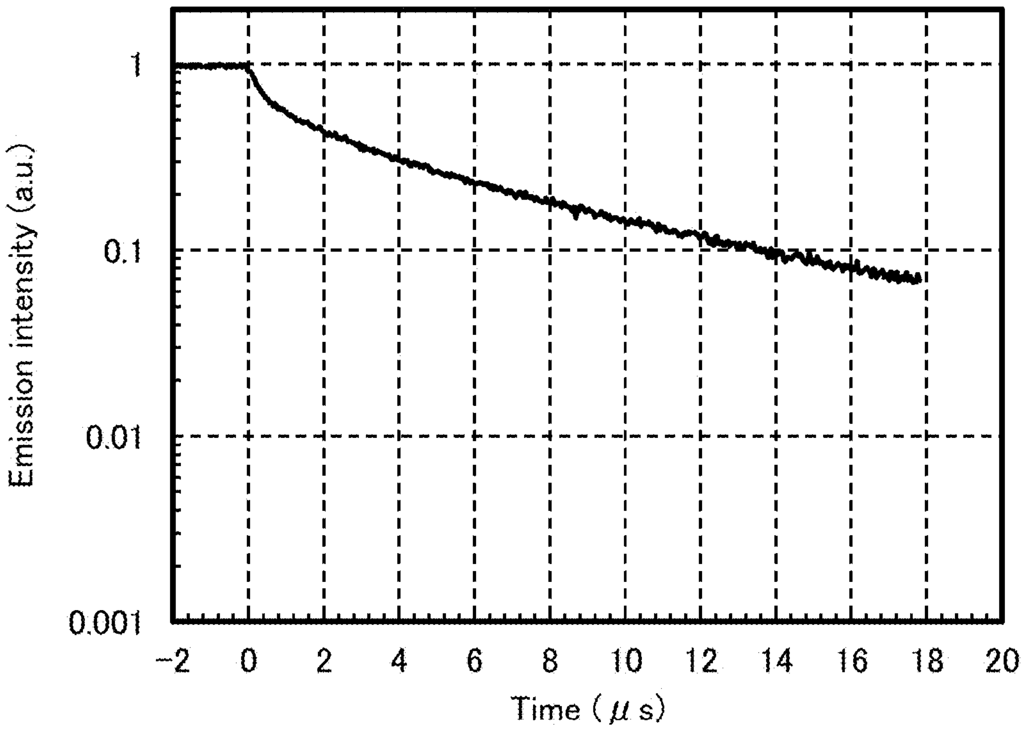
FIG. 49A and FIG. 49B are graphs showing transient EL characteristics of Light-emitting device 3.
Figure 49B:
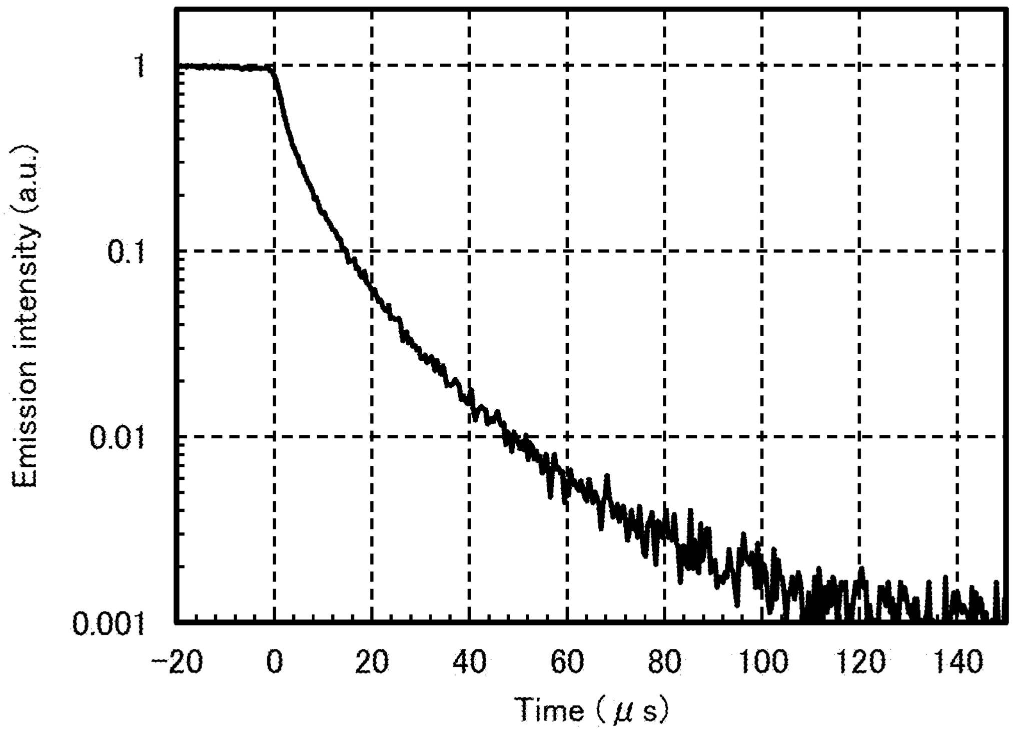

FIG. 49A and FIG. 49B show the measurement results of the transient EL characteristics of Light-emitting device 3. A picosecond fluorescence lifetime measurement system (manufactured by Hamamatsu Photonics K.K.) was used for the measurements. In the measurement, a square wave pulse voltage was applied to the light-emitting device, and time-resolved measurement of light emission, which was attenuated from the falling of the voltage, was performed with a streak camera. The measurement was conducted at room temperature (25° C.).

In FIG. 49A and FIG. 49B, the vertical axis represents the emission intensity normalized to that in a state where carriers were steadily injected (when the pulse voltage is ON). The horizontal axis represents time elapsed after the falling of the pulse voltage. Note that FIG. 49A and FIG. 49B differ in measurement time range.

From the transient EL characteristics shown in FIG. 49A and FIG. 49B, at least an emission component that attenuates promptly with a fluorescence lifetime (transient lifetime) of approximately 0.3 μs and an emission component that attenuates late with a fluorescence lifetime of approximately 10 μs were observed from Light-emitting device 3. Of these, the emission component with a fluorescence lifetime of 10 μs is delayed fluorescence based on reverse intersystem crossing, and Light-emitting device 3 is found to exhibit TADF. This indicates that using 4DPhA2CzBfpm as a light-emitting material causes TADF and allows triplet excitons to contribute to light emission, and accordingly Light-emitting device 3 can emit light with extremely favorable emission efficiency.

Example 8

In this example, Light-emitting device 4 using the organic compound of one embodiment of the present invention will be described. Structural formulae of organic compounds used in Light-emitting device 4 are shown below.

[Chemical Formula 39]

(i)

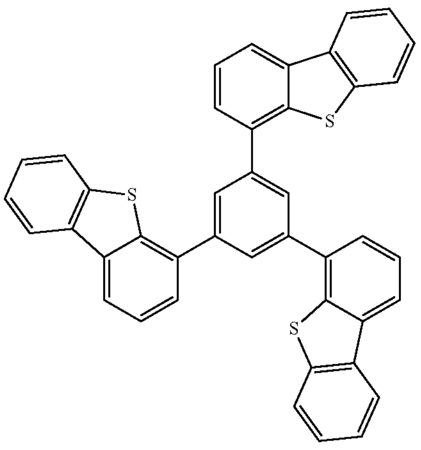

DBT3P-II

-continued (ii)

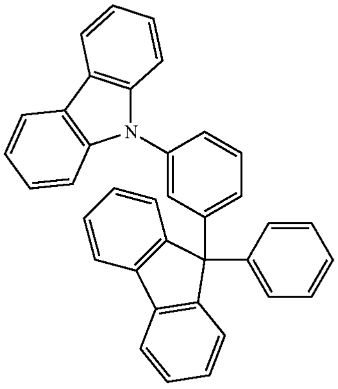

mCzFLP (iii)

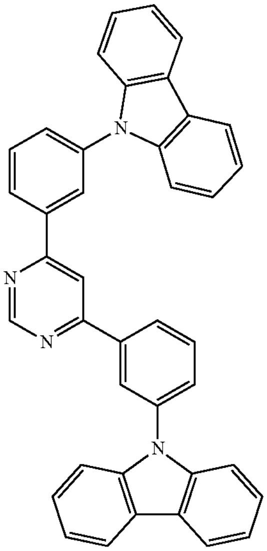

4,6mCzP2Pm (vi)

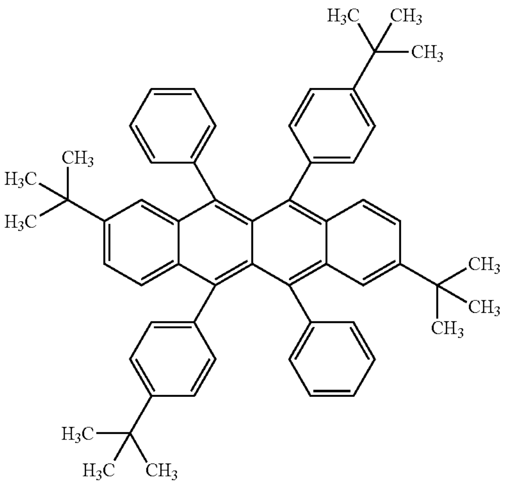

TBRb

-continued (100)

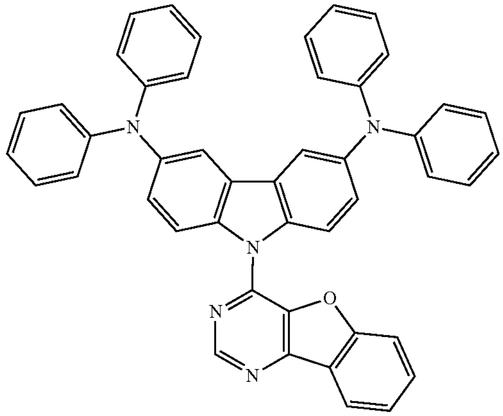

4DPhA2CzBfpm (iv)

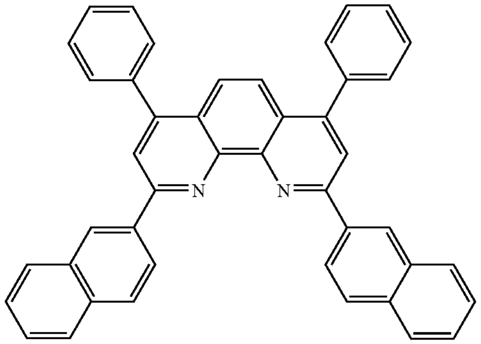

NBPhen (Method for Fabricating Light-Emitting Device 4)

First, indium tin oxide containing silicon oxide (ITSO) was deposited over a glass substrate by a sputtering method, so that the first electrode 101 was formed. Note that the film thickness was 70 nm and the area of the electrode was 2 mm×2 mm.

Next, in pretreatment for forming the light-emitting device over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to approximately $10^{-4}$ Pa, vacuum baking at 170° C. for 30 minutes was performed in a heating chamber in the vacuum evaporation apparatus, and then the substrate was cooled down for approximately 30 minutes.

Next, the substrate over which the first electrode 101 was formed was fixed to a substrate holder provided in the vacuum evaporation apparatus so that the surface over which the first electrode 101 was formed faced downward, and 4,4',4"-(benzene-1,3,5-triyl)tri(dibenzothiophene) (abbreviation: DBT3P-II) represented by Structural Formula (i) and molybdenum(VI) oxide were co-evaporated over the first electrode 101 to have a weight ratio of 1:0.5 (=DBT3P-II: molybdenum oxide) to a thickness of 40 nm by an evaporation method using resistance heating, whereby the hole-injection layer 111 was formed.

Next, as the hole-transport layer 112, 9-[3-(9-phenyl-9H-fluoren-9-yl)phenyl]9H-carbazole (abbreviation: mCzFLP) represented by Structural Formula (ii) was deposited over the hole-injection layer 111 by evaporation to a thickness of 20 nm.

Then, 4,6-bis[3-(9H-carbazol-9-yl)phenyl]pyrimidine (abbreviation: 4,6mCzP2Pm) represented by Structural Formula (iii), 4-[3,6-bis(N,N-diphenylamino)carbazol-9-yl]benzofuro[3,2-d]pyrimidine (abbreviation: 4DPhA2CzBfpm) represented by Structural Formula (100), and 2,8-di-tert-butyl-5,11-bis(4-tert-butylphenyl)-6,12-diphenyltetracene (abbreviation: TBRb) were deposited by co-evaporation to a thickness of 40 nm at a weight ratio of 1:1:0.01 (=4,6mCzP2Pm:4DPhA2CzBfpm:TBRb), so that the light-emitting layer 113 was formed.

After that, over the light-emitting layer 113, 4,6mCzP2Pm was formed to a thickness of 20 nm, and then, 2,9-di(2-naphthyl)-4,7-diphenyl-1,10-phenanthroline (abbreviation: NBPhen) represented by Structural Formula (iv) was deposited by evaporation to a thickness of 15 nm, whereby the electron-transport layer 114 was formed.

After the formation of the electron-transport layer 114, lithium fluoride (LiF) was deposited by evaporation to a thickness of 1 nm to form the electron-injection layer 115, and then aluminum was deposited by evaporation to a thickness of 200 nm to form the second electrode 102, whereby a light-emitting device 4 of this example was fabricated.

The element structure of the light-emitting device is listed in the following table.

in current excitation and indicates that energy from triplet excitons contributes to light emission.

Light-emitting device 4, in which the HOMO and LUMO of 4DPhA2CzBfpm used as one of the host materials are present in the spatially divided state in a molecule as described in Example 4, is an organic compound with small $\Delta E_{ST}$ as in the measurement in Example 1. This indicates that 4DPhACzBfpm is a substance that easily exhibits causes reverse intersystem crossing.

FIG. 56 shows the measurement results of the transient EL characteristics of Light-emitting device 4. A picosecond fluorescence lifetime measurement system (manufactured by Hamamatsu Photonics K.K.) was used for the measurements. In the measurement, a square wave pulse voltage was applied to the light-emitting device, and time-resolved measurement of light emission, which was attenuated from the falling of the voltage, was performed with a streak camera. The measurement was conducted at room temperature (25° C.).

Figure 56A:
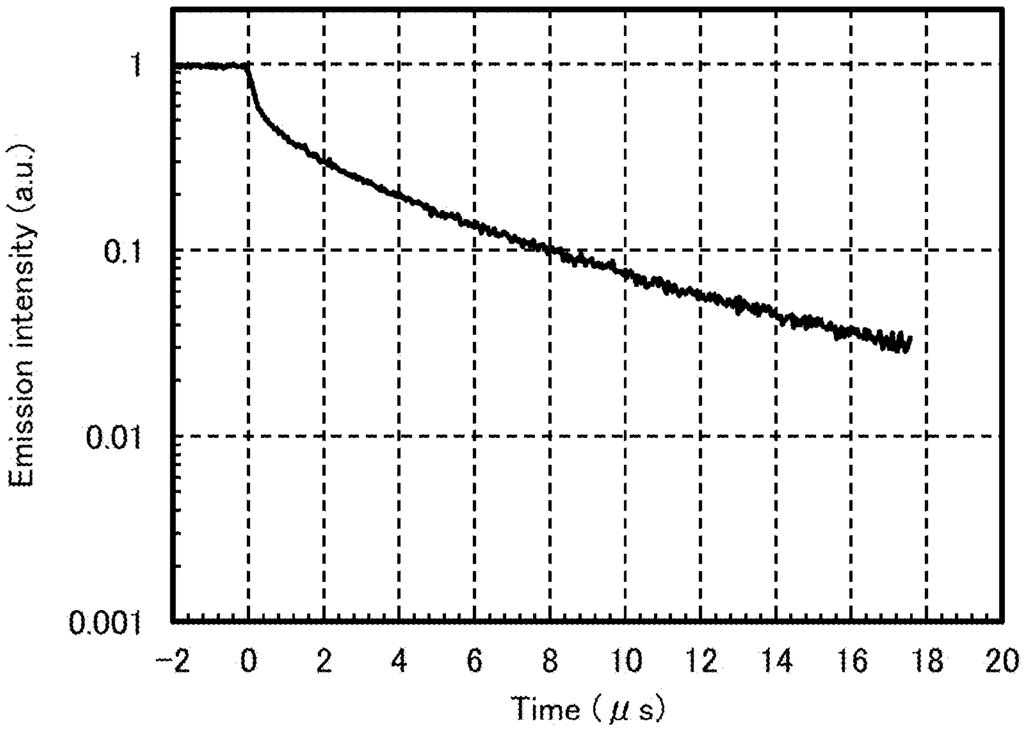
FIG. 56A and FIG. 56B are graphs showing transient EL characteristics of Light-emitting device 4.
Figure 56B:
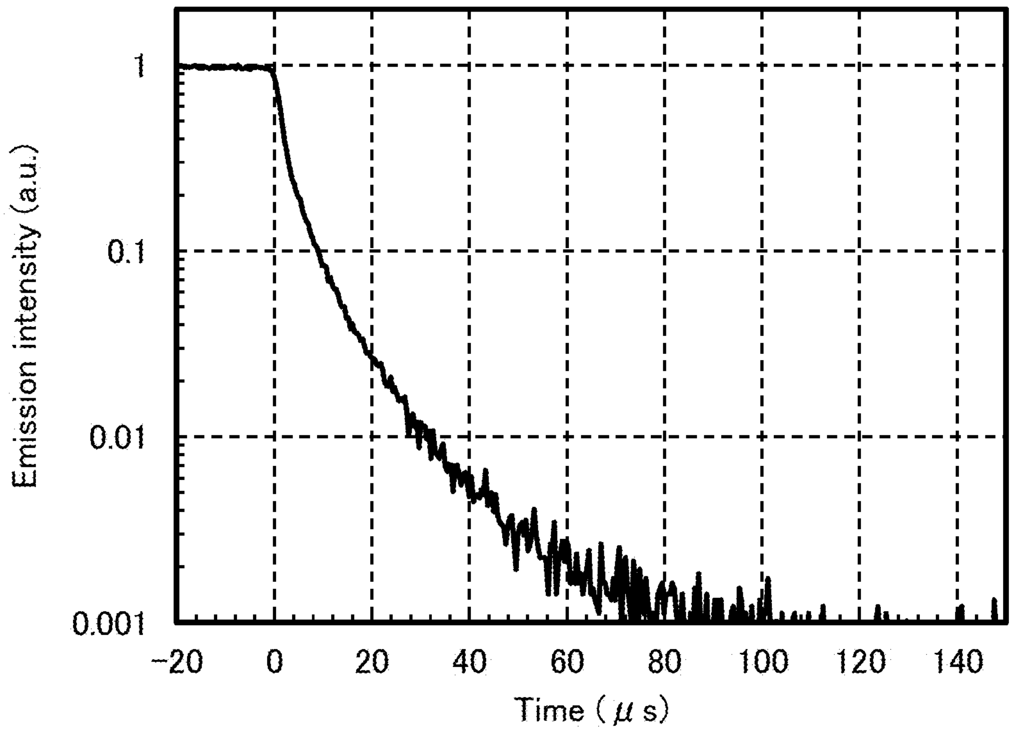

In FIG. 56A and FIG. 56B, the vertical axis represents the emission intensity normalized to that in a state where carriers were steadily injected (when the pulse voltage is ON). The horizontal axis represents time elapsed after the falling of the pulse voltage. Note that FIG. 56A and FIG. 56B differ in measurement time range.

TABLE 7

| | Hole-injection layer 40 nm | Hole-transport layer 20 nm | Light-emitting layer 40 nm | Electron-transport layer 1 20 nm | Electron-transport layer 2 15 nm |
|---|---|---|---|---|---|
| Light-emitting device 4 | DBT3P-II:molybdenum oxide (1:0.5) | mCzFLP | 4,6mCzP2Pm:4DPhA2CzBfpm:TBRb (1:1:0.01) | 4,6mCzP2Pm | NBPhen |

The light-emitting device was subjected to sealing with a glass substrate (a sealant was applied to surround the element, and at the time of sealing, UV treatment was performed first and heat treatment was performed at 80° C. for one hour) in a glove box containing a nitrogen atmosphere so that the light-emitting device was not exposed to the air. Then, the initial characteristics were measured.

Figure 50:
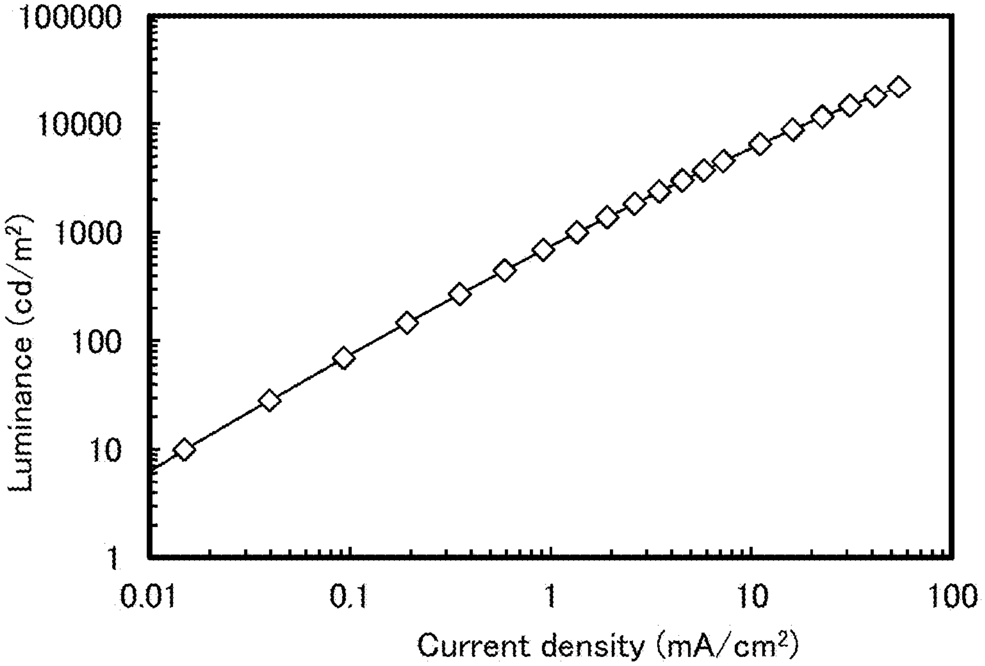
FIG. 50 is a graph showing luminance-current density characteristics of Light-emitting device 4.
Figure 51:
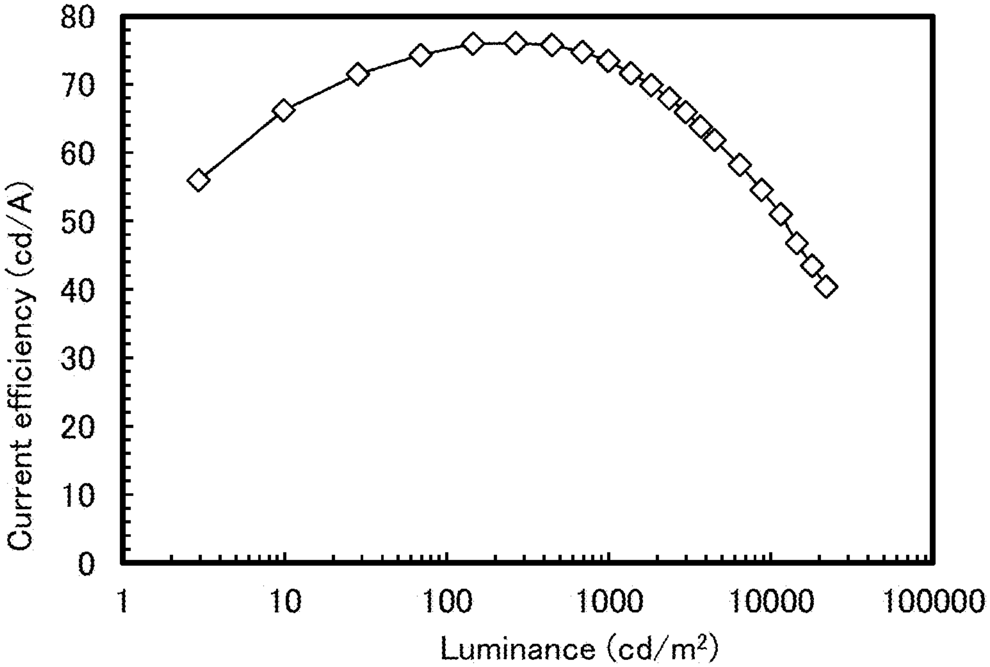
FIG. 51 is a graph showing current efficiency-luminance characteristics of Light-emitting device 4.
Figure 52:
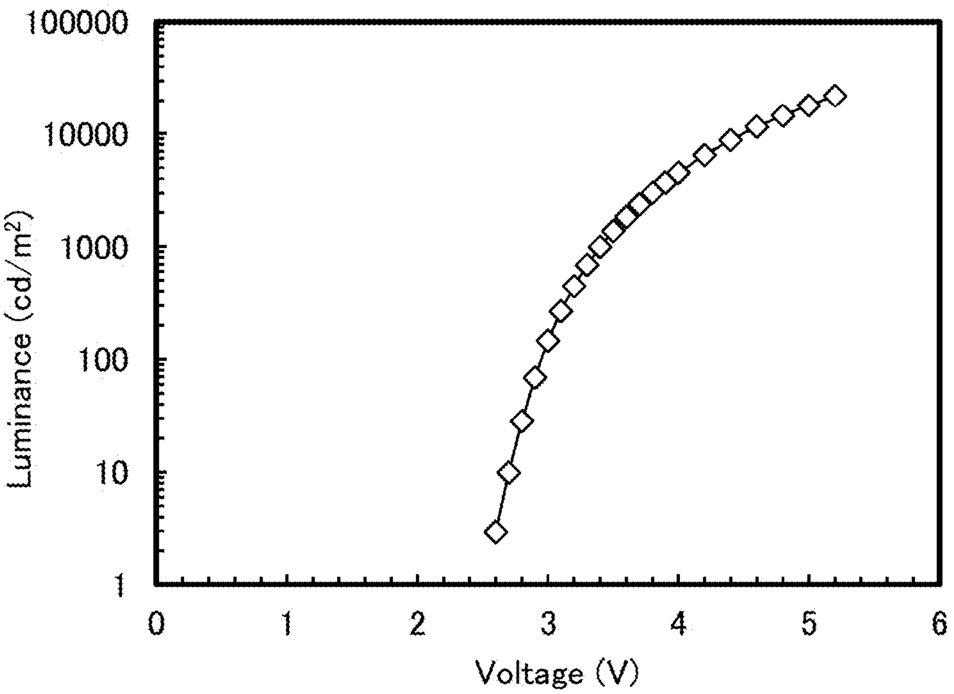
FIG. 52 is a graph showing luminance-voltage characteristics of Light-emitting device 4.
Figure 53:
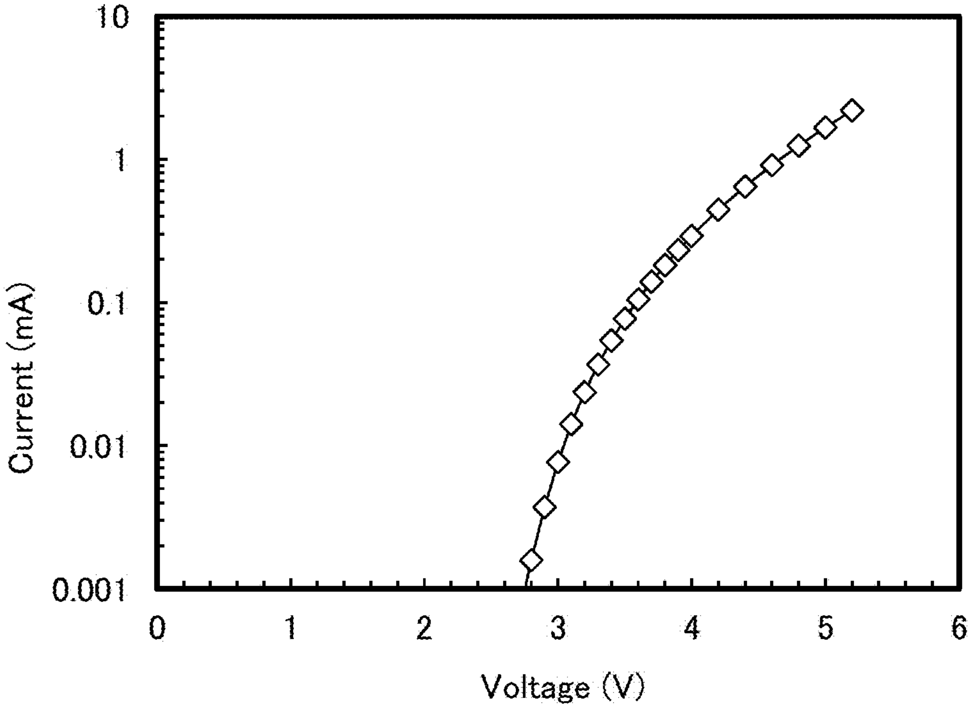
FIG. 53 is a graph showing current-voltage characteristics of Light-emitting device 4.
Figure 54:
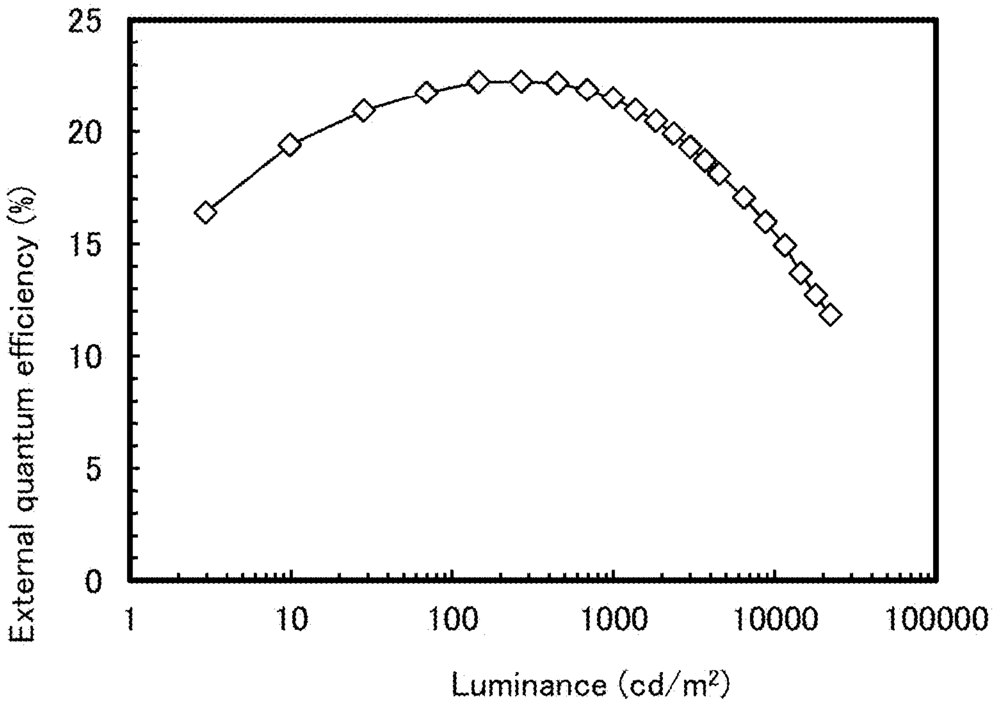
FIG. 54 is a graph showing external quantum efficiency-luminance characteristics of Light-emitting device 4.

FIG. 50 shows the luminance-current density characteristics of Light-emitting device 4; FIG. 51, the current efficiency-luminance characteristics; FIG. 52, the luminance-voltage characteristics; FIG. 53, the current-voltage characteristics; FIG. 54, the external quantum efficiency-luminance characteristics; and FIG. 55, the emission spectrum. Main characteristics of Light-emitting device 4 at approximately 1000 cd/m$^2$ are listed below.

From the transient EL characteristics shown in FIG. 56A and FIG. 56B, at least an emission component that attenuates promptly with a fluorescence lifetime (transient lifetime) of approximately 0.2 μs and an emission component that attenuates late with a fluorescence lifetime of approximately 8 μs were observed from Light-emitting device 4. Of these, the emission component with a fluorescence lifetime of 8 μs is delayed fluorescence.

Note that TBRb is a fluorescent light-emitting substance not having a TADF property. This indicates that, in Light-emitting device 4, a singlet excited state is generated by reverse intersystem crossing from the triplet excited state to the singlet excited state of 4DPhA2CzBfpm and light is emitted from TBRb by energy transfer from the singlet

TABLE 8

| | Voltage (V) | Current (mA) | Current density (mA/cm$^2$) | Chromaticity x | Chromaticity y | Current efficiency (cd/A) | External efficiency (%) |
|---|---|---|---|---|---|---|---|
| Light-emitting device 4 | 3.4 | 0.05 | 1.4 | 0.42 | 0.56 | 73.4 | 21.5 |

Figure 55:
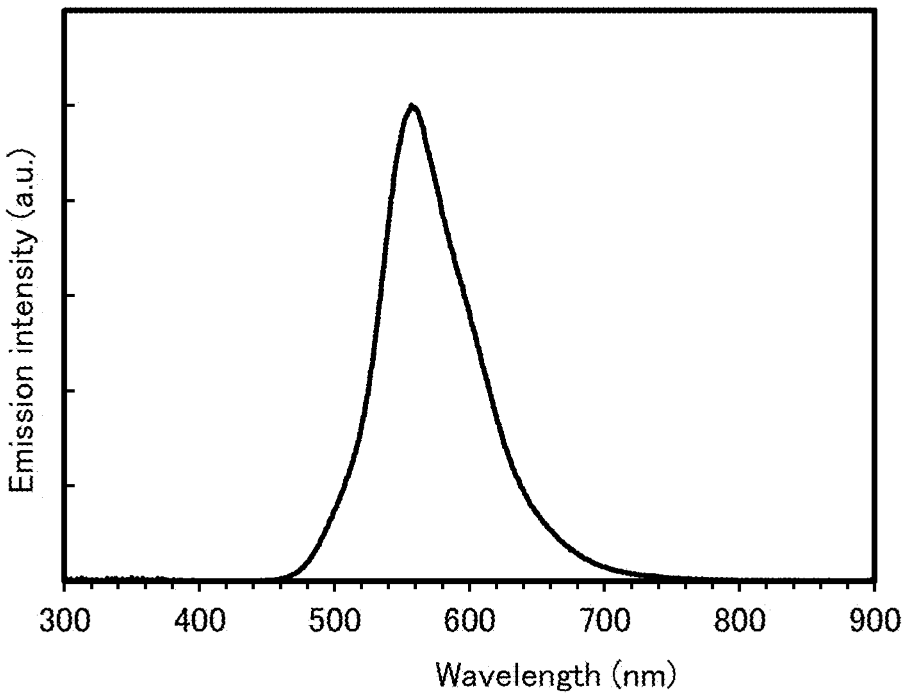
FIG. 55 is a graph showing an emission spectrum of Light-emitting device 4.

As can be seen from each of FIG. 55 and the chromaticity, TBRb in Light-emitting device 4 emits light. It is found from FIG. 50 to FIG. 54 that Light-emitting device 4 of one embodiment of the present invention is a light-emitting element having favorable characteristics with very high efficiency such as high external quantum efficiency of a maximum of 20% or higher. This is a value significantly exceeding the theoretical limit of fluorescent light emission excited state to TBRb. Thus, Light-emitting device 4 is found to be an exciton capture type fluorescent element and achieves high efficiency.

REFERENCE NUMERALS

101: first electrode, 102: second electrode, 103: EL layer, 111: hole-injection layer, 112: hole-transport layer, 113:

light-emitting layer, 114: electron-transport layer, 115: electron-injection layer, 116: charge-generation layer, 117: P-type layer, 118: electron-relay layer, 119: electron-injection buffer layer, 400: substrate, 401: first electrode, 403: EL layer, 404: second electrode, 405: sealant, 406: sealant, 407: sealing substrate, 412: pad, 420: IC chip, 501: anode, 502: cathode, 511: first light-emitting unit, 512: second light-emitting unit, 513: charge-generation layer, 601: driver circuit portion (source line driver circuit), 602: pixel portion, 603: driver circuit portion (gate line driver circuit), 604: sealing substrate, 605: sealant, 607: space, 608: wiring, 609: FPC (flexible printed circuit), 610: element substrate, 611: switching FET, 612: current control FET, 613: first electrode, 614: insulator, 616: EL layer, 617: second electrode, 618: light-emitting device, 730: insulating film, 770: planarization insulating film, 772: conductive film, 782: light-emitting device, 783: droplet discharge apparatus, 784: droplet, 785: layer, 786: EL layer, 788: conductive film, 951: substrate, 952: electrode, 953: insulating layer, 954: partition layer, 955: EL layer, 956: electrode, 1001: substrate, 1002: base insulating film, 1003: gate insulating film, 1006: gate electrode, 1007: gate electrode, 1008: gate electrode, 1020: first interlayer insulating film, 1021: second interlayer insulating film, 1022: electrode, 1024W: first electrode, 1024R: first electrode, 1024G: first electrode, 1024B: first electrode, 1025: partition, 1028: EL layer, 1029: second electrode, 1031: sealing substrate, 1032: sealant, 1033: transparent base material, 1034R: red coloring layer, 1034G: green coloring layer, 1034B: blue coloring layer, 1035: black matrix, 1036: overcoat layer, 1037: third interlayer insulating film, 1040: pixel portion, 1041: driver circuit portion, 1042: peripheral portion, 1400: droplet discharge apparatus, 1402: substrate, 1403: droplet discharge means, 1404: imaging means, 1405: head, 1406: dotted line, 1407: control means, 1408: storage medium, 1409: image processing means, 1410: computer, 1411: marker, 1412: head, 1413: material supply source, 1414: material supply source, 1415: material supply source, 1416: head, 2001: housing, 2002: light source, 2100: robot, 2110: arithmetic device, 2101: illuminance sensor, 2102: microphone, 2103: upper camera, 2104: speaker, 2105: display, 2106: lower camera, 2107: obstacle sensor, 2108: moving mechanism, 3001: lighting device, 5000: housing, 5001: display portion, 5002: display portion, 5003: speaker, 5004: LED lamp, 5006: connection terminal, 5007: sensor, 5008: microphone, 5012: support, 5013: earphone, 5100: cleaning robot, 5101: display, 5102: camera, 5103: brush, 5104: operation button, 5150: portable information terminal, 5151: housing, 5152: display region, 5153: bend portion, 5120: dust, 5200: display region, 5201: display region, 5202: display region, 5203: display region, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7210: second display portion, 7401: housing, 7402: display portion, 7403: operation button, 7404: external connection port, 7405: speaker, 7406: microphone, 9310: portable information terminal, 9311: display panel, 9313: hinge, 9315: housing This application is based on Japanese Patent Application Serial No. 2020-023394 filed on Feb. 14, 2020, the entire contents are hereby incorporated herein by reference.

The invention claimed is:

1. An organic compound represented by General Formula (G1):

(G1)

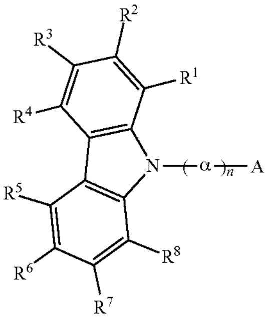

wherein in General Formula (G1), $R^1$ to $R^8$ are each independently any one of hydrogen, an alkyl group having 1 to 6 carbon atoms, a cycloalkyl group having 3 to 7 carbon atoms, and a substituted or unsubstituted diarylamino group; at least one of $R^1$ to $R^8$ is the substituted or unsubstituted diarylamino group; α is a substituted or unsubstituted phenylene group; n is an integer of 0 to 4; and A is a group represented by General Formula (g1):

(g1)

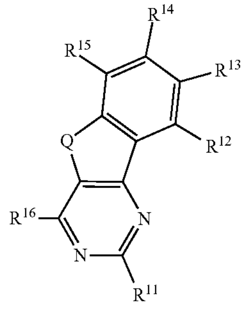

wherein in General Formula (g1), one of $R^{11}$ and $R^{16}$ is a bond; $R^{12}$ to $R^{15}$ and the other of $R^{11}$ and $R^{16}$ are each independently any of hydrogen, an alkyl group having 1 to 6 carbon atoms, a cycloalkyl group having 3 to 7 carbon atoms, and a substituted or unsubstituted aryl group having 6 to 13 carbon atoms in a ring; and Q represents an oxygen atom or a sulfur atom.

2. An organic compound represented by General Formula (G2):

(G2)

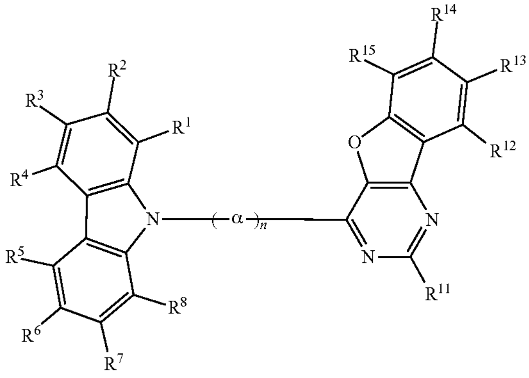

wherein in General Formula (G2), $R^1$ to $R^8$ are each independently any one of hydrogen, an alkyl group having 1 to 6 carbon atoms, a cycloalkyl group having 3 to 7 carbon atoms, and a substituted or unsubstituted diarylamino group; at least one of $R^1$ to $R^8$ is the substituted or unsubstituted diarylamino group; α is a substituted or unsubstituted phenylene group; n is an integer of 0 to 4; $R^{11}$ to $R^{15}$ are each independently any of hydrogen, an alkyl group having 1 to 6 carbon atoms, a cycloalkyl group having 3 to 7 carbon atoms, and a substituted or unsubstituted aryl group having 6 to 13 carbon atoms in a ring; and Q represents an oxygen atom or a sulfur atom.

3. The organic compound according to claim 1, wherein the substituted or unsubstituted diarylamino group is a group represented by General Formula (g2):

(g2)

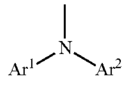

wherein in General Formula (g2), $Ar^1$ and $Ar^2$ each independently represent a substituted or unsubstituted aryl group having 6 to 13 carbon atoms in a ring.

4. The organic compound according to claim 3, wherein one or both of $R^3$ and $R^6$ are groups represented by General Formula (g2).

5. An organic compound represented by General Formula (G3):

(G3)

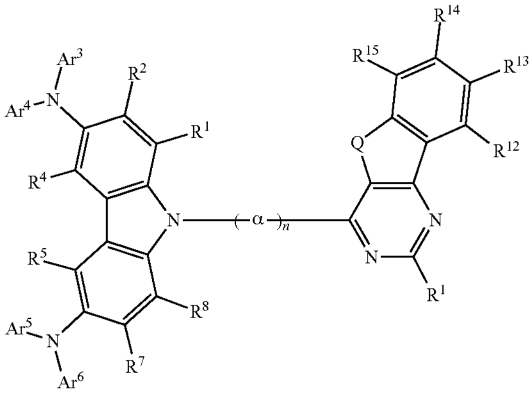

wherein in General Formula (G3), $Ar^3$ to $Ar^6$ are each independently any of a substituted or unsubstituted aryl group having 6 to 13 carbon atoms in a ring; $R^1$, $R^2$, $R^4$, $R^5$, $R^7$, and $R^8$ are each independently any one of hydrogen, an alkyl group having 1 to 6 carbon atoms, and a cycloalkyl group having 3 to 7 carbon atoms; α represents a substituted or unsubstituted phenylene group; n is an integer of 0 to 4; $R^{11}$ to $R^{15}$ are each independently any of hydrogen, an alkyl group having 1 to 6 carbon atoms, a cycloalkyl group having 3 to 7 carbon atoms, and a substituted or unsubstituted aryl group having 6 to 13 carbon atoms in a ring; and Q represents an oxygen atom or a sulfur atom.

6. The organic compound according to claim 5, wherein the organic compound is represented by General Formula (G4):

(G4)

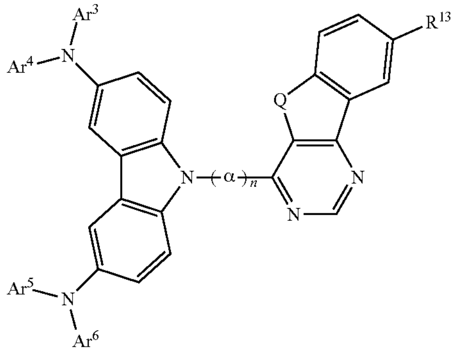

wherein in General Formula (G4), $Ar^3$ to $Ar^6$ are each independently any of a substituted or unsubstituted aryl group having 6 to 13 carbon atoms in a ring; α is a substituted or unsubstituted phenylene group; n is an integer of 0 to 4; $R^{13}$ is any of hydrogen, an alkyl group having 1 to 6 carbon atoms, a cycloalkyl group having 3 to 7 carbon atoms, and a substituted or unsubstituted aryl group having 6 to 13 carbon atoms in a ring; and Q represents an oxygen atom or a sulfur atom.

7. The organic compound according to claim 5, wherein the organic compound is represented by General Formula (G5):

(G5)

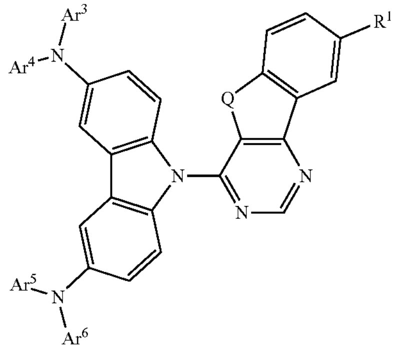

wherein in General Formula (G5), $Ar^3$ to $Ar^6$ are each independently any of a substituted or unsubstituted aryl group having 6 to 13 carbon atoms in a ring; $R^{13}$ is any of hydrogen, an alkyl group having 1 to 6 carbon atoms, a cycloalkyl group having 3 to 7 carbon atoms, and a substituted or unsubstituted aryl group having 6 to 13 carbon atoms in a ring; and Q represents an oxygen atom or a sulfur atom.

8. The organic compound according to claim 1, wherein the organic compound is represented by Structural Formula (100):

(100)

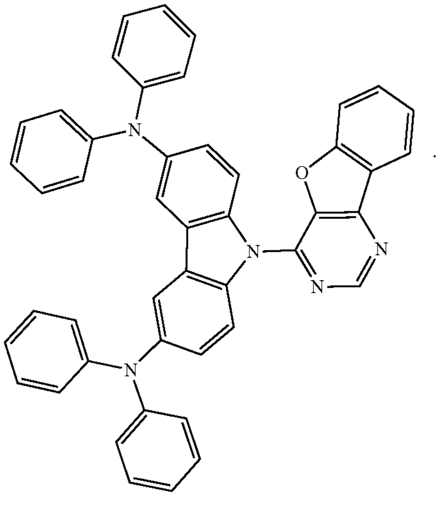

9. The organic compound according to claim 1, wherein the organic compound is represented by Structural Formula (101):

(101)

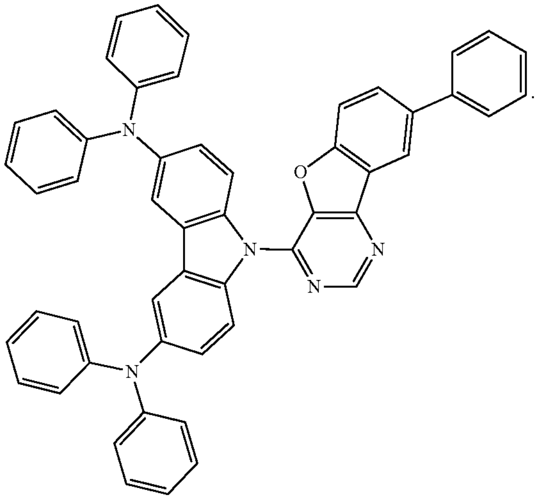

10. The organic compound according to claim 1, wherein the organic compound is represented by Structural Formula (102):

(102)

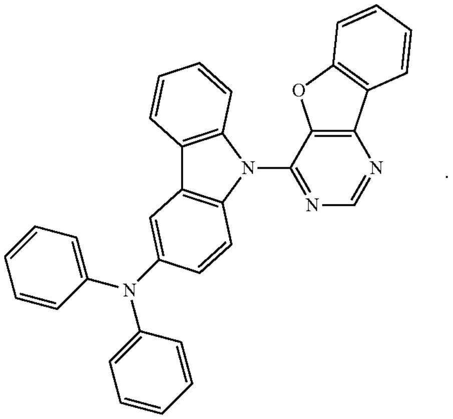

11. The organic compound according to claim 1, wherein a difference between a lowest singlet excited level and a lowest triplet excited level of the organic compound is less than or equal to 0.2 eV.

12. The organic compound according to claim 1, wherein a difference between a lowest singlet excited level and a lowest triplet excited level of the organic compound is less than or equal to 0.1 eV.

13. The organic compound according to claim 1, wherein Q is an oxygen atom.

14. An electronic device comprising:

a first electrode;

a second electrode; and an organic layer between the first electrode and the second electrode, wherein the organic layer comprises the organic compound according to claim 1.

15. A light-emitting device comprising:

a first electrode;

a second electrode; and an organic layer between the first electrode and the second electrode, wherein the organic layer comprises the organic compound according to claim 1.

16. The light-emitting device according to claim 15, wherein the organic layer comprises a light-emitting layer, and wherein the organic compound is included in the light-emitting layer.

17. The light-emitting device according to claim 15, wherein light emission from the organic layer is delayed fluorescence.

18. The light-emitting device according to claim 17, wherein a transient lifetime of the delayed fluorescence is longer than or equal to 100 nanoseconds and shorter than or equal to 10 milliseconds.

19. The light-emitting device according to claim 16, wherein the light-emitting layer further comprises a fluorescent light-emitting material.

20. The light-emitting device according to claim 16, wherein the light-emitting layer further comprises a phosphorescent light-emitting material.

21. An electronic apparatus comprising the light-emitting device according to claim 15, and at least one of a sensor, an operation button, a speaker, and a microphone.

22. A light-emitting apparatus comprising the light-emitting device according to claim 15, and at least one of a transistor and a substrate.

23. A lighting device comprising the light-emitting device according to claim 15, and a housing.

* * * * *